(12) United States Patent
Chevrot et al.

(10) Patent No.: US 10,246,697 B2
(45) Date of Patent: Apr. 2, 2019

(54) COLISTIN SYNTHETASES AND CORRESPONDING GENE CLUSTER

(71) Applicants: Centre National de la Recherche Scientifique, Paris (FR); Universite La Rochelle, La Rochelle (FR)

(72) Inventors: Romain Chevrot, La Rochelle (FR); Fatoumata Tambadou, La Rochelle (FR); Thibault Caradec, Lille (FR); Sandrine Didelot, La Rochelle (FR); Cyrille Barthelemy, Saintes (FR)

(73) Assignees: Centre National de la Recherche Scientifique (CNRS), Paris (FR); Universite La Rochelle, La Rochelle (FR)

( * ) Notice: Subject to any disclaimer, the term of this patent is extended or adjusted under 35 U.S.C. 154(b) by 0 days.

(21) Appl. No.: 15/113,978

(22) PCT Filed: Jan. 26, 2015

(86) PCT No.: PCT/IB2015/050571
§ 371 (c)(1),
(2) Date: Jul. 25, 2016

(87) PCT Pub. No.: WO2015/111013
PCT Pub. Date: Jul. 30, 2015

(65) Prior Publication Data
US 2016/0348088 A1  Dec. 1, 2016

(30) Foreign Application Priority Data

Jan. 27, 2014 (FR) ...................................... 14 50641

(51) Int. Cl.
| C07K 7/62 | (2006.01) |
| C12N 9/00 | (2006.01) |
| C12N 15/52 | (2006.01) |
| C12P 21/02 | (2006.01) |

(52) U.S. Cl.
CPC .................. *C12N 9/93* (2013.01); *C07K 7/62* (2013.01); *C12N 15/52* (2013.01); *C12P 21/02* (2013.01)

(58) Field of Classification Search
None
See application file for complete search history.

(56) References Cited

U.S. PATENT DOCUMENTS

2010/0279347 A1* 11/2010 Park ........................ C12N 15/52
435/69.1

OTHER PUBLICATIONS

GenBank: EPY07789.1 "Gramicidin S synthetase II [Paenibacillus alvei TS15]" Submitted May 22, 2013. (Year: 2013).*
Tambadou et al. "Characterization of the colistin (polymyxin E1 and E2) biosynthetic gene cluster." Arch Microbiol. May 2015;197(4):521-32 (Year: 2015).*
GenBank AJM89735.1, "PmxA," Submitted (Dec. 11, 2014) downloaded from www.ncbi.nlm.nih.gov (Year: 2014).*
GenBank KP262070, "Paenibacillus alvei colistin (polymyxin E1 & E2) biosynthetic gene cluster, complete sequence" Submitted (Dec. 11, 2014) downloaded from www.ncbi.nlm.nih.gov (Year: 2014).*
Choi et al., *Identification of a Polymyxin Synthetase Gene Cluster of Paenibacillus polymyxa and Heterologous Expression of the Gene in Bacillus subtilis*, 191(10) Journal of Bacteriology 3350-3358 (May 2009).
Kline et al., *Synthesis and characterization of the colistin peptide polymyxin $E_1$ and related antimicrobial peptides*, 37 J. Peptide Res. 175-187 (2001).
Park et al., *Efficient Production of Polymyxin in the Surrogate Hose Bacillus subtilis by Introducing a Foreign ectB Gene and Disrupting the abrB Gene*, 78(12) Applied and Environmental Microbiology 4194-4199 (Jun. 2012).
Tambadou et al., *Characterization of the colistin (polymyxin E1 and E2) biosynthetic gene cluster*, 197 Arch Microbiol 521-532 (2015).

* cited by examiner

*Primary Examiner* — Christina Bradley
(74) *Attorney, Agent, or Firm* — Buchanan Ingersoll & Rooney PC

(57) ABSTRACT

PmxA synthetase involved in polymyxin E synthesis, comprising four adenylation sites, characterized in that the second adenylation site has at least 90% identity with the peptide sequence SEQ ID NO 1:

VTEAEKADLLGRFNDTTTEFPRGKTLIQLFEEQVERIPDAAAITLNEQE

LTYRELNERVNRLARTLRSHGISKGRLVAILAERSIEMVVGMLAAHKAG

AAYVPIDPEYPEERIRFLIEDSGGQVMLTQSRLRERLAGSDPVILLDDE

SFYHEDGTNLNTGIEATDLACVIYTSGTTGKPKGNPVSHRNIVRVVQNT

NYIDITERDHVLQLSSYSF<u>D</u>GAT<u>F</u>DIFGALTNGARLVLVPYETLLEIGR

LADLIQRERISVM<u>F</u>ITTAFFNILVDVNVDCLRDVRAI<u>L</u>F<u>G</u>GERVSVGHV

RKALAHIGPGRLNH<u>V</u>YGPTEST<u>V</u><u>Y</u>TTYLPVDFVDELAVTVPIGRPISNT

TVYIVDSRNKLLPIGVAGELCVGGEGLVRGYNNRPELTAEKFVDNPFVP

GERMYRTGDLAKWLPDGTIEYVGRTDDQVKIRGFRIELGEIEAQLQKVE

GIRKTTVFARENASGEKQLCAYYEADCELPAAELKSVLSKELPAYMIPA

Figure 1:
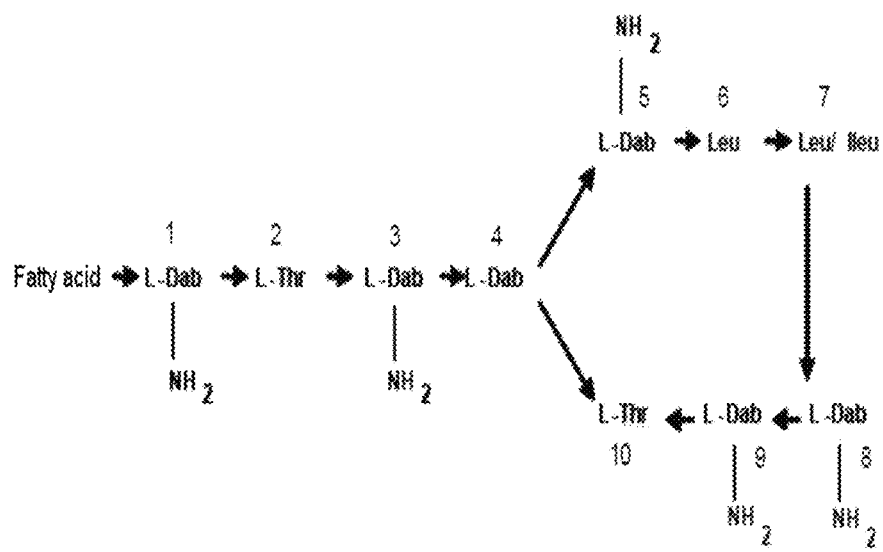

YLIQLERLPLTTNG<u>K</u>VDRRSLPAPEESLQPGGG, the underlined amino acids DGFFLGVVYK being conserved and forming a binding pocket specific for a leucine, isoleucine or valine residue.

4 Claims, 7 Drawing Sheets
Specification includes a Sequence Listing.

"Colistin" NRPS cluster

Amino acids incorporated by synthetases A, B & E

Leu-Leu-lleu-Dab-Dab    Thr    Dab-Thr-Dab-Dab-Dab

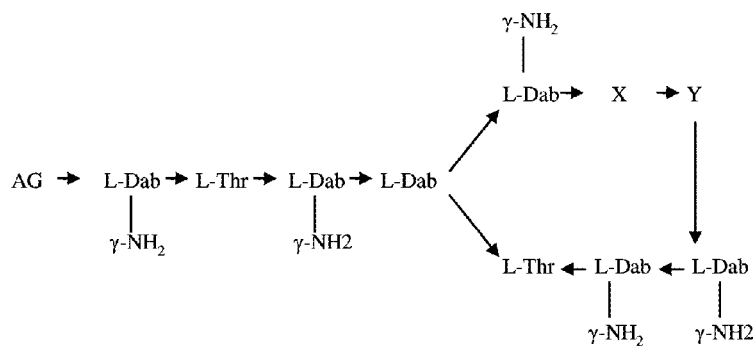

| Polymyxin B | X | Y | Fatty acid (FA) | Chemical formula and molecular mass |
|---|---|---|---|---|
| $B_1$ | D-Phe | L-Leu | 6-methyloctanoyl - $C_9H_{17}O$ | $C_{56}H_{98}N_{16}O_{13}$ – 1202.7498 Da |
| Ile-$B_1$ | D-Phe | L-Ile | 6-methyloctanoyl - $C_9H_{17}O$ | $C_{56}H_{98}N_{16}O_{13}$ – 1202.7498 Da |
| $B_2$ | D-Phe | L-Leu | 6-methylheptanoyl - $C_8H_{15}O$ | $C_{55}H_{96}N_{16}O_{13}$ – 1188.7342 Da |
| $B_3$ | D-Phe | L-Leu | Octanoyl - $C_8H_{15}O$ | $C_{55}H_{96}N_{16}O_{13}$ – 1188.7342 Da |
| $B_4$ | D-Phe | L-Leu | Heptanoyl - $C_7H_{13}O$ | $C_{54}H_{94}N_{16}O_{13}$ – 1174.7185 Da |
| $B_5$ | D-Phe | L-Leu | Nonanoyl - $C_9H_{17}O$ | $C_{56}H_{98}N_{16}O_{13}$ – 1202.7498 Da |
| $B_6$ | D-Phe | L-Leu | 3-OH-6-methyloctanoyl - $C_9H_{17}O_2$ | $C_{56}H_{98}N_{16}O_{14}$ – 1218.1447 Da |
| Polymyxin E | | | | |
| $E_1$ | D-Leu | L-Leu | 6-methyloctanoyl - $C_9H_{17}O$ | $C_{53}H_{100}N_{16}O_{13}$ – 1168.7655 Da |
| $E_2$ | D-Leu | L-Leu | 6-methylheptanoyl - $C_8H_{15}O$ | $C_{52}H_{98}N_{16}O_{13}$ – 1154.7498 Da |
| $E_3$ | D-Leu | L-Leu | Octanoyl - $C_8H_{15}O$ | $C_{52}H_{98}N_{16}O_{13}$ – 1154.7498 Da |
| $E_4$ | D-Leu | L-Leu | Heptanoyl - $C_7H_{13}O$ | $C_{51}H_{96}N_{16}O_{13}$ – 1140.7342 Da |
| $E_7$ | D-Leu | L-Leu | 7-methyloctanoyl - $C_9H_{17}O$ | $C_{53}H_{100}N_{16}O_{13}$ – 1168.7355 Da |
| Ile-$E_1$ | D-Leu | L-Ile | 6-methyloctanoyl - $C_9H_{17}O$ | $C_{53}H_{100}N_{16}O_{13}$ – 1168.7355 Da |
| Ile-$E_2$ | D-Leu | L-Ile | 6-methylheptanoyl - $C_8H_{15}O$ | $C_{52}H_{98}N_{16}O_{13}$ – 1154.7498 Da |
| Ile-$E_8$ | D-Leu | L-Ile | 7-methylnonanoyl - $C_{10}H_{19}O$ | $C_{54}H_{102}N_{16}O_{13}$ – 1182.7811 Da |
| Nval-$E_1$ | D-Leu | L-Norval | 6-methyloctanoyl - $C_9H_{17}O$ | $C_{51}H_{96}N_{16}O_{13}$ – 1140.7342 Da |
| Val-$E_1$ | D-Leu | L-Val | 6-methyloctanoyl - $C_9H_{17}O$ | $C_{52}H_{98}N_{16}O_{13}$ – 1154.7498 Da |
| Val-$E_2$ | D-Leu | L-Val | 6-methylheptanoyl - $C_8H_{15}O$ | $C_{51}H_{96}N_{16}O_{13}$ – 1140.7342 Da |

Legend: Dab = α,γ-diaminobutyric acid. Norval = norvaline.

FIGURE 3

BLR strain

Mutant 5

MAFEKETLFWNEKFGSDDYTLTRLPYSKAPSSQAPIMTTVGGSLSEKAAQRVLQMSKGAPLAAFMILLAGVQSLLHKYT
GASDILVGMPVIRKPTETRRSVNHTVILKSLLSAGSTFKTLLSELRTSLPETIQHQHIPFLKMTEKLDLQYADGIPIIH
TLVSLKELHLDEIGQNVVTDCSFEFSLTGGTIQLALSYNEHLYDSKFMTRIVGHLNRLLAVGLHELELDIVRVDM**LSED
EKFQLLQSFNDTEKDYPRDRTIHQLVEEQVKRVPEATAIVFEGRRLSYAELNERANRLARTLRSVGVLPNQLVGLMARR
SLETVVGILAVLKAGGAYVPIDPEYPEERIRYILENSNAQLLLTQRKLQQQVPFEGTVLALDDEQAYSDDGTNLEPASG
SNDLAYVIYTSGTTGKPKGVMLEHRGLVSLKLMFADRLGITEHDRIVQFASLSFDASCWEVFKALYFGATLYIPTAETI
LDNRLFESYMNEHAITAAILPPTYSAYLNPDRLPSLTKLVTGGSAVSAEFVQQWKPKVHYFNAYGPTEASIVTTLWDAN
EEQPERRVIPIGRPLANHRIFILDAHLQLVPPGVDGELCVAGVGLARGYLNHPELTAEKFVEHPFAPGERLYRTGDLAR
WLPDGNIEYLGRIDHQVKIRGFRIEIGEIEEQLLKIDSVQETMVIAREGKSGQELCAYLVADRPLTLGELRSALAQKLP
NYMIPAHFVQLPRMPLTPNDKIDRKALPAPEGNALTGGLY**VAPRNEAERTLVDVWQAVLNADRVGVTDHFFELGGDSIK
SIQVSSRLHQAGYKLDIRDLFKYPTISQLSLRVKPIGRTIDQGEITGETALTPIQHWFFESSFADPHHFNQSVMLYRKE
RFDEETVRQVLQKLAEHHDALRMVFRKTEQGFSERNRAIQEGGLFTLDVFDFKDAEDTAQALEAKATDIQAGIDLEKGP
LVKAGLFRCADGDHLLLAVHHAVVDGVSWRILMEDFALGYEQAGKSEEIRFPAKTDAYRTWSEQLAAYAQSPEIAKERA
YWQAVEQIAVPALPKDLEADVTTQQDSESLFVRLTSEETELLLKRVHRAYNTEMNDILVTALGIAVRKWTGHERVRINL
EGHGRESIGTDIDITRTVGWFTTKFPVVLEPETNRDLAYQIKQVKESLRRIPNKGLGYGVCRYLSKSEDGFVWGAEPEI
NFNYLGQFDDDVNQDEIGISSYSSGSPASDRQARSFVLDINGMVLDGALSLDLSYSRKQYRKVTMEAFAQRLEQSLREL
ITHCAGKENTELTPSDVQFKGLTIAELEQIGQRSVHVGEIENIYSLTPMQKGMWFHSALDRQTAAYFEQTRFTMRGALD
VQLFERSWTELAKRHLVLRANFVKGPAGEPLQIIYRDKPVGFEYEELLHLQADEKQAYLDKKAEDDKLRGFDLEHDALV
RVTILRTEEQSYHVLWSFQHILMDGWCLPQLTQELFETYSALASGKQPAGDKGSDYGAYIEWLEKQDDQAASGYWTAFL
AGYEGQTVLPGQKEAQPNGRFTADHVTAELGKDLSERMDRVAKQRLVTVNTLLQAAWGVMLQKYNGTNDAVFGSVVAGR
PAEIPGIESMIGLFINTVPVRVTSEADTVFADLMAKLQERALESGRYDYYPLYEIQARCVQKQNLINHIIAFENYPVDE
QMEQAGDQQHGDLTITDVQMEEQTNYNFNVTVVPGAEIEIRFDFNAEVFDKDSIERLKGHLVHLLEQVTDNPEITVGEL
EL**VTEAEKADLLGRFNDTTTEFPRGKTLIQLFEEQVERIPDAAAITLNEQELTYRELNERVNRLARTLRSHGISKGRLV
AILAERSIEMVVGMLAAHKAGAAYVPIDPEYPEERIRFLIEDSGGQVMLTQSRLRERLAGSDPVILLDDESFYHEDGTN
LNTGIEATDLACVIYTSGTTGKPKGNPVSHRNIVRVVQNTNYIDITERDHVLQLSSYSFDGATFDIFGALTNGARLVLV
PYETLLEIGRLADLIQRERISVMFITTAFFNILVDVNVDCLRDVRAILFGGERVSVGHVRKALAHIGPGRLNHVYGPTE
STVYTTYLPVDFVDELAVTVPIGRPISNTTVYIVDSRNKLLPIGVAGELCVGGEGLVRGYNNRPELTAEKFVDNPFVPG
ERMYRTGDLAKWLPDGTIEYVGRTDDQVKIRGFRIELGEIEAQLQKVEGIRKTTVFARENASGEKQLCAYYEADCELPA
AELKSVLSKELPAYMIPAYLIQLERLPLTTNGKVDRRSLPAPEESLQPGGG**STPPRTPLEASLAGIWKSVLGLVHIGVH
DNFFDMGGHSLRATTLVSKVHQELNVELPLRDVFRYSTIEEMALAISRIGEQSFSSIPLAGARAYYPLSSAQKRLFILN
QLEGADQSYNMPGVLLLEGSIDRSLLEKAFRGLIARHETLRTGFEIVQGEAVQRIYESVDFAVEYRHASEEETPEVVQA
FIRPFDLAKPPLLRAELVELAIERYLLMFDMHHIVSDGVSMDVLVEELVRLYGGESLEPLRIQYKDYAVWQQSDEQKVQ
LKREEAYWLDRYRGELPVLEMPTDYPRPAVQSFEGQTLTSFVDEATNEGLKQLAAQKGTTLYMVLLAAYTVLLHKYTGQ
DDLIVGTSIAGRTHGDTQPLIGMFVNTLALRNYPASEKSFLSYLEEVKETTLGAYEHQNYPFEELVDKVQVSRDLSRNP
LFDTMFSLQNLEDKEFKLEGLKLSPYPSEYGTAKFDLSVDVTEENGGLECIFEFATALYKESTIRRLSTHFGHLLAAIV
SRPDAKIAELNLLTAEENEQILGAFNPAQPEAAPAAAFHRLFEEQAERT**PEAEAVVYENDRLTYAELNERANRLAATLR
ASGIGRESIVGILSERSVDLLVAVLAVWKAGGAYVPIDPDYPADRVRFMLEDSGAKVLLTQTVLRERAEAWLGEEELAL
AAVLYLDDEASYSEERANAPIGSGMVSGKLTDAVDDGDVSHQKVGMGSFHEARPEDLAYVIYTSGTTGKPKGVMIEHRS
LVNTAAGYRREYRLDQFPVRLLQLASFSFDVFVGDIARTLYNGGTMVIVPKDDRIDPSRLHHWMERERVTIFESTPALI
VPFLEYVHEQGLDMSWMELLITSSDSCSVADYRILQERFGSFFRIINAYGVTEAAIDSSFYDEELTKLPQIGHVPIGKA
WLNAKFYIVDAHLNPVPVGVLGELVIGGVGVARGYLNRPELTEEKFVDSPFAAGERLYRTGDLARWMEDGNVDFIGRID
NQAKIRGYRIETGEIESQLLRVEGVREAVVLVRSDANGQKALCAYYTLDTGAELAVNDLRSTLAQELPGYMIPSYFVEL
EGLPLTPNGKIDRKALPAPEGEAGSGT**EYVAPRNELETKLAAIWQEVLGLAKEIGVHDNFFDIGGHSLRATTLVSKVHK
ELSVDLPLRDVFRHSTIESMAAAISRLDEQTFVAIPVADDREVYPQSFAQKRLFILNQLEGAELSYNMPEAMLLEGALD
RARFEEAFRKLVARHEMLRTGFEMVDGEASQRVYQDLNFAVEFYRVDEQEAEETVRRFVRPFDLAKPPLLRVGLVELAS
ERHILMYDMHHIISDGVSMEIFVEEFVRLYGGEQLEPLRIQYKDYTVWQHSQEQKERLQRQEAYWLNMFQGELPVLEMP
TDYPRPSVQSYEGHTLEFFFDASKTDGLKQLASETGTTLFMVLLAAYNVLLHKYSGQEDVIVGTPIAGRNHGDVQPLIG
MFLNTLAIRSYPASEKTFLSYLNEVKETTLHAFEHQNYPFEELVDKVQVTRDLSRNPLFDTLFTMQNTENEEFELEGLR
LIPYPSALDTAKFDISLDVGEENGGLDYSFEYATALYKRATIERLAKHYEQLLVTIISRPDAKIAELNLLTAEEKEQIL
GTFNPAQPEAAPAAAFHRLFEEQAERT**PEEAAVVYENDQLTYAELNERANRLAATLRASDIGRETIVGILAERSVDLL
SVLAVWKAGGAYVPLDPDYPADRVRFMLEDSGAKVLLTQMPLRERAEAWLGEEEALAAVLYLDDEASYSEERANAPIG
SGMVPGKLTDAVDDGDETHPNIGMGSFHEARPDDLAYVIYTSGTTGKPKGVMIEHRSLVNTAAGYRREYRLDQFPVRLL
QLASFSFDVFVGDIARTLYNGGTMVIVPKDDRIDPSRLHHWMERERVTIFESTPALIVPFLEYVHEQGLDISWMELLIT
SSDSCSVADYRILQERFGSLFRIINAYGVTEAAIDSSFYDEELAKLPQTGHVPIGKAWLNAKFYIVDAHLNPVPVGVLG
ELVIGGVGVARGYLNRPELTEEKFVDSPFAAGERLYRTGDLARWMEDGNVDFIGRIDNQAKIRGYRIETGEIESQLLRV
EGVREAVVLVRSDANGQKALCAYYTLDTGAELAVNDLRSTLAQELPGYMIPSYFVELEGLPLTPNGKIDRKALPAPEGE
AGSGT**EYVAPRNELETKLAAIWQEVLGLAKEIGVYDNFFDIGGHSLRATTLAGKVFKELNVNLPLRDVFRHSTIAAMAE
AIARMERLEHEDIPQAEEREYYPLSSAQKRLFIQHTLDGADQLYNMPELVQVEGEFDLDRLEAALRKLITRHESLRTGF
ELVKGKAVQRIYPQVDFAVEHHQADKEDAAQIEQIVRSFVRPFDLGKPPLLRAGVIELEPNLYILIFDMHHMVSDGVSM
AIVIDEFSSFYAGEELPSLRIQYKDYVVWQQSKAYRERIGRQEAYWLQTFKGELPTANLPMDYKRSAARSYEGAHLEFD
VEASLSMRLHELAAERKSTLFMVLLAAYTVLLSKYSGQEDLIVGTPVAGRTNADLEPVIGMFVNTLAIRNRPSGNKTFL
SYLEEVKETALGAFENQDYPFEELVERLNVKREPGRFPLFDAVFDLQNIEERDVELEGVSLKNYELDHLEEAKFDLTLF
MYENNGALSGGFFYATKLFKEAMIRTLTEDYLRVLSQIAENPQLELSRIECHKPAAGAKSAVDTIEFAF

FIGURE 5

A.
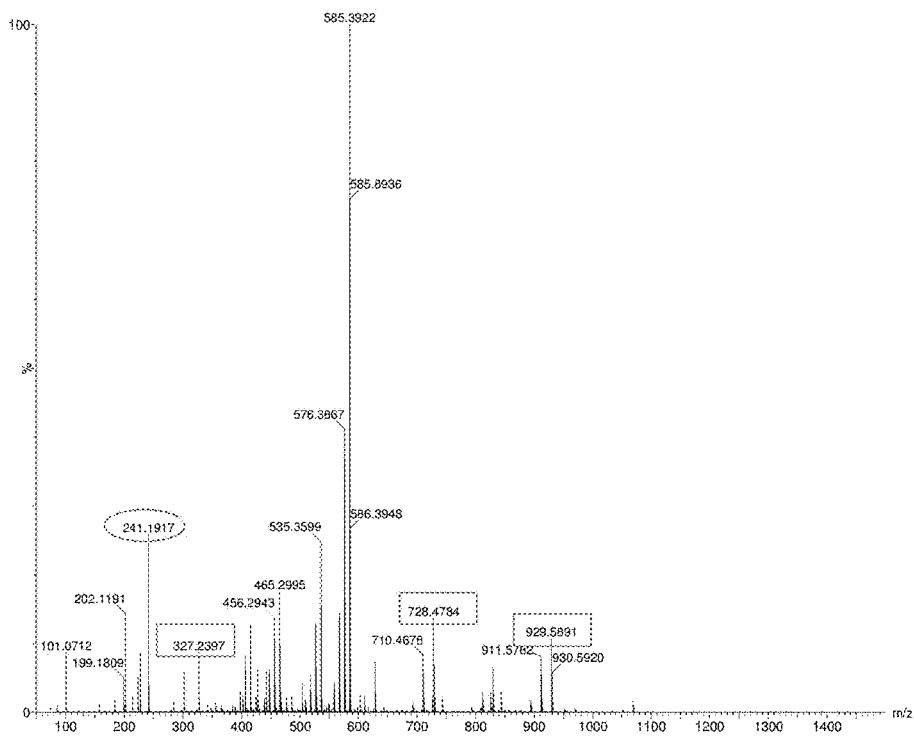
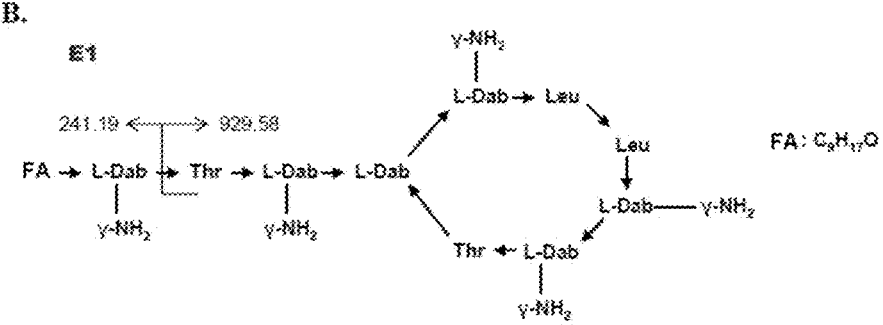
FIGURE 6

A.
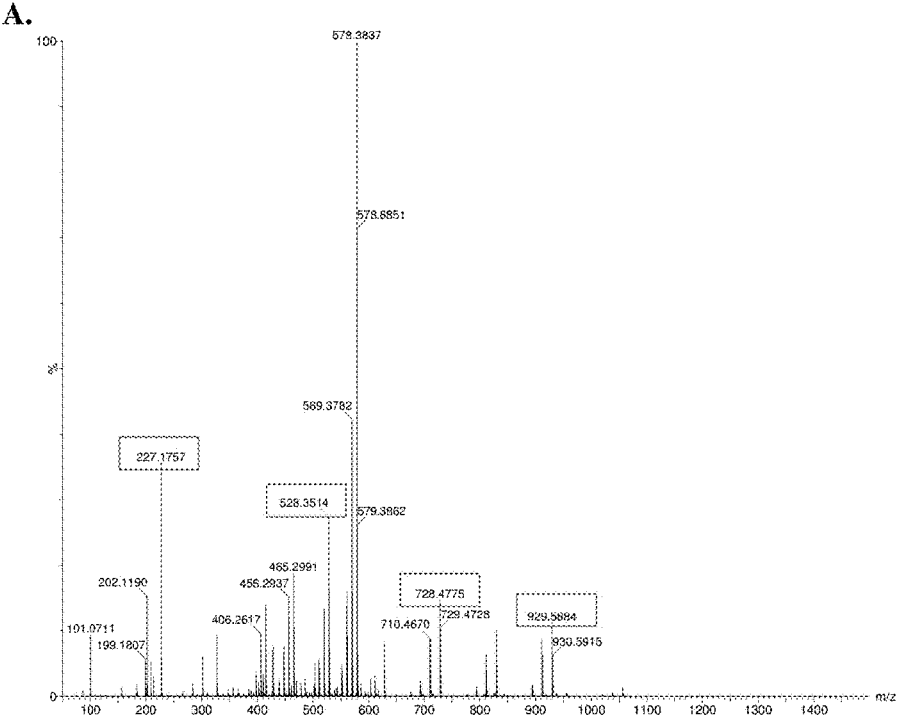
[M+2H]²⁺: 578.3837
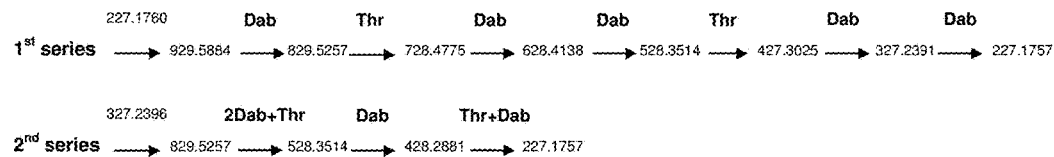
B.
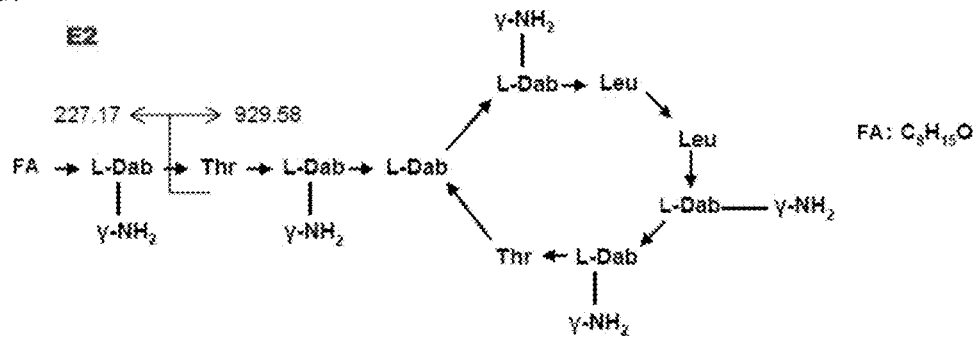
FIGURE 7

A.
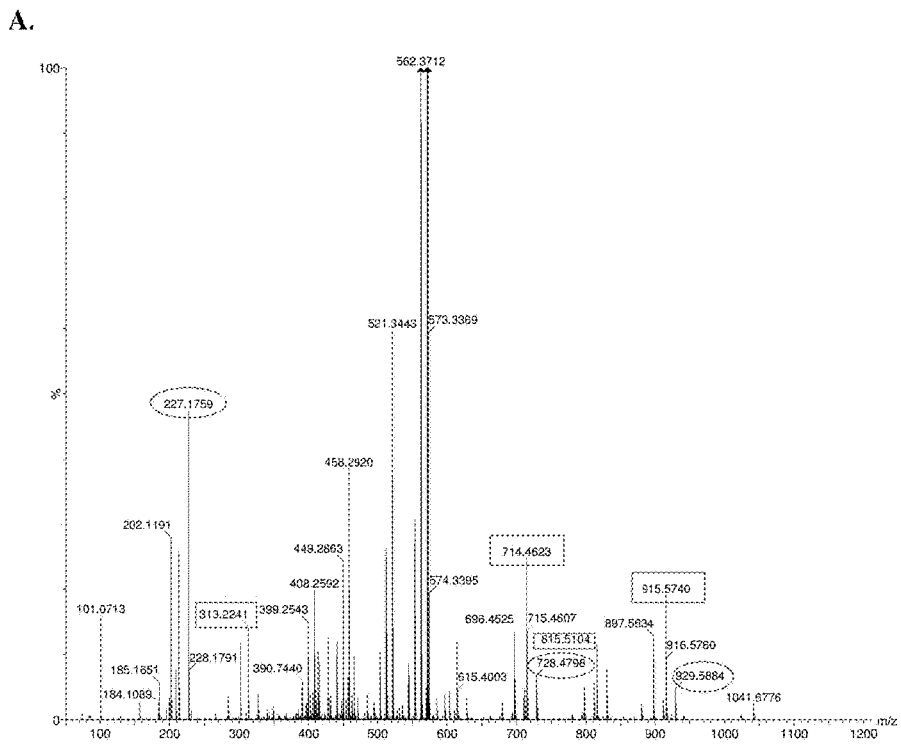
[M+2H]²⁺: 571.38
1st series: 227.1760 → 915.5740 —Dab→ 815.5104 —Thr→ 714.4623 —Dab→ 614.3993 —Dab→ 514.3352 —Thr→ 413.2866 —Dab→ 313.2241 —Dab→ 213.1603
2nd series: 213.1603 → 929.5884 —Dab→ 829.5252 —Thr→ 728.4798 —Dab→ 628.4152 —2Dab→ 428.2876 —Thr→ 327.2401 —Dab→ 227.1759
B.
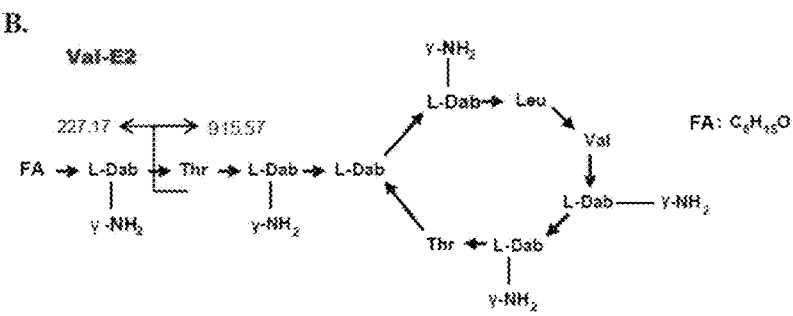
FIGURE 8

SEQUENCE LISTING

```
<160> NUMBER OF SEQ ID NOS: 32

<210> SEQ ID NO 1
<211> LENGTH: 523
<212> TYPE: PRT
<213> ORGANISM: Paenibacillus alvei

<400> SEQUENCE: 1

Val Thr Glu Ala Glu Lys Ala Asp Leu Leu Gly Arg Phe Asn Asp Thr
1               5                   10                  15

Thr Thr Glu Phe Pro Arg Gly Lys Thr Leu Ile Gln Leu Phe Glu Glu
            20                  25                  30
```

-continued

```
Gln Val Glu Arg Ile Pro Asp Ala Ala Ile Thr Leu Asn Glu Gln
         35                  40                  45
Glu Leu Thr Tyr Arg Glu Leu Asn Glu Arg Val Asn Arg Leu Ala Arg
 50                  55                  60
Thr Leu Arg Ser His Gly Ile Ser Lys Gly Arg Leu Val Ala Ile Leu
 65                  70                  75                  80
Ala Glu Arg Ser Ile Glu Met Val Val Gly Met Leu Ala Ala His Lys
                 85                  90                  95
Ala Gly Ala Ala Tyr Val Pro Ile Asp Pro Glu Tyr Pro Glu Glu Arg
             100                 105                 110
Ile Arg Phe Leu Ile Glu Asp Ser Gly Gly Gln Val Met Leu Thr Gln
         115                 120                 125
Ser Arg Leu Arg Glu Arg Leu Ala Gly Ser Asp Pro Val Ile Leu Leu
     130                 135                 140
Asp Asp Glu Ser Phe Tyr His Glu Asp Gly Thr Asn Leu Asn Thr Gly
145                 150                 155                 160
Ile Glu Ala Thr Asp Leu Ala Cys Val Ile Tyr Thr Ser Gly Thr Thr
                 165                 170                 175
Gly Lys Pro Lys Gly Asn Pro Val Ser His Arg Asn Ile Val Arg Val
             180                 185                 190
Val Gln Asn Thr Asn Tyr Ile Asp Ile Thr Glu Arg Asp His Val Leu
         195                 200                 205
Gln Leu Ser Ser Tyr Ser Phe Asp Gly Ala Thr Phe Asp Ile Phe Gly
     210                 215                 220
Ala Leu Thr Asn Gly Ala Arg Leu Val Leu Val Pro Tyr Glu Thr Leu
225                 230                 235                 240
Leu Glu Ile Gly Arg Leu Ala Asp Leu Ile Gln Arg Glu Arg Ile Ser
                 245                 250                 255
Val Met Phe Ile Thr Thr Ala Phe Phe Asn Ile Leu Val Asp Val Asn
             260                 265                 270
Val Asp Cys Leu Arg Asp Val Arg Ala Ile Leu Phe Gly Gly Glu Arg
         275                 280                 285
Val Ser Val Gly His Val Arg Lys Ala Leu Ala His Ile Gly Pro Gly
     290                 295                 300
Arg Leu Asn His Val Tyr Gly Pro Thr Glu Ser Thr Val Tyr Thr Thr
305                 310                 315                 320
Tyr Leu Pro Val Asp Phe Val Asp Glu Leu Ala Val Thr Val Pro Ile
                 325                 330                 335
Gly Arg Pro Ile Ser Asn Thr Arg Val Tyr Ile Val Asp Ser Arg Asn
             340                 345                 350
Lys Leu Leu Pro Ile Gly Val Ala Gly Glu Leu Cys Val Gly Gly Glu
         355                 360                 365
Gly Leu Val Arg Gly Tyr Asn Asn Arg Pro Glu Leu Thr Ala Glu Lys
     370                 375                 380
Phe Val Asp Asn Pro Phe Val Pro Gly Glu Arg Met Tyr Arg Thr Gly
385                 390                 395                 400
Asp Leu Ala Lys Trp Leu Pro Asp Gly Thr Ile Glu Tyr Val Gly Arg
                 405                 410                 415
Thr Asp Asp Gln Val Lys Ile Arg Gly Phe Arg Ile Glu Leu Gly Glu
             420                 425                 430
Ile Glu Ala Gln Leu Gln Lys Val Glu Gly Ile Arg Lys Thr Thr Val
         435                 440                 445
Phe Ala Arg Glu Asn Ala Ser Gly Glu Lys Gln Leu Cys Ala Tyr Tyr
```

```
            450                 455                 460
Glu Ala Asp Cys Glu Leu Pro Ala Ala Glu Leu Lys Ser Val Leu Ser
465                 470                 475                 480

Lys Glu Leu Pro Ala Tyr Met Ile Pro Ala Tyr Leu Ile Gln Leu Glu
                485                 490                 495

Arg Leu Pro Leu Thr Thr Asn Gly Lys Val Asp Arg Arg Ser Leu Pro
            500                 505                 510

Ala Pro Glu Glu Ser Leu Gln Pro Gly Gly Gly
        515                 520

<210> SEQ ID NO 2
<211> LENGTH: 10
<212> TYPE: PRT
<213> ORGANISM: Paenibacillus alvei

<400> SEQUENCE: 2

Asp Ala Trp Ile Val Gly Ala Ile Val Lys
1               5                   10

<210> SEQ ID NO 3
<211> LENGTH: 10
<212> TYPE: PRT
<213> ORGANISM: Paenibacillus alvei

<400> SEQUENCE: 3

Asp Gly Phe Phe Leu Gly Val Val Tyr Lys
1               5                   10

<210> SEQ ID NO 4
<211> LENGTH: 10
<212> TYPE: PRT
<213> ORGANISM: Paenibacillus alvei

<400> SEQUENCE: 4

Asp Val Gly Glu Ile Ser Ala Ile Asp Lys
1               5                   10

<210> SEQ ID NO 5
<211> LENGTH: 10
<212> TYPE: PRT
<213> ORGANISM: Paenibacillus alvei

<400> SEQUENCE: 5

Asp Val Gly Glu Ile Ser Ala Ile Asp Lys
1               5                   10

<210> SEQ ID NO 6
<211> LENGTH: 4967
<212> TYPE: PRT
<213> ORGANISM: Paenibacillus alvei

<400> SEQUENCE: 6

Met Ala Phe Glu Lys Glu Thr Leu Phe Trp Asn Glu Lys Phe Gly Ser
1               5                   10                  15

Asp Asp Tyr Thr Leu Thr Arg Leu Pro Tyr Ser Lys Ala Pro Ser Ser
                20                  25                  30

Gln Ala Pro Ile Met Thr Thr Val Gly Gly Ser Leu Ser Glu Lys Ala
            35                  40                  45

Ala Gln Arg Val Leu Gln Met Ser Lys Gly Ala Pro Leu Ala Ala Phe
        50                  55                  60

Met Ile Leu Leu Ala Gly Val Gln Ser Leu Leu His Lys Tyr Thr Gly
```

-continued

```
                65                  70                  75                  80
Ala Ser Asp Ile Leu Val Gly Met Pro Val Ile Arg Lys Pro Thr Glu
                        85                  90                  95
Thr Arg Arg Ser Val Asn His Thr Val Ile Leu Lys Ser Leu Leu Ser
                       100                 105                 110
Ala Gly Ser Thr Phe Lys Thr Leu Leu Ser Glu Leu Arg Thr Ser Leu
                       115                 120                 125
Pro Glu Thr Ile Gln His Gln His Ile Pro Phe Leu Lys Met Thr Glu
                       130                 135                 140
Lys Leu Asp Leu Gln Tyr Ala Asp Gly Ile Pro Ile Ile His Thr Leu
145                                150                 155                 160
Val Ser Leu Lys Glu Leu His Leu Asp Glu Ile Gly Gln Asn Val Val
                       165                 170                 175
Thr Asp Cys Ser Phe Glu Phe Ser Leu Thr Gly Gly Thr Ile Gln Leu
                       180                 185                 190
Ala Leu Ser Tyr Asn Glu His Leu Tyr Asp Ser Lys Phe Met Thr Arg
                       195                 200                 205
Ile Val Gly His Leu Asn Arg Leu Leu Ala Val Gly Leu His Glu Leu
                       210                 215                 220
Glu Leu Asp Ile Val Arg Val Asp Met Leu Ser Glu Asp Glu Lys Phe
225                                230                 235                 240
Gln Leu Leu Gln Ser Phe Asn Asp Thr Glu Lys Asp Tyr Pro Arg Asp
                       245                 250                 255
Arg Thr Ile His Gln Leu Val Glu Glu Val Lys Arg Val Pro Glu
                       260                 265                 270
Ala Thr Ala Ile Val Phe Glu Gly Arg Arg Leu Ser Tyr Ala Glu Leu
                       275                 280                 285
Asn Glu Arg Ala Asn Arg Leu Ala Arg Thr Leu Arg Ser Val Gly Val
                       290                 295                 300
Leu Pro Asn Gln Leu Val Gly Leu Met Ala Arg Arg Ser Leu Glu Thr
305                                310                 315                 320
Val Val Gly Ile Leu Ala Val Leu Lys Ala Gly Gly Ala Tyr Val Pro
                       325                 330                 335
Ile Asp Pro Glu Tyr Pro Glu Glu Arg Ile Arg Tyr Ile Leu Glu Asn
                       340                 345                 350
Ser Asn Ala Gln Leu Leu Leu Thr Gln Arg Lys Leu Gln Gln Gln Val
                       355                 360                 365
Pro Phe Glu Gly Thr Val Leu Ala Leu Asp Asp Glu Gln Ala Tyr Ser
                       370                 375                 380
Asp Asp Gly Thr Asn Leu Glu Pro Ala Ser Gly Ser Asn Asp Leu Ala
385                                390                 395                 400
Tyr Val Ile Tyr Thr Ser Gly Thr Thr Gly Lys Pro Lys Gly Val Met
                       405                 410                 415
Leu Glu His Arg Gly Leu Val Ser Leu Lys Leu Met Phe Ala Asp Arg
                       420                 425                 430
Leu Gly Ile Thr Glu His Asp Arg Ile Val Gln Phe Ala Ser Leu Ser
                       435                 440                 445
Phe Asp Ala Ser Cys Trp Glu Val Phe Lys Ala Leu Tyr Phe Gly Ala
                       450                 455                 460
Thr Leu Tyr Ile Pro Thr Ala Glu Thr Ile Leu Asp Asn Arg Leu Phe
465                                470                 475                 480
Glu Ser Tyr Met Asn Glu His Ala Ile Thr Ala Ala Ile Leu Pro Pro
                       485                 490                 495
```

```
Thr Tyr Ser Ala Tyr Leu Asn Pro Asp Arg Leu Pro Ser Leu Thr Lys
            500                 505                 510

Leu Val Thr Gly Gly Ser Ala Val Ser Ala Glu Phe Val Gln Gln Trp
        515                 520                 525

Lys Pro Lys Val His Tyr Phe Asn Ala Tyr Gly Pro Thr Glu Ala Ser
    530                 535                 540

Ile Val Thr Thr Leu Trp Asp Ala Asn Glu Glu Gln Pro Glu Arg Arg
545                 550                 555                 560

Val Ile Pro Ile Gly Arg Pro Leu Ala Asn His Arg Ile Phe Ile Leu
                565                 570                 575

Asp Ala His Leu Gln Leu Val Pro Pro Gly Val Asp Gly Glu Leu Cys
            580                 585                 590

Val Ala Gly Val Gly Leu Ala Arg Gly Tyr Leu Asn His Pro Glu Leu
        595                 600                 605

Thr Ala Glu Lys Phe Val Glu His Pro Phe Ala Pro Gly Glu Arg Leu
    610                 615                 620

Tyr Arg Thr Gly Asp Leu Ala Arg Trp Leu Pro Asp Gly Asn Ile Glu
625                 630                 635                 640

Tyr Leu Gly Arg Ile Asp His Gln Val Lys Ile Arg Gly Phe Arg Ile
                645                 650                 655

Glu Ile Gly Glu Ile Glu Glu Gln Leu Leu Lys Ile Asp Ser Val Gln
            660                 665                 670

Glu Thr Met Val Ile Ala Arg Glu Gly Lys Ser Gly Gln Glu Leu Cys
        675                 680                 685

Ala Tyr Leu Val Ala Asp Arg Pro Leu Thr Leu Gly Glu Leu Arg Ser
    690                 695                 700

Ala Leu Ala Gln Lys Leu Pro Asn Tyr Met Ile Pro Ala His Phe Val
705                 710                 715                 720

Gln Leu Pro Arg Met Pro Leu Thr Pro Asn Asp Lys Ile Asp Arg Lys
                725                 730                 735

Ala Leu Pro Ala Pro Glu Gly Asn Ala Leu Thr Gly Gly Leu Tyr Val
            740                 745                 750

Ala Pro Arg Asn Glu Ala Glu Arg Thr Leu Val Asp Val Trp Gln Ala
        755                 760                 765

Val Leu Asn Ala Asp Arg Val Gly Val Thr Asp His Phe Phe Glu Leu
    770                 775                 780

Gly Gly Asp Ser Ile Lys Ser Ile Gln Val Ser Ser Arg Leu His Gln
785                 790                 795                 800

Ala Gly Tyr Lys Leu Asp Ile Arg Asp Leu Phe Lys Tyr Pro Thr Ile
                805                 810                 815

Ser Gln Leu Ser Leu Arg Val Lys Pro Ile Gly Arg Thr Ile Asp Gln
            820                 825                 830

Gly Glu Ile Thr Gly Glu Thr Ala Leu Thr Pro Ile Gln His Trp Phe
        835                 840                 845

Phe Glu Ser Ser Phe Ala Asp Pro His His Phe Asn Gln Ser Val Met
    850                 855                 860

Leu Tyr Arg Lys Glu Arg Phe Asp Glu Thr Val Arg Gln Val Leu
865                 870                 875                 880

Gln Lys Leu Ala Glu His His Asp Ala Leu Arg Met Val Phe Arg Lys
                885                 890                 895

Thr Glu Gln Gly Phe Ser Glu Arg Asn Arg Ala Ile Gln Glu Gly Gly
            900                 905                 910
```

```
Leu Phe Thr Leu Asp Val Phe Asp Phe Lys Asp Ala Glu Asp Thr Ala
            915                 920                 925

Gln Ala Leu Glu Ala Lys Ala Thr Asp Ile Gln Ala Gly Ile Asp Leu
            930                 935                 940

Glu Lys Gly Pro Leu Val Lys Ala Gly Leu Phe Arg Cys Ala Asp Gly
945                 950                 955                 960

Asp His Leu Leu Leu Ala Val His His Ala Val Val Asp Gly Val Ser
            965                 970                 975

Trp Arg Ile Leu Met Glu Asp Phe Ala Leu Gly Tyr Glu Gln Ala Gly
            980                 985                 990

Lys Ser Glu Glu Ile Arg Phe Pro Ala Lys Thr Asp Ala Tyr Arg Thr
            995                 1000                1005

Trp Ser Glu Gln Leu Ala Ala Tyr Ala Gln Ser Pro Glu Ile Ala Lys
            1010                1015                1020

Glu Arg Ala Tyr Trp Gln Ala Val Glu Gln Ile Ala Val Pro Ala Leu
1025                1030                1035                1040

Pro Lys Asp Leu Glu Ala Asp Val Thr Thr Gln Gln Asp Ser Glu Ser
            1045                1050                1055

Leu Phe Val Arg Leu Thr Ser Glu Thr Glu Leu Leu Leu Lys Arg
            1060                1065                1070

Val His Arg Ala Tyr Asn Thr Glu Met Asn Asp Ile Leu Val Thr Ala
            1075                1080                1085

Leu Gly Ile Ala Val Arg Lys Trp Thr Gly His Glu Arg Val Arg Ile
            1090                1095                1100

Asn Leu Glu Gly His Gly Arg Glu Ser Ile Gly Thr Asp Ile Asp Ile
1105                1110                1115                1120

Thr Arg Thr Val Gly Trp Phe Thr Thr Lys Phe Pro Val Val Leu Glu
            1125                1130                1135

Pro Glu Thr Asn Arg Asp Leu Ala Tyr Gln Ile Lys Gln Val Lys Glu
            1140                1145                1150

Ser Leu Arg Arg Ile Pro Asn Lys Gly Leu Gly Tyr Gly Val Cys Arg
            1155                1160                1165

Tyr Leu Ser Lys Ser Glu Asp Gly Phe Val Trp Gly Ala Glu Pro Glu
            1170                1175                1180

Ile Asn Phe Asn Tyr Leu Gly Gln Phe Asp Asp Val Asn Gln Asp
1185                1190                1195                1200

Glu Ile Gly Ile Ser Ser Tyr Ser Ser Gly Ser Pro Ala Ser Asp Arg
            1205                1210                1215

Gln Ala Arg Ser Phe Val Leu Asp Ile Asn Gly Met Val Leu Asp Gly
            1220                1225                1230

Ala Leu Ser Leu Asp Leu Ser Tyr Ser Arg Lys Gln Tyr Arg Lys Val
            1235                1240                1245

Thr Met Glu Ala Phe Ala Gln Arg Leu Glu Gln Ser Leu Arg Glu Leu
            1250                1255                1260

Ile Thr His Cys Ala Gly Lys Glu Asn Thr Glu Leu Thr Pro Ser Asp
1265                1270                1275                1280

Val Gln Phe Lys Gly Leu Thr Ile Ala Glu Leu Glu Gln Ile Gly Gln
            1285                1290                1295

Arg Ser Val His Val Gly Glu Ile Glu Asn Ile Tyr Ser Leu Thr Pro
            1300                1305                1310

Met Gln Lys Gly Met Trp Phe His Ser Ala Leu Asp Arg Gln Thr Ala
            1315                1320                1325

Ala Tyr Phe Glu Gln Thr Arg Phe Thr Met Arg Gly Ala Leu Asp Val
```

```
            1330            1335            1340

Gln Leu Phe Glu Arg Ser Trp Thr Glu Leu Ala Lys Arg His Leu Val
1345                1350            1355            1360

Leu Arg Ala Asn Phe Val Lys Gly Pro Ala Gly Glu Pro Leu Gln Ile
                1365            1370            1375

Ile Tyr Arg Asp Lys Pro Val Gly Phe Glu Tyr Glu Leu Leu His
            1380            1385            1390

Leu Gln Ala Asp Glu Lys Gln Ala Tyr Leu Asp Lys Lys Ala Glu Asp
            1395            1400            1405

Asp Lys Leu Arg Gly Phe Asp Leu Glu His Asp Ala Leu Val Arg Val
        1410            1415            1420

Thr Ile Leu Arg Thr Glu Glu Gln Ser Tyr His Val Leu Trp Ser Phe
1425            1430            1435            1440

Gln His Ile Leu Met Asp Gly Trp Cys Leu Pro Gln Leu Thr Gln Glu
                1445            1450            1455

Leu Phe Glu Thr Tyr Ser Ala Leu Ala Ser Gly Lys Gln Pro Ala Gly
                1460            1465            1470

Asp Lys Gly Ser Asp Tyr Gly Ala Tyr Ile Glu Trp Leu Glu Lys Gln
            1475            1480            1485

Asp Asp Gln Ala Ala Ser Gly Tyr Trp Thr Ala Phe Leu Ala Gly Tyr
            1490            1495            1500

Glu Gly Gln Thr Val Leu Pro Gly Gln Lys Glu Ala Gln Pro Asn Gly
1505            1510            1515            1520

Arg Phe Thr Ala Asp His Val Thr Ala Glu Leu Gly Lys Asp Leu Ser
                1525            1530            1535

Glu Arg Met Asp Arg Val Ala Lys Gln Arg Leu Val Thr Val Asn Thr
            1540            1545            1550

Leu Leu Gln Ala Ala Trp Gly Val Met Leu Gln Lys Tyr Asn Gly Thr
            1555            1560            1565

Asn Asp Ala Val Phe Gly Ser Val Val Ala Gly Arg Pro Ala Glu Ile
        1570            1575            1580

Pro Gly Ile Glu Ser Met Ile Gly Leu Phe Ile Asn Thr Val Pro Val
1585            1590            1595            1600

Arg Val Thr Ser Glu Ala Asp Thr Val Phe Ala Asp Leu Met Ala Lys
                1605            1610            1615

Leu Gln Glu Arg Ala Leu Glu Ser Gly Arg Tyr Asp Tyr Tyr Pro Leu
            1620            1625            1630

Tyr Glu Ile Gln Ala Arg Cys Val Gln Lys Gln Asn Leu Ile Asn His
            1635            1640            1645

Ile Ile Ala Phe Glu Asn Tyr Pro Val Asp Glu Gln Met Glu Gln Ala
        1650            1655            1660

Gly Asp Gln Gln His Gly Asp Leu Thr Ile Thr Asp Val Gln Met Glu
1665            1670            1675            1680

Glu Gln Thr Asn Tyr Asn Phe Asn Val Thr Val Val Pro Gly Ala Glu
                1685            1690            1695

Ile Glu Ile Arg Phe Asp Phe Asn Ala Glu Val Phe Asp Lys Asp Ser
            1700            1705            1710

Ile Glu Arg Leu Lys Gly His Leu Val His Leu Leu Glu Gln Val Thr
            1715            1720            1725

Asp Asn Pro Glu Ile Thr Val Gly Glu Leu Glu Leu Val Thr Glu Ala
        1730            1735            1740

Glu Lys Ala Asp Leu Leu Gly Arg Phe Asn Asp Thr Thr Thr Glu Phe
1745            1750            1755            1760
```

-continued

```
Pro Arg Gly Lys Thr Leu Ile Gln Leu Phe Glu Gln Val Glu Arg
            1765                1770                1775
Ile Pro Asp Ala Ala Ile Thr Leu Asn Glu Gln Glu Leu Thr Tyr
            1780                1785                1790
Arg Glu Leu Asn Glu Arg Val Asn Arg Leu Ala Arg Thr Leu Arg Ser
            1795                1800                1805
His Gly Ile Ser Lys Gly Arg Leu Val Ala Ile Leu Ala Glu Arg Ser
            1810                1815                1820
Ile Glu Met Val Val Gly Met Leu Ala Ala His Lys Ala Gly Ala Ala
1825                1830                1835                1840
Tyr Val Pro Ile Asp Pro Glu Tyr Pro Glu Arg Ile Arg Phe Leu
            1845                1850                1855
Ile Glu Asp Ser Gly Gly Gln Val Met Leu Thr Gln Ser Arg Leu Arg
            1860                1865                1870
Glu Arg Leu Ala Gly Ser Asp Pro Val Ile Leu Leu Asp Asp Glu Ser
            1875                1880                1885
Phe Tyr His Glu Asp Gly Thr Asn Leu Asn Thr Gly Ile Glu Ala Thr
            1890                1895                1900
Asp Leu Ala Cys Val Ile Tyr Thr Ser Gly Thr Thr Gly Lys Pro Lys
1905                1910                1915                1920
Gly Asn Pro Val Ser His Arg Asn Ile Val Arg Val Val Gln Asn Thr
            1925                1930                1935
Asn Tyr Ile Asp Ile Thr Glu Arg Asp His Val Leu Gln Leu Ser Ser
            1940                1945                1950
Tyr Ser Phe Asp Gly Ala Thr Phe Asp Ile Phe Gly Ala Leu Thr Asn
            1955                1960                1965
Gly Ala Arg Leu Val Leu Val Pro Tyr Glu Thr Leu Leu Glu Ile Gly
            1970                1975                1980
Arg Leu Ala Asp Leu Ile Gln Arg Glu Arg Ile Ser Val Met Phe Ile
1985                1990                1995                2000
Thr Thr Ala Phe Phe Asn Ile Leu Val Asp Val Asn Val Asp Cys Leu
            2005                2010                2015
Arg Asp Val Arg Ala Ile Leu Phe Gly Gly Glu Arg Val Ser Val Gly
            2020                2025                2030
His Val Arg Lys Ala Leu Ala His Ile Gly Pro Gly Arg Leu Asn His
            2035                2040                2045
Val Tyr Gly Pro Thr Glu Ser Thr Val Tyr Thr Thr Tyr Leu Pro Val
            2050                2055                2060
Asp Phe Val Asp Glu Leu Ala Val Thr Val Pro Ile Gly Arg Pro Ile
2065                2070                2075                2080
Ser Asn Thr Thr Val Tyr Ile Val Asp Ser Arg Asn Lys Leu Leu Pro
            2085                2090                2095
Ile Gly Val Ala Gly Glu Leu Cys Val Gly Gly Glu Gly Leu Val Arg
            2100                2105                2110
Gly Tyr Asn Asn Arg Pro Glu Leu Thr Ala Glu Lys Phe Val Asp Asn
            2115                2120                2125
Pro Phe Val Pro Gly Glu Arg Met Tyr Arg Thr Gly Asp Leu Ala Lys
            2130                2135                2140
Trp Leu Pro Asp Gly Thr Ile Glu Tyr Val Gly Arg Thr Asp Asp Gln
2145                2150                2155                2160
Val Lys Ile Arg Gly Phe Arg Ile Glu Leu Gly Glu Ile Glu Ala Gln
            2165                2170                2175
```

-continued

Leu Gln Lys Val Glu Gly Ile Arg Lys Thr Thr Val Phe Ala Arg Glu
            2180                2185                2190

Asn Ala Ser Gly Glu Lys Gln Leu Cys Ala Tyr Tyr Glu Ala Asp Cys
            2195                2200                2205

Glu Leu Pro Ala Ala Glu Leu Lys Ser Val Leu Ser Lys Glu Leu Pro
            2210                2215                2220

Ala Tyr Met Ile Pro Ala Tyr Leu Ile Gln Leu Glu Arg Leu Pro Leu
2225                2230                2235                2240

Thr Thr Asn Gly Lys Val Asp Arg Arg Ser Leu Pro Ala Pro Glu Glu
            2245                2250                2255

Ser Leu Gln Pro Gly Gly Gly Ser Thr Pro Pro Arg Thr Pro Leu Glu
            2260                2265                2270

Ala Ser Leu Ala Gly Ile Trp Lys Ser Val Leu Gly Leu Val His Ile
            2275                2280                2285

Gly Val His Asp Asn Phe Phe Asp Met Gly Gly His Ser Leu Arg Ala
            2290                2295                2300

Thr Thr Leu Val Ser Lys Val His Gln Glu Leu Asn Val Glu Leu Pro
2305                2310                2315                2320

Leu Arg Asp Val Phe Arg Tyr Ser Thr Ile Glu Glu Met Ala Leu Ala
            2325                2330                2335

Ile Ser Arg Ile Gly Glu Gln Ser Phe Ser Ser Ile Pro Leu Ala Gly
            2340                2345                2350

Ala Arg Ala Tyr Tyr Pro Leu Ser Ser Ala Gln Lys Arg Leu Phe Ile
            2355                2360                2365

Leu Asn Gln Leu Glu Gly Ala Asp Gln Ser Tyr Asn Met Pro Gly Val
            2370                2375                2380

Leu Leu Leu Glu Gly Ser Ile Asp Arg Ser Leu Leu Glu Lys Ala Phe
2385                2390                2395                2400

Arg Gly Leu Ile Ala Arg His Glu Thr Leu Arg Thr Gly Phe Glu Ile
            2405                2410                2415

Val Gln Gly Glu Ala Val Gln Arg Ile Tyr Glu Ser Val Asp Phe Ala
            2420                2425                2430

Val Glu Tyr Arg His Ala Ser Glu Glu Glu Thr Pro Glu Val Val Gln
            2435                2440                2445

Ala Phe Ile Arg Pro Phe Asp Leu Ala Lys Pro Pro Leu Leu Arg Ala
2450                2455                2460

Glu Leu Val Glu Leu Ala Ile Glu Arg Tyr Leu Leu Met Phe Asp Met
2465                2470                2475                2480

His His Ile Val Ser Asp Gly Val Ser Met Asp Val Leu Val Glu Glu
            2485                2490                2495

Leu Val Arg Leu Tyr Gly Gly Glu Ser Leu Glu Pro Leu Arg Ile Gln
            2500                2505                2510

Tyr Lys Asp Tyr Ala Val Trp Gln Gln Ser Asp Glu Gln Lys Val Gln
            2515                2520                2525

Leu Lys Arg Glu Glu Ala Tyr Trp Leu Asp Arg Tyr Arg Gly Glu Leu
            2530                2535                2540

Pro Val Leu Glu Met Pro Thr Asp Tyr Pro Arg Pro Ala Val Gln Ser
2545                2550                2555                2560

Phe Glu Gly Gln Thr Leu Thr Ser Phe Val Asp Glu Ala Thr Asn Glu
            2565                2570                2575

Gly Leu Lys Gln Leu Ala Ala Gln Lys Gly Thr Thr Leu Tyr Met Val
            2580                2585                2590

Leu Leu Ala Ala Tyr Thr Val Leu Leu His Lys Tyr Thr Gly Gln Asp

-continued

```
            2595                2600                2605

Asp Leu Ile Val Gly Thr Ser Ile Ala Gly Arg Thr His Gly Asp Thr
            2610                2615                2620

Gln Pro Leu Ile Gly Met Phe Val Asn Thr Leu Ala Leu Arg Asn Tyr
2625                2630                2635                2640

Pro Ala Ser Glu Lys Ser Phe Leu Ser Tyr Leu Glu Glu Val Lys Glu
                2645                2650                2655

Thr Thr Leu Gly Ala Tyr Glu His Gln Asn Tyr Pro Phe Glu Glu Leu
                2660                2665                2670

Val Asp Lys Val Gln Val Ser Arg Asp Leu Ser Arg Asn Pro Leu Phe
            2675                2680                2685

Asp Thr Met Phe Ser Leu Gln Asn Leu Glu Asp Lys Glu Phe Lys Leu
            2690                2695                2700

Glu Gly Leu Lys Leu Ser Pro Tyr Pro Ser Gly Tyr Gly Thr Ala Lys
2705                2710                2715                2720

Phe Asp Leu Ser Val Asp Val Thr Glu Glu Asn Gly Gly Leu Glu Cys
                2725                2730                2735

Ile Phe Glu Phe Ala Thr Ala Leu Tyr Lys Glu Ser Thr Ile Arg Arg
                2740                2745                2750

Leu Ser Thr His Phe Gly His Leu Leu Ala Ala Ile Val Ser Arg Pro
            2755                2760                2765

Asp Ala Lys Ile Ala Glu Leu Asn Leu Leu Thr Ala Glu Glu Asn Glu
            2770                2775                2780

Gln Ile Leu Gly Ala Phe Asn Pro Ala Gln Pro Glu Ala Ala Pro Ala
2785                2790                2795                2800

Ala Ala Phe His Arg Leu Phe Glu Glu Gln Ala Glu Arg Thr Pro Glu
                2805                2810                2815

Ala Glu Ala Val Val Tyr Glu Asn Asp Arg Leu Thr Tyr Ala Glu Leu
                2820                2825                2830

Asn Glu Arg Ala Asn Arg Leu Ala Ala Thr Leu Arg Ala Ser Gly Ile
            2835                2840                2845

Gly Arg Glu Ser Ile Val Gly Ile Leu Ser Glu Arg Ser Val Asp Leu
            2850                2855                2860

Leu Val Ala Val Leu Ala Val Trp Lys Ala Gly Gly Ala Tyr Val Pro
2865                2870                2875                2880

Leu Asp Pro Asp Tyr Pro Ala Asp Arg Val Arg Phe Met Leu Glu Asp
                2885                2890                2895

Ser Gly Ala Lys Val Leu Leu Thr Gln Thr Val Leu Arg Glu Arg Ala
                2900                2905                2910

Glu Ala Trp Leu Gly Glu Glu Leu Ala Leu Ala Ala Val Leu Tyr
            2915                2920                2925

Leu Asp Asp Glu Ala Ser Tyr Ser Glu Glu Arg Ala Asn Ala Pro Ile
            2930                2935                2940

Gly Ser Gly Met Val Ser Gly Lys Leu Thr Asp Ala Val Asp Asp Gly
2945                2950                2955                2960

Asp Val Ser His Gln Lys Val Gly Met Gly Ser Phe His Glu Ala Arg
                2965                2970                2975

Pro Glu Asp Leu Ala Tyr Val Ile Tyr Thr Ser Gly Thr Thr Gly Lys
                2980                2985                2990

Pro Lys Gly Val Met Ile Glu His Arg Ser Leu Val Asn Thr Ala Ala
            2995                3000                3005

Gly Tyr Arg Arg Glu Tyr Arg Leu Asp Gln Phe Pro Val Arg Leu Leu
            3010                3015                3020
```

-continued

```
Gln Leu Ala Ser Phe Ser Phe Asp Val Phe Val Gly Asp Ile Ala Arg
3025                3030                3035                3040

Thr Leu Tyr Asn Gly Gly Thr Met Val Ile Val Pro Lys Asp Asp Arg
            3045                3050                3055

Ile Asp Pro Ser Arg Leu His His Trp Met Glu Arg Glu Arg Val Thr
        3060                3065                3070

Ile Phe Glu Ser Thr Pro Ala Leu Ile Val Pro Phe Leu Glu Tyr Val
    3075                3080                3085

His Glu Gln Gly Leu Asp Met Ser Trp Met Glu Leu Leu Ile Thr Ser
3090                3095                3100

Ser Asp Ser Cys Ser Val Ala Asp Tyr Arg Ile Leu Gln Glu Arg Phe
3105                3110                3115                3120

Gly Ser Phe Phe Arg Ile Ile Asn Ala Tyr Gly Val Thr Glu Ala Ala
            3125                3130                3135

Ile Asp Ser Ser Phe Tyr Asp Glu Glu Leu Thr Lys Leu Pro Gln Ile
        3140                3145                3150

Gly His Val Pro Ile Gly Lys Ala Trp Leu Asn Ala Lys Phe Tyr Ile
    3155                3160                3165

Val Asp Ala His Leu Asn Pro Val Pro Val Gly Val Leu Gly Glu Leu
    3170                3175                3180

Val Ile Gly Gly Val Gly Val Ala Arg Gly Tyr Leu Asn Arg Pro Glu
3185                3190                3195                3200

Leu Thr Glu Glu Lys Phe Val Asp Ser Pro Phe Ala Ala Gly Glu Arg
            3205                3210                3215

Leu Tyr Arg Thr Gly Asp Leu Ala Arg Trp Met Glu Asp Gly Asn Val
        3220                3225                3230

Asp Phe Ile Gly Arg Ile Asp Asn Gln Ala Lys Ile Arg Gly Tyr Arg
    3235                3240                3245

Ile Glu Thr Gly Glu Ile Glu Ser Gln Leu Leu Arg Val Glu Gly Val
3250                3255                3260

Arg Glu Ala Val Val Leu Val Arg Ser Asp Ala Asn Gly Gln Lys Ala
3265                3270                3275                3280

Leu Cys Ala Tyr Tyr Thr Leu Asp Thr Gly Ala Glu Leu Ala Val Asn
            3285                3290                3295

Asp Leu Arg Ser Thr Leu Ala Gln Glu Leu Pro Gly Tyr Met Ile Pro
        3300                3305                3310

Ser Tyr Phe Val Glu Leu Glu Gly Leu Pro Leu Thr Pro Asn Gly Lys
    3315                3320                3325

Ile Asp Arg Lys Ala Leu Pro Ala Pro Glu Gly Glu Ala Gly Ser Gly
    3330                3335                3340

Thr Glu Tyr Val Ala Pro Arg Asn Glu Leu Glu Thr Lys Leu Ala Ala
3345                3350                3355                3360

Ile Trp Gln Glu Val Leu Gly Leu Ala Lys Glu Ile Gly Val His Asp
            3365                3370                3375

Asn Phe Phe Asp Ile Gly Gly His Ser Leu Arg Ala Thr Thr Leu Val
        3380                3385                3390

Ser Lys Val His Lys Glu Leu Ser Val Asp Leu Pro Leu Arg Asp Val
    3395                3400                3405

Phe Arg His Ser Thr Ile Glu Ser Met Ala Ala Ala Ile Ser Arg Leu
    3410                3415                3420

Asp Glu Gln Thr Phe Val Ala Ile Pro Val Ala Asp Asp Arg Glu Val
3425                3430                3435                3440
```

-continued

Tyr Pro Gln Ser Phe Ala Gln Lys Arg Leu Phe Ile Leu Asn Gln Leu
                3445                3450                3455

Glu Gly Ala Glu Leu Ser Tyr Asn Met Pro Glu Ala Met Leu Leu Glu
    3460                3465                3470

Gly Ala Leu Asp Arg Ala Arg Phe Glu Glu Ala Phe Arg Lys Leu Val
    3475                3480                3485

Ala Arg His Glu Met Leu Arg Thr Gly Phe Glu Met Val Asp Gly Glu
    3490                3495                3500

Ala Ser Gln Arg Val Tyr Gln Asp Leu Asn Phe Ala Val Glu Phe Tyr
3505                3510                3515                3520

Arg Val Asp Glu Gln Glu Ala Glu Thr Val Arg Arg Phe Val Arg
                3525                3530                3535

Pro Phe Asp Leu Ala Lys Pro Pro Leu Leu Arg Val Gly Leu Val Glu
                3540                3545                3550

Leu Ala Ser Glu Arg His Ile Leu Met Tyr Asp Met His His Ile Ile
                3555                3560                3565

Ser Asp Gly Val Ser Met Glu Ile Phe Val Glu Phe Val Arg Leu
    3570                3575                3580

Tyr Gly Gly Glu Gln Leu Glu Pro Leu Arg Ile Gln Tyr Lys Asp Tyr
3585                3590                3595                3600

Thr Val Trp Gln His Ser Gln Glu Gln Lys Glu Arg Leu Gln Arg Gln
                3605                3610                3615

Glu Ala Tyr Trp Leu Asn Met Phe Gln Gly Glu Leu Pro Val Leu Glu
                3620                3625                3630

Met Pro Thr Asp Tyr Pro Arg Pro Ser Val Gln Ser Tyr Glu Gly His
                3635                3640                3645

Thr Leu Glu Phe Phe Phe Asp Ala Ser Lys Thr Asp Gly Leu Lys Gln
                3650                3655                3660

Leu Ala Ser Glu Thr Gly Thr Thr Leu Phe Met Val Leu Leu Ala Ala
3665                3670                3675                3680

Tyr Asn Val Leu Leu His Lys Tyr Ser Gly Gln Glu Asp Val Ile Val
                3685                3690                3695

Gly Thr Pro Ile Ala Gly Arg Asn His Gly Asp Val Gln Pro Leu Ile
                3700                3705                3710

Gly Met Phe Leu Asn Thr Leu Ala Ile Arg Ser Tyr Pro Ala Ser Glu
                3715                3720                3725

Lys Thr Phe Leu Ser Tyr Leu Asn Glu Val Lys Glu Thr Thr Leu His
                3730                3735                3740

Ala Phe Glu His Gln Asn Tyr Pro Phe Glu Glu Leu Val Asp Lys Val
3745                3750                3755                3760

Gln Val Thr Arg Asp Leu Ser Arg Asn Pro Leu Phe Asp Thr Leu Phe
                3765                3770                3775

Thr Met Gln Asn Thr Glu Asn Glu Glu Phe Glu Leu Glu Gly Leu Arg
                3780                3785                3790

Leu Ile Pro Tyr Pro Ser Ala Leu Asp Thr Ala Lys Phe Asp Ile Ser
                3795                3800                3805

Leu Asp Val Gly Glu Glu Asn Gly Gly Leu Asp Tyr Ser Phe Glu Tyr
                3810                3815                3820

Ala Thr Ala Leu Tyr Lys Arg Ala Thr Ile Glu Arg Leu Ala Lys His
3825                3830                3835                3840

Tyr Glu Gln Leu Leu Val Thr Ile Ile Ser Arg Pro Asp Ala Lys Ile
                3845                3850                3855

Ala Glu Leu Asn Leu Leu Thr Ala Glu Glu Lys Glu Gln Ile Leu Gly

```
                    3860              3865              3870
Thr Phe Asn Pro Ala Gln Pro Glu Ala Ala Pro Ala Ala Phe His
           3875              3880              3885

Arg Leu Phe Glu Glu Gln Ala Glu Arg Thr Pro Glu Glu Ala Val
           3890              3895              3900

Val Tyr Glu Asn Asp Gln Leu Thr Tyr Ala Glu Leu Asn Glu Arg Ala
3905              3910              3915              3920

Asn Arg Leu Ala Ala Thr Leu Arg Ala Ser Asp Ile Gly Arg Glu Thr
           3925              3930              3935

Ile Val Gly Ile Leu Ala Glu Arg Ser Val Asp Leu Leu Val Ser Val
           3940              3945              3950

Leu Ala Val Trp Lys Ala Gly Ala Tyr Val Pro Leu Asp Pro Asp
           3955              3960              3965

Tyr Pro Ala Asp Arg Val Arg Phe Met Leu Glu Asp Ser Gly Ala Lys
           3970              3975              3980

Val Leu Leu Thr Gln Met Pro Leu Arg Glu Arg Ala Glu Ala Trp Leu
3985              3990              3995              4000

Gly Glu Glu Glu Leu Ala Leu Ala Ala Val Leu Tyr Leu Asp Asp Glu
           4005              4010              4015

Ala Ser Tyr Ser Glu Glu Arg Ala Asn Ala Pro Ile Gly Ser Gly Met
           4020              4025              4030

Val Pro Gly Lys Leu Thr Asp Ala Val Asp Asp Gly Asp Glu Thr His
           4035              4040              4045

Pro Asn Ile Gly Met Gly Ser Phe His Glu Ala Arg Pro Asp Asp Leu
           4050              4055              4060

Ala Tyr Val Ile Tyr Thr Ser Gly Thr Thr Gly Lys Pro Lys Gly Val
4065              4070              4075              4080

Met Ile Glu His Arg Ser Leu Val Asn Thr Ala Ala Gly Tyr Arg Arg
           4085              4090              4095

Glu Tyr Arg Leu Asp Gln Phe Pro Val Arg Leu Leu Gln Leu Ala Ser
           4100              4105              4110

Phe Ser Phe Asp Val Phe Val Gly Asp Ile Ala Arg Thr Leu Tyr Asn
           4115              4120              4125

Gly Gly Thr Met Val Ile Val Pro Lys Asp Asp Arg Ile Asp Pro Ser
           4130              4135              4140

Arg Leu His His Trp Met Glu Arg Glu Arg Val Thr Ile Phe Glu Ser
4145              4150              4155              4160

Thr Pro Ala Leu Ile Val Pro Phe Leu Glu Tyr Val His Glu Gln Gly
           4165              4170              4175

Leu Asp Ile Ser Trp Met Glu Leu Leu Ile Thr Ser Ser Asp Ser Cys
           4180              4185              4190

Ser Val Ala Asp Tyr Arg Ile Leu Gln Glu Arg Phe Gly Ser Leu Phe
           4195              4200              4205

Arg Ile Ile Asn Ala Tyr Gly Val Thr Glu Ala Ala Ile Asp Ser Ser
           4210              4215              4220

Phe Tyr Asp Glu Glu Leu Ala Lys Leu Pro Gln Thr Gly His Val Pro
4225              4230              4235              4240

Ile Gly Lys Ala Trp Leu Asn Ala Lys Phe Tyr Ile Val Asp Ala His
           4245              4250              4255

Leu Asn Pro Val Pro Val Gly Val Leu Gly Glu Leu Val Ile Gly Gly
           4260              4265              4270

Val Gly Val Ala Arg Gly Tyr Leu Asn Arg Pro Glu Leu Thr Glu Glu
           4275              4280              4285
```

```
Lys Phe Val Asp Ser Pro Phe Ala Gly Glu Arg Leu Tyr Arg Thr
    4290            4295            4300

Gly Asp Leu Ala Arg Trp Met Glu Asp Gly Asn Val Asp Phe Ile Gly
4305            4310            4315            4320

Arg Ile Asp Asn Gln Ala Lys Ile Arg Gly Tyr Arg Ile Glu Thr Gly
        4325            4330            4335

Glu Ile Glu Ser Gln Leu Leu Arg Val Glu Gly Val Arg Glu Ala Val
            4340            4345            4350

Val Leu Val Arg Ser Asp Ala Asn Gly Gln Lys Ala Leu Cys Ala Tyr
                4355            4360            4365

Tyr Thr Leu Asp Thr Gly Ala Glu Leu Ala Val Asn Asp Leu Arg Ser
            4370            4375            4380

Thr Leu Ala Gln Glu Leu Pro Gly Tyr Met Ile Pro Ser Tyr Phe Val
4385            4390            4395            4400

Glu Leu Glu Gly Leu Pro Leu Thr Pro Asn Gly Lys Ile Asp Arg Lys
                4405            4410            4415

Ala Leu Pro Ala Pro Glu Gly Glu Ala Gly Ser Gly Thr Glu Tyr Val
            4420            4425            4430

Ala Pro Arg Asn Glu Leu Glu Thr Lys Leu Ala Ala Ile Trp Gln Glu
        4435            4440            4445

Val Leu Gly Leu Ala Lys Glu Ile Gly Val Tyr Asp Asn Phe Phe Asp
4450            4455            4460

Ile Gly Gly His Ser Leu Arg Ala Thr Thr Leu Ala Gly Lys Val Phe
4465            4470            4475            4480

Lys Glu Leu Asn Val Asn Leu Pro Leu Arg Asp Val Phe Arg His Ser
                4485            4490            4495

Thr Ile Ala Ala Met Ala Glu Ala Ile Ala Arg Met Glu Arg Leu Glu
            4500            4505            4510

His Glu Asp Ile Pro Gln Ala Glu Glu Arg Glu Tyr Tyr Pro Leu Ser
            4515            4520            4525

Ser Ala Gln Lys Arg Leu Phe Ile Gln His Thr Leu Asp Gly Ala Asp
        4530            4535            4540

Gln Leu Tyr Asn Met Pro Glu Leu Val Gln Val Glu Gly Glu Phe Asp
4545            4550            4555            4560

Leu Asp Arg Leu Glu Ala Ala Leu Arg Lys Leu Ile Thr Arg His Glu
            4565            4570            4575

Ser Leu Arg Thr Gly Phe Glu Leu Val Lys Gly Lys Ala Val Gln Arg
        4580            4585            4590

Ile Tyr Pro Gln Val Asp Phe Ala Val Glu His His Gln Ala Asp Lys
    4595            4600            4605

Glu Asp Ala Ala Gln Ile Glu Gln Ile Val Arg Ser Phe Val Arg Pro
4610            4615            4620

Phe Asp Leu Gly Lys Pro Pro Leu Leu Arg Ala Gly Val Ile Glu Leu
4625            4630            4635            4640

Glu Pro Asn Leu Tyr Ile Leu Ile Phe Asp Met His His Met Val Ser
            4645            4650            4655

Asp Gly Val Ser Met Ala Ile Val Ile Asp Glu Phe Ser Ser Phe Tyr
            4660            4665            4670

Ala Gly Glu Glu Leu Pro Ser Leu Arg Ile Gln Tyr Lys Asp Tyr Val
            4675            4680            4685

Val Trp Gln Gln Ser Lys Ala Tyr Arg Glu Arg Ile Gly Arg Gln Glu
    4690            4695            4700
```

Ala Tyr Trp Leu Gln Thr Phe Lys Gly Glu Leu Pro Thr Ala Asn Leu
4705                4710                4715                4720

Pro Met Asp Tyr Lys Arg Ser Ala Ala Arg Ser Tyr Glu Gly Ala His
            4725                4730                4735

Leu Glu Phe Asp Val Glu Ala Ser Leu Ser Met Arg Leu His Glu Leu
        4740                4745                4750

Ala Ala Glu Arg Lys Ser Thr Leu Phe Met Val Leu Leu Ala Ala Tyr
    4755                4760                4765

Thr Val Leu Leu Ser Lys Tyr Ser Gly Gln Glu Asp Leu Ile Val Gly
4770                4775                4780

Thr Pro Val Ala Gly Arg Thr Asn Ala Asp Leu Glu Pro Val Ile Gly
4785                4790                4795                4800

Met Phe Val Asn Thr Leu Ala Ile Arg Asn Arg Pro Ser Gly Asn Lys
            4805                4810                4815

Thr Phe Leu Ser Tyr Leu Glu Glu Val Lys Glu Thr Ala Leu Gly Ala
        4820                4825                4830

Phe Glu Asn Gln Asp Tyr Pro Phe Glu Glu Leu Val Glu Arg Leu Asn
    4835                4840                4845

Val Lys Arg Glu Pro Gly Arg Phe Pro Leu Phe Asp Ala Val Phe Asp
4850                4855                4860

Leu Gln Asn Ile Glu Glu Arg Asp Val Glu Leu Glu Gly Val Ser Leu
4865                4870                4875                4880

Lys Asn Tyr Glu Leu Asp His Leu Glu Glu Ala Lys Phe Asp Leu Thr
            4885                4890                4895

Leu Phe Met Tyr Glu Asn Asn Gly Ala Leu Ser Gly Gly Phe Phe Tyr
        4900                4905                4910

Ala Thr Lys Leu Phe Lys Glu Ala Met Ile Arg Thr Leu Thr Glu Asp
    4915                4920                4925

Tyr Leu Arg Val Leu Ser Gln Ile Ala Glu Asn Pro Gln Leu Glu Leu
4930                4935                4940

Ser Arg Ile Glu Cys His Lys Pro Ala Ala Gly Ala Lys Ser Ala Val
4945                4950                4955                4960

Asp Thr Ile Glu Phe Ala Phe
            4965

<210> SEQ ID NO 7
<211> LENGTH: 14901
<212> TYPE: DNA
<213> ORGANISM: Paenibacillus alvei

<400> SEQUENCE: 7

```
atggcttttg aaaagaaac gttgttttgg aacgaaaaat tcggtagtga cgattatacc        60
ttgacgcggc tgccttacag caaagctcca agctcccagg cgcccattat gacaaccgtc       120
ggcggttcgc tttcggagaa agcggcgcag cgcgtccttc aaatgagcaa gggcgctccg       180
ctggccgctt ttatgatttt gctcgccggt gttcagtcac tcttgcataa atatacaggc       240
gcttctgaca ttctggtcgg catgccggtt atacggaaac cgacggagac gcgccgatcc       300
gttaatcata cggtcatttt gaaaagcttg ctttcggcgg gatcgacttt taaaacgctt       360
ctgagcgagc tgagaacttc gttgccggaa acgattcagc atcaacatat tccgttcttg       420
aaaatgacgg agaagctgga tctgcaatat gcagacggga tacccatcat ccatacgcta       480
gtatcccta aggagctgca tctggatgaa attgggcaaa acgtggtcac ggattgttcc        540
tttgaattca gcttaaccgg cgggacgata cagctagcgc tctcatataa cgagcactta       600
```

```
tatgactcca agttcatgac tcggatcgtc ggccatctga atcgcctgct ggccgtgggg    660
cttcacgagt tggagctgga catcgtgcgg gtggacatgc tgtcggagga cgagaaattt    720
caattgctgc aaagctttaa cgataccgag aaggactatc ctcgagatcg gacgattcat    780
cagctcgtgg aggagcaggt gaagagggtg cccgaagcaa cggcgattgt ctttgagggg    840
cggcggcttt cgtacgctga gctgaacgaa cgggcgaacc ggctggcgcg gacgctgcga    900
tcggtcggcg tgctgcccaa tcagctggta ggcttgatgg ccaggagatc gctggagacg    960
gtcgttggca ttctggcggt tctgaaagct ggcggtgcct acgtgccgat cgacccggaa   1020
tacccggaag aacgcatccg ctacattctg gagaactcga acgcgcagct gctgctgact   1080
caaagaaagc tgcaacagca ggtgccgttc aagggactg tgttggcgct ggatgacgag    1140
caggcctaca gcgatgatgg aacgaatctg gagccggcca gcggttcgaa tgatctggct   1200
tatgtcatct atacgtcagg tacgacgggc aaacccaaag gggtcatgct ggagcatcgc   1260
ggtttggtca gcttgaaact gatgttcgcg gacaggctcg gcatcacgga gcatgaccgg   1320
atcgttcaat tcgccagcct gtcgttcgac gcgtcctgct gggaagtgtt caaagcgctc   1380
tattttggcg cgactttgta cataccgacg gccgagacga ttctcgacaa ccgcctgttt   1440
gagagttata tgaacgagca tgcgattacg gcggcgattt tgcctccgac gtacagcgct   1500
tatttgaacc cggaccgcct tcccagctta acgaagctcg taacgggagg ctcggcggta   1560
tcggccgaat tcgtgcagca gtggaaaccg aaggtccact atttcaatgc ttacggccct   1620
accgaagctt cgattgttac gacgctttgg gatgcgaatg aggagcagcc agagcgcaga   1680
gtcattccga ttgggcgccc gctggccaat caccggattt ttattttgga tgcccacctg   1740
cagcttgtgc ctccgggagt ggacggcgag ctgtgcgtgg caggcgtggg gcttgcgaga   1800
ggttacctga accatccgga gctgacggca gaaaagttcg tggaacatcc gttcgcgccg   1860
ggagaacgcc tttatcggac gggagatctc gcccgatggc tgccggacgg aaatattgag   1920 tacttggggcc ggatcgacca tcaggtgaaa atccgtggat tccggatcga gatcggcgag   1980
attgaagagc agcttctgaa gatcgactcc gtgcaggaga cgatggtaat cgcgcgggaa   2040
ggcaaaagcg gcaagaatt gtgcgcttat ctggtcgcgg accgcccgct tacgctcggc    2100
gagctgagaa gcgcgctggc gcaaaaattg ccgaattaca tgattccggc gcattttgtt   2160
cagcttccgc gaatgccgct cacgccgaac gacaaaatcg accgcaaggc tttgcccgcc   2220
ccggaaggaa acgcgctgac cggcggcttg tacgtagctc cccgcaatga agccgagcgg   2280
acacttgtcg atgtgtggca ggcggtattg aacgccgatc gtgttggggt aacggatcat   2340
ttcttcgagc tgggtggaga ctcgatcaag tccattcaag tatcttcgcg gcttcatcaa   2400
gccgggtaca agctggatat tcgggattt ttcaaatatc cgactatctc acagctcagc    2460
ctgcgtgtga accgatcgg acgtaccatc gatcaaggcg aaataacggg cgaaacggcg    2520
ctgacgccga ttcagcattg gttttcgag agctccttg cggatccgca tcatttcaac     2580
cagtcggtga tgctgtaccg gaaggaacgc ttcgacgaag agacggtgcg tcaggtactg   2640
caaaagctgg ccgagcatca tgacgccttg cggatggtgt ccgcaaaac ggaacaaggg    2700 tttagcgaaa ggaaccgcgc gattcaggaa ggcgggctgt tcacgctgga cgtgttcgac   2760
ttcaaggatg cggaggatac cgcacaggct ctggaagcga aggcaacgga tattcaagcg   2820
ggcatcgatc tggagaaagg gccctcgtg aaggcgggac tgttccgatg cgcggacggc    2880
gatcatttac tgctcgcggt tcatcatgcc gtggtggacg gcgtgtcttg gcgcattttg   2940
atggaggatt tcgctctggg ttacgagcag gccggcaaaa gcgaggaaat tcgtttcccg   3000
```

```
gcgaaaacgg atgcgtaccg cacttggtcc gagcagctgg ccgcttacgc gcaaagcccg      3060
gagatagcaa aggaacgggc ttattggcag gccgtggaac aaattgcggt tccggccttg      3120
ccgaaggatc tggaggcgga cgttacgacg cagcaggaca gcgaatcgct gttcgtccgt      3180
ttgacttccg aagaaacgga gctgctgctg aagcgggtac accggccta caacaccgaa       3240 atgaacgata ttttggtaac ggcgctcggc atagctgttc gcaagtggac gggacacgaa      3300
cgggtgcgga tcaatctcga aggacacgga cgcgaatcga tcggaacgga tatcgacatc      3360
acgcgcacag tcggctggtt tacgaccaag tttccggtcg tcctggagcc ggaaaccaac      3420
cgggatttgg cctatcagat aaacaggtc aaggaaagct tgcgtcgcat tccgaacaag       3480
gggcttgggt acggtgtatg ccgctatctc tccaaatcgg aggatggctt tgtttgggc      3540 gcagagccgg aaattaattt taactacctc ggccagttcg acgatgatgt caaccaggac      3600
gagatcggca tatcttctta ttccagcggc agcccggcca gcgaccggca ggcccgcagc      3660
tttgtgctgg atatcaacgg catggtgctg acggcgctc tatcgctcga tctcagctac       3720
agccggaagc agtatcgcaa ggtaacgatg gaagccttcg ctcagcggct tgagcaaagt      3780
ctccgagagc tcattaccca ctgcgcaggc aagaaaaaca ccgaattgac gcctagcgac      3840
gtgcaattta aaggcttgac catcgcggaa ttggagcaaa tcggccagcg ctcggtccat      3900
gtcggggaaa tcgagaatat ttactcgctt acgccgatgc agaagggcat gtggttccac      3960
agcgcgcttg accggcagac ggccgcttac ttcgagcaga cgcggtttac gatgcgggga      4020
gcgctcgacg ttcagctttt cgagaggagc tggacggagc ttgcgaaacg tcatctggtg      4080
ctgcgggcga attttgtgaa aggaccagcg ggcgagccgc tgcagatcat ataccgcgac      4140
aaaccagtcg gctttgaata tgaagagctg ctacatttgc aggcggacga gaaacaagcg      4200
tatttggata aaaaggccga ggatgacaag cttcgcggct tcgacctgga acatgacgcg      4260
ctcgttcggg ttacgatcct gcgcaccgaa gagcagagcc atcatgtgct gtggagtttc      4320
cagcatattt tgatggacgg ctggtgcctg ccgcaactga cgcaggagct gtttgagaca      4380
tactcggcct tggcatccgg caagcagcca gcggagata aggggtcgga ttatggcgct       4440
tatatcgaat ggctggagaa acaggacgat caggcggcat ccggctattg gacggcgttc      4500
ctggcaggtt acgaagggca aactgtactc ccggggcaaa aggaagcgca gccgaacggt      4560
agatttacgg ctgatcacgt caccgccgag ctgggcaagg acttgagcga gcggatggat      4620
cgggtggcga acagcgcct ggttacagtc aatacgctgc tgcaagccgc ttggggcgtg       4680
atgctgcaaa aatataacgg aacaaacgat gccgtattcg gcagcgtcgt ggccggaaga      4740
ccggcggaaa tcccgggtat agagtccatg attggactgt ttatcaatac ggtgccggtt      4800
cgcgtcacga gcgaagcgga caccgtgttc gctgacctga tggcaaagct ccaagagcgg      4860
gcgctggagt ccgggcgtta tgattactat ccgctgtatg aaattcaagc ccgctgcgtg      4920
caaaagcaaa acctgatcaa ccatatcatc gctttcgaga actatccggt ggatgagcag      4980
atggagcagg cgggcgacca gcagcacggc gacctgacga tcactgacgt tcagatggag      5040
gagcagacga actataactt caatgtgacc gtggtgccag gagccgagat cgaaattcgg      5100
ttcgatttta acgccgaagt gtttgataaa gacagcatcg aacggctcaa ggggcatctc      5160
gtccatctgc tggagcaggt gacggataac ccggaaatta ccgtgggaga gctggaactt      5220
gtgacggagg cggaaaaggc cgaccttctc ggacgattta cgacaccac cacgcgaattt       5280 ccgcgcggga agacgctcat tcaattgttc gaagagcagg tagagcgcat cccggatgca      5340
```

```
gccgccatca ccttgaatga gcaagagctg acctaccgcg agctcaacga acgtgtcaac    5400
cgccttgccc gtaccttgcg tagccacggg atatccaaag gtcgtctggt cgccattttg    5460
gctgagcgtt ccattgaaat ggtggtgggc atgctggcgg cacacaaagc cggagcggct    5520
tacgtaccga ttgacccaga atatcccgag gagcgtatcc gtttcttgat cgaggattcg    5580
ggagggcagg tcatgctgac gcaaagccgc ttgcgcgagc gcctggcggg ttcggacccc    5640
gtgatcttac tggatgacga gtccttctat cacgaggacg gcacaaatct aaatacgggc    5700
atcgaagcga cagatctggc ctgcgtcatc tatacgtcag gcacgacggg caagccgaaa    5760
ggcaaccctg tttcgcaccg caacatcgtg cgggtcgtgc aaaatacgaa ttatatcgac    5820
atcaccgagc gggatcatgt cctccagctt tcgagctatt cgttcgacgg agcgactttc    5880
gatattttcg gcgctttgac caacggggcg cggctggtgc tggttcccta cgagactttg    5940
ctggaaatcg gccggctggc ggatctcatc cagcgcgagc gcatctcggt catgtttatt    6000
acgacggctt tcttcaacat ccttgtagat gtgaacgtcg actgcctgcg ggatgtcagg    6060
gcgattttgt tcggaggaga gcgtgtgtcg gtcggccatg tgcgcaaagc gctcgcccat    6120
atcggaccgg gcaggctcaa ccatgtgtac ggcccgacgg aaagcacggt ttataccacg    6180
taccttccgg tcgacttcgt cgatgagttg gcggttaccg tacccattgg acggccgatc    6240
agcaatacga cggtgtatat cgtcgacagc cggaacaaac ttctgccgat cggcgtggcc    6300
ggggaacttt gcgtcggcgg agaaggcttg gtaaggggct acaataaccg gccggagctg    6360
acggcggaga aatttgtgga caatccgttt gtgccgggag agcgcatgta ccggacgggg    6420
gatttggcga aatggctgcc ggacggcacg atcgaatacg tgggacggac ggacgaccaa    6480
gtgaaaatcc gcggcttccg aattgagcta ggcgagatcg aagctcagct tcagaaagtg    6540
gagggaattc ggaaaacgac ggtattcgcg agggaaaacg cctccggcga gaagcagctt    6600
tgcgcctatt atgaagcgga ctgcgagctt ccggcggccg aactgaagag cgtgctttcc    6660
aaggaactgc cggcctatat gatcccggcg tacctgatcc agttggagcg gctcccgctg    6720
acgacgaacg gcaaggtcga ccgccgatca ctcccggcgc cggaggagag cttgcagccg    6780
ggcggaggaa gtactccgcc tcggactccg ctggaagcca gcttggccgg aatttggaaa    6840
agcgtgctcg gactagtgca cattggcgtt catgacaact tcttcgacat gggcggacat    6900
tccctgcggg cgacgacact ggtgagcaag gtgcatcagg agctgaacgt cgaactgcct    6960
ctgcgcgacg tattccgcta ctcgacgatc gaggagatgg ctctcgccat ctcccggatc    7020
ggagagcagt cgttctcgtc gattccgctg gcaggcgcaa gagcatatta tccgcttttcc    7080
tcagctcaga agcggctgtt tatcctgaat cagctggaag gggccgatca gagctacaac    7140
atgccgggcg tgctgctgtt ggaaggatcg attgaccgga gcctgctgga gaaggctttc    7200
cgcggactga tcgcacggca cgaaacgctg cgaaccggct tgagatcgt acaaggcgaa    7260
gcagtacagc gcatttacga gagcgtcgac tttgccgtcg agtaccgtca tgcgagcgag    7320
gaagaaacgc ctgaagtcgt gcaggccttc atccggcctt cgacttggc aaagcctccg    7380
ctgctgcggg cggagctcgt agagctggca atcgaacgtt atttgctgat gttcgacatg    7440
caccatatcg tctccgacgg ggtttcgatg gacgtgttag tcgaggaact cgttcgtctg    7500
tacggcggcg agtcattaga gcctttgcgc attcaataca aggactatgc ggtatggcag    7560
cagtcggacg agcaaaaagt gcagttgaaa cgcgaggaag cttactggtt ggaccgttac    7620
cggggcgagc tgccggttct ggaaatgccg acggactatc cgcgtcctgc cgtgcagagc    7680
tttgagggac aaacgctgac gtccttcgtg gacgaggcaa cgaacgaagg cttaaagcaa    7740
```

```
ctggccgctc aaaaaggaac gacgctgtat atggtactgc ttgcggcata taccgtgctt   7800
ttgcataaat acacaggtca ggacgatttg atcgtcggaa cgtcgattgc gggcagaacg   7860
cacggagaca cgcagccttt gatcggaatg ttcgtcaata cgctggcact ccgcaattat   7920
ccggcttcgg agaagagctt cctgtcgtat cttgaagaag tgaaagaaac gaccttaggc   7980
gcttacgagc atcagaatta tccgttcgaa gagctcgttg ataaagtgca ggtcagccgg   8040
gatttgagcc gcaacccgct gtttgacacg atgttctccc tgcaaaactt ggaggataaa   8100
gagtttaagc tggaagggct gaaattgtcc ccgtacccta gtgaatacgg cacggccaag   8160
ttcgatctga gtgtggatgt tacgaagaa acggcggct tggagtgcat ctttgaattc    8220
gcaacggctc tttataaaga aagcacgatc cggcggctgt cgactcattt tggacatttg   8280
cttgcggcga tcgtaagtcg tccggatgcg aagatcgccg agctgaactt gttgacggca   8340
gaggaaaatg agcaaattct cggcgcgttc aacccggcgc agccggaagc ggctcctgcg   8400
gccgcgttcc accggctgtt cgaagaacag gcggagcgca cgccgaaagc ggaggccgtc   8460
gtgtacgaga cgaccggct gacgtatgcg gagctgaacg agcgggcgaa ccgcttggcg    8520
gctacgctgc gcgcaagcgg catcggccgg gagtcgatcg tcggcattct ctccgagcgt   8580
tcggtggact tgctggtggc cgtgctggcc gtctggaaag cgggcggggc gtatgtgccg   8640
ctcgacccgg attatccggc ggaccgcgtg cggttcatgc ttgaagacag tggagcgaag   8700
gtgctgctga cgcaaacggt gctgcgagag cgcgccgaag cctggctcgg cgaagaggag   8760
ctggcgctgg cagcggtgct gtacctggac gacgaagcgt cgtacagcga ggagcgggcg   8820
aatgcgccga ttggttccgg catggtctcc ggcaagctga cggatgctgt ggacgacggc   8880
gatgtgagcc atcagaaggt cggcatgggc agcttccatg aagcccgtcc ggaggatctg   8940
gcgtacgtga tctatacgtc gggaacgacg ggcaagccga agggcgtaat gatcgagcac   9000
cgcagcctgg tgaacacggc ggcgggctat cggcgggaat accggttgga tcagttcccg   9060
gtgcggctgc tgcagctcgc aagcttctcg ttcgacgtat tcgtgggcga tatcgcgcgg   9120
acgctgtata acggaggcac gatggtgatt gtgccgaagg acgaccggat cgatccgtct   9180
cgtctgcacc actggatgga gcgggagcgg gtcaccatct tcgaatcgac gccggcgctg   9240
atcgtgccgt tcctggagta cgtgcacgag caggggctgg atatgagctg gatggagctg   9300
ttgatcacga gttcggacag ctgcagcgtg gcggattacc ggatcttgca ggaacgtttc   9360
ggctcgttct tccggatcat caacgcatac ggcgtgacgg aagcggcgat cgactccagc   9420
ttctacgacg aggagctgac gaagctgccg cagataggcc atgtaccgat tggaaaagcg   9480
tggctgaatg cgaaattcta catcgtggat gcgcatctga cccggtgcc ggtcggggtg    9540
ctgggcgagc tggtcatcgg cggagtcggt gtggcgcgag ggtatttgaa ccgtccggag   9600
ctgacggaag agaagttcgt agacagtccg ttcgccgcgg cgagcggct gtaccgcacg    9660
ggagacttgg cgccggtgga tggaggacggg aacgtggact tcatcggccg gatcgacaac  9720
caagcgaaaa tccggggcta ccggatcgag acgggtgaga tcgagtcgca gctgctgcgg   9780
gtggaaggcg tgcgcgaagc ggtggtgctg gttcgaagtg acgcaaacgg gcagaaggcg   9840
ttatgcgcgt attacacgct ggataccgga gcggaactgg cagtgaacga tctgcgcagc   9900
acgctggcgc aggagctgcc gggctacatg atcccgtcgt acttcgtgga gctggagggc   9960
ctgcctctga cgccgaacgg aaagattgac cggaaggcgc tgccggcgcc ggaaggagaa   10020
gcgggaagcg gaacggagta cgtcgcaccg cgcaatgagc tggaaacaaa gctggcggcg   10080
```

```
atttggcagg aggtgctggg gcttgcgaag gagattggcg ttcacgacaa cttcttcgac   10140
atcggcggcc actccctgcg ggcgacgacg ctggtcagca aggtgcacaa ggaactgagc   10200
gtggatctgc cgctgcgcga cgtgttccgc cattccacga tcgagagcat ggcggccgcc   10260
atttcccggc tggatgagca gacattcgtt gccattccgg tggcggatga ccgggaggtg   10320
tacccgcaat cttttgctca aaaacgtctc tttatcctga atcaactgga aggcgcggag   10380
cttagctaca acatgccgga ggcgatgctg ctggagggg ctttggatcg ggcaaggttc     10440
gaagaagcat tccgtaagct cgtggcgcgg catgaaatgc tgcgcaccgg gttcgaaatg   10500
gtggatggcg aagcatcgca gcgggtttac caggacttga attttgctgt ggagttctat   10560
cgagtagatg agcaagaggc cgaagagacg gttcgccgtt ttgtccgtcc gtttgacttg   10620
gcgaagcctc cgctgctgag ggtaggcctt gtcgagctgg cttcggaacg ccatattcta   10680
atgtacgaca tgcatcatat tatttccgac ggtgtctcca tggaaatctt tgttgaagaa   10740
ttcgtccgct tgtacggcgg tgagcaattg gagcctcttc gcattcagta caaagactac   10800
acagtttggc agcattcgca ggagcagaag gaacggcttc agcgtcagga ggcgtactgg   10860
ctgaacatgt tccaaggcga gcttccggtg ctggaaatgc caaccgacta tccgcgtccg   10920
tccgtgcaga gctacgaagg ccacacgctg gagttttttct tcgacgcttc gaaaaccgac   10980
ggcctgaagc aactggcctc ggaaacgggc acgacgctgt ttatggtgct gcttgcggcg   11040
tataacgtcc ttctgcataa atattcaggt caggaagatg tgatcgttgg tacgccgatt   11100
gccggaagga atcatggaga tgtgcagccg ttgatcggaa tgttcttaaa cacgctggcg   11160
atccgcagtt atccggcttc ggagaagaca ttcctgtcat acctgaacga agtcaaagaa   11220
acgaccctcc atgccttcga gcatcaaaac tatccgttcg aagaattggt agacaaggtg   11280
caagtcaccc gtgatttaag ccgtaatccg ctttttcgaca cgctgtttac gatgcagaat   11340
acggagaatg aagaatttga gctggaaggg cttcgcctga ttccttatcc gagcgcactg   11400
gataccgcaa agtttgatat cagcttggat gtgggcgagg agaacggcgg cttggattac   11460
agcttcgaat atgcgacggc tctctacaaa agggcgacga ttgaacggct ggcgaagcat   11520
tacgagcagc tgctcgtgac gatcataagc cgtccagatg cgaagatcgc cgagctgaac   11580
ttgctgacgg cagaggaaaa agaacaaatt cttggcacat tcaaccccgc gcagccggaa   11640
gcggctcctg cggccgcgtt ccaccggctg ttcgaggaac aggcggaacg aacgccggaa   11700
gaggcggccg tcgtgtacga gaacgaccag ctgacgtatg cggagctgaa cgagcgggcg   11760
aaccgcttag cggccacgct gcgcgcaagc gacatcggcc gggagacgat cgtcggcatt   11820
ctcgccgagc gttcggtgga tctgctggtg tccgtgctgg ccgtctggaa agcgggcggg   11880
gcatatgtgc cgctcgaccc ggattatccg gcggatcgcg tgcggttcat gcttgaagac   11940
agtggagcga aggtactgtt gacgcaaatg ccgctgcgag aacgcgccga agcctggctc   12000
ggcgaagagg agctggcgct ggcagcggtg ctgtacctcg acgacgaagc atcgtacagc   12060
gaggagcggg cgaatgcgcc gattggctcc ggcatggtcc ccgcaagct gacggatgct    12120 gtggatgacg gcgatgagac ccatccgaat attggcatgg cagcttcca tgaagcccgt    12180 ccggatgatc tggcgtatgt gatctatacg tcgggaacga cgggcaagcc gaaaggcgtg   12240
atgatcgagc accgcagcct ggtgaacacg gcggcgggct accggcggga ataccggttg   12300
gatcagttcc cggtacggct gctgcagctc gccagcttct cgtttgacgt gttcgtggga   12360
gatatcgcgc ggacgctgta caacggaggc acgatggtga ttgtgccgaa ggacgaccgg   12420
atcgatccgt ctcgtctgca ccactggatg gagcgagagc gggtcaccat tttcgaatca   12480
```

```
acgccggcgc tgatcgtgcc gttcttagag tacgtgcacg agcaggggct ggatatcagt   12540
tggatggagc tgttgatcac gagttcggac agctgcagcg tggcggatta ccggatcttg   12600
caggaacgct tcggctcgtt attccggatc atcaacgcat acggcgtgac ggaagcggcg   12660
atcgactcca gcttctatga cgaggagctg gcgaagctgc cgcagacagg ccatgtaccg   12720
attggaaaag cgtggctgaa tgcgaaattc tacatcgtgg atgcgcatct gaacccggtg   12780
ccggtcgggg tgctgggcga gctggtaatc ggcggagtcg gtgtggcgcg agggtatttg   12840
aaccgtccgg agctgacgga agagaagttc gtagacagtc cgttcgccgc aggcgagcgg   12900
ctgtaccgca cgggagactt ggcgcggtgg atggaggacg ggaacgtgga cttcatcggc   12960
cggatcgaca accaagcgaa atccggggc taccggatcg aaacgggtga gatcgagtcg   13020
cagctgctgc gggtggaagg cgtgcgcgaa gcggtggtgc tggttcgaag tgacgcaaac   13080
gggcagaagg cgttatgcgc gtattacacg ctggataccg gagcggaact ggcagtgaac   13140
gatctgcgca gcacgctggc gcaggagctg ccgggctaca tgatcccgtc gtacttcgtg   13200
gagctggagg gcctgcctct gacgccgaac ggaaagattg accggaaggc gctgccggcg   13260
ccggaaggag aagcgggaag cggaacggag tacgtcgcac cgcgcaatga gctgaaaaca   13320
aagctggcgg cgatttggca ggaggtgctg gggcttgcga aggagattgg cgtttacgac   13380
aacttcttcg acatcggtgg tcactccctg cgggcaacga cgctggcggg caaagtattt   13440
aaggaattaa acgtcaacct gccgctgcgt gacgtatttc gtcactcgac gattgcagcg   13500
atggccgagg cgatcgcccg aatggaacgg ctggagcatg aggacattcc tcaagcggag   13560
gagagagagt attaccctct gtcctctgcg cagaaacggc tgttcattca gcacacgctg   13620
gatggagcgg atcagcttta caacatgccg gaactggtgc aggtggaagg cgagtttgat   13680
ttagaccggt tggaagccgc cttgcggaaa ttgataacac ggcatgaatc gctgcgtacc   13740
ggttttgaac tcgtgaaggg caaagcggtt cagcggattt acccgcaggt cgattttgct   13800
gtcgagcatc atcaagcgga taagaggat gcggctcaaa tcgagcagat cgtccgcagc   13860
ttcgttcgtc catttgatct cggcaagccg ccgctgctgc gcgccggggt catcgagctg   13920
gagccgaacc tgtatattct cattttcgac atgcaccata tggtgtccga cggcgtatca   13980
atggcgattg tgatcgatga gttctcgagt ttctacgccg gggaagagct gccgtcactg   14040
cgcattcaat acaaggatta tgtcgtttgg cagcagtcga aggcctaccg agaacggatc   14100
gggcggcagg aagcgtactg gctgcaaacc ttcaaggcg agctgccgac ggcgaacctg   14160
ccgatggact acaaacggtc tgcagctcgc agctacgaag gtgcacatct ggagtttgac   14220
gtcgaagcct ctctctctat gcggctgcac gaattggcgg cagagcgtaa agcacgctg   14280 ttcatggtgc tgcttgcggc ttataccgtg ctgctgtcca aatacagcgg gcaggaggac   14340
ttgatcgtgg gcaccccggt ggcgggaaga acgaacgccg atttggaacc ggtcatcgga   14400
atgtttgtca atacactggc gatccgcaat cgtccgtcgg caacaaaac gttttgtcc   14460 tacctggaag aagtgaagga aacggctttg ggtgctttcg agaaccagga ttatccattt   14520
gaggagctcg tggaacgttt gaatgtgaag cgggagccgg ccgcttccc gctgttcgat   14580 gccgttttcg acttgcaaaa tatcgaagaa cgagacgtcg agctgaagg ggtcagcctg   14640 aagaattacg agcttgacca tttggaagaa gcgaagttcg atctgacgct gtttatgtat   14700
gaaaacaacg gggcgctgag cggggcttc ttctacgcca ccaagctgtt caaagaagcc   14760
atgatccgca ccttgaccga ggattacctg agggtactgt ctcaaattgc ggaaaatccg   14820
```

```
caacttgagc taagtcggat tgaatgtcat aaaccggcgg ctggcgcaaa gagtgccgtc    14880
gatacgatcg aatttgcgtt c                                             14901

<210> SEQ ID NO 8
<211> LENGTH: 3306
<212> TYPE: DNA
<213> ORGANISM: Paenibacillus alvei

<400> SEQUENCE: 8
atgaaatctt tatttgaaaa ggaagaaagg tactggagcg gcaagtttga cgccgatgac      60
aacctgagct tccttcccta cagtcaatcc tccaaattat ccgccgacgg ggaagctgcg     120
gccgagccgg gcttgcttca ccgtaccctg ccgagcgaac tctcggagag aatcattcgc     180
ctcgccaacg gttcggatt t ggctatgtac atgattgttt tggcaggagt aaaaagcctg    240
ctgttcaaat ataccgggca ggaccaagtg ctggtcggca tgccttctta tagcgcagac     300
cccgacggga ctccgccgcc gcatgacatc ttggtgatca agacggccgt aagccatcag     360
actacgctga aaacgctgct cggggggcatc aaagcctcca ttggcgaggc gctggagcat     420
cagcacctgc cttttcagaa aatggtggag ccgctccatc tggactatac ggggatggc     480 ctcccggtcg ttaacaccgt tgcatccttc gccccgattc atcccgaacc gctgggtaac     540
cgggtggcgg ccgatacggt ttttcgcttc gatcgccaaa accactccat cgagctggaa     600
ataagctttg acgggcagcg gtacgagcgg gcatttgtgg aacaggcggc cgaccatttt    660
gttcggctac tgtccttgct tttatttcag cctgatctgg agcttggaca agccgatgtg     720
ctgtccccag acgagaggga gacgctgctg aagcgattta atgacaccga accgggttc     780 gagcggggga aaacgattca tggcttgttc gaagagcagg cggagcttta cccggacaac     840
gtggccgccg tcatgaatga gcggcagctg acttaccgcg aactgaacga gcgatccaac     900
cgccttgcgc ggaagctgcg ggagacggga gtagaagcgg atcagctggt agcgattctg     960
gctgaacgct cgctcgatat ggtcgtcggc attctggcga ttcttaaagc gggcggagcc    1020
tacgtgcctg ttgatcccga ctacccggag gagcgcatcc gcttcatgat cgaggattcg    1080
ggcgcgccgt tattgttgat tcaaaagcat ctgcacgaga gaccgacttt cgcaggaacg    1140
cgcctcgagt tggatgattt cgtgtggaac gacagagggg tggactccga aggtaggctg    1200
gatgcttcga acctggagcc gatttccggg ccgggcaatc tggcttatgt tatctacacg    1260
tcgggaacga ccggcagacc gaaaggaaca ttaatcgagc ataagaacgt cgtgcggctc    1320
ctgttcaacg acaagaacct gttcgacttc gggccatccg acacgtggac gctgttccac    1380
tcgttctgct tcgatttctc cgtctgggaa atgtacggag cgctgctgta cggaggcaag    1440
ctggtcatcg taccgccgct cacggcgaaa aatccggctg atttcctggt gctgctgggc    1500
cacgaacagg tcacgatttt gaaccagacg ccaacgtact tctaccagct gctgcgtaag    1560
gtcttggcgg accatccgta cgatctgcgg attcgcaacg tcatcttcgg gggcgaagcg    1620
ctgagtccgc tgctgctcaa gggcttcaag acgaagtacc ggagacgaa gctgatcaat    1680 atgtacggca ttaccgagac gacagttcac gttacgtata aggaaatcac ctgggtcgaa    1740
atggaggcgc gaagagcaa tatcggcaag ccgatcccga cgctgagggt gtacgtcctt    1800
gatgaaaacc gccgcccagt gccgatcggc gtagcaggcg aaatgtacgt ggccggggaa    1860
ggcctggcga gaggatacct gaaccgtccg gatctgacgg cggagaagtt cgtcgattcc    1920
ccgtttgcgg aggggggagaa actataccgc tcgggcgact ggcggttttg gctgccggac    1980
ggcaacatcg aatatctggg ccgaatcgac caccaagtga aaatccgcgg gtaccggatc    2040
```

```
gagctggacg aaatcgagac gcagttgctg aagattgccg ccgtgcaaga agccaaggtg    2100
ctcgaccgcg acgacgcgaa cggccaaaag cagcttgtcg cttactacgt cgcggaaatg    2160
aggctggcgg cgcatgaact caaggaggag ctcgccaaac agcttccagg gtatatgatt    2220
ccttcgcact tcgtgcagct ttcgcggatg cctctaaccc cgaacggaaa aatcgaccgc    2280
aaagcgctgc cagcgccgga ggaagtcgcg gccttaggag cggaatatgt cgcgccgaga    2340
acgctgctcg aaatgaagat tgcccgcgtc tggcaggata cgcttggcgt tccgcaggtc    2400
ggcgtaaagg ataactttt tgatttgggt ggcaattcgt taagtctgat gaggctcgtt    2460
caagccgttt acgatgaaac gggcattgag attccgctga atcgccaatt tcatcatgta    2520
accgttgaag ccatggcttt cgaagagggg gatctgggcc tggataaagg gggagactcc    2580
ttcataaagc tgaataaagc aggagatctg aacgtgttct gcttccctcc gggcagcggc    2640
ttcggcatcg gttaccgaga gctcgcaagc aggctcgacg ccagttcgt gctctacggc    2700 attgatttta tcgacgatac cgccgattac gaggccatgc tgaaccgtta tgttgacgag    2760
attgtccgca tccagccgga aggaccttac gtgctgctcg gctactgctt cggaggcaac    2820
ctgacgttcg aggtagccaa aacgatggag aaaagagggt atcccgtaac ggacgtgctc    2880
atggtggact cgtggattaa ggagacgctg acgccttccg aaacgtcaga gaaagagctt    2940
gaagaaatgc ttgccgattt cgacgaagaa gagaaggaat taatgagcaa tccgctcgtg    3000
cgggagcggg ttcatcagaa ggtcaaagcg actttggcgt acgaagcgca gcttattaac    3060
tccggcacga tcccggcccg gatttacgaa ctgattgcga aggacagcga agcgttccgc    3120
ttggagcacc aattgccgtc ctggcggggg gcaacgacgc aagcttacac cgattaccgg    3180
ctggagggcg cgcacgagga attgctggaa ctcgcgcgcg tggacgaaac ggccgttgtc    3240
atccgggata tcttagagca agtcaagcgg cagatcgaag tggaggccgg ggtactgcat    3300
ggaagc                                                              3306
```

<210> SEQ ID NO 9
<211> LENGTH: 18876
<212> TYPE: DNA
<213> ORGANISM: Paenibacillus alvei

<400> SEQUENCE: 9

```
atggaaatta tgaatccggg aacgtccatc acgatgcttt ccgcgaccta ccagattacg      60
ggccagatcg acacacagct tctggagcaa gctgcggcgg agatcgtcaa aacctatgac     120
gctttccgaa tacgcattag cggggatttg cagaatccaa cgcagtggtt cgaagagccg     180
gagaatgtcc aagccaggat aagccgcctc gaaataggca caaccgaaca attctatgct     240
tgggtgaaag aagtaagcga aaaaccggcc agcgtgttcg acgaacacct ctaccaattt     300
acgattatcc attttgcgaa cggccaagta tggctcaatt tgacggtaaa tcatattatc     360
gccgacggct tgtccgtcac tgctttgctg catgcggtga tggaaaaata catggaactg     420
cgcaaaggca tctccagcag ttaccaggcc ccttcttatc tggattatat ttccgcggag     480
cgtgaatatg agcaatcgca gcgttatcaa aaaggcaagg aatactggct gacgaagtac     540
agcactttgc ctgaaacgac cggctttaaa tcgtatccgc cattctcgat cggcagcgaa     600
tccaataaac gggccaccac tttggacggt tcccggtatg aacgcattct ggcctttagc     660
gaacaatatc aggtcagctt atatacgtta tttctgtccg cgatgtatgc cttgctatac     720
aagctgaccg acagcaccga tgttccggtc ggcacggtgt tcgccaatcg caccagcaag     780
```

```
aaggaaaaag aaacgatcgg catgttcgtc agcaccgtgg ctacacggat tcatctgaat    840
ccagacgggg acgtgctttc cttgatccaa gcggtttcca aggagaatac ggcggatctg    900
cggtatcaaa ataccctta taaccaattg atccaggatt tacgcgaaca cacggccgc     960
aacgatcttt cgggactgtt ccgtacgtct ctggaatatc tgcctttgaa atcgtggaa    1020
tacgaagaaa tcaaggtacg cctggaggct cacttcgcta agcacgagat ggatgatttg   1080
ctgctgcgtt tcgaccatat gctgaatgaa ggccatgtca ttctccacgc ttcctatcgc   1140
actggcttgt tcgagacagc cgagattgat cggattatgg aacagtatgt aaccgttctg   1200
gaccagtttc ttcagactcc cgaactgccg gtacgcgaaa tttctctgct gagcgatgag   1260
gagagacagt gcattctggg cgttttaac ccgccggtgg cagggctgag cgagggagag    1320
gcgtttcatc ggtacgttga aaagtttgcc cgcgaaattc cagatcatcc ggcagttgtc   1380
tacatggata cacagctgac ctacggtgaa ttgaacgaac gtgccgagcg gctggcttct   1440
ctccttcgcg agcagggcgt gggaaaggag acgattacgg ggatctgggc ggagcgttcg   1500
gtggaactgc tgatcggggt gctcgccgtt tggaaagccg gcggagccta tgtaccgctt   1560
gaccccgatt atccggcgga gcggattgag tacatgctca gcgatagcgg tgcgtcggtg   1620
ctgcttacgc agcgtcatct gttggagcgg gccgaaggtt ggttggccga tgaccggctg   1680
aaactacaag ctgtctatgc tatggacgat gaacagattt ataacaggga tgccttagcc   1740
gtggaatttg agtctgccga tagtgccccg caagacttgg cttatgtgat ttacacctcg   1800
ggtacgacgg gacgcccgaa aggcgtcatg atcgaacatg gtagtctctt gaatacggcg   1860
gatgcgtacc gtcgcgagta ccggttggat cagttcccgg tgcggctgct gcagttggcc   1920
agcttttcgt ttgacgtgtt tgtcggagac atcgctcgga cgctgtataa cggaggtacg   1980
atggtgattg tgccaaagga tgaccggatt gatccgaacc gcttatacgg ctggattcgg   2040
gaccaaaaca ttacggtatt cgaatcgacg cctgcgctca tcctgccatt catgcagcat   2100
atttatgaag aagggctgga cgttagctcc atgcagttgc tgattaccag ctcggatgct   2160
tgcagtgtca ccgattaccg attgctgcag gaaagattcg gcggacaatt ccgcatcatc   2220
aacagctatg gcgttaccga agcggccatt gacagcagct tttacgatga gacgctggac   2280
aagctgccgt cgtcgggtca tgtgccgatc ggcaaagctt ggctgaacgc ccggttttac   2340
attgtcgatg ccgcgttaaa accggttcct gtagggggttc cggcgagct tgtcatcgga   2400
ggcgctgggg tggcgcgcgg atactggaac cgtccggacc taacggccga aagtttgcg    2460
gacagcccgt ttgtgcctgg cgaacgtttg tatcggacag gcgatttggc ccgctggctg   2520
aagacggca acgtcgactt catcggccga attgactatc aggtgaaaat tcgcgggttc    2580
cggatcgaac tcgcgaaat tgaaacggcc ttgctgcgtt tcccgggcgt caagcaggct    2640
gtggtgacag accgtacaga taagcagggg caaaagtatt tgtgtggcta cgtggcggca   2700
gatacttcct tgcagctgag cgatctgctg tcccaattga agcaagagct gccggcccat   2760
atggttccgg cccggctggt gtctcttgat aagcttccac ttactccgaa cggcaaaatt   2820
gaccgtaaag cgctgcctga accgaccgga gaggtagaag caggccgtga gtatgtggct   2880
cctcgcacaa cgctggaaac aagacttgct ctcatttggc agcaggtgct gggtattgcg   2940
cgagttggag tcgaagacga tttctttgac ctgggtggtc attccttgcg ggcctccacg   3000
ctggtttcca agattcggaa agagctgcaa gtcgaggttc cgctgcggga cgttttccgc   3060
tacaccacga tcaaacagct ggcccaaaga atcggcggtt taaagcagca ggagacgtat   3120
gaaattacaa aggcggctga ggccgagtac tatccggttt catccgagca aaagcgtctg   3180
```

```
tacgtcctgc gccagcttga cggggccgag cgcagctaca atatgtcggg ggcgcttctt    3240
ctcgaaggca agctggatcg gacgcgcgta gagtacgcgt tccgggcgct gattcagcgt    3300
catgagacgc tgcgtaccgg gatcgagcag gttcaaggcg aacttgtcca gcgcatctat    3360
gacgaggtgg agtttgctgt ggattatttc caggcgagtg agcggaagt ggagcaaggg     3420 gtggaagctt actatcgccc gtttgatctg accaagccgc cacttctccg catcggcctg    3480
atcgaagtca ccgaggatcg ccacattctg ctgttcgata tgcaccatat cgtctcggac    3540
ggcatatcga cagcgctgct cttcgacgag ttcagccgcc tgtatcgggg cgaggagctg    3600
gctccgctgc gcattcaata caaagattat gccgtttggc agcattccga agcttacgcg    3660
caactgctcc agccgcagaa ggagtactgg ctggagcagc tgtcaggcga gctgccggtc    3720
ttggagctgc cgacggattt cccgcggcca gcggtgcaaa gctttgacgg ccggaccgtg    3780 aagtttata tcgggaaaga gcggacggag aagctgaaag agctggcgtc acggacggga     3840
acgaccctgt acatggtgct gctgtcggct tataccatcc ttatgcataa atattcgggt    3900
caggaagatc tgatcgtcgg aacgccaatt gccggaagaa cgcaggatga agtgcagccg    3960
atcgtaggga tgtttatcaa cacgctgacc attcgcagcc gtccggagcg ttccaagcca    4020
tacctttcgt acctggaaga aatcaaggac atcacgctcg gggctttcga acaccaaaat    4080
tatttgttcg aagacttggt ggaaagtctt cacattccgc gcgcgaccgg ccggaatccg    4140
ctctttgata cgttcttctc cctgcaaaat acggagaacg agcaaattgt cattgagggg    4200
ctggagcaat cgttttatcc gctggaaaac cgaacatcca agttcgagct gctcctggac    4260
atttctgagc aggacggtca gctcgaatgc cggttggagt acgaacggc tttgtataaa     4320 caggagaccg cggaacggtt cgccaaacat tatgacaagc tgttagaaac catcgcagca    4380
gcgccggacg gggatattgc ctcgctggaa atgctcacgg aggaggaaat ccgcgaacta    4440
gtacgtggtt tcaacgattc ggaggcggac tacccgcggc agcagacgat tcacggcttg    4500
ttcgaagagc aggcagagct ttacccggac aacgtggccg ccgtcatgaa cgagcggcag    4560
ctgacctacc gcgagctgaa cgagcgatcc aaccgccttg cgcggaagct gcgggagacg    4620
ggagtagaag cggatcaact ggtagcgatt ctggccgaac gctcgctcga tatggttgtc    4680
ggcattctgg cgattcttaa agcgggcgga gcctacgtgc ctgtcgatcc cgactacccg    4740
gaggagcgta tccgcttcat gatcgaggat tcgggcgcgc cgttattgct gattcaaaag    4800
catttgcacg agaagaccga cttcgcagga acacgcctcg aattggatga tttcgtttgg    4860
ggcgacagag gtgcggactc cgaaggtgcg ctggatgctt cgaatctgga tccgatttcc    4920
gggccgggca acctagccta tgtcatctac acatcgggaa cgaccggcag accgaaagga    4980
actttgatcg agcataagaa cgtcgtgcgc ctcctgttca cgacaagaa tctgttcgac     5040 ttcgggccgt ccgacacgtg gacgctgttc cactcgttct gcttcgattt ctccgtctgg    5100
gaaatgtacg gagcactgct gtacggaggc aagctggtca tcgtaccgcc gctcatggcg    5160
aaaaatccgg ccgatttcct agcgctgctg ggccgcgaac agatcacgat tttgaaccag    5220
acgccaacgt acttctacca gctgctgcgt gaggtcttgg cggaccatcc gtacgatctg    5280
cggattcgca acgtcatctt cggggggcgaa gcactgagtc cgctgctgct caagggcttc    5340
aagacgaagt acccggagac gaagctgatc aatatgtacg gcattaccga gacgacggtt    5400
cacgttacgt ataaggaaat cacgtgggtc gaaatggagg cggcgaagag caatatcggc    5460
aagccgatcc cgacgctgag ggtgtacgtc cttgatgaaa ccgccgccc tgtgccgatc     5520
```

```
ggcgtagcgg gcgaaatgta tgtggccggg aaggccttg cgagaggata cctgaaccgt    5580
ccggatctga cggcggagaa gtttgtcgat tccccgtttg cggaggggga gaaactgtac    5640
cgctcgggcg acttggcggc ttggcagccg gacggcaaca tcgaatacct gggccggatc    5700
gaccaccagg taaaaatccg cgggtaccgg atcgagctgg atgaaatcga gacgcagctt    5760
ctgaacgttg agggcgtgga agaagcggtg gtgcttgctc gtcaggacgg tggggcgag     5820
aaggcgcttg tcgcctactt tgtggcgaac cggacactga cggtcagtga aatgagaacc    5880
tcactggcca aggaaatgcc ggggtacatg atcccgtcgt acttcgtgca gctggagcgt    5940
atgccgctga cgtccaacgg caaagtggat cgcaaagccc tgccggagcc gcaaggcggc    6000
ttgcaaacgg gcgtcgaata tgtagcgccg cgtaaccgga cggagtccca gcttgtgaag    6060
atctgggagg aagtgctggg ttactccggc attggagtca tggacaattt cttcgagctt    6120
ggaggccact ccttgcgggc gacgaacctt gtcagcaaga ttcggaagga aatgaacgtc    6180
gaatttccgc tgcgcgatgt gttccgctat atgacggtag agtcgatggc cggggctatt    6240
gccagcttgg aggaaacgcg gcatagctcg attccgaaag cggaagagag agcgtactat    6300
ccggtttcct ccgcacaaaa aaggttgtac gtcctgaacc agctggatgg ctcggagctg    6360
aattacaacc tcccaagcgc cttgcaattg aaagggcgtt tgaacgaggc caaagtggaa    6420
aaggcgctga ctactttggt ggcccggcac gatatgctgc gcaccggttt tgaaatcgta    6480
gatgggagc cggtacagcg tattcatccg ctcgcagctt tcaaggtcga aagcttcaa     6540
gcaagtgaag atcaggttgc ggccattctt gaaggcttca ttcagccttt tgacttgacc    6600
cagccgcctt tgctgcgtgc cctgctgatc gaactggaga aagagaaatt cctgcttgcg    6660
ctggatattc atcatattgg ttccgacggc ctctccatgg acgtgctgct gcgcgaattc    6720
gtgcggcttt acaatgggga agaattgccg gtgctacgga ttcaatacaa ggattacgcc    6780
gtttggcagc aatccgagga acagcgccag cgtatcaaac agcaggagga atactggcgt    6840
ggggtattca actctgagct tccggttctt gagctgcctc tcgacttctc ccgtccggcc    6900
gtccagcagt ttgacggtcg aacgctcacg tttacgctgg atgcggagaa aagcgaagct    6960
ctcaaacggt tgccggcga ttcggagcg acgctttaca tgcttttgct ggctgcgtac     7020
tccgtattgc ttcataaata tgcgggacag gaagatatcg tggtcggaac tccgattgcc    7080
gcccgatctc acactgactt acagccgatt atcggcatgt tcgtcaatac gcttgccctt    7140
cgcttgggac cggcggcgga gcggacgttc ctggattact tacaggaagt gaaggaaacg    7200
acgctaggag cctacgagca ccaggactat ccgtttgagg agctggtgga agctcttcag    7260
gtgagccggg atttaagccg gaatccgctg tttgacacca tgttttcttt gcaaaagcac    7320
gaaagcttgg atttaaccct ggaaggcttg caatggtcgc tgttcgacat cgaggaaaag    7380
acggcaaagt ttgatcttag ctttgatatc gtggaagccg ataacgagtt ggtttgcaag    7440
atcgagtacg ctacctcgtt gtttagacag gaaacgatgg tacggctggc gggtcattac    7500
gagcagcttt tggcgtcgat cctggctcag ccgggtgcgc ggatttcgga tttggacata    7560
ttgacggaca gcgaaaagca tgatttgctg gtcgggtttg acgtgtcgtc ttcggctctt    7620
gcgaagcaat ccgccgcaga gggtacaggt ttggaagcgg atgaatcgtg gagagagagg    7680
acgttccacg agctgttcga ggagcaggcg gagcgcactc ctggagcgct ggctgttatc    7740
tacgaagaca gcaagctgac gtatgcggag ctgaacgcca aagcgaatcg tctggcgtat    7800
gcactgcggg cgcgcggggt gaagccgag caggtggtcg gcattctggc cggccgttcg    7860
gcggagctgt tgatcggggt gctcgccgta tggaaagcgg gtggcgctta tgtgccgctt    7920
```

```
gatccggact atccggcgga gcggatcgag tatatgctca cggacagcgg ggcgtcggtt    7980
ctgctcacgc agacccgcct gctggagcag gcggaagttt ggcgcagcga cggagctcta    8040
gcgttgcaaa cggtgcttgc acttgacgac gctgcgacgt acagtctcgg agcggcagaa    8100
gtggctgtgg gcgtacaagc tttgggcgaa gcaggcgcag aggcggaggc tttggcgcaa    8160
gcgcaaacgg ctgctgccga gacgtccgcc acggcagaag ccgagcagaa cgtactggcg    8220
gcggatctcg catcgaatcc ggcgaatgtg aacaagccgc gcgatttggc ttacgtcatc    8280
tacacctccg gtacgactgg ccgtccgaag ggtgtggcgg tggaacaccg cagcctggtg    8340
aacacggcgc cgggctatcg gcgggactac cgcctggatc agttcccgat ccggctgctg    8400
caactcgcca gcttctcgtt tgacgtgttc gtcggcgaca ttgcgcggac gctgtacaac    8460
ggcggcacca tggtcatcgt gccgaaggac gaccggattg atccaacccg cctatacggc    8520
tggattcgcg actacgccgt gacggtgttc gaatcgactc cggcgctgat cgtgccgttc    8580
atggagcatg tgtatgccga gggtctggat ctcagctcga tgcagttgct gctcacaagc    8640
tcggatgcgt gcagcgtagc ggattaccgc accttgcagg agcgcttcgg ctcgcagttc    8700
cgtattatta acagctacgg cgtcacgaaa gcggcgattg actccagctt ctatgacgag    8760
ccgctggaga agctgccgaa gacgggcagc gtgccgatcg ggaaagcgtg gctgaacgca    8820
aagttctaca tcgtggatgc gagtctgaag ccggtgccga tcggggtgtt gggcgagctg    8880
gttatcggcg gagcgggtgt ggcccgcggt tacttgaacc gcccggattt gacggcggag    8940
aaattcgtag acagcccgtt cactgcaggg gagcggctgt accggacggg cgacctggcg    9000
cgctggatgc cggacggcaa cgttgacttc atcggccgga tcgacaacca ggtaaaaatt    9060
cgcggctatc ggatcgagct tggtgaaatt gaagcggcta tgaaaaattt tgccggcgtt    9120
cgtcaagcgc ttgtcatcga ccggacggac gagcggggc agaaatattt gtgcgggtat    9180
gtcgtagcgg attccagctt cgatctggaa gggcttgtgg cccatctgga cgctgcactg    9240
ccttcccata tggtgccttc gcgtatcatg cgcctggatc aaatgccgct tacgccgaac    9300
gggaagatcg accgtaaagg gctgcctgtg ccggaaggaa gcattcgtgc cgaggctgca    9360
tacacggcgc ctcgtactcc tgctgagcaa gcacttgcgt tggtctggca gtcagtgctg    9420
ggcgtggatc aggtcggcac gatgacaat ttctttgcgc tcggcggcga ttcgatcaag    9480
gccttgcagg tatcgtcccg tcttttgcaa acggggtaca agctgatcat gaaagatttg    9540
ttccattacc cgacgatttc cgcccttagt ttgcagctgc aaacggcgga gagaacggca    9600
agccaggccg aagtgacggg ggaggtcatc ttgaccccga ttcagcgctg gttctttgaa    9660
caaaatccgg ccgacgtgca tcacagcaac caggcattca tgcagttctc caagctaggc    9720
ttcgacgaag aagcttttacg ccaagcggtg cgtcaacttg tcgtgcatca cgatgctctc    9780
cgtacggttt accgccaaac cgaaaacagc tataccgcct ggaaccgcgg cgccggggag    9840
aacgaagcac tgttcgatct ggaagttgta gatttcaggg gagtctgcga cgtgaaaggc    9900
gcggtagagg ctaaggcgaa tgatattcaa gcgagcatcg atctggaaaa cggcccgctg    9960
gtgaagctcg gcttgttccg ctgcgacgac ggcgaccacc tgctcatcgc gatccatcac   10020
ttggtcgtag acgcgtatc atggcggatt ctgcttgaag attttgctgc cggatatgag   10080
caggtgctgc aagggcagcc gatccgtctg ccgctcaaaa cggattcatt ccaaacgtgg   10140
gcgaaacagc tcgctgatta tgcgaacgat ccggcgatgg aaagcgaaag agagtattgg   10200
cagcatatcg agcaattgag ctatgagccg cttccaaaag atttttgaaca aggcagatcc   10260
```

```
acgctgaagg acagcggtct cgtgaccgtt cgctggacag cggaggaaac cgaacagctg    10320
ctgaagcacg cacaccgtgc ttaccgtacg gaaatgaacg atttgctgct tgccgcgctt    10380
ggcctcgcgg tacaagcttg gagcggccgg ggacgcgtgc tggtgaatct cgaaggccac    10440
ggccgggaag atattttgcc ggatgtggac attacacgca cggtaggctg gtttacaagc    10500
caattccctg tcgttctgga gccgggtcac gcccaggagc tcggtcatca gctgaaacag    10560
gttaaagaaa gcttgcgccg cattccgaac aaaggaatca gctatggcat cctgcgctat    10620
ttgtcggcgc cgcgtgacgg cgagtgcttc gctttggagc cggagatcag ctttaactat    10680
ttgggtcagt tcgaccagga ttacgaaagc agcggctcgc agccgtctcc gttcagcccg    10740
ggctccgact caagcccgaa cgcagtgatg gattttgtcc tagatatcaa cggtatggtg    10800
tcggaaggag tgctggaact cacgatccgt tatggggaaa cccagtataa acgggaaacg    10860
gtagagcgcc tgggcaccct gcttcaattg agcttgcgtg aagtcatcaa ccattgcgta    10920
tcgaaagagc ggccggagct tacgcctagc gacgtactgc ttcaagatgt gacggtggag    10980
gaactggagc ggttggctga acatacggcg gcgctcggcg aactggagaa tgtatacacc    11040
ctgactccgc tgcaaaaagg gatgttgttc cacagcctgc tggatgccga ttcggaagct    11100
tacttcgaac aggtgacctt cgatctgaac ggaagcctga atgtcgaagc cttcacccaa    11160
ggattggata cgctggtgca gcggaatgag gcactgcgga ccaactttat taccggctgg    11220
agggacgagc cgattcaagt ggtattccgc gagcggaagt gtgaagtgta cttcgaagat    11280
attcgctcgg caagcgatga agacccggag aagacgatag ccgatttcgt cagcgcggat    11340
aaagcgaaca agttcgattt ggctcaaggc tctcttatgc gcgtgaccgt tttgcgcacg    11400
ggcgacgagt cttaccatgt gatctggagt caccatcaca ttttgatgga cggctggtgc    11460
atgtccttca tgatcaagga agtgttcgac acctacttcg cgttccaaga gaagcggacg    11520
ctggagcttc ctccggttac ctcgtactcc cggtatatcg aatggctgga agctcaagat    11580
gccgcgaaag cttcgcgtta ctggtccgaa tatttggcgg gttacgatca gcagaccaag    11640
ctgccccagg agaaaacgca gctgaagcag gcgcttttg aagcggctga atcgatgtg     11700 gaactcagca aggaactgac cgggcaaatc gagcgggtgg cgcgccagca gcaggtgacg    11760
ctcaatacgt tcatgcagac cgtatgggga ctggttctgc agatatacaa caacagcgag    11820
gatgtcgtat tcggctccgt cgtatccggg cgtccggcgg aaattccggg catcgaaagc    11880
atgatcggcc tgtttattaa tacgatcccg gttcgtattc aaggcaaagc cgaggagacg    11940
gtagccgata tcttgagaaa aacccaggat caagcactgg catcgggagc ttacgaaacg    12000
ttcccgctgt tcgaaattca gtcgctgagc gagcaaaagc gcgacttgat caaccatatt    12060
atggtttttg aaaattatcc gatggaagaa cagattgagc aggtcgtcgg cggtgacaaa    12120
gaagcgctga aaatcgctaa tatccagtcg ccagagcaaa cgaactacga cctggacatt    12180
accgtcattc cggaagagcc tattttgctg cggtttacgt acaatgcgct gacgtacaga    12240
gaggaagaca tcaggctgat ccacggtcat tttgcccagg cactggagaa ggttgcggct    12300
aacccgaata tccgcgtgaa tcagttggag cttttgacgg cggcggaaaa agaccaaatt    12360
ctcggtgcgt ttaacccggc gcagccgaaa gcggctcctg cggccgcgtt ccaccggctg    12420
ttcgaggaac aggcggaacg cacgccggaa gaggcggccg tcgtgtatga aatgaccgg     12480 ctgacgtatg cggagctgaa cgagcgggcg aaccgcttgg cggccacgct gcgcgcaagc    12540
ggcatcggcc gggagacgat cgtcggcatt ctcgccgagc gttcggtgga cttgctggtg    12600
gccgtgctgg ccgtctggaa agcgggcggg gcatatgtgc cgctcgaccc ggattatccg    12660
```

```
gcagaccgcg tgcggttcat gcttgaagac agtggagcga aggtactgtt gacgcaaata   12720
ccgctgcgag aacgcgccga agcctggctc ggcgaagagg agctggcgct ggcagcggtg   12780
ctgtacctcg acgacgaagc gtcgtacagc gaggagcggg cgaatgcgcc gattggttcc   12840
ggcatggtct ccggccagct gacggatgct gtggatgacg cgatgagac ccatccgaat    12900 attggcatgg gcagcttcca tgaagctcgt ccggaggatc tggcgtatgt gatctatacg   12960
tcgggaacga cgggcaagcc gaaaggcgtg atgatcgagc accgcagcct ggtgaacacg   13020
gcagcgggct accggcggga ataccggttg gatcagttcc cggtacggct gctgcagctc   13080
gcaagcttct cgttcgacgt gttcgtggga gatatcgcgc ggacgctgta taacggaggc   13140
acgatggtga ttgtgccgaa ggacgatcgg atcgatccgt ctcgtctgca ccactggatg   13200
gagcgggagc gggtcaccat tttcgaatca acgccggcgc tgatcgtgcc gttcttagag   13260
tacgtgcacg agcaggggct ggatatgagc tggatggagc tgttgatcac gagttcggac   13320
agctgcagcg tggcggatta ccggaccttg caggaacgct tcggctcgtt attccggatc   13380
atcaacgcat acggcgtgac ggaagcggcg atcgactcca gcttctacga cgaggagctg   13440
acgaagctgc cgcagacagg acatgtgccg atcggtaaag cgtggctgaa tgcgaaattc   13500
tacatcgtgg acgcgcatct gaacccggtg ccggtcgggg tgctgggcga gctggtcatt   13560
ggcggagtcg gggtagcacg cgggtacttg aaccgtccgg agctgacgga agagaagttc   13620
gtagacagtc cgttcgccgc gggcgagcgg ctgtaccgca cgggagactt ggcgcggtgg   13680
atggaggacg ggaacgtgga cttcatcggc cggatcgaca accaggcgaa aatccggggc   13740
taccggattg agacgggcga agtcgaagcg aagatgctga gtgtaggtgg tgtgaaggaa   13800
gcggtcgttg tcgtcaggga agatcaagaa ggtcagaaag ctttgtgcgc ttattataca   13860
gtggaagaag gcatgacggc ggcagacctg aagcgtgcga tttccagcga gctgccgggg   13920
tacatgatcc cgtcgtattt cgtggagctg gagcgtctgc ctttgacgcc gaacggaaag   13980
atcgaccgga aggcgctgcc ggcaccggaa ggggcagcag gcggaggccg cgaatacgtg   14040
gcgccacgca ccgaactgga ggcgaagctg gccgccattt ggcaggaggt gcttgttagg   14100
gagaaggcag taggtgtaac ggacaacttc tttgacctcg gcggacactc cctgcgggct   14160
acgacgcttg tcagcaaaat gcataaggag ctaggcattg aattcccgct acgcgacgta   14220
ttccgctact cgacggttga ggaaatggcc gcggctatgg agtggctgga gatcggctcg   14280
ttcatagcta ttccggctgc ggaacctagc gagtattatc cgctatcatc cgctcagaaa   14340
cgtctctata tcttgaacca gctggaagga ggcgagctga gctacaacat accgggagca   14400
atgctgctcg aaggggagct cgaccggcag cggtttgaag aagcgttccg cgggctcgta   14460
gctcgtcatg aaaacgctgcg taccggattt gagatggtaa aaggcgaagc ggttcaacgg   14520
atttatgaag aagctgcttt ccaggtggaa tatgtgcaga ttagcgggga acgggtggaa   14580
gaaacggtgc gccaattcgt tcgtccattt gatctggcga agccgccact tctgcgtgta   14640
ggccttgccg aactggcgcc ggaccggcac attctgatgt tcgatacgca tcatatcgta   14700
tctgacggcg tttcgatgga cgtactgatt gaagagttcg tccgcttgta cagcggggag   14760
ccgttggagc cgctacgcat tcagtacaaa gattatgcgt tatggcagca atcggacgag   14820
cagaaagctc agcttgccaa gcaggaagcc tactggctcg acatgttccg cggagaactg   14880
ccggttttgg aattgccaac ggactaccca cgcccagcta tgcagagcta cgagggtcgc   14940
acactgcaat tgtttatgaa tagggagaaa agcgagggtc tgaaacggct tgcagccgag   15000
```

```
aacggcgcaa cgctttacat ggttctgctt gctggttata caatattatt gcataaatat   15060
actagtcaag aagacgtagt ggtcggtacg ccgattgcgg gaagaaatca cagtgacgtt   15120
cagccgctga tcggaatgtt cgtcaatact ctggccatcc gcagttatcc gactgcgggt   15180
aagacgttcc ttgactactt gaaggaaatc aaggagacga cgctgggtgc ttttgaacat   15240
cagaattatc cgtttgagga actggtggat aaggtgaacg tagctcgtga tttaagccgc   15300
aatccgctgt tcgatacgat gtttgctttg cagaatacag agaatttgga aatccagctt   15360
cccggactcc atttgtcgac gtatgccagc gaagaaattg tttctaaatt cgatctcagc   15420
ttggacgtca cggagatcga ggaaggcttg gaatatctgt ttgaatacgc cactgctctt   15480
tataaaaccg aaacggtgga gaaattggcc gctcactact tgcagctgct tgaatctatt   15540
ctctgcaacc cttctgcgac tattgccgag ctgggcattt tgacaccagc ggaaaaagaa   15600
caaattctcg gcgcgttcaa cccggcgcag ccggaagcgg ctcctgcggc ggcgttccac   15660
cggctgttcg aggaacaggc ggagcgcacg ccggaagcgg aggctgtcgt gtacgagaac   15720
gaccggctga tttatgcgga gctgaacgag cgggcgaacc gcttggcggc tacgctgcgc   15780
gcaagcggca tcggccggga gtcgatcgtc ggcattctcg ccgagcgttc ggtggacttg   15840
ctggtggccg tgctggccgt ctggaaagcg gcgggggcgt atgtgccgct cgacccggat   15900
tatccggcgg accgcgtgcg gttcatgctt gaagacagcg gagcgaaggt tctgctgacg   15960
caaaaggtgc tgcgagagcg cgccgaagcc tggctcggcg aagaggagct gacgctggca   16020
gcggtgctgt acctcgacga cgaagcgtcg tacagcgagg tgcgggcgaa tgcgccgatt   16080
ggctccggca tggtctccgg caagctgatg gatgctgtga atgacggcga tgggacccat   16140
ccgaatgttg acatgggcag cttccatgaa gcccgtccgg aggatctggc gtacgtgatc   16200
tatacgtcgg gaacgacggg caagccgaag ggcgtgatga tcgagcaccg cagcctggtg   16260
aacacggcag cgggctaccg gcgggaatac cggttggatc agttcccggt gcggctgctg   16320
cagctcgcaa gcttctcgtt cgacgtattc gtgggcgata tcgcgcggac gctgtataac   16380
ggaggcacga tggtgattgt gacgaaggac gaccggatcg atccgtctcg tctgcaccac   16440
tggatggagc gggagcgggt caccatcttc gaatcgacgc cggcgctaat cgtgccgttc   16500
ctggagtacg tgcacgagca ggggctggat atgagctgga tggagctgtt gatcacgagt   16560
tcggacagct gcagcgtggc ggattaccgg accttgcagg aacgcttcgg ctcgttgttc   16620
cggatcatca atgcttatgg cgtgacggaa gcggcgatcg actccagctt ctacgacgag   16680
gagctgacga agctgccaca gacaggccat gtgccgatcg gcaaagcgtg gctgaatgcg   16740
aaattctaca tcgtggacgc gcatctgaac ccggtgccgg tcggggtgct gggcgagctg   16800
gtcatcggcg gagtcggagt ggcgcgaggg tacttgaacc gtccggagct gacggaagag   16860
aagttcgtag acagtccgtt cgccgcgggc gagcgactgt accgcacggg agacttggcg   16920
cggtggatgg aggacgggaa cgtggacttc atcggccgga tcgacaacca ggcgaaaatc   16980
cgggggtacc ggattgagac gggcgaagtc gaagcgaagc tgctaagtgt ggaaggcgtg   17040
cgcgaagcgg tggtgctggt tcgaagtgac gcgaacgggc agaaagcgct gtgtgcgtac   17100
tacacaattg atggcgaatt tacagcggca gacctgaaac gggcgattgc cagcgagctg   17160
ccggggtaca tgatcccgtc gtacttcgtg gagctggagc gcctgcctct gacgccgaac   17220
gggaaaatcg accggaaggc gctgccggcg ccggaagggg gagcaaacgc aggccgcgaa   17280
tacgtggcgc cgcgcaccga actggaggcg aaactggtcg ccatctggca ggacgtgctc   17340
gggccggtca cgattggcgt aacggacaac ttcttcgacc tcggtgggca ctccctgcgg   17400
```

```
gcgacgacgc tggtcagcaa ggtgcacaag gagctgagcg tggacctgcc gttgcgcgat    17460
gtgttccggc actcgaccat cgaagcgatg gccgaagcga taagccaatt ggagcggcag    17520
gaacacctct ccattccggt tctggataag agggattact atccgctttc ctccgtgcag    17580
aaacggctgt atatccagca gcagatggaa ggcgccgagc ttagctacaa tatgtccggc    17640
atgacggttc tcgtcgggcg tttggaacgg aatcaattcg aggcggcgct caaaggattg    17700
atagctcgtc acgaaatttt gcgaaccggc ttcgaaatgg tcgacggcga accggtacaa    17760
cggatttatc cggacttgaa gtttgccgtc gagtatacga aagcgatgga aagtgaaacg    17820
aagagcatcg tagacggctt tgtacgcgtc tttgatttgg agcggccgcc gctgctgcgt    17880
gtgggcttag tcgaaatgga agcggaacgg catttgctca tgctggacat tcatcatatc    17940
gtcacggatg gcatgtcgat gggtatcttc gtcgaagagc tgctgcgcct gtataacggc    18000
gagaatctgg aaccacttcg gattcaatac aaggaattcg ccgcttggca gcagtccgaa    18060
cctgtaaaag agcggctgaa acgtcaggaa gcctactggc tggacgtgct ggaaggcgaa    18120
ctgccgacgc ttgaactgcc aacggacttt gtcagacctg ccgctcgcag ctttgaggga    18180
gatgtgctgc ctttcagcat cgacaagcag atgaccgaca gcttgcagcg catcgccgat    18240
gagaacggtg gcacccttta tggtgttta tcggcggtct attcaatcct gctcagcaag    18300
tactcgggac aagaagattt cattgtaggc acgccggttt caggccgcac acatgcagac    18360
ctggagccgc tcatcggaat gtttgtcaac actttggcga ttcgccatta tccgtccggg    18420
gagaagacgt tcctcgctta cttgaacgaa gtcaaagaaa cgatgctggg ggcctacgat    18480
caccaggatt atccgttcga ggagcttgtg aaaaagctgc aggttccgcg agatctaagc    18540
cgcaatcctg tattcgatgt catgtttgct ctggaaacca aggaagataa cgttcaaaac    18600
ttcggggata tcaggatcga atcttatccg gaaactcata cggtttccca atttgatcta    18660
accttgatca tttcgttgct ggatgaggga atgaacgggc agtttgaata tgccaccaag    18720
ttgttcacac gcaatctgat cgacaatttc gctcaggacc tgctcgtaat catctctcaa    18780
atttgcgaac agccttcggt gctgctgaag atatttccc  tgaacgggca atccgaacag    18840
gagcaagatg tgctagaggc cattgatatt attttc                               18876
```

<210> SEQ ID NO 10
<211> LENGTH: 41169
<212> TYPE: DNA
<213> ORGANISM: Paenibacillus alvei

<400> SEQUENCE: 10

```
atgtttgaaa aggcggggag catggctgta gcgttgctgc ggcatatgct ccgccggatt      60
gcttttaccg atgtagagag ggggacgatc caggtggctt ttgaaaaaga aacgttgttt     120
tggaacgaaa aattcggtag tgacgattat accttgacgc ggctgcctta cagcaaagct     180
ccaagctccc aggcgcccat tatgacaacc gtcggcggtt cgctttcgga aaagcggcg     240 cagcgcgtcc ttcaaatgag caagggcgct ccgctggccg ctttatgat tttgctcgcc     300 ggtgttcagt cactcttgca taaatataca ggcgcttctg acattctggt cggcatgccg     360
gttatacgga aaccgacgga gacgcgccga tccgttaatc atacggtcat tttgaaaagc     420
ttgctttcgg cgggatcgac ttttaaaacg cttctgagcg agctgagaac ttcgttgccg     480
gaaacgattc agcatcaaca tattccgttc ttgaaaatga cggagaagct ggatctgcaa     540
tatgcagacg ggatacccat catccatacg ctagtatccc ttaaggagct gcatctggat     600
```

```
gaaattgggc aaaacgtggt cacgattgt tcctttgaat tcagcttaac cggcgggacg    660
atacagctag cgctctcata taacgagcac ttatatgact ccaagttcat gactcggatc    720
gtcggccatc tgaatcgcct gctggccgtg gggcttcacg agttggagct ggacatcgtg    780
cgggtggaca tgctgtcgga ggacgagaaa tttcaattgc tgcaaagctt taacgatacc    840
gagaaggact atcctcgaga tcggacgatt catcagctcg tggaggagca ggtgaagagg    900
gtgcccgaag caacgcgat tgtctttgag gggcggcggc tttcgtacgc tgagctgaac    960
gaacgggcga accggctggc gcggacgctg cgatcggtcg gcgtgctgcc caatcagctg   1020
gtaggcttga tggccaggag atcgctggag acggtcgttg gcattctggc ggttctgaaa   1080
gctggcggtg cctacgtgcc gatcgacccg gaatacccgg aagaacgcat ccgctacatt   1140
ctggagaact cgaacgcgca gctgctgctg actcaaagaa agctgcaaca gcaggtgccg   1200
ttcgaaggga ctgtgttggc gctggatgac gagcaggcct acagcgatga tggaacgaat   1260
ctggagccgg ccagcggttc gaatgatctg gcttatgtca tctatacgtc aggtacgacg   1320
ggcaaaccca aggggtcat gctggagcat cgcggtttgg tcagcttgaa actgatgttc   1380
gcggacaggc tcggcatcac ggagcatgac cggatcgttc aattcgccag cctgtcgttc   1440
gacgcgtcct gctgggaagt gttcaaagcg ctctattttg gcgcgacttt gtacataccg   1500
acggccgaga cgattctcga caaccgcctg tttgagagtt atatgaacga gcatgcgatt   1560
acggcggcga ttttgcctcc gacgtacagc gcttatttga acccgaccg ccttcccagc   1620
ttaacgaagc tcgtaacggg aggctcggcg gtatcggccg aattcgtgca gcagtggaaa   1680
ccgaaggtcc actatttcaa tgcttacggc cctaccgaag cttcgattgt tacgacgctt   1740
tgggatgcga atgaggagca gccagagcgc agagtcattc cgattgggcg cccgctggcc   1800
aatcaccgga tttttatttt ggatgcccac ctgcagcttg tgcctccggg agtggacggc   1860
gagctgtgcg tggcaggcgt ggggcttgcg agaggttacc tgaaccatcc ggagctgacg   1920
gcagaaaagt tcgtggaaca tccgttcgcg ccggggagaac gcctttatcg gacgggagat   1980
ctcgcccgat ggctgccgga cggaaatatt gagtacttgg gccggatcga ccatcaggtg   2040
aaaatccgtg gattccggat cgagatcggc gagattgaag agcagcttct gaagatcgac   2100
tccgtgcagg agacgatggt aatcgcgcgg gaaggcaaaa gcgggcaaga attgtgcgct   2160
tatctggtcg cggaccgccc gcttacgctc ggcgagctga aagcgcgct ggcgcaaaaa   2220
ttgccgaatt acatgattcc ggcgcatttt gttcagcttc cgcgaatgcc gctcacgccg   2280
aacgacaaaa tcgaccgcaa ggctttgccc gccccggaag gaaacgcgct gaccggcggc   2340
ttgtacgtag ctccccgcaa tgaagccgag cggacacttg tcgatgtgtg gcaggcggta   2400
ttgaacgccg atcgtgttgg ggtaacggat catttcttcg agctgggtgg agactcgatc   2460
aagtccattc aagtatcttc gcggcttcat caagccgggt acaagctgga tattcgggat   2520
ttgttcaaat atccgactat ctcacagctc agcctgcgtg tgaaaccgat cggacgtacc   2580
atcgatcaag gcgaaataac gggcgaaacg gcgctgacgc cgattcagca ttggtttttc   2640
gagagctcct ttgcggatcc gcatcatttc aaccagtcgg tgatgctgta ccggaaggaa   2700
cgcttcgacg aagagacggt gcgtcaggta ctgcaaaagc tggccgagca tcatgacgcc   2760
ttgcggatgg tgttccgcaa aacggaacaa gggtttagcg aaaggaaccg cgcgattcag   2820
gaaggcgggc tgttcacgct ggacgtgttc gacttcaagg atgcggagga taccgcacag   2880
gctctggaag cgaaggcaac ggatattcaa gcgggcatcg atctggagaa agggccctc   2940
gtgaaggcgg gactgttccg atgcgcggac ggcgatcatt tactgctcgc ggttcatcat   3000
```

```
gccgtggtgg acggcgtgtc ttggcgcatt ttgatggagg atttcgctct gggttacgag    3060
caggccggca aaagcgagga aattcgtttc ccggcgaaaa cggatgcgta ccgcacttgg    3120
tccgagcagc tggccgctta cgcgcaaagc ccggagatag caaaggaacg ggcttattgg    3180
caggccgtgg aacaaattgc ggttccggcc ttgccgaagg atctggaggc ggacgttacg    3240
acgcagcagg acagcgaatc gctgttcgtc cgtttgactt ccgaagaaac ggagctgctg    3300
ctgaagcggg tacaccgggc ctacaacacc gaaatgaacg atattttggt aacggcgctc    3360
ggcatagctg ttcgcaagtg gacgggacac gaacgggtgc ggatcaatct cgaaggacac    3420
ggacgcgaat cgatcggaac ggatatcgac atcacgcgca cagtcggctg gtttacgacc    3480
aagtttccgg tcgtcctgga gccggaaacc aaccgggatt tggcctatca gattaaacag    3540
gtcaaggaaa gcttgcgtcg cattccgaac aaggggcttg ggtacggtgt atgccgctat    3600
ctctccaaat cggaggatgg ctttgtttgg ggcgcagagc cggaaattaa tttaactac     3660 ctcggccagt tcgacgatga tgtcaaccag gacgagatcg gcatatcttc ttattccagc    3720
ggcagcccgg ccagcgaccg gcaggcccgc agctttgtgc tggatatcaa cggcatggtg    3780
ctggacggcg ctctatcgct cgatctcagc tacagccgga agcagtatcg caaggtaacg    3840
atggaagcct tcgctcagcg gcttgagcaa agtctccgag agctcattac ccactgcgca    3900
ggcaaagaaa acaccgaatt gacgcctagc gacgtgcaat ttaaaggctt gaccatcgcg    3960
gaattggagc aaatcggcca gcgctcggtc catgtcgggg aaatcgagaa tatttactcg    4020
cttacgccga tgcagaaggg catgtggttc cacagcgcgc ttgaccggca gacggccgct    4080
tacttcgagc agacgcggtt tacgatgcgg ggagcgctcg acgttcagct tttcgagagg    4140
agctggacgg agcttgcgaa acgtcatctg gtgctgcggg cgaattttgt gaaaggacca    4200
gcgggcgagc cgctgcagat catataccgc gacaaaccag tcggctttga atatgaagag    4260
ctgctacatt tgcaggcgga cgagaaacaa gcgtatttgg ataaaaaggc cgaggatgac    4320
aagcttcgcg gcttcgacct ggaacatgac gcgctcgttc gggttacgat cctgcgcacc    4380
gaagagcaga gctatcatgt gctgtggagt ttccagcata ttttgatgga cggctggtgc    4440
ctgccgcaac tgacgcagga gctgtttgag acatactcgg ccttggcatc cggcaagcag    4500
ccagcgggag ataaggggtc ggattatggc gcttatatcg aatggctgga gaaacaggac    4560
gatcaggcgg catccggcta ttggacgcgg ttcctggcag gttacgaagg gcaaactgta    4620
ctcccggggc aaaaggaagc gcagccgaac ggtagattta cggctgatca cgtcaccgcc    4680
gagctgggca aggacttgag cgagcggatg gatcgggtgg cgaaacagcg cctggttaca    4740
gtcaatacgc tgctgcaagc cgcttggggc gtgatgctgc aaaaatataa cggaacaaac    4800
gatgccgtat tcggcagcgt cgtggccgga agaccggcgg aaatcccggg tatagagtcc    4860
atgattggac tgtttatcaa tacggtgccg gttcgcgtca cgagcgaagc ggacaccgtg    4920
ttcgctgacc tgatggcaaa gctccaagag cgggcgctgg agtccgggcg ttatgattac    4980
tatccgctgt atgaaattca agcccgctgc gtgcaaaagc aaaacctgat caaccatatc    5040
atcgctttcg agaactatcc ggtggatgag cagatggagc aggcgggcga ccagcagcac    5100
ggcgacctga cgatcactga cgttcagatg gaggagcaga cgaactataa cttcaatgtg    5160
accgtggtgc caggagccga gatcgaaatt cggttcgatt ttaacgccga agtgtttgat    5220
aaagacagca tcgaacggct caaggggcat ctcgtccatc tgctgagcag ggtgacggat    5280 aaccccggaaa ttaccgtggg agagctggaa cttgtgacgg aggcggaaaa ggccgacctt    5340
```

```
ctcggacgat ttaacgacac caccacggaa tttccgcgcg ggaagacgct cattcaattg    5400
ttcgaagagc aggtagagcg catcccggat gcagccgcca tcaccttgaa tgagcaagag    5460
ctgacctacc gcgagctcaa cgaacgtgtc aaccgccttg cccgtacctt gcgtagccac    5520
gggatatcca aaggtcgtct ggtcgccatt ttggctgagc gttccattga atggtggtg    5580
ggcatgctgg cggcacacaa agccggagcg gcttacgtac cgattgaccc agaatatccc    5640
gaggagcgta tccgtttctt gatcgaggat tcgggagggc aggtcatgct gacgcaaagc    5700
cgcttgcgcg agcgcctggc gggttcggac cccgtgatct tactgatga cgagtccttc    5760
tatcacgagg acggcacaaa tctaaatacg ggcatcgaag cgacagatct ggcctgcgtc    5820
atctatacgt caggcacgac gggcaagccg aaaggcaacc ctgtttcgca ccgcaacatc    5880
gtgcgggtcg tgcaaaatac gaattatatc gacatcaccg agcgggatca tgtcctccag    5940
ctttcgagct attcgttcga cggagcgact ttcgatattt tcggcgcttt gaccaacggg    6000
gcgcggctgg tgctggttcc ctacgagact ttgctggaaa tcggccggct ggcggatctc    6060
atccagcgcg agcgcatctc ggtcatgttt attacgacgg ctttcttcaa catccttgta    6120
gatgtgaacg tcgactgcct gcgggatgtc agggcgattt tgttcggagg agagcgtgtg    6180
tcggtcggcc atgtgcgcaa agcgctcgcc catatcggac cgggcaggct caaccatgtg    6240
tacggcccga cggaaagcac ggtttatacc acgtaccttc cggtcgactt cgtcgatgag    6300
ttggcggtta ccgtacccat tggacggccg atcagcaata cgacggtgta tatcgtcgac    6360
agccggaaca aacttctgcc gatcggcgtg gccggggaac tttgcgtcgg cggagaaggc    6420
ttggtaaggg gctacaataa ccggccggag ctgacggcgg agaaatttgt ggacaatccg    6480
tttgtgccgg gagagcgcat gtaccggacg ggggatttgg cgaaatggct gccggacggc    6540
acgatcgaat acgtgggacg gacgacgac caagtgaaaa tccgcggctt ccgaattgag    6600
ctaggcgaga tcgaagctca gcttcagaaa gtggagggaa ttcggaaaac gacggtattc    6660
gcgagggaaa acgcctccgg cgagaagcag ctttgcgcct attatgaagc ggactgcgag    6720
cttccggcgg ccgaactgaa gagcgtgctt tccaaggaac tgccggccta tatgatcccg    6780
gcgtacctga tccagttgga gcggctcccg ctgacgacga acggcaaggt cgaccgccga    6840
tcactcccgg cgccggagga gagcttgcag ccgggcggag gaagtactcc gcctcggact    6900
ccgctggaag ccagcttggc cggaatttgg aaaagcgtgc tcggactagt gcacattggc    6960
gttcatgaca acttcttcga catgggcgga cattccctgc gggcgacgac actggtgagc    7020
aaggtgcatc aggagctgaa cgtcgaactg cctctgcgcg acgtattccg ctactcgacg    7080
atcgaggaga tggctctcgc catctcccgg atcggagagc agtcgttctc gtcgattccg    7140
ctggcaggcg caagagcata ttatccgctt tcctcagctc agaagcggct gtttatcctg    7200
aatcagctgg aaggggccga tcagagctac aacatgccgg gcgtgctgct gttggaagga    7260
tcgattgacc ggagcctgct ggagaaggct ttccgcggac tgatcgcacg gcacgaaacg    7320
ctgcgaaccg gctttgagat cgtacaaggc gaagcagtac agcgcattta cgagagcgtc    7380
gactttgccg tcgagtaccg tcatgcgagc gaggaagaaa cgcctgaagt cgtgcaggcc    7440
ttcatccggc ctttcgactt ggcaaagcct ccgctgctgc gggcggagct cgtagagctg    7500
gcaatcgaac gttatttgct gatgttcgac atgcaccata tcgtctccga cggggtttcg    7560
atggacgtgt tagtcgagga actcgttcgt ctgtacggcg gcgagtcatt agagcctttg    7620
cgcattcaat acaaggacta tgcggtatgg cagcagtcgg acgagcaaaa agtgcagttg    7680
aaacgcgagg aagcttactg gttggaccgt taccggggcg agctgccggt tctggaaatg    7740
```

```
ccgacggact atccgcgtcc tgccgtgcag agctttgagg gacaaacgct gacgtccttc    7800
gtggacgagg caacgaacga aggcttaaag caactggccg ctcaaaaagg aacgacgctg    7860
tatatggtac tgcttgcggc atataccgtg cttttgcata aatacacagg tcaggacgat    7920
ttgatcgtcg gaacgtcgat tgcgggcaga acgcacggag acacgcagcc tttgatcgga    7980
atgttcgtca atacgctggc actccgcaat tatccggctt cggagaagag cttcctgtcg    8040
tatcttgaag aagtgaaaga aacgacctta ggcgcttacg agcatcagaa ttatccgttc    8100
gaagagctcg ttgataaagt gcaggtcagc cgggatttga gccgcaaccc gctgtttgac    8160
acgatgttct ccctgcaaaa cttggaggat aaagagttta agctggaagg gctgaaattg    8220
tccccgtacc ctagtgaata cggcacggcc aagttcgatc tgagtgtgga tgttacggaa    8280
gaaaacggcg gcttggagtg catctttgaa ttcgcaacgg ctctttataa agaaagcacg    8340
atccggcggc tgtcgactca ttttggacat ttgcttgcgg cgatcgtaag tcgtccggat    8400
gcgaagatcg ccgagctgaa cttgttgacg gcagaggaaa atgagcaaat tctcggcgcg    8460
ttcaacccgg cgcagccgga agcggctcct gcggccgcgt tccaccggct gttcgaagaa    8520
caggcggagc gcacgccgga agcggaggcc gtcgtgtacg agaacgaccg gctgacgtat    8580
gcggagctga acgagcgggc gaaccgcttg gcggctacgc tgcgcgcaag cggcatcggc    8640
cgggagtcga tcgtcggcat tctctccgag cgttcggtgg acttgctggt ggccgtgctg    8700
gccgtctgga aagcgggcgg ggcgtatgtg ccgctcgacc cggattatcc ggcggaccgc    8760
gtgcggttca tgcttgaaga cagtggacgg aaggtgctgc tgacgcaaac ggtgctgcga    8820
gagcgcgccg aagcctggct cggcgaagag gagctggcgc tggcagcggt gctgtacctg    8880
gacgacgaag cgtcgtacag cgaggagcgg gcgaatgcgc cgattggttc cggcatggtc    8940
tccggcaagc tgacggatgc tgtggacgac ggcgatgtga gccatcagaa ggtcggcatg    9000
ggcagcttcc atgaagcccg tccggaggat ctggcgtacg tgatctatac gtcgggaacg    9060
acgggcaagc cgaagggcgt aatgatcgag caccgcagcc tggtgaacac ggcggcgggc    9120
tatcggcggg aataccggtt ggatcagttc ccggtgcggc tgctgcagct cgcaagcttc    9180
tcgttcgacg tattcgtggg cgatatcgcg cggacgctgt ataacggagg cacgatggtg    9240
attgtgccga aggacgaccg gatcgatccg tctcgtctgc accactggat ggagcgggag    9300
cgggtcacca tcttcgaatc gacgccgcg ctgatcgtgc cgttcctgga gtacgtgcac    9360
gagcaggggc tggatatgag ctggatggag ctgttgatca cgagttcgga cagctgcagc    9420
gtggcggatt accggatctt gcaggaacgt ttcggctcgt tcttccggat catcaacgca    9480
tacggcgtga cggaagcggc gatcgactcc agcttctacg acgaggagct gacgaagctg    9540
ccgcagatag gccatgtacc gattggaaaa gcgtggctga atgcgaaatt ctacatcgtg    9600
gatgcgcatc tgaacccggt gccggtcggg gtgctgggcg agctggtcat cggcggagtc    9660
ggtgtggcgc gagggtattt gaaccgtccg gagctgacgg aagagaagtt cgtagacagt    9720
ccgttcgccg cgggcgagcg gctgtaccgc acgggagact ggcgcggtg gatggaggac    9780
gggaacgtgg acttcatcgg ccggatcgac aaccaagcga aaatccgggg ctaccggatc    9840
gagacgggtg agatcgagtc gcagctgctg cgggtggaag gcgtgcgcga agcggtggtg    9900
ctggttcgaa gtgacgcaaa cgggcagaag gcgttatgcg cgtattacac gctggatacc    9960
ggagcggaac tggcagtgaa cgatctgcgc agcacgctgg cgcaggagct gccgggctac   10020
atgatcccgt cgtacttcgt ggagctggag ggcctgcctc tgacgccgaa cggaaagatt   10080
```

```
gaccggaagg cgctgccggc gccggaagga gaagcgggaa gcggaacgga gtacgtcgca  10140
ccgcgcaatg agctggaaac aaagctggcg gcgatttggc aggaggtgct ggggcttgcg  10200
aaggagattg gcgttcacga caacttcttc gacatcggcg gccactccct gcgggcgacg  10260
acgctggtca gcaaggtgca caaggaactg agcgtggatc tgccgctgcg cgacgtgttc  10320
cgccattcca cgatcgagag catggcggcc gccatttccc ggctggatga gcagacattc  10380
gttgccattc cggtggcgga tgaccgggag gtgtacccgc aatcttttgc tcaaaaacgt  10440
ctctttatcc tgaatcaact ggaaggcgcg gagcttagct acaacatgcc ggaggcgatg  10500
ctgctggagg gggctttgga tcgggcaagg ttcgaagaag cattccgtaa gctcgtggcg  10560
cggcatgaaa tgctgcgcac cgggttcgaa atggtggatg gcgaagcatc gcagcgggtt  10620
taccaggact tgaattttgc tgtggagttc tatcgagtag atgagcaaga ggccgaagag  10680
acggttcgcc gttttgtccg tccgtttgac ttggcgaagc ctccgctgct gagggtaggc  10740
cttgtcgagc tggcttcgga acgccatatt ctaatgtacg acatgcatca tattatttcc  10800
gacggtgtct ccatgaaaat ctttgttgaa gaattcgtcc gcttgtacgg cggtgagcaa  10860
ttggagcctc ttcgcattca gtacaaagac tacacagttt ggcagcattc gcaggagcag  10920
aaggaacggc ttcagcgtca ggaggcgtac tggctgaaca tgttccaagg cgagcttccg  10980
gtgctggaaa tgccaaccga ctatccgcgt ccgtccgtgc agagctacga aggccacacg  11040
ctggagtttt cttcgacgc ttcgaaaacc gacggcctga gcaactggc ctcggaaacg  11100
ggcacgacgc tgtttatggt gctgcttgcg gcgtataacg tccttctgca taaatattca  11160
ggtcaggaag atgtgatcgt tggtacgccg attgccggaa ggaatcatgg agatgtgcag  11220
ccgttgatcg gaatgttctt aaacacgctg gcgatccgca gttatccggc ttcggagaag  11280
acattcctgt catacctgaa cgaagtcaaa gaaacgaccc tccatgcctt cgagcatcaa  11340
aactatccgt tcgaagaatt ggtagacaag gtgcaagtca cccgtgattt aagccgtaat  11400
ccgcttttcg acacgctgtt tacgatgcag aatacggaga tgaagaatt tgagctggaa  11460
gggcttcgcc tgattcctta tccgagcgca ctggataccg caaagtttga tatcagcttg  11520
gatgtgggcg aggagaacgg cggcttggat tacagcttcg aatatgcgac ggctctctac  11580
aaaagggcga cgattgaacg gctggcgaag cattacgagc agctgctcgt gacgatcata  11640
agccgtccag atgcgaagat cgccgagctg aacttgctga cggcagagga aaaagaacaa  11700
attcttggca cattcaaccc cgcgcagccg gaagcggctc ctgcggccgc gttccaccgg  11760
ctgttcgaga acaggcgga acgaacgccg gaagaggcgg ccgtcgtgta cgagaacgac  11820
cagctgacgt atgcggagct gaacgagcgg gcgaaccgct tagcggccac gctgcgcgca  11880
agcgacatcg gccgggagac gatcgtcggc attctcgccg agcgttcggt ggatctgctg  11940
gtgtccgtgc tggccgtctg gaaagcgggc ggggcatatg tgccgctcga cccggattat  12000
ccggcggatc gcgtgcggtt catgcttgaa gacagtggag cgaaggtact gttgacgcaa  12060
atgccgctgc gagaacgcgc cgaagcctgg ctcggcgaag aggagctggc gctggcagcg  12120
gtgctgtacc tcgacgacga agcatcgtac agcgaggagc gggcgaatgc gccgattggc  12180
tccggcatgg tccccggcaa gctgacggat gctgtggatg acggcgatga gacccatccg  12240
aatattggca tgggcagctt ccatgaagcc cgtccggatg atctggcgta tgtgatctat  12300
acgtcgggaa cgacgggcaa gccgaaaggc gtgatgatcg agcaccgcag cctggtgaac  12360
acggcggcgc gctaccggcg ggaataccgg ttgatcagt tccgggtacg gctgctgcag  12420
ctcgccagct tctcgtttga cgtgttcgtg ggagatatcg cgcggacgct gtacaacgga  12480
```

```
ggcacgatgg tgattgtgcc gaaggacgac cggatcgatc cgtctcgtct gcaccactgg   12540
atggagcgag agcgggtcac cattttcgaa tcaacgccgg cgctgatcgt gccgttctta   12600
gagtacgtgc acgagcaggg gctggatatc agttggatgg agctgttgat cacgagttcg   12660
gacagctgca gcgtggcgga ttaccggatc ttgcaggaac gcttcggctc gttattccgg   12720
atcatcaacg catacggcgt gacggaagcg gcgatcgact ccagcttcta tgacgaggag   12780
ctggcgaagc tgccgcagac aggccatgta ccgattggaa aagcgtggct gaatgcgaaa   12840
ttctacatcg tggatgcgca tctgaacccg gtgccggtcg gggtgctggg cgagctggta   12900
atcggcggag tcgtgtggc gcgagggtat ttgaaccgtc cggagctgac ggaagagaag   12960
ttcgtagaca gtccgttcgc cgcaggcgag cggctgtacc gcacgggaga cttggcgcgg   13020
tggatggagg acgggaacgt ggacttcatc ggccggatcg acaaccaagc gaaaatccgg   13080
ggctaccgga tcgaaacggg tgagatcgag tcgcagctgc tgcgggtgga aggcgtgcgc   13140
gaagcggtgg tgctggttcg aagtgacgca aacgggcaga aggcgttatg cgcgtattac   13200
acgctggata ccggagcgga actggcagtg aacgatctgc gcagcacgct ggcgcaggag   13260
ctgccgggct acatgatccc gtcgtacttc gtggagctgg agggcctgcc tctgacgccg   13320
aacggaaaga ttgaccggaa ggcgctgccg gcgccggaag gagaagcggg aagcggaacg   13380
gagtacgtcg caccgcgcaa tgagctgaaa acaaagctgg cggcgatttg caggaggtg   13440 ctggggcttg cgaaggagat tggcgtttac gacaacttct tcgacatcgg tggtcactcc   13500
ctgcgggcaa cgacgctggc gggcaaagta tttaaggaat taaacgtcaa cctgccgctg   13560
cgtgacgtat ttcgtcactc gacgattgca gcgatggccg aggcgatcgc ccgaatggaa   13620
cggctggagc atgaggacat tcctcaagcg gaggagagag agtattaccc tctgtcctct   13680
gcgcagaaac ggctgttcat tcagcacacg ctggatggag cggatcagct ttacaacatg   13740
ccggaactgg tgcaggtgga aggcgagttt gatttagacc ggttggaagc cgccttgcgg   13800
aaattgataa cacggcatga atcgctgcgt accggttttg aactcgtgaa gggcaaagcg   13860
gttcagcgga tttacccgca ggtcgatttt gctgtcgagc atcatcaagc ggataaagag   13920
gatgcggctc aaatcgagca gatcgtccgc agcttcgttc gtccatttga tctcggcaag   13980
ccgccgctgc tgcgcgccgg ggtcatcgag ctggagccga acctgtatat tctcattttc   14040
gacatgcacc atatggtgtc cgacggcgta tcaatgcgca ttgtgatcga tgagttctcg   14100
agtttctacg ccggggaaga gctgccgtca ctgcgcattc aatacaagga ttatgtcgtt   14160
tggcagcagt cgaaggccta ccgagaacgg atcgggcggc aggaagcgta ctggctgcaa   14220
accttcaaag gcgagctgcc gacggcgaac ctgccgatgg actacaaacg gtctgcagct   14280
cgcagctacg aaggtgcaca tctggagttt gacgtcgaag cctctctctc tatgcggctg   14340
cacgaattgg cggcagagcg taaaagcacg ctgttcatgg tgctgcttgc ggcttatacc   14400
gtgctgctgt ccaaatacag cgggcaggag gacttgatcg tgggcacccc ggtggcggga   14460
agaacgaacg ccgatttgga accggtcatc ggaatgtttg tcaatacact ggcgatccgc   14520
aatcgtccgt cgggcaacaa aacgttttg tcctacctgg aagaagtgaa ggaaacggct   14580
ttgggtgctt tcgagaacca ggattatcca tttgaggagc tcgtgaacg tttgaatgtg   14640 aagcgggagc cgggccgctt cccgctgttc gatgccgttt tcgacttgca aaatatcgaa   14700
gaacgagacg tcgagctgga aggggtcagc ctgaagaatt acgagcttga ccatttggaa   14760
gaagcgaagt tcgatctgac gctgtttatg tatgaaaaca acggggcgct gagcgggggc   14820
```

```
ttcttctacg ccaccaagct gttcaaagaa gccatgatcc gcaccttgac cgaggattac    14880
ctgagggtac tgtctcaaat tgcggaaaat ccgcaacttg agctaagtcg gattgaatgt    14940
cataaaccgg cggctggcgc aaagagtgcc gtcgatacga tcgaatttgc gttctaatcc    15000
tataagtgcg cctccgccgt caagcgaaag cggcgcgcat cccaaggaag acggcgaaca    15060
acgtccaagc ccgtaaacgc gcaggccgaa agcaagcttt tcggatctgc gctggggcat    15120
ggtttacttc attttaggg gaggtacgaa tgaaatcttt atttgaaaag gaagaaaggt    15180
actggagcgg caagtttgac gccgatgaca acctgagctt ccttccctac agtcaatcct    15240
ccaaattatc cgccgacggg gaagctgcgg ccgagccggg cttgcttcac cgtaccctgc    15300
cgagcgaact ctcggagaga atcattcgcc tcgccaacgg ttcggatttg gctatgtaca    15360
tgattgtttt ggcaggagta aaaagcctgc tgttcaaata taccgggcag gaccaagtgc    15420
tggtcggcat gccttcttat agcgcagacc ccgacgggac tccgccgccg catgacatct    15480
tggtgatcaa gacggccgta agccatcaga ctacgctgaa aacgctgctc ggggcatca    15540 aagcctccat tggcgaggcg ctggagcatc agcacctgcc ttttcagaaa atggtggagc    15600
cgctccatct ggactatacg ggggatggcc tcccggtcgt taacaccgtt gcatccttcg    15660
ccccgattca tcccgaaccg ctgggtaacc gggtggcggc cgatacggtt tttcgcttcg    15720
atcgccaaaa ccactccatc gagctggaaa taagctttga cgggcagcgg tacgagcggg    15780
catttgtgga acaggcggcc gaccattttg ttcggctact gtccttgctt ttatttcagc    15840
ctgatctgga gcttggacaa gccgatgtgc tgtccccaga cgagagggag acgctgctga    15900
agcgatttaa tgacaccgaa accgggttcg agcggggaa aacgattcat ggcttgttcg    15960
aagagcaggc ggagctttac ccggacaacg tggccgccgt catgaatgag cggcagctga    16020
cttaccgcga actgaacgag cgatccaacc gccttgcgcg gaagctgcgg gagacgggag    16080
tagaagcgga tcagctggta gcgattctgg ctgaacgctc gctcgatatg gtcgtcggca    16140
ttctggcgat tcttaaagcg ggcggagcct acgtgcctgt tgatcccgac tacccggagg    16200
agcgcatccg cttcatgatc gaggattcgg gcgcgccgtt attgttgatt caaaagcatc    16260
tgcacgagaa gaccgacttc gcaggaacgc gcctcgagtt ggatgatttc gtgtggaacg    16320 acagagggt ggactccgaa ggtaggctgg atgcttcgaa cctggagccg atttccgggc    16380
cgggcaatct ggcttatgtt atctacacgt cgggaacgac cggcagaccg aaaggaacat    16440
taatcgagca taagaacgtc gtgcggctcc tgttcaacga caagaacctg ttcgacttcg    16500
ggccatccga cacgtggacg ctgttccact cgttctgctt cgatttctcc gtctgggaaa    16560
tgtacggagc gctgctgtac ggaggcaagc tggtcatcgt accgccgctc acggcgaaaa    16620
atccggctga tttcctggtg ctgctgggcc acgaacaggt cacgattttg aaccagacgc    16680
caacgtactt ctaccagctg ctgcgtaagg tcttggcgga ccatccgtac gatctgcgga    16740
ttcgcaacgt catcttcggg ggcgaagcgc tgagtccgct gctgctcaag gcttcaaga    16800 cgaagtaccc ggagacgaag ctgatcaata tgtacggcat taccgagacg acagttcacg    16860
ttacgtataa ggaaatcacc tgggtcgaaa tggaggcggc gaagagcaat atcggcaagc    16920
cgatcccgac gctgagggtg tacgtccttg atgaaaaccg ccgcccagtg ccgatcggcg    16980
tagcaggcga aatgtacgtg gccggggaag gcctggcgag aggatacctg aaccgtccgg    17040
atctgacggg ggagaagttc gtcgattccc cgtttgcgga gggggagaaa ctataccgct    17100
cgggcgactt ggcggtttgg ctgccggacg gcaacatcga atatctgggc cgaatcgacc    17160
accaagtgaa aatccgcggg taccggatcg agctggacga aatcgagacg cagttgctga    17220
```

```
agattgccgc cgtgcaagaa gccaaggtgc tcgaccgcga cgacgcgaac ggccaaaagc    17280
agcttgtcgc ttactacgtc gcggaaatga ggctggcggc gcatgaactc aaggaggagc    17340
tcgccaaaca gcttccaggg tatatgattc cttcgcactt cgtgcagctt tcgcggatgc    17400
ctctaacccc gaacggaaaa atcgaccgca aagcgctgcc agcgccggag gaagtcgcgg    17460
ccttaggagc ggaatatgtc gcgccgagaa cgctgctcga aatgaagatt gcccgcgtct    17520
ggcaggatac gcttggcgtt ccgcaggtcg gcgtaaagga taactttttt gatttgggtg    17580
gcaattcgtt aagtctgatg aggctcgttc aagccgttta cgatgaaacg ggcattgaga    17640
ttccgctgaa tcgccaattt catcatgtaa ccgttgaagc catggctttc gaagaggggg    17700
atctgggcct ggataaaggg ggagactcct tcataaagct gaataaagca ggagatctga    17760
acgtgttctg cttccctccg ggcagcggct tcggcatcgg ttaccgagag ctcgcaagca    17820
ggctcgacgg ccagttcgtg ctctacggca ttgattttat cgacgatacc gccgattacg    17880
aggccatgct gaaccgttat gttgacgaga ttgtccgcat ccagccggaa ggaccttacg    17940
tgctgctcgg ctactgcttc ggaggcaacc tgacgttcga ggtagccaaa acgatggaga    18000
aaagagggta tcccgtaacg gacgtgctca tggtggactc gtggattaag gagacgctga    18060
cgccttccga aacgtcagag aaagagcttg aagaaatgct tgccgatttc gacgaagaag    18120
agaaggaatt aatgagcaat ccgctcgtgc gggagcgggt tcatcagaag gtcaaagcga    18180
ctttggcgta cgaagcgcag cttattaact ccggcacgat cccggcccgg atttacgaac    18240
tgattgcgaa ggacagcgaa gcgttccgct tggagcacca attgccgtcc tggcgggggg    18300
caacgacgca agcttacacc gattaccggc tggagggcgc gcacgaggaa ttgctggaac    18360
tcgcgcgcgt ggacgaaacg gccgttgtca tccgggatat cttagagcaa gtcaagcggc    18420
agatcgaagt ggaggccggg gtactgcatg gaagctgacc gacagccgtc cgttcaagaa    18480
caaggcacag cggtgccttc caagcgccaa accgcttacg ccacctggaa agcgttccgc    18540
tggctgatgt cctatgtaag ccgtcacata ggctggatga ccgtcggtac cttgtccgca    18600
attgccgccg ccgttattga gatatggacg ggaagtttga tcgagcagct gaccacccag    18660
gccgagaagg gggcggggcc actcgttctg caaatcgtat acacggtctt tgtggtcatc    18720
ttgatcggtg tgccggcgaa gttttttcatg agcttcggcg tggagcgaag cagcgcctct    18780
gcggttcagg atatccgcaa ccatgtcatg cgtcatatcg gcaaactacc ggtctcctat    18840
ttggaaaagc agcactctgg cgacgtgttg tcgcggatca acaacgacct gcagcttatc    18900
cagcagttta tgattcggga ccttgcccag tggttttatc atccgctatt gttcatcggc    18960
tgtttcgctt atttgatcta cctccaatgg gagctgatgc tgtccagcct gctgttattt    19020
cctgtagcgc tgctggtctc ccaatggatc ggcaagcagt tggagcggtt gacggaggaa    19080
gcccaggcga atatgggccg aatgaatgtc aacctccagg atacgcttgg gggtatgcct    19140
gttgtaaaaa gctacctgct atccggcatg ttatctcgct cctaccaagt gctgctgcaa    19200
ttgacggccc aaaaaaagct ggccgtgaaa aagcgggaag cctgggtcaa cccgctgctt    19260
tccacgctga tgatcagccc gatcattttc gccgtcagtt acggaagcta tttgatctac    19320
aacgggcagc taggcgcagg agagttgatc gccttcctgt atttgctgaa tctgtgtctg    19380
gagccgctgg agcatattcc cgagctcatc acgcggacgt tcgaaatggc cggtgccctg    19440
agaagagtct ccgaaatcgt cgagcagccg accgaaacgg aaaatggccg ttcgcttccg    19500
aaagcgagcg ccgcccccat cgagtttcag aacgtaacct tcgggtatga ggagagttcc    19560
```

```
ccgatcctgc ggaatgttag cttctcggtg ccggaaggga agacgatcgc gcttgtcgga   19620
gcgagcggcg gagggaaaag cacggtgttt aagcttgtat gcggctttta tccgcttccg   19680
gaggatcagg gggagatccg cgtattcggc agcctgatcc acggcgccga tccggagcag   19740
cttcggtcac attttccgt agtaacccag gattcatatt tgtttagcgg cacgatcgcc   19800
gaaaatatcg gcttcgggcg ggaagaagcg tcgatggaca agattatcga agccgccaaa   19860
gccgctcaag cgcattcttt cattatgcag cttgagggcg gctaccaaac gtatgtcgga   19920
gagcgcggag gcttcttgtc cggtgggcag cgccagcgta ttgcaatggc ccgggccttt   19980
ctaaaggatg ctcctgtttt gctgctggac gagccaacgt cggctcttga tccggagtcg   20040
gaaagcgcgg ttcagaaagc gctgggcgta ttgatgaagc agagaacgac catggttatt   20100
gcccaccggc tttctacagt acaaaatgcc gacgaaattt gggtcatgga acaaggaaat   20160
attgtggaaa agggcactca tgaacaattg ctggagatga agggactgta cgcccagtca   20220
tactaccagg aatttactga gattgccgaa cgcaggagg tggcgtacac atgaaaaagg   20280
gcggatggct ctcacaagtg aaagaacttg gctacttgct gaccttatg aaccgccagc   20340 gcaaaactca gtacgccatt ggcctggccg taacggcgct cacccagaca ttttccctga   20400
tcgctttcag tttggtcgta cataacttgg ttgatttcgc cgtgtcccga gataagtccc   20460
tgatggtgga agccttatt attttgggcg cggccctgtt cctggaaaat gtgatttctc   20520
catggttcat ttacttatac cagcgcagtg ttgagctgac tgtgctgaat atccgcaaac   20580
gtctttatga caagttgtgc cgggtgcggc cgagattcct agagcagacg caccatgggg   20640
acttgctatc gcgggtgaac aacgacgtaa cgaccgttga gtttacattc tcgcaggttt   20700
acttcgtttt gctgcttcaa gttgtctttt gcatcggctc cattgtctct atgatgttga   20760
tcgattggcg gtttgccggc gtatccttcg tcattctgct gctgtcctcc gtggtcagcc   20820
tgaaatttgc gcgggatatt cgcgccctgt ccgaacaagg cttacagacg ctcggaaaaa   20880
tgaccgaaaa attcaaagat tttatgggcg gcattcaaat tgtgaagctg ttccgcatcc   20940
gcacgattta cggccagtac gaggcgttga cgaacaaat gacgcagacg cttcggcaaa   21000
ccgcgcagaa aaacggcatg caggctgcgg tgaaccattt tatcagctac gtcacgttct   21060
gcggcatcat agtcatcggc agtcttcttt atgcctacgg actgatgggc atgggaagcg   21120
tcgctgccct ggcggttctg caagtgaatc tgacgcacgc cttgttgaac ttggggatcg   21180
ttctgtcgat gacccagaat tcgctcgcgg gcgctcaccg gattcaagag gtactaagag   21240
aggaagagga accggagcgt ctaggatctc ctctcagcga gctcgtgtcg gaggctgcgg   21300
tggagtttcg cgatgtagag ttttcctatc aggcggataa aaaggtgctt gtcgacatgt   21360
ccatgcaggt gtttcccggc caggtcgccg ctatcgtggg ggccagcggc agcggcaaaa   21420
gtacgctgat caagctgctg ctcggctttt atcctgtgga cagcggagaa atcctgctcc   21480
aaggcaaacc gttcggccat tacacgctgg acgaaatccg gaggcagatt gcatacgttc   21540
cacaggaacc gttcttattt accggcacga ttgaggaaaa cattcgctac ggcaacccgg   21600
atgcaacgga tgaagaagta attgaagcgg ctaaagcggc gtacgctcat catttcattc   21660
aggaacttcc tgaacagtat aaaacgccgg tgggagagag aggagcgtcg ttgtcgggcg   21720
gacaaaggca gcgaattgcg atcgcccggg cgattctcaa aaacgccccg attctgctgc   21780
tggacgaagc gacttctgcg ctggataacg aatcccagca ttgggtacag caggctctga   21840
acgtattgat gaaggggcgc accaccattc tgatcgccca tcgtctcagc actgtggaac   21900
atgcggattt gattaccgtt atgaaccaag ggacggtcgt cgagcgtggc cgccatcagg   21960
```

```
acctgctggc gcacgggggg tattacgccc ggctgtacgg ctagacccgc tttacggcgg    22020
gaggcttccg acttgcgaat gcgacagagc cttttagtaa ctaaggtatg actttataac    22080
tggtatttac cagaaaacgt agacacgaac aaggggggaag agtccacagg agccattccg   22140
ggaatgacct gcgtggttct tcttaagagt gactaagtga gatctaggta caaagcctat    22200
ctataagaat ctctaaaacg ggagtgtgtc gatgtgagag ataataccaa cgggcaatat    22260
gaattaacgc aagcccagcg ccgaatatgg ttcatgaaaa ttatgaatcc gggaacgtcc    22320
atcacgatgc tttccgcgac ctaccagatt acgggccaga tcgacacaca gcttctggag   22380
caagctgcgg cggagatcgt caaaacctat gacgctttcc gaatacgcat tagcggggat    22440
ttgcagaatc caacgcagtg gttcgaagag ccggagaatg tccaagccag gataagccgc    22500
ctcgaaatag gcacaaccga acaattctat gcttgggtga aagaagtaag cgaaaaaccg   22560
gccagcgtgt tcgacgaaca cctctaccaa tttacgatta tccattttgc gaacggccaa    22620
gtatggctca atttgacggt aaatcatatt atcgccgacg gcttgtccgt cactgctttg    22680
ctgcatgcgg tgatggaaaa atacatggaa ctgcgcaaag gcatctccag cagttaccag    22740
gccccttctt atctggatta tatttccgcg gagcgtgaat atgagcaatc gcagcgttat   22800
caaaaaggca aggaatactg gctgacgaag tacagcactt tgcctgaaac gaccggcttt    22860
aaatcgtatc cgccattctc gatcggcagc gaatccaata acgggccac cactttggac    22920 ggttcccggt atgaacgcat tctggccttt agcgaacaat atcaggtcag cttatatacg    22980
ttatttctgt ccgcgatgta tgccttgcta tacaagctga ccgacagcac cgatgttccg    23040
gtcggcacgg tgttcgccaa tcgcaccagc aagaaggaaa aagaaacgat cggcatgttc    23100
gtcagcaccg tggctacacg gattcatctg aatccagacg gggacgtgct ttccttgatc    23160
caagcggttt ccaaggagaa tacggcggat ctgcggtatc aaaaataccc ttataaccaa    23220
ttgatccagg atttacgcga acaacacggc cgcaacgatc tttcgggact gttccgtacg    23280
tctctggaat atctgccttt gaaaatcgtg gaatacgaag aaatcaaggt acgcctggag    23340
gctcacttcg ctaagcacga gatggatgat ttgctgctgc gtttcgacca tatgctgaat    23400
gaaggccatg tcattctcca cgcttcctat cgcactggct tgttcgagac agccgagatt    23460
gatcggatta tggaacagta tgtaaccgtt ctggaccagt ttcttcagac tcccgaactg    23520
ccggtacgcg aaatttctct gctgagcgat gaggagagac agtgcattct gggcgttttt    23580
aacccgccgg tggcagggct gagcgaggga gaggcgtttc atcggtacgt tgaaaagttt    23640 gccccgcgaaa ttccagatca tccggcagtt gtctacatgg atacacagct gacctacggt    23700
gaattgaacg aacgtgccga gcggctggct tctctccttc gcgagcaggg cgtgggaaag    23760
gagacgatta cggggatctg ggcggagcgt tcggtgaac tgctgatcgg ggtgctcgcc    23820
gtttggaaag ccggcggagc ctatgtaccg cttgacccc gattatccggc ggagcggatt    23880 gagtacatgc tcagcgatag cggtgcgtcg gtgctgctta cgcagcgtca tctgttggag    23940
cgggccggag gttggttggc cgatgaccgg ctgaaactac aagctgtcta tgctatggac    24000
gatgaacaga tttataacag ggatgcctta gccgtggaat ttgagtctgc cgatagtgcc    24060
ccgcaagact tggcttatgt gatttacacc tcggtacga cgggacgccc gaaaggcgtc    24120
atgatcgaac atggtagtct cttgaatacg gcggatgcgt accgtcgcga gtaccggttg    24180
gatcagttcc cggtgcggct gctgcagttg gccagctttt cgtttgacgt gtttgtcgga    24240
gacatcgctc ggacgctgta taacggaggt acgatggtga ttgtgccaaa ggatgaccgg    24300
```

```
attgatccga accgcttata cggctggatt cgggaccaaa acattacggt attcgaatcg    24360
acgcctgcgc tcatcctgcc attcatgcag catatttatg aagaagggct ggacgttagc    24420
tccatgcagt tgctgattac cagctcggat gcttgcagtg tcaccgatta ccgattgctg    24480
caggaaagat tcggcggaca attccgcatc atcaacagct atggcgttac cgaagcggcc    24540
attgacagca gcttttacga tgagacgctg acaagctgc cgtcgtcggg tcatgtgccg     24600
atcggcaaag cttggctgaa cgcccggttt tacattgtcg atgccgcgtt aaaaccggtt    24660
cctgtagggg ttccgggcga gcttgtcatc ggaggcgctg gggtggcgcg cggatactgg    24720
aaccgtccgg acctaacggc cgagaagttt gcggacagcc cgtttgtgcc tggcgaacgt    24780
ttgtatcgga caggcgattt ggcccgctgg ctggaagacg gcaacgtcga cttcatcggc    24840
cgaattgact atcaggtgaa aattcgcggg ttccggatcg aactcggcga aattgaaacg    24900
gccttgctgc gtttcccggg cgtcaagcag gctgtggtga cagaccgtac agataagcag    24960
gggcaaaagt atttgtgtgg ctacgtggcg gcagatactt ccttgcagct gagcgatctg    25020
ctgtcccaat tgaagcaaga gctgccggcc catatggttc cggcccggct ggtgtctctt    25080
gataagcttc cacttactcc gaacggcaaa attgaccgta aagcgctgcc tgaaccgacc    25140
ggagaggtag aagcaggccg tgagtatgtg ctcctcgca caacgctgga aacaagactt     25200
gctctcattt ggcagcaggt gctgggtatt gcgcgagttg gagtcgaaga cgatttctt    25260 gacctgggtg gtcattcctt gcgggcctcc acgctggttt ccaagattcg gaaagagctg    25320
caagtcgagg ttccgctgcg ggacgttttc cgctacacca cgatcaaaca gctggcccaa    25380
agaatcggcg gtttaaagca gcaggagacg tatgaaatta caaaggcggc tgaggccgag    25440
tactatccgg tttcatccga gcaaaagcgt ctgtacgtcc tgcgccagct tgacggggcc    25500
gagcgcagct acaatatgtc ggcggcgctt cttctcgaag gcaagctgga tcggacgcgc    25560
gtagagtacg cgttccgggc gctgattcag cgtcatgaga cgctgcgtac cgggatcgag    25620
caggttcaag gcgaacttgt ccagcgcatc tatgacgagg tggagtttgc tgtggattat    25680
ttccaggcga gtgagcggga agtggagcaa ggggtggaag cttactatcg cccgtttgat    25740
ctgaccaagc cgcccacttct ccgcatcggc ctgatcgaag tcaccgagga tcgccacatt    25800
ctgctgttcg atatgcacca tatcgtctcg gacggcatat cgacagcgct gctcttcgac    25860
gagttcagcc gcctgtatcg gggcgaggag ctggctccgc tgcgcattca atacaaagat    25920
tatgccgttt ggcagcattc cgaagcttac gcgcaactgc tccagccgca gaaggagtac    25980
tggctggagc agctgtcagg cgagctgccg gtcttggagc tgccgacgga ttttcccgcgg   26040 ccagcggtgc aaagctttga cggccggacc gtgaagtttt atatcgggaa agagcggacg    26100
gagaagctga aagagctggc gtcacggacg ggaacgaccc tgtacatggt gctgctgtcg    26160
gcttatacca tccttatgca taaatattcg ggtcaggaag atctgatcgt cggaacgcca    26220
attgccggaa gaacgcagga tgaagtcag ccgatcgtag ggatgtttat caacacgctg      26280
accattcgca gccgtccgga gcgttccaag ccataccttt cgtacctgga agaaatcaag    26340
gacatcacgc tcggggcttt cgaacaccaa aattatttgt tcgaagactt ggtggaaagt    26400
cttcacattc cgcgcgcgac cggccggaat ccgctctttg atacgttctt ctccctgcaa    26460
aatacggaga acgagcaaat tgtcattgag gggctggagc aatcgttta ccgctggaa     26520 aaccgaacat ccaagttcga gctgctcctg gacatttctg agcaggacgg tcagctcgaa    26580
tgccggttgg agtacgcaac ggctttgtat aaacaggaga ccgcggaacg gttcgccaaa    26640
cattatgaca agctgttaga aaccatcgca gcagcgccgg acggggatat tgcctcgctg    26700
```

```
gaaatgctca cggaggagga aatccgcgaa ctagtacgtg gtttcaacga ttcggaggcg   26760
gactacccgc ggcagcagac gattcacggc ttgttcgaag agcaggcaga gctttacccg   26820
gacaacgtgg ccgccgtcat gaacgagcgg cagctgacct accgcgagct gaacgagcga   26880
tccaaccgcc ttgcgcggaa gctgcgggag acgggagtag aagcggatca actggtagcg   26940
attctggccg aacgctcgct cgatatggtt gtcggcattc tggcgattct aaagcgggc    27000 ggagcctacg tgcctgtcga tcccgactac ccggaggagc gtatccgctt catgatcgag   27060
gattcgggcg cgccgttatt gctgattcaa aagcatttgc acgagaagac cgacttcgca   27120
ggaacacgcc tcgaattgga tgatttcgtt tgggcgaca gaggtgcgga ctccgaaggt     27180
gcgctggatg cttcgaatct ggatccgatt ccgggccgg gcaacctagc ctatgtcatc     27240
tacacatcgg gaacgaccgg cagaccgaaa ggaactttga tcgagcataa gaacgtcgtg   27300
cgcctcctgt tcaacgacaa gaatctgttc gacttcgggc cgtccgacac gtggacgctg   27360
ttccactcgt tctgcttcga tttctccgtc tgggaaatgt acggagcact gctgtacgga   27420
ggcaagctgg tcatcgtacc gccgctcatg gcgaaaaatc cggccgattt cctagcgctg   27480
ctgggccgcg aacagatcac gattttgaac cagacgccaa cgtacttcta ccagctgctg   27540
cgtgaggtct tggcggacca tccgtacgat ctgcggattc gcaacgtcat cttcggggc    27600 gaagcactga gtccgctgct gctcaagggc ttcaagacga agtacccgga gacgaagctg   27660
atcaatatgt acggcattac cgagacgacg gttcacgtta cgtataagga aatcacgtgg   27720
gtcgaaatgg aggcggcgaa gagcaatatc ggcaagccga tcccgacgct gagggtgtac   27780
gtccttgatg aaaaccgccg ccctgtgccg atcggcgtag cgggcgaaat gtatgtggcc   27840
ggggaaggcc ttgcgagagg atacctgaac cgtccggatc tgacggcgga gaagtttgtc   27900
gattccccgt ttgcggaggg ggagaaactg taccgctcgg gcgacttggc ggcttggcag   27960
ccggacggca acatcgaata cctgggccgg atcgaccacc aggtaaaaat ccgcgggtac   28020
cggatcgagc tggatgaaat cgagacgcag cttctgaacg ttgagggcgt ggaagaagcg   28080
gtggtgcttg ctcgtcagga cggtgggggc gagaaggcgc ttgtcgccta ctttgtggcg   28140
aaccggacac tgacggtcag tgaaatgaga acctcactgg ccaaggaaat gccggggtac   28200
atgatcccgt cgtacttcgt gcagctggag cgtatgccgc tgacgtccaa cggcaaagtg   28260
gatcgcaaag ccctgccgga ccgcaaggc ggcttgcaaa cgggcgtcga atatgtagcg    28320
ccgcgtaacc ggacggagtc ccagcttgtg aagatctggg aggaagtgct gggttactcc   28380
ggcattggag tcatggacaa tttcttcgag cttggaggcc actccttgcg ggcgacgaac   28440
cttgtcagca agattcggaa ggaaatgaac gtcgaatttc cgctgcgcga tgtgttccgc   28500
tatatgacgg tagagtcgat ggccgggget attgccagct tggaggaaac gcggcatagc   28560
tcgattccga aagcggaaga gagagcgtac tatccggttt cctccgcaca aaaaaggttg   28620
tacgtcctga ccagctgga tggctcgag ctgaattaca acctcccaag cgccttgcaa    28680
ttgaaagggg ctttgaacga ggccaaagtg aaaaggcgc tgactacttt ggtggcccgg    28740
cacgatatgc tgcgcaccgg ttttgaaatc gtagatgggg agccggtaca gcgtattcat   28800
ccgctcgcag ctttcaaggt cgagaagctt caagcaagtg aagatcaggt tgcggccatt    28860
cttgaaggct tcattcagcc ttttgacttg acccagccgc ctttgctgcg tgccctgctg   28920
atcgaactga agaaagagaa attcctgctt gcgctggata ttcatcatat tggttccgac   28980
ggcctctcca tggacgtgct gctgcgcgaa ttcgtgcggc tttacaatgg ggaagaattg   29040
```

| | |
|---|---|
| ccggtgctac ggattcaata caaggattac gccgtttggc agcaatccga ggaacagcgc | 29100 |
| cagcgtatca aacagcagga ggaatactgg cgtggggtat tcaactctga gcttccggtt | 29160 |
| cttgagctgc ctctcgactt ctcccgtccg gccgtccagc agtttgacgg tcgaacgctc | 29220 |
| acgtttacgc tggatgcgga gaaaagcgaa gctctcaaac ggcttgccgg cgattcggga | 29280 |
| gcgacgcttt acatgctttt gctggctgcg tactccgtat tgcttcataa atatgcggga | 29340 |
| caggaagata tcgtggtcgg aactccgatt gccgcccgat ctcacactga cttacagccg | 29400 |
| attatcggca tgttcgtcaa tacgcttgcc cttcgcttgg gaccggcggc ggagcggacg | 29460 |
| ttcctggatt acttacagga agtgaaggaa acgacgctag gagcctacga gcaccaggac | 29520 |
| tatccgtttg aggagctggt ggaagctctt caggtgagcc gggatttaag ccggaatccg | 29580 |
| ctgtttgaca ccatgttttc tttgcaaaag cacgaaagct tggatttaac cctggaaggc | 29640 |
| ttgcaatggt cgctgttcga catcgaggaa aagacggcaa agtttgatct tagctttgat | 29700 |
| atcgtggaag ccgataacga gttggttttgc aagatcgagt acgctacctc gttgtttaga | 29760 |
| caggaaacga tggtacggct ggcgggtcat tacgagcagc ttttggcgtc gatcctggct | 29820 |
| cagccgggtg cgcggatttc ggatttggac atattgacgg acagcgaaaa gcatgatttg | 29880 |
| ctggtcgggt ttgacgtgtc gtcttcggct cttgcgaagc aatccgccgc agagggtaca | 29940 |
| ggtttggaag cggatgaatc gtggagagag aggacgttcc acgagctgtt cgaggagcag | 30000 |
| gcggagcgca ctcctggagc gctggctgtt atctacgaag acagcaagct gacgtatgcg | 30060 |
| gagctgaacg ccaaagcgaa tcgtctggcg tatgcactgc gggcgcgcgg ggtgaagccg | 30120 |
| gagcaggtgg tcggcattct ggccggccgt tcggcggagc tgttgatcgg ggtgctcgcc | 30180 |
| gtatggaaag cgggtggcgc ttatgtgccg cttgatccgg actatccggc ggagcggatc | 30240 |
| gagtatatgc tcacggacag cggggcgtcg gttctgctca cgcagacccg cctgctggag | 30300 |
| caggcggaag tttggcgcag cgacggagct ctagcgttgc aaacggtgct tgcacttgac | 30360 |
| gacgctgcga cgtacagtct cggagcggca gaagtggctg tgggcgtaca agcttttggc | 30420 |
| gaagcaggcg cagaggcgga ggctttggcg caagcgcaaa cggctgctgc cgagacgtcc | 30480 |
| gccacggcag aagccgagca gaacgtactg gcggcggatc tcgcatcgaa tccggcgaat | 30540 |
| gtgaacaagc cgcgcgattt ggcttacgtc atctacacct ccggtacgac tggccgtccg | 30600 |
| aagggtgtgg cggtggaaca ccgcagcctg gtgaacacgg cggcgggcta tcggcgggac | 30660 |
| taccgcctgg atcagttccc gatccggctg ctgcaactcg ccagcttctc gtttgacgtg | 30720 |
| ttcgtcggcg acattgcgcg gacgctgtac aacggcggca ccatggtcat cgtgccgaag | 30780 |
| gacgaccgga ttgatccaac ccgcctatac ggctggattc gcgactacgc cgtgacggtg | 30840 |
| ttcgaatcga ctccggcgct gatcgtgccg ttcatggagc atgtgtatgc cgagggtctg | 30900 |
| gatctcagct cgatgcagtt gctgctcaca agctcggatg cgtgcagcgt agcggattac | 30960 |
| cgcacccttgc aggagcgctt cggctcgcag ttccgtatta ttaacagcta cggcgtcacg | 31020 |
| gaagcggcga ttgactccag cttctatgac gagccgctgg agaagctgcc gaagacgggc | 31080 |
| agcgtgccga tcgggaaagc gtggctgaac gcaaagttct acatcgtgga tgcgagtctg | 31140 |
| aagccggtgc cgatcggggt gttgggcgag ctggttatcg gcggagcggg tgtggcccgc | 31200 |
| ggttacttga accgcccgga tttgacggcg gagaaattcg tagacagccc gttcactgca | 31260 |
| ggggagcgga tgtaccggac gggcgacctg cgcgcgctgga tgccggacgg caacgttgac | 31320 |
| ttcatcggcc ggatcgacaa ccaggtaaaa attcgcggct atcggatcga gcttggtgaa | 31380 |
| attgaagcgg ctatgaaaaa ttttgccggc gttcgtcaag cgcttgtcat cgaccggacg | 31440 |

```
gacgagcggg ggcagaaata tttgtgcggg tatgtcgtag cggattccag cttcgatctg    31500
gaagggcttg tggcccatct ggacgctgca ctgccttccc atatggtgcc ttcgcgtatc    31560
atgcgcctgg atcaaatgcc gcttacgccg aacgggaaga tcgaccgtaa agggctgcct    31620
gtgccggaag gaagcattcg tgccgaggct gcatacacgg cgcctcgtac tcctgctgag    31680
caagcacttg cgttggtctg gcagtcagtg ctgggcgtgg atcaggtcgg cacgatggac    31740
aatttctttg cgctcggcgg cgattcgatc aaggccttgc aggtatcgtc ccgtcttttg    31800
caaacggggt acaagctgat catgaaagat ttgttccatt acccgacgat ttccgccctt    31860
agtttgcagc tgcaaacggc ggagagaacg gcaagccagg ccgaagtgac gggggaggtc    31920
atcttgaccc cgattcagcg ctggttcttt gaacaaaatc cggccgacgt gcatcacagc    31980
aaccaggcat tcatgcagtt ctccaagcta ggcttcgacg aagaagcttt acgccaagcg    32040
gtgcgtcaac ttgtcgtgca tcacgatgct ctccgtacgg tttaccgcca aaccgaaaac    32100
agctataccg cctggaaccg cggcgccggg gagaacgaag cactgttcga tctggaagtt    32160
gtagatttca ggggagtctg cgacgtgaaa ggcgcggtag aggctaaggc gaatgatatt    32220
caagcgagca tcgatctgga aaacggcccg ctggtgaagc tcggcttgtt ccgctgcgac    32280
gacggcgacc acctgctcat cgcgatccat cacttggtcg tagacggcgt atcatggcgg    32340
attctgcttg aagattttgc tgccggatat gagcaggtgc tgcaagggca gccgatccgt    32400
ctgccgctca aaacggattc attccaaacg tgggcgaaac agctcgctga ttatgcgaac    32460
gatccggcga tggaaagcga aagagagtat tggcagcata tcgagcaatt gagctatgag    32520
ccgcttccaa aagattttga acaaggcaga tccacgctga aggacagcgg tctcgtgacc    32580
gttcgctgga cagcggagga aaccgaacag ctgctgaagc acgcacaccg tgcttaccgt    32640
acggaaatga acgatttgct gcttgccgcg cttggcctcg cggtacaagc ttggagcggc    32700
cggggacgcg tgctggtgaa tctcgaaggc cacggccggg aagatatttt gccggatgtg    32760
gacattacac gcacggtagg ctggtttaca agccaattcc ctgtcgttct ggagccgggt    32820
cacgcccagg agctcggtca tcagctgaaa caggttaaag aaagcttgcg ccgcattccg    32880
aacaaaggaa tcagctatgg catcctgcgc tatttgtcgg cgccgcgtga cggcgagtgc    32940
ttcgctttgg agccggagat cagctttaac tatttgggtc agttcgacca ggattacgaa    33000
agcagcggct cgcagccgtc tccgttcagc ccgggctccg actcaagccc gaacgcagtg    33060
atggattttg tcctagatat caacggtatg gtgtcggaag gagtgctgga actcacgatc    33120
cgttatgggg aaacccagta taaacgggaa acggtagagc gcctgggcac cctgcttcaa    33180
ttgagcttgc gtgaagtcat caaccattgc gtatcgaaag agcggccgga gcttacgcct    33240
agcgacgtac tgcttcaaga tgtgacggtg gaggaactgg agcggttggc tgaacatacg    33300
gcggcgctcg gcgaactgga gaatgtatac accctgactc cgctgcaaaa agggatgttg    33360
ttccacagcc tgctggatgc cgattcggaa gcttacttcg aacaggtgac cttcgatctg    33420
aacggaagcc tgaatgtcga agccttcacc caaggattgg atacgctggt gcagcggaat    33480
gaggcactgc ggaccaactt tattaccggc tggagggacg agccgattca agtggtattc    33540
cgcgagcgga agtgtgaagt gtacttcgaa gatattcgct cggcaagcga tgaagacccg    33600
gagaagacga tagccgattt cgtcagcgcg gataaagcga acaagttcga tttggctcaa    33660
ggctctctta tgcgcgtgac cgttttgcgc acgggcgacg agtcttacca tgtgatctgg    33720
agtcaccatc acattttgat ggacggctgg tgcatgtcct tcatgatcaa ggaagtgttc    33780
```

```
gacacctact tcgcgttcca agagaagcgg acgctggagc ttcctccggt tacctcgtac   33840
tcccggtata tcgaatggct ggaagctcaa gatgccgcga aagcttcgcg ttactggtcc   33900
gaatatttgg cgggttacga tcagcagacc aagctgcccc aggagaaaac gcagctgaag   33960
cagggcgctt ttgaagcggc tgaaatcgat gtggaactca gcaaggaact gaccgggcaa   34020
atcgagcggg tggcgcgcca gcagcaggtg acgctcaata cgttcatgca gaccgtatgg   34080
ggactggttc tgcagatata caacaacagc gaggatgtcg tattcggctc cgtcgtatcc   34140
gggcgtccgg cggaaattcc gggcatcgaa agcatgatcg gcctgtttat taatacgatc   34200
ccggttcgta ttcaaggcaa agccgaggag acggtagccg atatcttgag aaaaacccag   34260
gatcaagcac tggcatcggg agcttacgaa acgttcccgc tgttcgaaat tcagtcgctg   34320
agcgagcaaa agcgcgactt gatcaaccat attatggttt ttgaaaatta tccgatggaa   34380
gaacagattg agcaggtcgt cggcggtgac aaagaagcgc tgaaaatcgc taatatccag   34440
tcgccagagc aaacgaacta cgacctggac attaccgtca ttccggaaga gcctattttg   34500
ctgcggttta cgtacaatgc gctgacgtac agagaggaag acatcaggct gatccacggt   34560
cattttgccc aggcactgga gaaggttgcg gctaacccga atatccgcgt gaatcagttg   34620
gagcttttga cggcggcgga aaaagaccaa attctcggtg cgtttaaccc ggcgcagccg   34680
gaagcggctc ctgcggccgc gttccaccgg ctgttcgagg aacaggcgga acgcacgccg   34740
gaagaggcgg ccgtcgtgta tgagaatgac cggctgacgt atgcggagct gaacgagcgg   34800
gcgaaccgct tggcggccac gctgcgcgca agcggcatcg gccgggagac gatcgtcggc   34860
attctcgccg agcgttcggt ggacttgctg gtggccgtgc tggccgtctg gaaagcgggc   34920
ggggcatatg tgccgctcga cccggattat ccggcagacc gcgtgcggtt catgcttgaa   34980
gacagtggag cgaaggtact gttgacgcaa ataccgctgc gagaacgcgc cgaagcctgg   35040
ctcggcgaag aggagctggc gctggcagcg gtgctgtacc tcgacgacga agcgtcgtac   35100
agcgaggagc gggcgaatgc gccgattggt tccggcatgg tctccggcca gctgacggat   35160
gctgtggatg acggcgatga gacccatccg aatattggca tgggcagctt ccatgaagct   35220
cgtccggagg atctggcgta tgtgatctat acgtcgggaa cgacgggcaa gccgaaaggc   35280
gtgatgatcg agcaccgcag cctggtgaac acggcagcgg gctaccggcg gaataccgg    35340
ttggatcagt tcccggtacg gctgctgcag ctcgcaagct tctcgttcga cgtgttcgtg   35400
ggagatatcg cgcggacgct gtataacgga ggcacgatgg tgattgtgcc gaaggacgat   35460
cggatcgatc cgtctcgtct gcaccactgg atggagcggg agcgggtcac catttttcgaa  35520
tcaacgccgg cgctgatcgt gccgttctta gagtacgtgc acgagcaggg gctggatatg   35580
agctggatgg agctgttgat cacgagttcg gacagctgca gcgtggcgga ttaccggacc   35640
ttgcaggaac gcttcggctc gttattccgg atcatcaacg catacggcgt gacggaagcg   35700
gcgatcgact ccagcttcta cgacgaggag ctgacgaagc tgccgcagac aggacatgtg   35760
ccgatcggta aagcgtggct gaatgcgaaa ttctacatcg tggacgcgca tctgaacccg   35820
gtgccggtcg gggtgctggg cgagctggtc attggcggag tcggggtagc acgcgggtac   35880
ttgaaccgtc cggagctgac ggaagagaag ttcgtagaca gtccgttcgc cgcgggcgag   35940
cggctgtacc gcacgggaga cttggcgcgg tggatggagg acgggaacgt ggacttcatc   36000
ggccggatcg acaaccaggc gaaaatccgg ggctaccgga ttgagacggg cgaagtcgaa   36060
gcgaagatgc tgagtgtagg tggtgtgaag gaagcggtcg ttgtcgtcag ggaagatcaa   36120
gaaggtcaga aagctttgtg cgcttattat acagtggaag aaggcatgac ggcggcagac   36180
```

```
ctgaagcgtg cgatttccag cgagctgccg gggtacatga tcccgtcgta tttcgtggag   36240
ctggagcgtc tgcctttgac gccgaacgga aagatcgacc ggaaggcgct gccggcaccg   36300
gaaggggcag caggcggagg ccgcgaatac gtggcgccac gcaccgaact ggaggcgaag   36360
ctggccgcca tttggcagga ggtgcttgtt agggagaagg cagtaggtgt aacggacaac   36420
ttctttgacc tcggcggaca ctccctgcgg gctacgacgc ttgtcagcaa aatgcataag   36480
gagctaggca ttgaattccc gctacgcgac gtattccgct actcgacggt tgaggaaatg   36540
gccgcggcta tggagtggct ggagatcggc tcgttcatag ctattccggc tgcggaacct   36600
agcgagtatt atccgctatc atccgctcag aaacgtctct atatcttgaa ccagctggaa   36660
ggaggcgagc tgagctacaa cataccggga gcaatgctgc tcgaagggga gctcgaccgg   36720
cagcggtttg aagaagcgtt ccgcgggctc gtagctcgtc atgaaacgct gcgtaccgga   36780
tttgagatgg taaaaggcga agcggttcaa cggatttatg aagaagctgc tttccaggtg   36840
gaatatgtgc agattagcgg ggaacgggtg aagaaacgg tgcgccaatt cgttcgtcca   36900
tttgatctgg cgaagccgcc acttctgcgt gtaggccttg ccgaactggc gccggaccgg   36960
cacattctga tgttcgatac gcatcatatc gtatctgacg gcgtttcgat ggacgtactg   37020
attgaagagt tcgtccgctt gtacagcggg gagccgttgg agccgctacg cattcagtac   37080
aaagattatg cggtatggca gcaatcggac gagcagaaag ctcagcttgc caagcaggaa   37140
gcctactggc tcgacatgtt ccgcggagaa ctgccggttt tggaattgcc aacggactac   37200
ccacgcccag ctatgcagag ctacgagggt cgcacactgc aattgtttat gaataggag   37260 aaaagcgagg gtctgaaacg gcttgcagcc gagaacggcg caacgcttta catggttctg   37320
cttgctggtt atacaatatt attgcataaa tatactagtc aagaagacgt agtggtcggt   37380
acgccgattg cgggaagaaa tcacagtgac gttcagccgc tgatcggaat gttcgtcaat   37440
actctggcca tccgcagtta tccgactgcg ggtaagacgt tccttgacta cttgaaggaa   37500
atcaaggaga cgacgctggg tgcttttgaa catcagaatt atccgtttga ggaactggtg   37560
gataaggtga acgtagctcg tgatttaagc cgcaatccgc tgttcgatac gatgtttgct   37620
ttgcagaata cagagaattt ggaaatccag cttcccggac tccatttgtc gacgtatgcc   37680
agcgaagaaa ttgttttctaa attcgatctc agcttggacg tcacggagat cgaggaaggc   37740
ttggaatatc tgtttgaata cgccactgct ctttataaaa ccgaaacggt ggagaaattg   37800
gccgctcact acttgcagct gcttgaatct attctctgca accttctgc gactattgcc   37860 gagctgggca ttttgacacc agcggaaaaa gaacaaattc tcggcgcgtt caacccggcg   37920
cagccggaag cggctcctgc ggcggcgttc caccggctgt tcgaggaaca ggcggagcgc   37980
acgccggaag cggaggctgt cgtgtacgag aacgaccggc tgatttatgc ggagctgaac   38040
gagcgggcga accgcttggc ggctacgctg cgcgcaagcg gcatcggccg ggagtcgatc   38100
gtcggcattc tcgccgagcg ttcggtggac ttgctggtgg ccgtgctggc cgtctgaaa   38160 gcgggcgggg cgtatgtgcc gctcgacccg gattatccgg cggaccgcgt gcggttcatg   38220
cttgaagaca gcggagcgaa ggttctgctg acgcaaaagg tgctgcgaga gcgcgccgaa   38280
gcctggctcg cgcgaagagga gctgacgctg gcagcggtgc tgtacctcga cgacgaagcg   38340
tcgtacagcg aggtgcgggc gaatgcgccg attggctccg gcatggtctc cggcaagctg   38400
atggatgctg tgaatgacgg cgatgggacc catccgaatg ttgacatggg cagcttccat   38460
gaagcccgtc cggaggatct ggcgtacgtg atctatacgt cgggaacgac gggcaagccg   38520
```

```
aagggcgtga tgatcgagca ccgcagcctg gtgaacacgg cagcgggcta ccggcgggaa    38580
taccggttgg atcagttccc ggtgcggctg ctgcagctcg caagcttctc gttcgacgta    38640
ttcgtgggcg atatcgcgcg gacgctgtat aacggaggca cgatggtgat tgtgacgaag    38700
gacgaccgga tcgatccgtc tcgtctgcac cactggatgg agcgggagcg ggtcaccatc    38760
ttcgaatcga cgccggcgct aatcgtgccg ttcctggagt acgtgcacga gcagggctg    38820 gatatgagct ggatggagct gttgatcacg agttcggaca gctgcagcgt ggcggattac    38880
cggaccttgc aggaacgctt cggctcgttg ttccggatca tcaatgctta tggcgtgacg    38940
gaagcggcga tcgactccag cttctacgac gaggagctga cgaagctgcc acagacaggc    39000
catgtgccga tcggcaaagc gtggctgaat gcgaaattct acatcgtgga cgcgcatctg    39060
aacccggtgc cggtcgggt gctgggcgag ctggtcatcg gcggagtcgg agtggcgcga    39120
gggtacttga accgtccgga gctgacggaa agaagttcg tagacagtcc gttcgccgcg    39180
ggcgagcgac tgtaccgcac gggagacttg gcgcggtgga tggaggacgg gaacgtggac    39240
ttcatcggcc ggatcgacaa ccaggcgaaa atccgggggt accggattga gacgggcgaa    39300
gtcgaagcga agctgctaag tgtggaaggc gtgcgcgaag cggtggtgct ggttcgaagt    39360
gacgcgaacg gcagaaagc gctgtgtgcg tactacacaa ttgatggcga atttacagcg    39420
gcagacctga acgggcgat tgccagcgag ctgccggggt acatgatccc gtcgtacttc    39480
gtggagctga gcgcctgcc tctgacgccg aacgggaaaa tcgaccggaa ggcgctgccg    39540
gcgccggaag ggggagcaaa cgcaggccgc gaatacgtgg cgccgcgcac cgaactggag    39600
gcgaaactgg tcgccatctg gcaggacgtg ctcgggccgg tcacgattgg cgtaacggac    39660
aacttcttcg acctcggtgg gcactccctg cgggcgacga cgctggtcag caaggtgcac    39720
aaggagctga gcgtggacct gccgttgcgc gatgtgttcc ggcactcgac catcgaagcg    39780
atggccgaag cgataagcca attggagcgg caggaacacc tctccattcc ggttctggat    39840
aagagggatt actatccgct ttcctccgtg cagaaacggc tgtatatcca gcagcagatg    39900
gaaggcgccg agcttagcta caatatgtcc ggcatgacgg ttctcgtcgg gcgtttggaa    39960
cggaatcaat tcgaggcggc gctcaaagga ttgatagctc gtcacgaaat tttgcgaacc    40020
ggcttcgaaa tggtcgacgg cgaaccggta caacggattt atccggactt gaagtttgcc    40080
gtcgagtata cgaaagcgat ggaaagtgaa acgaagagca tcgtagacgg ctttgtacgc    40140
gtctttgatt tggagcggcc gccgctgctg cgtgtgggct tagtcgaaat ggaagcggaa    40200
cggcatttgc tcatgctgga cattcatcat atcgtcacgg atggcatgtc gatgggtatc    40260
ttcgtcgaag agctgctgcg cctgtataac ggcgagaatc tggaaccact tcggattcaa    40320
tacaaggaat tcgccgcttg gcagcagtcc gaacctgtaa aagagcggct gaaacgtcag    40380
gaagcctact ggctggacgt gctggaaggc gaactgccga cgcttgaact gccaacggac    40440
tttgtcagac ctgccgctcg cagctttgag ggagatgtgc tgcctttcag catcgacaag    40500
cagatgaccg acagcttgca gcgcatcgcc gatgagaacg tggcaccct ttatatggtg    40560 ttatcggcgg tctattcaat cctgctcagc aagtactcgg gacaagaaga tttcattgta    40620
ggcacgccgg tttcaggccg cacacatgca gacctggagc cgctcatcgg aatgtttgtc    40680
aacactttgg cgattcgcca ttatccgtcc ggggagaaga cgttcctcgc ttacttgaac    40740
gaagtcaaag aaacgatgct gggggcctac gatcaccagg attatccgtt cgaggagctt    40800
gtgaaaaagc tgcaggttcc gcgagatcta agccgcaatc ctgtattcga tgtcatgttt    40860
gctctggaaa ccaaggaaga taacgttcaa aacttcgggg atatcaggat cgaatcttat    40920
```

```
ccggaaactc atacggtttc ccaatttgat ctaaccttga tcatttcgtt gctggatgag   40980
ggaatgaacg ggcagtttga atatgccacc aagttgttca cacgcaatct gatcgacaat   41040
ttcgctcagg acctgctcgt aatcatctct caaatttgcg aacagccttc ggtgctgctg   41100
aaggatattt ccctgaacgg gcaatccgaa caggagcaag atgtgctaga ggccattgat   41160
attatttc                                                            41169
```

<210> SEQ ID NO 11
<211> LENGTH: 1102
<212> TYPE: PRT
<213> ORGANISM: Paenibacillus alvei

<400> SEQUENCE: 11

```
Met Lys Ser Leu Phe Glu Lys Glu Glu Arg Tyr Trp Ser Gly Lys Phe
1               5                   10                  15

Asp Ala Asp Asp Asn Leu Ser Phe Leu Pro Tyr Ser Gln Ser Ser Lys
                20                  25                  30

Leu Ser Ala Asp Gly Glu Ala Ala Glu Pro Gly Leu Leu His Arg
            35                  40                  45

Thr Leu Pro Ser Glu Leu Ser Glu Arg Ile Ile Arg Leu Ala Asn Gly
    50                  55                  60

Ser Asp Leu Ala Met Tyr Met Ile Val Leu Ala Gly Val Lys Ser Leu
65                  70                  75                  80

Leu Phe Lys Tyr Thr Gly Gln Asp Gln Val Leu Val Gly Met Pro Ser
                85                  90                  95

Tyr Ser Ala Asp Pro Asp Gly Thr Pro Pro His Asp Ile Leu Val
            100                 105                 110

Ile Lys Thr Ala Val Ser His Gln Thr Thr Leu Lys Thr Leu Leu Gly
        115                 120                 125

Gly Ile Lys Ala Ser Ile Gly Glu Ala Leu Glu His Gln His Leu Pro
    130                 135                 140

Phe Gln Lys Met Val Glu Pro Leu His Leu Asp Tyr Thr Gly Asp Gly
145                 150                 155                 160

Leu Pro Val Val Asn Thr Val Ala Ser Phe Ala Pro Ile His Pro Glu
                165                 170                 175

Pro Leu Gly Asn Arg Val Ala Ala Asp Thr Val Phe Arg Phe Asp Arg
            180                 185                 190

Gln Asn His Ser Ile Glu Leu Glu Ile Ser Phe Asp Gly Gln Arg Tyr
        195                 200                 205

Glu Arg Ala Phe Val Glu Gln Ala Ala Asp His Phe Val Arg Leu Leu
    210                 215                 220

Ser Leu Leu Leu Phe Gln Pro Asp Leu Glu Leu Gly Gln Ala Asp Val
225                 230                 235                 240

Leu Ser Pro Asp Glu Arg Glu Thr Leu Leu Lys Arg Phe Asn Asp Thr
                245                 250                 255

Glu Thr Gly Phe Glu Arg Gly Lys Thr Ile His Gly Leu Phe Glu Glu
            260                 265                 270

Gln Ala Glu Leu Tyr Pro Asp Asn Val Ala Ala Val Met Asn Glu Arg
        275                 280                 285

Gln Leu Thr Tyr Arg Glu Leu Asn Glu Arg Ser Asn Arg Leu Ala Arg
    290                 295                 300

Lys Leu Arg Glu Thr Gly Val Glu Ala Asp Gln Leu Val Ala Ile Leu
305                 310                 315                 320
```

```
Ala Glu Arg Ser Leu Asp Met Val Val Gly Ile Leu Ala Ile Leu Lys
                325                 330                 335
Ala Gly Gly Ala Tyr Val Pro Val Asp Pro Asp Tyr Pro Glu Glu Arg
            340                 345                 350
Ile Arg Phe Met Ile Glu Asp Ser Gly Ala Pro Leu Leu Leu Ile Gln
        355                 360                 365
Lys His Leu His Glu Lys Thr Asp Phe Ala Gly Thr Arg Leu Glu Leu
    370                 375                 380
Asp Asp Phe Val Trp Asn Asp Arg Gly Val Asp Ser Glu Gly Arg Leu
385                 390                 395                 400
Asp Ala Ser Asn Leu Glu Pro Ile Ser Gly Pro Gly Asn Leu Ala Tyr
                405                 410                 415
Val Ile Tyr Thr Ser Gly Thr Thr Gly Arg Pro Lys Gly Thr Leu Ile
            420                 425                 430
Glu His Lys Asn Val Val Arg Leu Leu Phe Asn Asp Lys Asn Leu Phe
        435                 440                 445
Asp Phe Gly Pro Ser Asp Thr Trp Thr Leu Phe His Ser Phe Cys Phe
    450                 455                 460
Asp Phe Ser Val Trp Glu Met Tyr Gly Ala Leu Leu Tyr Gly Gly Lys
465                 470                 475                 480
Leu Val Ile Val Pro Pro Leu Thr Ala Lys Asn Pro Ala Asp Phe Leu
                485                 490                 495
Val Leu Leu Gly His Glu Gln Val Thr Ile Leu Asn Gln Thr Pro Thr
            500                 505                 510
Tyr Phe Tyr Gln Leu Leu Arg Lys Val Leu Ala Asp His Pro Tyr Asp
        515                 520                 525
Leu Arg Ile Arg Asn Val Ile Phe Gly Gly Glu Ala Leu Ser Pro Leu
    530                 535                 540
Leu Leu Lys Gly Phe Lys Thr Lys Tyr Pro Glu Thr Lys Leu Ile Asn
545                 550                 555                 560
Met Tyr Gly Ile Thr Glu Thr Thr Val His Val Thr Tyr Lys Glu Ile
                565                 570                 575
Thr Trp Val Glu Met Glu Ala Ala Lys Ser Asn Ile Gly Lys Pro Ile
            580                 585                 590
Pro Thr Leu Arg Val Tyr Val Leu Asp Glu Asn Arg Arg Pro Val Pro
        595                 600                 605
Ile Gly Val Ala Gly Glu Met Tyr Val Ala Gly Glu Gly Leu Ala Arg
    610                 615                 620
Gly Tyr Leu Asn Arg Pro Asp Leu Thr Ala Glu Lys Phe Val Asp Ser
625                 630                 635                 640
Pro Phe Ala Glu Gly Glu Lys Leu Tyr Arg Ser Gly Asp Leu Ala Val
                645                 650                 655
Trp Leu Pro Asp Gly Asn Ile Glu Tyr Leu Gly Arg Ile Asp His Gln
            660                 665                 670
Val Lys Ile Arg Gly Tyr Arg Ile Glu Leu Asp Glu Ile Glu Thr Gln
        675                 680                 685
Leu Leu Lys Ile Ala Ala Val Gln Glu Ala Lys Val Leu Asp Arg Asp
    690                 695                 700
Asp Ala Asn Gly Gln Lys Gln Leu Val Ala Tyr Tyr Val Ala Glu Met
705                 710                 715                 720
Arg Leu Ala Ala His Glu Leu Lys Glu Glu Leu Ala Lys Gln Leu Pro
                725                 730                 735
Gly Tyr Met Ile Pro Ser His Phe Val Gln Leu Ser Arg Met Pro Leu
```

740                 745                 750
Thr Pro Asn Gly Lys Ile Asp Arg Lys Ala Leu Pro Ala Pro Glu Glu
            755                 760                 765

Val Ala Leu Gly Ala Glu Tyr Val Ala Pro Arg Thr Leu Leu Glu
    770                 775                 780

Met Lys Ile Ala Arg Val Trp Gln Asp Thr Leu Gly Val Pro Gln Val
785                 790                 795                 800

Gly Val Lys Asp Asn Phe Phe Asp Leu Gly Gly Asn Ser Leu Ser Leu
            805                 810                 815

Met Arg Leu Val Gln Ala Val Tyr Asp Glu Thr Gly Ile Glu Ile Pro
        820                 825                 830

Leu Asn Arg Gln Phe His His Val Thr Val Glu Ala Met Ala Phe Glu
            835                 840                 845

Glu Gly Asp Leu Gly Leu Asp Lys Gly Asp Ser Phe Ile Lys Leu
    850                 855                 860

Asn Lys Ala Gly Asp Leu Asn Val Phe Cys Phe Pro Pro Gly Ser Gly
865                 870                 875                 880

Phe Gly Ile Gly Tyr Arg Glu Leu Ala Ser Arg Leu Asp Gly Gln Phe
            885                 890                 895

Val Leu Tyr Gly Ile Asp Phe Ile Asp Asp Thr Ala Asp Tyr Glu Ala
        900                 905                 910

Met Leu Asn Arg Tyr Val Asp Glu Ile Val Arg Ile Gln Pro Glu Gly
            915                 920                 925

Pro Tyr Val Leu Leu Gly Tyr Cys Phe Gly Gly Asn Leu Thr Phe Glu
    930                 935                 940

Val Ala Lys Thr Met Glu Lys Arg Gly Tyr Pro Val Thr Asp Val Leu
945                 950                 955                 960

Met Val Asp Ser Trp Ile Lys Glu Thr Leu Thr Pro Ser Glu Thr Ser
            965                 970                 975

Glu Lys Glu Leu Glu Glu Met Leu Ala Asp Phe Asp Glu Glu Lys
        980                 985                 990

Glu Leu Met Ser Asn Pro Leu Val Arg Glu Arg Val His Gln Lys Val
            995                 1000                1005

Lys Ala Thr Leu Ala Tyr Glu Ala Gln Leu Ile Asn Ser Gly Thr Ile
    1010                1015                1020

Pro Ala Arg Ile Tyr Glu Leu Ile Ala Lys Asp Ser Glu Ala Phe Arg
1025                1030                1035                1040

Leu Glu His Gln Leu Pro Ser Trp Arg Gly Ala Thr Thr Gln Ala Tyr
            1045                1050                1055

Thr Asp Tyr Arg Leu Glu Gly Ala His Glu Glu Leu Leu Glu Leu Ala
        1060                1065                1070

Arg Val Asp Glu Thr Ala Val Val Ile Arg Asp Ile Leu Glu Gln Val
            1075                1080                1085

Lys Arg Gln Ile Glu Val Glu Ala Gly Val Leu His Gly Ser
    1090                1095                1100

<210> SEQ ID NO 12
<211> LENGTH: 608
<212> TYPE: PRT
<213> ORGANISM: Paenibacillus alvei

<400> SEQUENCE: 12

Met Glu Ala Asp Arg Gln Pro Ser Val Gln Glu Gln Gly Thr Ala Val
1               5                   10                  15

-continued

```
Pro Ser Lys Arg Gln Thr Ala Tyr Ala Thr Trp Lys Ala Phe Arg Trp
            20                  25                  30

Leu Met Ser Tyr Val Ser Arg His Ile Gly Trp Met Thr Val Gly Thr
        35                  40                  45

Leu Ser Ala Ile Ala Ala Val Ile Glu Ile Trp Thr Gly Ser Leu
    50                  55                  60

Ile Glu Gln Leu Thr Thr Gln Ala Glu Lys Gly Ala Gly Pro Leu Val
65                  70                  75                  80

Leu Gln Ile Val Tyr Thr Val Phe Val Ile Leu Ile Gly Val Pro
                85                  90                  95

Ala Lys Phe Phe Met Ser Phe Gly Val Glu Arg Ser Ser Ala Ser Ala
                100                 105                 110

Val Gln Asp Ile Arg Asn His Val Met Arg His Ile Gly Lys Leu Pro
            115                 120                 125

Val Ser Tyr Leu Glu Lys Gln His Ser Gly Asp Val Leu Ser Arg Ile
            130                 135                 140

Asn Asn Asp Leu Gln Leu Ile Gln Gln Phe Met Ile Arg Asp Leu Ala
145                 150                 155                 160

Gln Trp Phe Tyr His Pro Leu Leu Phe Ile Gly Cys Phe Ala Tyr Leu
                165                 170                 175

Ile Tyr Leu Gln Trp Glu Leu Met Leu Ser Ser Leu Leu Phe Pro
            180                 185                 190

Val Ala Leu Leu Val Ser Gln Trp Ile Gly Lys Gln Leu Glu Arg Leu
            195                 200                 205

Thr Glu Glu Ala Gln Ala Asn Met Gly Arg Met Asn Val Asn Leu Gln
    210                 215                 220

Asp Thr Leu Gly Gly Met Pro Val Val Lys Ser Tyr Leu Leu Ser Gly
225                 230                 235                 240

Met Leu Ser Arg Ser Tyr Gln Val Leu Leu Gln Leu Thr Ala Gln Lys
                245                 250                 255

Lys Leu Ala Val Lys Lys Arg Glu Ala Trp Val Asn Pro Leu Leu Ser
                260                 265                 270

Thr Leu Met Ile Ser Pro Ile Ile Phe Ala Val Ser Tyr Gly Ser Tyr
    275                 280                 285

Leu Ile Tyr Asn Gly Gln Leu Gly Ala Gly Glu Leu Ile Ala Phe Leu
    290                 295                 300

Tyr Leu Leu Asn Leu Cys Leu Glu Pro Leu Glu His Ile Pro Glu Leu
305                 310                 315                 320

Ile Thr Arg Thr Phe Glu Met Ala Gly Ala Leu Arg Arg Val Ser Glu
                325                 330                 335

Ile Val Glu Gln Pro Thr Glu Thr Glu Asn Gly Arg Ser Leu Pro Lys
            340                 345                 350

Ala Ser Ala Ala Pro Ile Glu Phe Gln Asn Val Thr Phe Gly Tyr Glu
            355                 360                 365

Glu Ser Ser Pro Ile Leu Arg Asn Val Ser Phe Ser Val Pro Glu Gly
            370                 375                 380

Lys Thr Ile Ala Leu Val Gly Ala Ser Gly Gly Lys Ser Thr Val
385                 390                 395                 400

Phe Lys Leu Val Cys Gly Phe Tyr Pro Leu Pro Glu Asp Gln Gly Glu
                405                 410                 415

Ile Arg Val Phe Gly Ser Leu Ile His Gly Ala Asp Pro Glu Gln Leu
            420                 425                 430

Arg Ser His Phe Ser Val Val Thr Gln Asp Ser Tyr Leu Phe Ser Gly
```

```
                435                 440                 445
Thr Ile Ala Glu Asn Ile Gly Phe Gly Arg Glu Ala Ser Met Asp
450                 455                 460
Lys Ile Ile Glu Ala Ala Lys Ala Ala Gln Ala His Ser Phe Ile Met
465                 470                 475                 480
Gln Leu Glu Gly Gly Tyr Gln Thr Tyr Val Gly Glu Arg Gly Phe
                485                 490                 495
Leu Ser Gly Gly Gln Arg Gln Arg Ile Ala Met Ala Arg Ala Phe Leu
                500                 505                 510
Lys Asp Ala Pro Val Leu Leu Asp Glu Pro Thr Ser Ala Leu Asp
                515                 520                 525
Pro Glu Ser Glu Ser Ala Val Gln Lys Ala Leu Gly Val Leu Met Lys
                530                 535                 540
Gln Arg Thr Thr Met Val Ile Ala His Arg Leu Ser Thr Val Gln Asn
545                 550                 555                 560
Ala Asp Glu Ile Trp Val Met Glu Gln Gly Asn Ile Val Glu Lys Gly
                565                 570                 575
Thr His Glu Gln Leu Leu Glu Met Lys Gly Leu Tyr Ala Gln Ser Tyr
                580                 585                 590
Tyr Gln Glu Phe Thr Glu Ile Ala Glu Arg Arg Glu Val Ala Tyr Thr
                595                 600                 605

<210> SEQ ID NO 13
<211> LENGTH: 577
<212> TYPE: PRT
<213> ORGANISM: Paenibacillus alvei

<400> SEQUENCE: 13

Met Lys Lys Gly Gly Trp Leu Ser Gln Val Lys Glu Leu Gly Tyr Leu
1               5                   10                  15
Leu Thr Phe Met Asn Arg Gln Arg Lys Thr Gln Tyr Ala Ile Gly Leu
                20                  25                  30
Ala Val Thr Ala Leu Thr Gln Thr Phe Phe Leu Ile Ala Phe Ser Leu
                35                  40                  45
Val Val His Asn Leu Val Asp Phe Ala Val Ser Arg Asp Lys Ser Leu
                50                  55                  60
Met Val Glu Ala Phe Ile Ile Leu Gly Ala Ala Leu Phe Leu Glu Asn
65              70                  75                  80
Val Ile Ser Pro Trp Phe Ile Tyr Leu Tyr Gln Arg Ser Val Glu Leu
                85                  90                  95
Thr Val Leu Asn Ile Arg Lys Arg Leu Tyr Asp Lys Leu Cys Arg Val
                100                 105                 110
Arg Pro Arg Phe Leu Glu Gln Thr His His Gly Asp Leu Leu Ser Arg
                115                 120                 125
Val Asn Asn Asp Val Thr Thr Val Glu Phe Thr Phe Ser Gln Val Tyr
                130                 135                 140
Phe Val Leu Leu Leu Gln Val Val Phe Cys Ile Gly Ser Ile Val Ser
145             150                 155                 160
Met Met Leu Ile Asp Trp Arg Phe Ala Gly Val Ser Phe Val Ile Leu
                165                 170                 175
Leu Leu Ser Ser Val Val Ser Leu Lys Phe Ala Arg Asp Ile Arg Ala
                180                 185                 190
Leu Ser Glu Gln Gly Leu Gln Thr Leu Gly Lys Met Thr Glu Lys Phe
                195                 200                 205
```

Lys Asp Phe Met Gly Gly Ile Gln Ile Val Lys Leu Phe Arg Ile Arg
210                 215                 220

Thr Ile Tyr Gly Gln Tyr Glu Ala Leu Asn Glu Gln Met Thr Gln Thr
225                 230                 235                 240

Leu Arg Gln Thr Ala Gln Lys Asn Gly Met Gln Ala Ala Val Asn His
            245                 250                 255

Phe Ile Ser Tyr Val Thr Phe Cys Gly Ile Val Ile Gly Ser Leu
            260                 265                 270

Leu Tyr Ala Tyr Gly Leu Met Gly Met Gly Ser Val Ala Ala Leu Ala
            275                 280                 285

Val Leu Gln Val Asn Leu Thr His Ala Leu Leu Asn Leu Gly Ile Val
290                 295                 300

Leu Ser Met Thr Gln Asn Ser Leu Ala Gly Ala His Arg Ile Gln Glu
305                 310                 315                 320

Val Leu Arg Glu Glu Glu Pro Glu Arg Leu Gly Ser Pro Leu Ser
            325                 330                 335

Glu Leu Val Ser Glu Ala Ala Val Glu Phe Arg Asp Val Glu Phe Ser
            340                 345                 350

Tyr Gln Ala Asp Lys Lys Val Leu Val Asp Met Ser Met Gln Val Phe
            355                 360                 365

Pro Gly Gln Val Ala Ala Ile Val Gly Ala Ser Gly Ser Gly Lys Ser
370                 375                 380

Thr Leu Ile Lys Leu Leu Leu Gly Phe Tyr Pro Val Asp Ser Gly Glu
385                 390                 395                 400

Ile Leu Leu Gln Gly Lys Pro Phe Gly His Tyr Thr Leu Asp Glu Ile
            405                 410                 415

Arg Arg Gln Ile Ala Tyr Val Pro Gln Glu Pro Phe Leu Phe Thr Gly
            420                 425                 430

Thr Ile Glu Glu Asn Ile Arg Tyr Gly Asn Pro Asp Ala Thr Asp Glu
            435                 440                 445

Glu Val Ile Glu Ala Ala Lys Ala Ala Tyr Ala His His Phe Ile Gln
450                 455                 460

Glu Leu Pro Glu Gln Tyr Lys Thr Pro Val Gly Glu Arg Gly Ala Ser
465                 470                 475                 480

Leu Ser Gly Gly Gln Arg Gln Arg Ile Ala Ile Ala Arg Ala Ile Leu
            485                 490                 495

Lys Asn Ala Pro Ile Leu Leu Leu Asp Glu Ala Thr Ser Ala Leu Asp
            500                 505                 510

Asn Glu Ser Gln His Trp Val Gln Gln Ala Leu Asn Val Leu Met Lys
            515                 520                 525

Gly Arg Thr Thr Ile Leu Ile Ala His Arg Leu Ser Thr Val Glu His
530                 535                 540

Ala Asp Leu Ile Thr Val Met Asn Gln Gly Thr Val Val Glu Arg Gly
545                 550                 555                 560

Arg His Gln Asp Leu Leu Ala His Gly Gly Tyr Tyr Ala Arg Leu Tyr
            565                 570                 575

Gly

<210> SEQ ID NO 14
<211> LENGTH: 6292
<212> TYPE: PRT
<213> ORGANISM: Paenibacillus alvei

<400> SEQUENCE: 14

-continued

```
Met Glu Ile Met Asn Pro Gly Thr Ser Ile Thr Met Leu Ser Ala Thr
1               5                   10                  15

Tyr Gln Ile Thr Gly Gln Ile Asp Thr Gln Leu Leu Glu Gln Ala Ala
            20                  25                  30

Ala Glu Ile Val Lys Thr Tyr Asp Ala Phe Arg Ile Arg Ile Ser Gly
            35                  40                  45

Asp Leu Gln Asn Pro Thr Gln Trp Phe Glu Pro Glu Asn Val Gln
    50                  55                  60

Ala Arg Ile Ser Arg Leu Glu Ile Gly Thr Thr Glu Gln Phe Tyr Ala
65                  70                  75                  80

Trp Val Lys Glu Val Ser Glu Lys Pro Ala Ser Val Phe Asp Glu His
                85                  90                  95

Leu Tyr Gln Phe Thr Ile Ile His Phe Ala Asn Gly Gln Val Trp Leu
            100                 105                 110

Asn Leu Thr Val Asn His Ile Ile Ala Asp Gly Leu Ser Val Thr Ala
            115                 120                 125

Leu Leu His Ala Val Met Glu Lys Tyr Met Glu Leu Arg Lys Gly Ile
    130                 135                 140

Ser Ser Ser Tyr Gln Ala Pro Ser Tyr Leu Asp Tyr Ile Ser Ala Glu
145                 150                 155                 160

Arg Glu Tyr Glu Gln Ser Gln Arg Tyr Gln Lys Gly Lys Glu Tyr Trp
                165                 170                 175

Leu Thr Lys Tyr Ser Thr Leu Pro Glu Thr Thr Gly Phe Lys Ser Tyr
            180                 185                 190

Pro Pro Phe Ser Ile Gly Ser Glu Ser Asn Lys Arg Ala Thr Thr Leu
    195                 200                 205

Asp Gly Ser Arg Tyr Glu Arg Ile Leu Ala Phe Ser Glu Gln Tyr Gln
    210                 215                 220

Val Ser Leu Tyr Thr Leu Phe Leu Ser Ala Met Tyr Ala Leu Leu Tyr
225                 230                 235                 240

Lys Leu Thr Asp Ser Thr Asp Val Pro Val Gly Thr Val Phe Ala Asn
            245                 250                 255

Arg Thr Ser Lys Lys Glu Lys Glu Thr Ile Gly Met Phe Val Ser Thr
            260                 265                 270

Val Ala Thr Arg Ile His Leu Asn Pro Asp Gly Asp Val Leu Ser Leu
    275                 280                 285

Ile Gln Ala Val Ser Lys Glu Asn Thr Ala Asp Leu Arg Tyr Gln Lys
    290                 295                 300

Tyr Pro Tyr Asn Gln Leu Ile Gln Asp Leu Arg Glu Gln His Gly Arg
305                 310                 315                 320

Asn Asp Leu Ser Gly Leu Phe Arg Thr Ser Leu Glu Tyr Leu Pro Leu
            325                 330                 335

Lys Ile Val Glu Tyr Glu Ile Lys Val Arg Leu Glu Ala His Phe
            340                 345                 350

Ala Lys His Glu Met Asp Asp Leu Leu Leu Arg Phe Asp His Met Leu
    355                 360                 365

Asn Glu Gly His Val Ile Leu His Ala Ser Tyr Arg Thr Gly Leu Phe
    370                 375                 380

Glu Thr Ala Glu Ile Asp Arg Ile Met Glu Gln Tyr Val Thr Val Leu
385                 390                 395                 400

Asp Gln Phe Leu Gln Thr Pro Glu Leu Pro Val Arg Glu Ile Ser Leu
            405                 410                 415

Leu Ser Asp Glu Glu Arg Gln Cys Ile Leu Gly Val Phe Asn Pro Pro
```

-continued

```
            420                 425                 430
Val Ala Gly Leu Ser Glu Gly Glu Ala Phe His Arg Tyr Val Glu Lys
            435                 440                 445

Phe Ala Arg Glu Ile Pro Asp His Pro Ala Val Val Tyr Met Asp Thr
            450                 455                 460

Gln Leu Thr Tyr Gly Glu Leu Asn Glu Arg Ala Glu Arg Leu Ala Ser
465                 470                 475                 480

Leu Leu Arg Glu Gln Gly Val Gly Lys Glu Thr Ile Thr Gly Ile Trp
            485                 490                 495

Ala Glu Arg Ser Val Glu Leu Leu Ile Gly Val Leu Ala Val Trp Lys
            500                 505                 510

Ala Gly Gly Ala Tyr Val Pro Leu Asp Pro Asp Tyr Pro Ala Glu Arg
            515                 520                 525

Ile Glu Tyr Met Leu Ser Asp Ser Gly Ala Ser Val Leu Leu Thr Gln
            530                 535                 540

Arg His Leu Leu Glu Arg Ala Gly Gly Trp Leu Ala Asp Asp Arg Leu
545                 550                 555                 560

Lys Leu Gln Ala Val Tyr Ala Met Asp Asp Glu Gln Ile Tyr Asn Arg
            565                 570                 575

Asp Ala Leu Ala Val Glu Phe Glu Ser Ala Asp Ser Ala Pro Gln Asp
            580                 585                 590

Leu Ala Tyr Val Ile Tyr Thr Ser Gly Thr Thr Gly Arg Pro Lys Gly
            595                 600                 605

Val Met Ile Glu His Gly Ser Leu Leu Asn Thr Ala Asp Ala Tyr Arg
            610                 615                 620

Arg Glu Tyr Arg Leu Asp Gln Phe Pro Val Arg Leu Leu Gln Leu Ala
625                 630                 635                 640

Ser Phe Ser Phe Asp Val Phe Val Gly Asp Ile Ala Arg Thr Leu Tyr
            645                 650                 655

Asn Gly Gly Thr Met Val Ile Val Pro Lys Asp Asp Arg Ile Asp Pro
            660                 665                 670

Asn Arg Leu Tyr Gly Trp Ile Arg Asp Gln Asn Ile Thr Val Phe Glu
            675                 680                 685

Ser Thr Pro Ala Leu Ile Leu Pro Phe Met Gln His Ile Tyr Glu Glu
            690                 695                 700

Gly Leu Asp Val Ser Ser Met Gln Leu Leu Ile Thr Ser Ser Asp Ala
705                 710                 715                 720

Cys Ser Val Thr Asp Tyr Arg Leu Leu Gln Glu Arg Phe Gly Gly Gln
            725                 730                 735

Phe Arg Ile Ile Asn Ser Tyr Gly Val Thr Glu Ala Ala Ile Asp Ser
            740                 745                 750

Ser Phe Tyr Asp Glu Thr Leu Asp Lys Leu Pro Ser Ser Gly His Val
            755                 760                 765

Pro Ile Gly Lys Ala Trp Leu Asn Ala Arg Phe Tyr Ile Val Asp Ala
            770                 775                 780

Ala Leu Lys Pro Val Pro Val Gly Val Pro Gly Glu Leu Val Ile Gly
785                 790                 795                 800

Gly Ala Gly Val Ala Arg Gly Tyr Trp Asn Arg Pro Asp Leu Thr Ala
            805                 810                 815

Glu Lys Phe Ala Asp Ser Pro Phe Val Pro Gly Glu Arg Leu Tyr Arg
            820                 825                 830

Thr Gly Asp Leu Ala Arg Trp Leu Glu Asp Gly Asn Val Asp Phe Ile
            835                 840                 845
```

```
Gly Arg Ile Asp Tyr Gln Val Lys Ile Arg Gly Phe Arg Ile Glu Leu
    850                 855                 860

Gly Glu Ile Glu Thr Ala Leu Leu Arg Phe Pro Gly Val Lys Gln Ala
865                 870                 875                 880

Val Val Thr Asp Arg Thr Asp Lys Gln Gly Gln Lys Tyr Leu Cys Gly
            885                 890                 895

Tyr Val Ala Ala Asp Thr Ser Leu Gln Leu Ser Asp Leu Leu Ser Gln
                900                 905                 910

Leu Lys Gln Glu Leu Pro Ala His Met Val Pro Ala Arg Leu Val Ser
        915                 920                 925

Leu Asp Lys Leu Pro Leu Thr Pro Asn Gly Lys Ile Asp Arg Lys Ala
    930                 935                 940

Leu Pro Glu Pro Thr Gly Glu Val Glu Ala Gly Arg Glu Tyr Val Ala
945                 950                 955                 960

Pro Arg Thr Thr Leu Glu Thr Arg Leu Ala Leu Ile Trp Gln Gln Val
            965                 970                 975

Leu Gly Ile Ala Arg Val Gly Val Glu Asp Asp Phe Phe Asp Leu Gly
                980                 985                 990

Gly His Ser Leu Arg Ala Ser Thr Leu Val Ser Lys Ile Arg Lys Glu
        995                 1000                1005

Leu Gln Val Glu Val Pro Leu Arg Asp Val Phe Arg Tyr Thr Thr Ile
    1010                1015                1020

Lys Gln Leu Ala Gln Arg Ile Gly Gly Leu Lys Gln Gln Glu Thr Tyr
1025                1030                1035                1040

Glu Ile Thr Lys Ala Ala Glu Ala Glu Tyr Tyr Pro Val Ser Ser Glu
            1045                1050                1055

Gln Lys Arg Leu Tyr Val Leu Arg Gln Leu Asp Gly Ala Glu Arg Ser
                1060                1065                1070

Tyr Asn Met Ser Ala Ala Leu Leu Leu Glu Gly Lys Leu Asp Arg Thr
        1075                1080                1085

Arg Val Glu Tyr Ala Phe Arg Ala Leu Ile Gln Arg His Glu Thr Leu
    1090                1095                1100

Arg Thr Gly Ile Glu Gln Val Gln Gly Glu Leu Val Gln Arg Ile Tyr
1105                1110                1115                1120

Asp Glu Val Glu Phe Ala Val Asp Tyr Phe Gln Ala Ser Glu Arg Glu
            1125                1130                1135

Val Glu Gln Gly Val Glu Ala Tyr Tyr Arg Pro Phe Asp Leu Thr Lys
                1140                1145                1150

Pro Pro Leu Leu Arg Ile Gly Leu Ile Glu Val Thr Glu Asp Arg His
        1155                1160                1165

Ile Leu Leu Phe Asp Met His His Ile Val Ser Asp Gly Ile Ser Thr
    1170                1175                1180

Ala Leu Leu Phe Asp Glu Phe Ser Arg Leu Tyr Arg Gly Glu Glu Leu
1185                1190                1195                1200

Ala Pro Leu Arg Ile Gln Tyr Lys Asp Tyr Ala Val Trp Gln His Ser
            1205                1210                1215

Glu Ala Tyr Ala Gln Leu Leu Gln Pro Gln Lys Glu Tyr Trp Leu Glu
                1220                1225                1230

Gln Leu Ser Gly Glu Leu Pro Val Leu Glu Leu Pro Thr Asp Phe Pro
        1235                1240                1245

Arg Pro Ala Val Gln Ser Phe Asp Gly Arg Thr Val Lys Phe Tyr Ile
    1250                1255                1260
```

-continued

```
Gly Lys Glu Arg Thr Glu Lys Leu Lys Glu Leu Ala Ser Arg Thr Gly
1265                1270                1275                1280

Thr Thr Leu Tyr Met Val Leu Leu Ser Ala Tyr Thr Ile Leu Met His
            1285                1290                1295

Lys Tyr Ser Gly Gln Glu Asp Leu Ile Val Gly Thr Pro Ile Ala Gly
        1300                1305                1310

Arg Thr Gln Asp Glu Val Gln Pro Ile Val Gly Met Phe Ile Asn Thr
    1315                1320                1325

Leu Thr Ile Arg Ser Arg Pro Glu Arg Ser Lys Pro Tyr Leu Ser Tyr
1330                1335                1340

Leu Glu Glu Ile Lys Asp Ile Thr Leu Gly Ala Phe Glu His Gln Asn
1345                1350                1355                1360

Tyr Leu Phe Glu Asp Leu Val Glu Ser Leu His Ile Pro Arg Ala Thr
            1365                1370                1375

Gly Arg Asn Pro Leu Phe Asp Thr Phe Phe Ser Leu Gln Asn Thr Glu
        1380                1385                1390

Asn Glu Gln Ile Val Ile Glu Gly Leu Glu Gln Ser Phe Tyr Pro Leu
    1395                1400                1405

Glu Asn Arg Thr Ser Lys Phe Glu Leu Leu Leu Asp Ile Ser Glu Gln
1410                1415                1420

Asp Gly Gln Leu Glu Cys Arg Leu Glu Tyr Ala Thr Ala Leu Tyr Lys
1425                1430                1435                1440

Gln Glu Thr Ala Glu Arg Phe Ala Lys His Tyr Asp Lys Leu Leu Glu
            1445                1450                1455

Thr Ile Ala Ala Ala Pro Asp Gly Asp Ile Ala Ser Leu Glu Met Leu
        1460                1465                1470

Thr Glu Glu Ile Arg Glu Leu Val Arg Gly Phe Asn Asp Ser Glu
    1475                1480                1485

Ala Asp Tyr Pro Arg Gln Gln Thr Ile His Gly Leu Phe Glu Glu Gln
1490                1495                1500

Ala Glu Leu Tyr Pro Asp Asn Val Ala Ala Val Met Asn Glu Arg Gln
1505                1510                1515                1520

Leu Thr Tyr Arg Glu Leu Asn Glu Arg Ser Asn Arg Leu Ala Arg Lys
            1525                1530                1535

Leu Arg Glu Thr Gly Val Glu Ala Asp Gln Leu Val Ala Ile Leu Ala
        1540                1545                1550

Glu Arg Ser Leu Asp Met Val Val Gly Ile Leu Ala Ile Leu Lys Ala
    1555                1560                1565

Gly Gly Ala Tyr Val Pro Val Asp Pro Asp Tyr Pro Glu Glu Arg Ile
1570                1575                1580

Arg Phe Met Ile Glu Asp Ser Gly Ala Pro Leu Leu Leu Ile Gln Lys
1585                1590                1595                1600

His Leu His Glu Lys Thr Asp Phe Ala Gly Thr Arg Leu Glu Leu Asp
            1605                1610                1615

Asp Phe Val Trp Gly Asp Arg Gly Ala Asp Ser Glu Gly Ala Leu Asp
        1620                1625                1630

Ala Ser Asn Leu Asp Pro Ile Ser Gly Pro Gly Asn Leu Ala Tyr Val
    1635                1640                1645

Ile Tyr Thr Ser Gly Thr Thr Gly Arg Pro Lys Gly Thr Leu Ile Glu
1650                1655                1660

His Lys Asn Val Val Arg Leu Leu Phe Asn Asp Lys Asn Leu Phe Asp
1665                1670                1675                1680

Phe Gly Pro Ser Asp Thr Trp Thr Leu Phe His Ser Phe Cys Phe Asp
```

```
                    1685                1690                1695
Phe Ser Val Trp Glu Met Tyr Gly Ala Leu Leu Tyr Gly Gly Lys Leu
            1700                1705                1710

Val Ile Val Pro Pro Leu Met Ala Lys Asn Pro Ala Asp Phe Leu Ala
            1715                1720                1725

Leu Leu Gly Arg Glu Gln Ile Thr Ile Leu Asn Gln Thr Pro Thr Tyr
            1730                1735                1740

Phe Tyr Gln Leu Leu Arg Glu Val Leu Ala Asp His Pro Tyr Asp Leu
1745                1750                1755                1760

Arg Ile Arg Asn Val Ile Phe Gly Gly Glu Ala Leu Ser Pro Leu Leu
            1765                1770                1775

Leu Lys Gly Phe Lys Thr Lys Tyr Pro Glu Thr Lys Leu Ile Asn Met
            1780                1785                1790

Tyr Gly Ile Thr Glu Thr Thr Val His Val Thr Tyr Lys Glu Ile Thr
            1795                1800                1805

Trp Val Glu Met Glu Ala Ala Lys Ser Asn Ile Gly Lys Pro Ile Pro
            1810                1815                1820

Thr Leu Arg Val Tyr Val Leu Asp Glu Asn Arg Arg Pro Val Pro Ile
1825                1830                1835                1840

Gly Val Ala Gly Glu Met Tyr Val Ala Gly Glu Gly Leu Ala Arg Gly
            1845                1850                1855

Tyr Leu Asn Arg Pro Asp Leu Thr Ala Glu Lys Phe Val Asp Ser Pro
            1860                1865                1870

Phe Ala Glu Gly Glu Lys Leu Tyr Arg Ser Gly Asp Leu Ala Ala Trp
            1875                1880                1885

Gln Pro Asp Gly Asn Ile Glu Tyr Leu Gly Arg Ile Asp His Gln Val
            1890                1895                1900

Lys Ile Arg Gly Tyr Arg Ile Glu Leu Asp Glu Ile Glu Thr Gln Leu
1905                1910                1915                1920

Leu Asn Val Glu Gly Val Glu Glu Ala Val Val Leu Ala Arg Gln Asp
            1925                1930                1935

Gly Gly Gly Glu Lys Ala Leu Val Ala Tyr Phe Val Ala Asn Arg Thr
            1940                1945                1950

Leu Thr Val Ser Glu Met Arg Thr Ser Leu Ala Lys Glu Met Pro Gly
            1955                1960                1965

Tyr Met Ile Pro Ser Tyr Phe Val Gln Leu Glu Arg Met Pro Leu Thr
            1970                1975                1980

Ser Asn Gly Lys Val Asp Arg Lys Ala Leu Pro Glu Pro Gln Gly Gly
1985                1990                1995                2000

Leu Gln Thr Gly Val Glu Tyr Val Ala Pro Arg Asn Arg Thr Glu Ser
            2005                2010                2015

Gln Leu Val Lys Ile Trp Glu Glu Leu Gly Tyr Ser Gly Ile Gly
            2020                2025                2030

Val Met Asp Asn Phe Phe Glu Leu Gly Gly His Ser Leu Arg Ala Thr
            2035                2040                2045

Asn Leu Val Ser Lys Ile Arg Lys Glu Met Asn Val Glu Phe Pro Leu
            2050                2055                2060

Arg Asp Val Phe Arg Tyr Met Thr Val Glu Ser Met Ala Gly Ala Ile
2065                2070                2075                2080

Ala Ser Leu Glu Glu Thr Arg His Ser Ser Ile Pro Lys Ala Glu Glu
            2085                2090                2095

Arg Ala Tyr Tyr Pro Val Ser Ser Ala Gln Lys Arg Leu Tyr Val Leu
            2100                2105                2110
```

```
Asn Gln Leu Asp Gly Ser Glu Leu Asn Tyr Asn Leu Pro Ser Ala Leu
            2115                2120                2125

Gln Leu Lys Gly Ala Leu Asn Glu Ala Lys Val Glu Lys Ala Leu Thr
        2130                2135                2140

Thr Leu Val Ala Arg His Asp Met Leu Arg Thr Gly Phe Glu Ile Val
2145                2150                2155                2160

Asp Gly Glu Pro Val Gln Arg Ile His Pro Leu Ala Ala Phe Lys Val
                2165                2170                2175

Glu Lys Leu Gln Ala Ser Glu Asp Gln Val Ala Ala Ile Leu Glu Gly
            2180                2185                2190

Phe Ile Gln Pro Phe Asp Leu Thr Gln Pro Pro Leu Leu Arg Ala Leu
        2195                2200                2205

Leu Ile Glu Leu Glu Lys Glu Lys Phe Leu Leu Ala Leu Asp Ile His
    2210                2215                2220

His Ile Gly Ser Asp Gly Leu Ser Met Asp Val Leu Leu Arg Glu Phe
2225                2230                2235                2240

Val Arg Leu Tyr Asn Gly Glu Glu Leu Pro Val Leu Arg Ile Gln Tyr
                2245                2250                2255

Lys Asp Tyr Ala Val Trp Gln Gln Ser Glu Glu Gln Arg Gln Arg Ile
            2260                2265                2270

Lys Gln Gln Glu Glu Tyr Trp Arg Gly Val Phe Asn Ser Glu Leu Pro
        2275                2280                2285

Val Leu Glu Leu Pro Leu Asp Phe Ser Arg Pro Ala Val Gln Gln Phe
    2290                2295                2300

Asp Gly Arg Thr Leu Thr Phe Thr Leu Asp Ala Glu Lys Ser Glu Ala
2305                2310                2315                2320

Leu Lys Arg Leu Ala Gly Asp Ser Gly Ala Thr Leu Tyr Met Leu Leu
                2325                2330                2335

Leu Ala Ala Tyr Ser Val Leu Leu His Lys Tyr Ala Gly Gln Glu Asp
            2340                2345                2350

Ile Val Val Gly Thr Pro Ile Ala Ala Arg Ser His Thr Asp Leu Gln
        2355                2360                2365

Pro Ile Ile Gly Met Phe Val Asn Thr Leu Ala Leu Arg Leu Gly Pro
    2370                2375                2380

Ala Ala Glu Arg Thr Phe Leu Asp Tyr Leu Gln Glu Val Lys Glu Thr
2385                2390                2395                2400

Thr Leu Gly Ala Tyr Glu His Gln Asp Tyr Pro Phe Glu Glu Leu Val
                2405                2410                2415

Glu Ala Leu Gln Val Ser Arg Asp Leu Ser Arg Asn Pro Leu Phe Asp
            2420                2425                2430

Thr Met Phe Ser Leu Gln Lys His Glu Ser Leu Asp Leu Thr Leu Glu
        2435                2440                2445

Gly Leu Gln Trp Ser Leu Phe Asp Ile Glu Glu Lys Thr Ala Lys Phe
    2450                2455                2460

Asp Leu Ser Phe Asp Ile Val Glu Ala Asp Asn Glu Leu Val Cys Lys
2465                2470                2475                2480

Ile Glu Tyr Ala Thr Ser Leu Phe Arg Gln Glu Thr Met Val Arg Leu
                2485                2490                2495

Ala Gly His Tyr Glu Gln Leu Leu Ala Ser Ile Leu Ala Gln Pro Gly
            2500                2505                2510

Ala Arg Ile Ser Asp Leu Asp Ile Leu Thr Asp Ser Glu Lys His Asp
        2515                2520                2525
```

```
Leu Leu Val Gly Phe Asp Val Ser Ser Ala Leu Ala Lys Gln Ser
    2530                2535                2540

Ala Ala Glu Gly Thr Gly Leu Glu Ala Asp Glu Ser Trp Arg Glu Arg
2545                2550                2555                2560

Thr Phe His Glu Leu Phe Glu Glu Gln Ala Glu Arg Thr Pro Gly Ala
                2565                2570                2575

Leu Ala Val Ile Tyr Glu Asp Ser Lys Leu Thr Tyr Ala Glu Leu Asn
            2580                2585                2590

Ala Lys Ala Asn Arg Leu Ala Tyr Ala Leu Arg Ala Arg Gly Val Lys
        2595                2600                2605

Pro Glu Gln Val Val Gly Ile Leu Ala Gly Arg Ser Ala Glu Leu Leu
    2610                2615                2620

Ile Gly Val Leu Ala Val Trp Lys Ala Gly Gly Ala Tyr Val Pro Leu
2625                2630                2635                2640

Asp Pro Asp Tyr Pro Ala Glu Arg Ile Glu Tyr Met Leu Thr Asp Ser
                2645                2650                2655

Gly Ala Ser Val Leu Leu Thr Gln Thr Arg Leu Leu Glu Gln Ala Glu
            2660                2665                2670

Val Trp Arg Ser Asp Gly Ala Leu Ala Leu Gln Thr Val Leu Ala Leu
        2675                2680                2685

Asp Asp Ala Ala Thr Tyr Ser Leu Gly Ala Ala Glu Val Ala Val Gly
    2690                2695                2700

Val Gln Ala Leu Gly Glu Ala Gly Ala Glu Ala Glu Ala Leu Ala Gln
2705                2710                2715                2720

Ala Gln Thr Ala Ala Ala Glu Thr Ser Ala Thr Ala Glu Ala Glu Gln
                2725                2730                2735

Asn Val Leu Ala Ala Asp Leu Ala Ser Asn Pro Ala Asn Val Asn Lys
            2740                2745                2750

Pro Arg Asp Leu Ala Tyr Val Ile Tyr Thr Ser Gly Thr Thr Gly Arg
        2755                2760                2765

Pro Lys Gly Val Ala Val Glu His Arg Ser Leu Val Asn Thr Ala Ala
    2770                2775                2780

Gly Tyr Arg Arg Asp Tyr Arg Leu Asp Gln Phe Pro Ile Arg Leu Leu
2785                2790                2795                2800

Gln Leu Ala Ser Phe Ser Phe Asp Val Phe Val Gly Asp Ile Ala Arg
                2805                2810                2815

Thr Leu Tyr Asn Gly Gly Thr Met Val Ile Val Pro Lys Asp Asp Arg
            2820                2825                2830

Ile Asp Pro Thr Arg Leu Tyr Gly Trp Ile Arg Asp Tyr Ala Val Thr
        2835                2840                2845

Val Phe Glu Ser Thr Pro Ala Leu Ile Val Pro Phe Met Glu His Val
    2850                2855                2860

Tyr Ala Glu Gly Leu Asp Leu Ser Ser Met Gln Leu Leu Leu Thr Ser
2865                2870                2875                2880

Ser Asp Ala Cys Ser Val Ala Asp Tyr Arg Thr Leu Gln Glu Arg Phe
                2885                2890                2895

Gly Ser Gln Phe Arg Ile Ile Asn Ser Tyr Gly Val Thr Glu Ala Ala
            2900                2905                2910

Ile Asp Ser Ser Phe Tyr Asp Glu Pro Leu Glu Lys Leu Pro Lys Thr
        2915                2920                2925

Gly Ser Val Pro Ile Gly Lys Ala Trp Leu Asn Ala Lys Phe Tyr Ile
    2930                2935                2940

Val Asp Ala Ser Leu Lys Pro Val Pro Ile Gly Val Leu Gly Glu Leu
```

```
                    2945              2950              2955              2960
          Val Ile Gly Gly Ala Gly Val Ala Arg Gly Tyr Leu Asn Arg Pro Asp
                            2965              2970              2975
          Leu Thr Ala Glu Lys Phe Val Asp Ser Pro Phe Thr Ala Gly Glu Arg
                            2980              2985              2990
          Leu Tyr Arg Thr Gly Asp Leu Ala Arg Trp Met Pro Asp Gly Asn Val
                            2995              3000              3005
          Asp Phe Ile Gly Arg Ile Asp Asn Gln Val Lys Ile Arg Gly Tyr Arg
                  3010              3015              3020
          Ile Glu Leu Gly Glu Ile Glu Ala Ala Met Lys Asn Phe Ala Gly Val
          3025              3030              3035              3040
          Arg Gln Ala Leu Val Ile Asp Arg Thr Asp Glu Arg Gly Gln Lys Tyr
                            3045              3050              3055
          Leu Cys Gly Tyr Val Val Ala Asp Ser Ser Phe Asp Leu Glu Gly Leu
                  3060              3065              3070
          Val Ala His Leu Asp Ala Ala Leu Pro Ser His Met Val Pro Ser Arg
                  3075              3080              3085
          Ile Met Arg Leu Asp Gln Met Pro Leu Thr Pro Asn Gly Lys Ile Asp
                  3090              3095              3100
          Arg Lys Gly Leu Pro Val Pro Glu Gly Ser Ile Arg Ala Glu Ala Ala
          3105              3110              3115              3120
          Tyr Thr Ala Pro Arg Thr Pro Ala Glu Gln Ala Leu Ala Leu Val Trp
                            3125              3130              3135
          Gln Ser Val Leu Gly Val Asp Gln Val Gly Thr Met Asp Asn Phe Phe
                    3140              3145              3150
          Ala Leu Gly Gly Asp Ser Ile Lys Ala Leu Gln Val Ser Ser Arg Leu
                    3155              3160              3165
          Leu Gln Thr Gly Tyr Lys Leu Ile Met Lys Asp Leu Phe His Tyr Pro
                    3170              3175              3180
          Thr Ile Ser Ala Leu Ser Leu Gln Leu Gln Thr Ala Glu Arg Thr Ala
          3185              3190              3195              3200
          Ser Gln Ala Glu Val Thr Gly Glu Val Ile Leu Thr Pro Ile Gln Arg
                            3205              3210              3215
          Trp Phe Phe Glu Gln Asn Pro Ala Asp Val His His Ser Asn Gln Ala
                            3220              3225              3230
          Phe Met Gln Phe Ser Lys Leu Gly Phe Asp Glu Glu Ala Leu Arg Gln
                    3235              3240              3245
          Ala Val Arg Gln Leu Val Val His His Asp Ala Leu Arg Thr Val Tyr
                    3250              3255              3260
          Arg Gln Thr Glu Asn Ser Tyr Thr Ala Trp Asn Arg Gly Ala Gly Glu
          3265              3270              3275              3280
          Asn Glu Ala Leu Phe Asp Leu Glu Val Val Asp Phe Arg Gly Val Cys
                    3285              3290              3295
          Asp Val Lys Gly Ala Val Glu Lys Ala Asn Asp Ile Gln Ala Ser
                    3300              3305              3310
          Ile Asp Leu Glu Asn Gly Pro Leu Val Lys Leu Gly Leu Phe Arg Cys
                    3315              3320              3325
          Asp Asp Gly Asp His Leu Leu Ile Ala Ile His Leu Val Val Asp
                    3330              3335              3340
          Gly Val Ser Trp Arg Ile Leu Leu Glu Asp Phe Ala Ala Gly Tyr Glu
          3345              3350              3355              3360
          Gln Val Leu Gln Gly Gln Pro Ile Arg Leu Pro Leu Lys Thr Asp Ser
                    3365              3370              3375
```

```
Phe Gln Thr Trp Ala Lys Gln Leu Ala Asp Tyr Ala Asn Asp Pro Ala
            3380                3385                3390

Met Glu Ser Glu Arg Glu Tyr Trp Gln His Ile Glu Gln Leu Ser Tyr
            3395                3400            3405

Glu Pro Leu Pro Lys Asp Phe Glu Gln Gly Arg Ser Thr Leu Lys Asp
            3410                3415            3420

Ser Gly Leu Val Thr Val Arg Trp Thr Ala Glu Glu Thr Gln Leu
3425                3430            3435                3440

Leu Lys His Ala His Arg Ala Tyr Arg Thr Glu Met Asn Asp Leu Leu
            3445                3450                3455

Leu Ala Ala Leu Gly Leu Ala Val Gln Ala Trp Ser Gly Arg Gly Arg
            3460                3465            3470

Val Leu Val Asn Leu Glu Gly His Gly Arg Glu Asp Ile Leu Pro Asp
            3475                3480            3485

Val Asp Ile Thr Arg Thr Val Gly Trp Phe Thr Ser Gln Phe Pro Val
            3490                3495            3500

Val Leu Glu Pro Gly His Ala Gln Glu Leu Gly His Gln Leu Lys Gln
3505                3510            3515                3520

Val Lys Glu Ser Leu Arg Arg Ile Pro Asn Lys Gly Ile Ser Tyr Gly
            3525                3530            3535

Ile Leu Arg Tyr Leu Ser Ala Pro Arg Asp Gly Glu Cys Phe Ala Leu
            3540                3545            3550

Glu Pro Glu Ile Ser Phe Asn Tyr Leu Gly Gln Phe Asp Gln Asp Tyr
            3555                3560            3565

Glu Ser Ser Gly Ser Gln Pro Ser Pro Phe Ser Pro Gly Ser Asp Ser
            3570                3575            3580

Ser Pro Asn Ala Val Met Asp Phe Val Leu Asp Ile Asn Gly Met Val
3585                3590            3595                3600

Ser Glu Gly Val Leu Glu Leu Thr Ile Arg Tyr Gly Glu Thr Gln Tyr
            3605                3610            3615

Lys Arg Glu Thr Val Glu Arg Leu Gly Thr Leu Leu Gln Leu Ser Leu
            3620                3625            3630

Arg Glu Val Ile Asn His Cys Val Ser Lys Glu Arg Pro Glu Leu Thr
            3635                3640            3645

Pro Ser Asp Val Leu Leu Gln Asp Val Thr Val Glu Glu Leu Glu Arg
3650                3655            3660

Leu Ala Glu His Thr Ala Ala Leu Gly Glu Leu Glu Asn Val Tyr Thr
3665                3670            3675                3680

Leu Thr Pro Leu Gln Lys Gly Met Leu Phe His Ser Leu Leu Asp Ala
            3685                3690            3695

Asp Ser Glu Ala Tyr Phe Glu Gln Val Thr Phe Asp Leu Asn Gly Ser
            3700                3705            3710

Leu Asn Val Glu Ala Phe Thr Gln Gly Leu Asp Thr Leu Val Gln Arg
            3715                3720            3725

Asn Glu Ala Leu Arg Thr Asn Phe Ile Thr Gly Trp Arg Asp Glu Pro
            3730                3735            3740

Ile Gln Val Val Phe Arg Glu Arg Lys Cys Glu Val Tyr Phe Glu Asp
3745                3750            3755                3760

Ile Arg Ser Ala Ser Asp Glu Asp Pro Glu Lys Thr Ile Ala Asp Phe
            3765                3770            3775

Val Ser Ala Asp Lys Ala Asn Lys Phe Asp Leu Ala Gln Gly Ser Leu
            3780                3785            3790
```

-continued

Met Arg Val Thr Val Leu Arg Thr Gly Asp Glu Ser Tyr His Val Ile
    3795                3800                3805

Trp Ser His His His Ile Leu Met Asp Gly Trp Cys Met Ser Phe Met
    3810                3815                3820

Ile Lys Glu Val Phe Asp Thr Tyr Phe Ala Phe Gln Glu Lys Arg Thr
3825                3830                3835                3840

Leu Glu Leu Pro Pro Val Thr Ser Tyr Ser Arg Tyr Ile Glu Trp Leu
            3845                3850                3855

Glu Ala Gln Asp Ala Ala Lys Ala Ser Arg Tyr Trp Ser Glu Tyr Leu
        3860                3865                3870

Ala Gly Tyr Asp Gln Gln Thr Lys Leu Pro Gln Glu Lys Thr Gln Leu
    3875                3880                3885

Lys Gln Gly Ala Phe Glu Ala Ala Glu Ile Asp Val Glu Leu Ser Lys
3890                3895                3900

Glu Leu Thr Gly Gln Ile Glu Arg Val Ala Arg Gln Gln Val Thr
3905                3910                3915                3920

Leu Asn Thr Phe Met Gln Thr Val Trp Gly Leu Val Leu Gln Ile Tyr
        3925                3930                3935

Asn Asn Ser Glu Asp Val Val Phe Gly Ser Val Val Ser Gly Arg Pro
            3940                3945                3950

Ala Glu Ile Pro Gly Ile Glu Ser Met Ile Gly Leu Phe Ile Asn Thr
        3955                3960                3965

Ile Pro Val Arg Ile Gln Gly Lys Ala Glu Glu Thr Val Ala Asp Ile
    3970                3975                3980

Leu Arg Lys Thr Gln Asp Gln Ala Leu Ala Ser Gly Ala Tyr Glu Thr
3985                3990                3995                4000

Phe Pro Leu Phe Glu Ile Gln Ser Leu Ser Glu Gln Lys Arg Asp Leu
            4005                4010                4015

Ile Asn His Ile Met Val Phe Glu Asn Tyr Pro Met Glu Glu Gln Ile
        4020                4025                4030

Glu Gln Val Val Gly Gly Asp Lys Glu Ala Leu Lys Ile Ala Asn Ile
    4035                4040                4045

Gln Ser Pro Glu Gln Thr Asn Tyr Asp Leu Asp Ile Thr Val Ile Pro
    4050                4055                4060

Glu Glu Pro Ile Leu Leu Arg Phe Thr Tyr Asn Ala Leu Thr Tyr Arg
4065                4070                4075                4080

Glu Glu Asp Ile Arg Leu Ile His Gly His Phe Ala Gln Ala Leu Glu
            4085                4090                4095

Lys Val Ala Ala Asn Pro Asn Ile Arg Val Asn Gln Leu Glu Leu Leu
        4100                4105                4110

Thr Ala Ala Glu Lys Asp Gln Ile Leu Gly Ala Phe Asn Pro Ala Gln
    4115                4120                4125

Pro Glu Ala Ala Pro Ala Ala Ala Phe His Arg Leu Phe Glu Glu Gln
    4130                4135                4140

Ala Glu Arg Thr Pro Glu Glu Ala Ala Val Val Tyr Glu Asn Asp Arg
4145                4150                4155                4160

Leu Thr Tyr Ala Glu Leu Asn Glu Arg Ala Asn Arg Leu Ala Ala Thr
            4165                4170                4175

Leu Arg Ala Ser Gly Ile Gly Arg Glu Thr Ile Val Gly Ile Leu Ala
        4180                4185                4190

Glu Arg Ser Val Asp Leu Leu Val Ala Val Leu Ala Val Trp Lys Ala
    4195                4200                4205

Gly Gly Ala Tyr Val Pro Leu Asp Pro Asp Tyr Pro Ala Asp Arg Val

-continued

```
                4210                4215                4220
Arg Phe Met Leu Glu Asp Ser Gly Ala Lys Val Leu Thr Gln Ile
4225                4230                4235                4240
Pro Leu Arg Glu Arg Ala Glu Ala Trp Leu Gly Glu Glu Leu Ala
                4245                4250                4255
Leu Ala Ala Val Leu Tyr Leu Asp Asp Glu Ala Ser Tyr Ser Glu Glu
                4260                4265                4270
Arg Ala Asn Ala Pro Ile Gly Ser Gly Met Val Ser Gly Gln Leu Thr
                4275                4280                4285
Asp Ala Val Asp Asp Gly Asp Glu Thr His Pro Asn Ile Gly Met Gly
                4290                4295                4300
Ser Phe His Glu Ala Arg Pro Glu Asp Leu Ala Tyr Val Ile Tyr Thr
4305                4310                4315                4320
Ser Gly Thr Thr Gly Lys Pro Lys Gly Val Met Ile Glu His Arg Ser
                4325                4330                4335
Leu Val Asn Thr Ala Ala Gly Tyr Arg Arg Glu Tyr Arg Leu Asp Gln
                4340                4345                4350
Phe Pro Val Arg Leu Leu Gln Leu Ala Ser Phe Ser Phe Asp Val Phe
                4355                4360                4365
Val Gly Asp Ile Ala Arg Thr Leu Tyr Asn Gly Gly Thr Met Val Ile
                4370                4375                4380
Val Pro Lys Asp Asp Arg Ile Asp Pro Ser Arg Leu His His Trp Met
4385                4390                4395                4400
Glu Arg Glu Arg Val Thr Ile Phe Glu Ser Thr Pro Ala Leu Ile Val
                4405                4410                4415
Pro Phe Leu Glu Tyr Val His Glu Gln Gly Leu Asp Met Ser Trp Met
                4420                4425                4430
Glu Leu Leu Ile Thr Ser Ser Asp Ser Cys Ser Val Ala Asp Tyr Arg
                4435                4440                4445
Thr Leu Gln Glu Arg Phe Gly Ser Leu Phe Arg Ile Ile Asn Ala Tyr
                4450                4455                4460
Gly Val Thr Glu Ala Ala Ile Asp Ser Ser Phe Tyr Asp Glu Glu Leu
4465                4470                4475                4480
Thr Lys Leu Pro Gln Thr Gly His Val Pro Ile Gly Lys Ala Trp Leu
                4485                4490                4495
Asn Ala Lys Phe Tyr Ile Val Asp Ala His Leu Asn Pro Val Pro Val
                4500                4505                4510
Gly Val Leu Gly Glu Leu Val Ile Gly Gly Val Gly Val Ala Arg Gly
                4515                4520                4525
Tyr Leu Asn Arg Pro Glu Leu Thr Glu Glu Lys Phe Val Asp Ser Pro
                4530                4535                4540
Phe Ala Ala Gly Glu Arg Leu Tyr Arg Thr Gly Asp Leu Ala Arg Trp
4545                4550                4555                4560
Met Glu Asp Gly Asn Val Asp Phe Ile Gly Arg Ile Asp Asn Gln Ala
                4565                4570                4575
Lys Ile Arg Gly Tyr Arg Ile Glu Thr Gly Glu Val Glu Ala Lys Met
                4580                4585                4590
Leu Ser Val Gly Gly Val Lys Glu Ala Val Val Val Arg Glu Asp
                4595                4600                4605
Gln Glu Gly Gln Lys Ala Leu Cys Ala Tyr Tyr Thr Val Glu Glu Gly
                4610                4615                4620
Met Thr Ala Ala Asp Leu Lys Arg Ala Ile Ser Ser Glu Leu Pro Gly
4625                4630                4635                4640
```

```
Tyr Met Ile Pro Ser Tyr Phe Val Glu Leu Glu Arg Leu Pro Leu Thr
                4645                4650                4655

Pro Asn Gly Lys Ile Asp Arg Lys Ala Leu Pro Ala Pro Glu Gly Ala
                4660                4665                4670

Ala Gly Gly Gly Arg Glu Tyr Val Ala Pro Arg Thr Glu Leu Glu Ala
                4675                4680                4685

Lys Leu Ala Ala Ile Trp Gln Glu Val Leu Val Arg Glu Lys Ala Val
                4690                4695                4700

Gly Val Thr Asp Asn Phe Phe Asp Leu Gly Gly His Ser Leu Arg Ala
4705                4710                4715                4720

Thr Thr Leu Val Ser Lys Met His Lys Glu Leu Gly Ile Glu Phe Pro
                4725                4730                4735

Leu Arg Asp Val Phe Arg Tyr Ser Thr Val Glu Glu Met Ala Ala Ala
                4740                4745                4750

Met Glu Trp Leu Glu Ile Gly Ser Phe Ile Ala Ile Pro Ala Ala Glu
                4755                4760                4765

Pro Ser Glu Tyr Tyr Pro Leu Ser Ser Ala Gln Lys Arg Leu Tyr Ile
                4770                4775                4780

Leu Asn Gln Leu Glu Gly Gly Glu Leu Ser Tyr Asn Ile Pro Gly Ala
4785                4790                4795                4800

Met Leu Leu Glu Gly Glu Leu Asp Arg Gln Arg Phe Glu Glu Ala Phe
                4805                4810                4815

Arg Gly Leu Val Ala Arg His Glu Thr Leu Arg Thr Gly Phe Glu Met
                4820                4825                4830

Val Lys Gly Glu Ala Val Gln Arg Ile Tyr Glu Glu Ala Ala Phe Gln
                4835                4840                4845

Val Glu Tyr Val Gln Ile Ser Gly Glu Arg Val Glu Glu Thr Val Arg
                4850                4855                4860

Gln Phe Val Arg Pro Phe Asp Leu Ala Lys Pro Pro Leu Leu Arg Val
4865                4870                4875                4880

Gly Leu Ala Glu Leu Ala Pro Asp Arg His Ile Leu Met Phe Asp Thr
                4885                4890                4895

His His Ile Val Ser Asp Gly Val Ser Met Asp Val Leu Ile Glu Glu
                4900                4905                4910

Phe Val Arg Leu Tyr Ser Gly Glu Pro Leu Glu Pro Leu Arg Ile Gln
                4915                4920                4925

Tyr Lys Asp Tyr Ala Val Trp Gln Gln Ser Asp Glu Gln Lys Ala Gln
                4930                4935                4940

Leu Ala Lys Gln Glu Ala Tyr Trp Leu Asp Met Phe Arg Gly Glu Leu
4945                4950                4955                4960

Pro Val Leu Glu Leu Pro Thr Asp Tyr Pro Arg Pro Ala Met Gln Ser
                4965                4970                4975

Tyr Glu Gly Arg Thr Leu Gln Leu Phe Met Asn Arg Glu Lys Ser Glu
                4980                4985                4990

Gly Leu Lys Arg Leu Ala Ala Glu Asn Gly Ala Thr Leu Tyr Met Val
                4995                5000                5005

Leu Leu Ala Gly Tyr Thr Ile Leu Leu His Lys Tyr Thr Ser Gln Glu
                5010                5015                5020

Asp Val Val Val Gly Thr Pro Ile Ala Gly Arg Asn His Ser Asp Val
5025                5030                5035                5040

Gln Pro Leu Ile Gly Met Phe Val Asn Thr Leu Ala Ile Arg Ser Tyr
                5045                5050                5055
```

-continued

Pro Thr Ala Gly Lys Thr Phe Leu Asp Tyr Leu Lys Glu Ile Lys Glu
            5060                5065                5070

Thr Thr Leu Gly Ala Phe Glu His Gln Asn Tyr Pro Phe Glu Glu Leu
        5075                5080                5085

Val Asp Lys Val Asn Val Ala Arg Asp Leu Ser Arg Asn Pro Leu Phe
        5090                5095                5100

Asp Thr Met Phe Ala Leu Gln Asn Thr Glu Asn Leu Glu Ile Gln Leu
5105                5110                5115                5120

Pro Gly Leu His Leu Ser Thr Tyr Ala Ser Glu Glu Ile Val Ser Lys
            5125                5130                5135

Phe Asp Leu Ser Leu Asp Val Thr Glu Ile Glu Glu Gly Leu Glu Tyr
        5140                5145                5150

Leu Phe Glu Tyr Ala Thr Ala Leu Tyr Lys Thr Glu Thr Val Glu Lys
            5155                5160                5165

Leu Ala Ala His Tyr Leu Gln Leu Leu Glu Ser Ile Leu Cys Asn Pro
        5170                5175                5180

Ser Ala Thr Ile Ala Glu Leu Gly Ile Leu Thr Pro Ala Glu Lys Glu
5185                5190                5195                5200

Gln Ile Leu Gly Ala Phe Asn Pro Ala Gln Pro Glu Ala Ala Pro Ala
            5205                5210                5215

Ala Ala Phe His Arg Leu Phe Glu Glu Gln Ala Glu Arg Thr Pro Glu
        5220                5225                5230

Ala Glu Ala Val Val Tyr Glu Asn Asp Arg Leu Ile Tyr Ala Glu Leu
            5235                5240                5245

Asn Glu Arg Ala Asn Arg Leu Ala Ala Thr Leu Arg Ala Ser Gly Ile
        5250                5255                5260

Gly Arg Glu Ser Ile Val Gly Ile Leu Ala Glu Arg Ser Val Asp Leu
5265                5270                5275                5280

Leu Val Ala Val Leu Ala Val Trp Lys Ala Gly Gly Ala Tyr Val Pro
            5285                5290                5295

Leu Asp Pro Asp Tyr Pro Ala Asp Arg Val Arg Phe Met Leu Glu Asp
        5300                5305                5310

Ser Gly Ala Lys Val Leu Leu Thr Gln Lys Val Leu Arg Glu Arg Ala
            5315                5320                5325

Glu Ala Trp Leu Gly Glu Glu Leu Thr Leu Ala Ala Val Leu Tyr
        5330                5335                5340

Leu Asp Asp Glu Ala Ser Tyr Ser Glu Val Arg Ala Asn Ala Pro Ile
5345                5350                5355                5360

Gly Ser Gly Met Val Ser Gly Lys Leu Met Asp Ala Val Asn Asp Gly
            5365                5370                5375

Asp Gly Thr His Pro Asn Val Asp Met Gly Ser Phe His Glu Ala Arg
        5380                5385                5390

Pro Glu Asp Leu Ala Tyr Val Ile Tyr Thr Ser Gly Thr Thr Gly Lys
            5395                5400                5405

Pro Lys Gly Val Met Ile Glu His Arg Ser Leu Val Asn Thr Ala Ala
        5410                5415                5420

Gly Tyr Arg Arg Glu Tyr Arg Leu Asp Gln Phe Pro Val Arg Leu Leu
5425                5430                5435                5440

Gln Leu Ala Ser Phe Ser Phe Asp Val Phe Val Gly Asp Ile Ala Arg
            5445                5450                5455

Thr Leu Tyr Asn Gly Gly Thr Met Val Ile Val Thr Lys Asp Asp Arg
        5460                5465                5470

Ile Asp Pro Ser Arg Leu His His Trp Met Glu Arg Glu Arg Val Thr

-continued

```
            5475                5480                5485
Ile Phe Glu Ser Thr Pro Ala Leu Ile Val Pro Phe Leu Glu Tyr Val
            5490                5495                5500
His Glu Gln Gly Leu Asp Met Ser Trp Met Glu Leu Leu Ile Thr Ser
5505                5510                5515                5520
Ser Asp Ser Cys Ser Val Ala Asp Tyr Arg Thr Leu Gln Glu Arg Phe
                5525                5530                5535
Gly Ser Leu Phe Arg Ile Ile Asn Ala Tyr Gly Val Thr Glu Ala Ala
            5540                5545                5550
Ile Asp Ser Ser Phe Tyr Asp Glu Glu Leu Thr Lys Leu Pro Gln Thr
            5555                5560                5565
Gly His Val Pro Ile Gly Lys Ala Trp Leu Asn Ala Lys Phe Tyr Ile
            5570                5575                5580
Val Asp Ala His Leu Asn Pro Val Pro Val Gly Val Leu Gly Glu Leu
5585                5590                5595                5600
Val Ile Gly Gly Val Gly Val Ala Arg Gly Tyr Leu Asn Arg Pro Glu
                5605                5610                5615
Leu Thr Glu Glu Lys Phe Val Asp Ser Pro Phe Ala Ala Gly Glu Arg
            5620                5625                5630
Leu Tyr Arg Thr Gly Asp Leu Ala Arg Trp Met Glu Asp Gly Asn Val
            5635                5640                5645
Asp Phe Ile Gly Arg Ile Asp Asn Gln Ala Lys Ile Arg Gly Tyr Arg
            5650                5655                5660
Ile Glu Thr Gly Glu Val Glu Ala Lys Leu Leu Ser Val Glu Gly Val
5665                5670                5675                5680
Arg Glu Ala Val Val Leu Val Arg Ser Asp Ala Asn Gly Gln Lys Ala
                5685                5690                5695
Leu Cys Ala Tyr Tyr Thr Ile Asp Gly Glu Phe Thr Ala Ala Asp Leu
            5700                5705                5710
Lys Arg Ala Ile Ala Ser Glu Leu Pro Gly Tyr Met Ile Pro Ser Tyr
            5715                5720                5725
Phe Val Glu Leu Glu Arg Leu Pro Leu Thr Pro Asn Gly Lys Ile Asp
            5730                5735                5740
Arg Lys Ala Leu Pro Ala Pro Glu Gly Gly Ala Asn Ala Gly Arg Glu
5745                5750                5755                5760
Tyr Val Ala Pro Arg Thr Glu Leu Glu Ala Lys Leu Val Ala Ile Trp
                5765                5770                5775
Gln Asp Val Leu Gly Pro Val Thr Ile Gly Val Thr Asp Asn Phe Phe
            5780                5785                5790
Asp Leu Gly Gly His Ser Leu Arg Ala Thr Thr Leu Val Ser Lys Val
            5795                5800                5805
His Lys Glu Leu Ser Val Asp Leu Pro Leu Arg Asp Val Phe Arg His
5810                5815                5820
Ser Thr Ile Glu Ala Met Ala Glu Ala Ile Ser Gln Leu Glu Arg Gln
5825                5830                5835                5840
Glu His Leu Ser Ile Pro Val Leu Asp Lys Arg Asp Tyr Tyr Pro Leu
                5845                5850                5855
Ser Ser Val Gln Lys Arg Leu Tyr Ile Gln Gln Met Glu Gly Ala
            5860                5865                5870
Glu Leu Ser Tyr Asn Met Ser Gly Met Thr Val Leu Val Gly Arg Leu
            5875                5880                5885
Glu Arg Asn Gln Phe Glu Ala Ala Leu Lys Gly Leu Ile Ala Arg His
            5890                5895                5900
```

-continued

```
Glu Ile Leu Arg Thr Gly Phe Glu Met Val Asp Gly Glu Pro Val Gln
5905                5910                5915                5920

Arg Ile Tyr Pro Asp Leu Lys Phe Ala Val Glu Tyr Thr Lys Ala Met
            5925                5930                5935

Glu Ser Glu Thr Lys Ser Ile Val Asp Gly Phe Val Arg Val Phe Asp
        5940                5945                5950

Leu Glu Arg Pro Pro Leu Leu Arg Val Gly Leu Val Glu Met Glu Ala
            5955                5960                5965

Glu Arg His Leu Leu Met Leu Asp Ile His His Ile Val Thr Asp Gly
        5970                5975                5980

Met Ser Met Gly Ile Phe Val Glu Glu Leu Leu Arg Leu Tyr Asn Gly
5985                5990                5995                6000

Glu Asn Leu Glu Pro Leu Arg Ile Gln Tyr Lys Glu Phe Ala Ala Trp
            6005                6010                6015

Gln Gln Ser Glu Pro Val Lys Glu Arg Leu Lys Arg Gln Glu Ala Tyr
        6020                6025                6030

Trp Leu Asp Val Leu Glu Gly Glu Leu Pro Thr Leu Glu Leu Pro Thr
            6035                6040                6045

Asp Phe Val Arg Pro Ala Ala Arg Ser Phe Glu Gly Asp Val Leu Pro
        6050                6055                6060

Phe Ser Ile Asp Lys Gln Met Thr Asp Ser Leu Gln Arg Ile Ala Asp
6065                6070                6075                6080

Glu Asn Gly Gly Thr Leu Tyr Met Val Leu Ser Ala Val Tyr Ser Ile
            6085                6090                6095

Leu Leu Ser Lys Tyr Ser Gly Gln Glu Asp Phe Ile Val Gly Thr Pro
        6100                6105                6110

Val Ser Gly Arg Thr His Ala Asp Leu Glu Pro Leu Ile Gly Met Phe
        6115                6120                6125

Val Asn Thr Leu Ala Ile Arg His Tyr Pro Ser Gly Glu Lys Thr Phe
        6130                6135                6140

Leu Ala Tyr Leu Asn Glu Val Lys Glu Thr Met Leu Gly Ala Tyr Asp
6145                6150                6155                6160

His Gln Asp Tyr Pro Phe Glu Glu Leu Val Lys Lys Leu Gln Val Pro
            6165                6170                6175

Arg Asp Leu Ser Arg Asn Pro Val Phe Asp Val Met Phe Ala Leu Glu
            6180                6185                6190

Thr Lys Glu Asp Asn Val Gln Asn Phe Gly Asp Ile Arg Ile Glu Ser
        6195                6200                6205

Tyr Pro Glu Thr His Thr Val Ser Gln Phe Asp Leu Thr Leu Ile Ile
        6210                6215                6220

Ser Leu Leu Asp Glu Gly Met Asn Gly Gln Phe Glu Tyr Ala Thr Lys
6225                6230                6235                6240

Leu Phe Thr Arg Asn Leu Ile Asp Asn Phe Ala Gln Asp Leu Leu Val
            6245                6250                6255

Ile Ile Ser Gln Ile Cys Glu Gln Pro Ser Val Leu Leu Lys Asp Ile
        6260                6265                6270

Ser Leu Asn Gly Gln Ser Glu Gln Glu Gln Asp Val Leu Glu Ala Ile
        6275                6280                6285

Asp Ile Ile Phe
    6290

<210> SEQ ID NO 15
<211> LENGTH: 20
```

```
<212> TYPE: DNA
<213> ORGANISM: Artificial Sequence
<220> FEATURE:
<223> OTHER INFORMATION: A "forward

<400> SEQUENCE: 15
atggcttttg aaaaagaaac                                              20

<210> SEQ ID NO 16
<211> LENGTH: 20
<212> TYPE: DNA
<213> ORGANISM: Artificial Sequence
<220> FEATURE:
<223> OTHER INFORMATION: A "reverse

<400> SEQUENCE: 16
gaacgcaaat tcgatcgtat                                              20

<210> SEQ ID NO 17
<211> LENGTH: 20
<212> TYPE: DNA
<213> ORGANISM: Artificial Sequence
<220> FEATURE:
<223> OTHER INFORMATION: B "forward

<400> SEQUENCE: 17
atgaaatctt tatttgaaaa                                              20

<210> SEQ ID NO 18
<211> LENGTH: 20
<212> TYPE: DNA
<213> ORGANISM: Artificial Sequence
<220> FEATURE:
<223> OTHER INFORMATION: B "reverse

<400> SEQUENCE: 18
gcttccatgc agtaccccgg                                              20

<210> SEQ ID NO 19
<211> LENGTH: 20
<212> TYPE: DNA
<213> ORGANISM: Artificial Sequence
<220> FEATURE:
<223> OTHER INFORMATION: E "forward

<400> SEQUENCE: 19
atggaaatta tgaatccggg                                              20

<210> SEQ ID NO 20
<211> LENGTH: 20
<212> TYPE: DNA
<213> ORGANISM: Artificial Sequence
<220> FEATURE:
<223> OTHER INFORMATION: E "reverse

<400> SEQUENCE: 20
gaaaataata tcaatggcct                                              20

<210> SEQ ID NO 21
<211> LENGTH: 20
<212> TYPE: DNA
<213> ORGANISM: Artificial Sequence
<220> FEATURE:
<223> OTHER INFORMATION: C "forward

<400> SEQUENCE: 21
```

```
atggaagctg accgacagcc                                              20
```

<210> SEQ ID NO 22
<211> LENGTH: 20
<212> TYPE: DNA
<213> ORGANISM: Artificial Sequence
<220> FEATURE:
<223> OTHER INFORMATION: C "reverse

<400> SEQUENCE: 22

```
gtgtacgcca cctccctgcg                                              20
```

<210> SEQ ID NO 23
<211> LENGTH: 20
<212> TYPE: DNA
<213> ORGANISM: Artificial Sequence
<220> FEATURE:
<223> OTHER INFORMATION: D "forward

<400> SEQUENCE: 23

```
atgaaaaagg gcggatggct                                              20
```

<210> SEQ ID NO 24
<211> LENGTH: 20
<212> TYPE: DNA
<213> ORGANISM: Artificial Sequence
<220> FEATURE:
<223> OTHER INFORMATION: D "reverse

<400> SEQUENCE: 24

```
gccgtacagc cgggcgtaat                                              20
```

<210> SEQ ID NO 25
<211> LENGTH: 4998
<212> TYPE: PRT
<213> ORGANISM: Paenibacillus alvei

<400> SEQUENCE: 25

```
Met Phe Glu Lys Ala Gly Ser Met Ala Val Ala Leu Leu Arg His Met
1               5                   10                  15

Leu Arg Arg Ile Ala Phe Thr Asp Val Glu Arg Gly Thr Ile Gln Val
                20                  25                  30

Ala Phe Glu Lys Glu Thr Leu Phe Trp Asn Glu Lys Phe Gly Ser Asp
            35                  40                  45

Asp Tyr Thr Leu Thr Arg Leu Pro Tyr Ser Lys Ala Pro Ser Ser Gln
        50                  55                  60

Ala Pro Ile Met Thr Thr Val Gly Gly Ser Leu Ser Glu Lys Ala Ala
65                  70                  75                  80

Gln Arg Val Leu Gln Met Ser Lys Gly Ala Pro Leu Ala Ala Phe Met
                85                  90                  95

Ile Leu Leu Ala Gly Val Gln Ser Leu Leu His Lys Tyr Thr Gly Ala
                100                 105                 110

Ser Asp Ile Leu Val Gly Met Pro Val Ile Arg Lys Pro Thr Glu Thr
            115                 120                 125

Arg Arg Ser Val Asn His Thr Val Ile Leu Lys Ser Leu Leu Ser Ala
        130                 135                 140

Gly Ser Thr Phe Lys Thr Leu Leu Ser Glu Leu Arg Thr Ser Leu Pro
145                 150                 155                 160

Glu Thr Ile Gln His Gln His Ile Pro Phe Leu Lys Met Thr Glu Lys
                165                 170                 175
```

-continued

Leu Asp Leu Gln Tyr Ala Asp Gly Ile Pro Ile Ile His Thr Leu Val
            180                 185                 190

Ser Leu Lys Glu Leu His Leu Asp Glu Ile Gly Gln Asn Val Val Thr
        195                 200                 205

Asp Cys Ser Phe Glu Phe Ser Leu Thr Gly Gly Thr Ile Gln Leu Ala
    210                 215                 220

Leu Ser Tyr Asn Glu His Leu Tyr Asp Ser Lys Phe Met Thr Arg Ile
225                 230                 235                 240

Val Gly His Leu Asn Arg Leu Leu Ala Val Gly Leu His Glu Leu Glu
                245                 250                 255

Leu Asp Ile Val Arg Val Asp Met Leu Ser Glu Asp Glu Lys Phe Gln
            260                 265                 270

Leu Leu Gln Ser Phe Asn Asp Thr Glu Lys Asp Tyr Pro Arg Asp Arg
        275                 280                 285

Thr Ile His Gln Leu Val Glu Glu Gln Val Lys Arg Val Pro Glu Ala
    290                 295                 300

Thr Ala Ile Val Phe Glu Gly Arg Arg Leu Ser Tyr Ala Glu Leu Asn
305                 310                 315                 320

Glu Arg Ala Asn Arg Leu Ala Arg Thr Leu Arg Ser Val Gly Val Leu
                325                 330                 335

Pro Asn Gln Leu Val Gly Leu Met Ala Arg Arg Ser Leu Glu Thr Val
            340                 345                 350

Val Gly Ile Leu Ala Val Leu Lys Ala Gly Gly Ala Tyr Val Pro Ile
        355                 360                 365

Asp Pro Glu Tyr Pro Glu Glu Arg Ile Arg Tyr Ile Leu Glu Asn Ser
    370                 375                 380

Asn Ala Gln Leu Leu Leu Thr Gln Arg Lys Leu Gln Gln Val Pro
385                 390                 395                 400

Phe Glu Gly Thr Val Leu Ala Leu Asp Asp Glu Gln Ala Tyr Ser Asp
                405                 410                 415

Asp Gly Thr Asn Leu Glu Pro Ala Ser Gly Ser Asn Asp Leu Ala Tyr
            420                 425                 430

Val Ile Tyr Thr Ser Gly Thr Thr Gly Lys Pro Lys Gly Val Met Leu
        435                 440                 445

Glu His Arg Gly Leu Val Ser Leu Lys Leu Met Phe Ala Asp Arg Leu
    450                 455                 460

Gly Ile Thr Glu His Asp Arg Ile Val Gln Phe Ala Ser Leu Ser Phe
465                 470                 475                 480

Asp Ala Ser Cys Trp Glu Val Phe Lys Ala Leu Tyr Phe Gly Ala Thr
                485                 490                 495

Leu Tyr Ile Pro Thr Ala Glu Thr Ile Leu Asp Asn Arg Leu Phe Glu
            500                 505                 510

Ser Tyr Met Asn Glu His Ala Ile Thr Ala Ala Ile Leu Pro Pro Thr
        515                 520                 525

Tyr Ser Ala Tyr Leu Asn Pro Asp Arg Leu Pro Ser Leu Thr Lys Leu
    530                 535                 540

Val Thr Gly Gly Ser Ala Val Ser Ala Glu Phe Val Gln Gln Trp Lys
545                 550                 555                 560

Pro Lys Val His Tyr Phe Asn Ala Tyr Gly Pro Thr Glu Ala Ser Ile
                565                 570                 575

Val Thr Thr Leu Trp Asp Ala Asn Glu Glu Pro Glu Arg Arg Val
            580                 585                 590

Ile Pro Ile Gly Arg Pro Leu Ala Asn His Arg Ile Phe Ile Leu Asp

```
                595                 600                 605
Ala His Leu Gln Leu Val Pro Pro Gly Val Asp Gly Glu Leu Cys Val
610                 615                 620

Ala Gly Val Gly Leu Ala Arg Gly Tyr Leu Asn His Pro Glu Leu Thr
625                 630                 635                 640

Ala Glu Lys Phe Val Glu His Pro Phe Ala Pro Gly Glu Arg Leu Tyr
                645                 650                 655

Arg Thr Gly Asp Leu Ala Arg Trp Leu Pro Asp Gly Asn Ile Glu Tyr
                660                 665                 670

Leu Gly Arg Ile Asp His Gln Val Lys Ile Arg Gly Phe Arg Ile Glu
                675                 680                 685

Ile Gly Glu Ile Glu Glu Gln Leu Leu Lys Ile Asp Ser Val Gln Glu
690                 695                 700

Thr Met Val Ile Ala Arg Glu Gly Lys Ser Gly Gln Glu Leu Cys Ala
705                 710                 715                 720

Tyr Leu Val Ala Asp Arg Pro Leu Thr Leu Gly Glu Leu Arg Ser Ala
                725                 730                 735

Leu Ala Gln Lys Leu Pro Asn Tyr Met Ile Pro Ala His Phe Val Gln
                740                 745                 750

Leu Pro Arg Met Pro Leu Thr Pro Asn Asp Lys Ile Asp Arg Lys Ala
                755                 760                 765

Leu Pro Ala Pro Glu Gly Asn Ala Leu Thr Gly Gly Leu Tyr Val Ala
                770                 775                 780

Pro Arg Asn Glu Ala Glu Arg Thr Leu Val Asp Val Trp Gln Ala Val
785                 790                 795                 800

Leu Asn Ala Asp Arg Val Gly Val Thr Asp His Phe Phe Glu Leu Gly
                805                 810                 815

Gly Asp Ser Ile Lys Ser Ile Gln Val Ser Ser Arg Leu His Gln Ala
                820                 825                 830

Gly Tyr Lys Leu Asp Ile Arg Asp Leu Phe Lys Tyr Pro Thr Ile Ser
                835                 840                 845

Gln Leu Ser Leu Arg Val Lys Pro Ile Gly Arg Thr Ile Asp Gln Gly
                850                 855                 860

Glu Ile Thr Gly Glu Thr Ala Leu Thr Pro Ile Gln His Trp Phe Phe
865                 870                 875                 880

Glu Ser Ser Phe Ala Asp Pro His His Phe Asn Gln Ser Val Met Leu
                885                 890                 895

Tyr Arg Lys Glu Arg Phe Asp Glu Glu Thr Val Arg Gln Val Leu Gln
                900                 905                 910

Lys Leu Ala Glu His His Asp Ala Leu Arg Met Val Phe Arg Lys Thr
                915                 920                 925

Glu Gln Gly Phe Ser Glu Arg Asn Arg Ala Ile Glu Gly Gly Leu
                930                 935                 940

Phe Thr Leu Asp Val Phe Asp Phe Lys Asp Ala Glu Asp Thr Ala Gln
945                 950                 955                 960

Ala Leu Glu Ala Lys Ala Thr Asp Ile Gln Ala Gly Ile Asp Leu Glu
                965                 970                 975

Lys Gly Pro Leu Val Lys Ala Gly Leu Phe Arg Cys Ala Asp Gly Asp
                980                 985                 990

His Leu Leu Leu Ala Val His His Ala Val Val Asp Gly Val Ser Trp
                995                 1000                1005

Arg Ile Leu Met Glu Asp Phe Ala Leu Gly Tyr Glu Gln Ala Gly Lys
                1010                1015                1020
```

```
Ser Glu Glu Ile Arg Phe Pro Ala Lys Thr Asp Ala Tyr Arg Thr Trp
1025                1030                1035                1040

Ser Glu Gln Leu Ala Ala Tyr Ala Gln Ser Pro Glu Ile Ala Lys Glu
            1045                1050                1055

Arg Ala Tyr Trp Gln Ala Val Glu Gln Ile Ala Val Pro Ala Leu Pro
        1060                1065                1070

Lys Asp Leu Glu Ala Asp Val Thr Thr Gln Gln Asp Ser Glu Ser Leu
    1075                1080                1085

Phe Val Arg Leu Thr Ser Glu Glu Thr Glu Leu Leu Leu Lys Arg Val
1090                1095                1100

His Arg Ala Tyr Asn Thr Glu Met Asn Asp Ile Leu Val Thr Ala Leu
1105                1110                1115                1120

Gly Ile Ala Val Arg Lys Trp Thr Gly His Glu Arg Val Arg Ile Asn
            1125                1130                1135

Leu Glu Gly His Gly Arg Glu Ser Ile Gly Thr Asp Ile Asp Ile Thr
        1140                1145                1150

Arg Thr Val Gly Trp Phe Thr Thr Lys Phe Pro Val Val Leu Glu Pro
    1155                1160                1165

Glu Thr Asn Arg Asp Leu Ala Tyr Gln Ile Lys Gln Val Lys Glu Ser
1170                1175                1180

Leu Arg Arg Ile Pro Asn Lys Gly Leu Gly Tyr Gly Val Cys Arg Tyr
1185                1190                1195                1200

Leu Ser Lys Ser Glu Asp Gly Phe Val Trp Gly Ala Glu Pro Glu Ile
            1205                1210                1215

Asn Phe Asn Tyr Leu Gly Gln Phe Asp Asp Val Asn Gln Asp Glu
        1220                1225                1230

Ile Gly Ile Ser Ser Tyr Ser Ser Gly Ser Pro Ala Ser Asp Arg Gln
    1235                1240                1245

Ala Arg Ser Phe Val Leu Asp Ile Asn Gly Met Val Leu Asp Gly Ala
1250                1255                1260

Leu Ser Leu Asp Leu Ser Tyr Ser Arg Lys Gln Tyr Arg Lys Val Thr
1265                1270                1275                1280

Met Glu Ala Phe Ala Gln Arg Leu Glu Gln Ser Leu Arg Glu Leu Ile
            1285                1290                1295

Thr His Cys Ala Gly Lys Glu Asn Thr Glu Leu Thr Pro Ser Asp Val
        1300                1305                1310

Gln Phe Lys Gly Leu Thr Ile Ala Glu Leu Glu Gln Ile Gly Gln Arg
    1315                1320                1325

Ser Val His Val Gly Glu Ile Glu Asn Ile Tyr Ser Leu Thr Pro Met
1330                1335                1340

Gln Lys Gly Met Trp Phe His Ser Ala Leu Asp Arg Gln Thr Ala Ala
1345                1350                1355                1360

Tyr Phe Glu Gln Thr Arg Phe Thr Met Arg Gly Ala Leu Asp Val Gln
            1365                1370                1375

Leu Phe Glu Arg Ser Trp Thr Glu Leu Ala Lys Arg His Leu Val Leu
        1380                1385                1390

Arg Ala Asn Phe Val Lys Gly Pro Ala Gly Glu Pro Leu Gln Ile Ile
    1395                1400                1405

Tyr Arg Asp Lys Pro Val Gly Phe Glu Tyr Glu Glu Leu His Leu
1410                1415                1420

Gln Ala Asp Glu Lys Gln Ala Tyr Leu Asp Lys Lys Ala Glu Asp Asp
1425                1430                1435                1440
```

```
Lys Leu Arg Gly Phe Asp Leu Glu His Asp Ala Leu Val Arg Val Thr
            1445                1450                1455

Ile Leu Arg Thr Glu Glu Gln Ser Tyr His Val Leu Trp Ser Phe Gln
        1460                1465                1470

His Ile Leu Met Asp Gly Trp Cys Leu Pro Gln Leu Thr Gln Glu Leu
    1475                1480                1485

Phe Glu Thr Tyr Ser Ala Leu Ala Ser Gly Lys Gln Pro Ala Gly Asp
1490                1495                1500

Lys Gly Ser Asp Tyr Gly Ala Tyr Ile Glu Trp Leu Glu Lys Gln Asp
1505                1510                1515                1520

Asp Gln Ala Ala Ser Gly Tyr Trp Thr Ala Phe Leu Ala Gly Tyr Glu
            1525                1530                1535

Gly Gln Thr Val Leu Pro Gly Gln Lys Glu Ala Gln Pro Asn Gly Arg
        1540                1545                1550

Phe Thr Ala Asp His Val Thr Ala Glu Leu Gly Lys Asp Leu Ser Glu
    1555                1560                1565

Arg Met Asp Arg Val Ala Lys Gln Arg Leu Val Thr Val Asn Thr Leu
1570                1575                1580

Leu Gln Ala Ala Trp Gly Val Met Leu Gln Lys Tyr Asn Gly Thr Asn
1585                1590                1595                1600

Asp Ala Val Phe Gly Ser Val Val Ala Gly Arg Pro Ala Glu Ile Pro
            1605                1610                1615

Gly Ile Glu Ser Met Ile Gly Leu Phe Ile Asn Thr Val Pro Val Arg
        1620                1625                1630

Val Thr Ser Glu Ala Asp Thr Val Phe Ala Asp Leu Met Ala Lys Leu
    1635                1640                1645

Gln Glu Arg Ala Leu Glu Ser Gly Arg Tyr Asp Tyr Tyr Pro Leu Tyr
1650                1655                1660

Glu Ile Gln Ala Arg Cys Val Gln Lys Gln Asn Leu Ile Asn His Ile
1665                1670                1675                1680

Ile Ala Phe Glu Asn Tyr Pro Val Asp Glu Gln Met Glu Gln Ala Gly
            1685                1690                1695

Asp Gln Gln His Gly Asp Leu Thr Ile Thr Asp Val Gln Met Glu Glu
        1700                1705                1710

Gln Thr Asn Tyr Asn Phe Asn Val Thr Val Pro Gly Ala Glu Ile
    1715                1720                1725

Glu Ile Arg Phe Asp Phe Asn Ala Glu Val Phe Asp Lys Asp Ser Ile
        1730                1735                1740

Glu Arg Leu Lys Gly His Leu Val His Leu Leu Glu Gln Val Thr Asp
1745                1750                1755                1760

Asn Pro Glu Ile Thr Val Gly Glu Leu Glu Leu Val Thr Glu Ala Glu
            1765                1770                1775

Lys Ala Asp Leu Leu Gly Arg Phe Asn Asp Thr Thr Thr Glu Phe Pro
        1780                1785                1790

Arg Gly Lys Thr Leu Ile Gln Leu Phe Glu Glu Gln Val Glu Arg Ile
    1795                1800                1805

Pro Asp Ala Ala Ala Ile Thr Leu Asn Glu Gln Glu Leu Thr Tyr Arg
    1810                1815                1820

Glu Leu Asn Glu Arg Val Asn Arg Leu Ala Arg Thr Leu Arg Ser His
1825                1830                1835                1840

Gly Ile Ser Lys Gly Arg Leu Val Ala Ile Leu Ala Glu Arg Ser Ile
            1845                1850                1855

Glu Met Val Val Gly Met Leu Ala Ala His Lys Ala Gly Ala Ala Tyr
```

```
                1860            1865            1870
Val Pro Ile Asp Pro Glu Tyr Pro Glu Glu Arg Ile Arg Phe Leu Ile
        1875            1880            1885
Glu Asp Ser Gly Gly Gln Val Met Leu Thr Gln Ser Arg Leu Arg Glu
        1890            1895            1900
Arg Leu Ala Gly Ser Asp Pro Val Ile Leu Leu Asp Asp Glu Ser Phe
1905            1910            1915            1920
Tyr His Glu Asp Gly Thr Asn Leu Asn Thr Gly Ile Glu Ala Thr Asp
            1925            1930            1935
Leu Ala Cys Val Ile Tyr Thr Ser Gly Thr Thr Gly Lys Pro Lys Gly
            1940            1945            1950
Asn Pro Val Ser His Arg Asn Ile Val Arg Val Val Gln Asn Thr Asn
        1955            1960            1965
Tyr Ile Asp Ile Thr Glu Arg Asp His Val Leu Gln Leu Ser Ser Tyr
        1970            1975            1980
Ser Phe Asp Gly Ala Thr Phe Asp Ile Phe Gly Ala Leu Thr Asn Gly
1985            1990            1995            2000
Ala Arg Leu Val Leu Val Pro Tyr Glu Thr Leu Leu Glu Ile Gly Arg
            2005            2010            2015
Leu Ala Asp Leu Ile Gln Arg Glu Arg Ile Ser Val Met Phe Ile Thr
        2020            2025            2030
Thr Ala Phe Phe Asn Ile Leu Val Asp Val Asn Val Asp Cys Leu Arg
        2035            2040            2045
Asp Val Arg Ala Ile Leu Phe Gly Gly Glu Arg Val Ser Val Gly His
        2050            2055            2060
Val Arg Lys Ala Leu Ala His Ile Gly Pro Gly Arg Leu Asn His Val
2065            2070            2075            2080
Tyr Gly Pro Thr Glu Ser Thr Val Tyr Thr Thr Tyr Leu Pro Val Asp
            2085            2090            2095
Phe Val Asp Glu Leu Ala Val Thr Val Pro Ile Gly Arg Pro Ile Ser
            2100            2105            2110
Asn Thr Thr Val Tyr Ile Val Asp Ser Arg Asn Lys Leu Leu Pro Ile
        2115            2120            2125
Gly Val Ala Gly Glu Leu Cys Val Gly Gly Glu Gly Leu Val Arg Gly
        2130            2135            2140
Tyr Asn Asn Arg Pro Glu Leu Thr Ala Glu Lys Phe Val Asp Asn Pro
2145            2150            2155            2160
Phe Val Pro Gly Glu Arg Met Tyr Arg Thr Gly Asp Leu Ala Lys Trp
            2165            2170            2175
Leu Pro Asp Gly Thr Ile Glu Tyr Val Gly Arg Thr Asp Asp Gln Val
            2180            2185            2190
Lys Ile Arg Gly Phe Arg Ile Glu Leu Gly Glu Ile Glu Ala Gln Leu
        2195            2200            2205
Gln Lys Val Glu Gly Ile Arg Lys Thr Thr Val Phe Ala Arg Glu Asn
        2210            2215            2220
Ala Ser Gly Glu Lys Gln Leu Cys Ala Tyr Tyr Glu Ala Asp Cys Glu
2225            2230            2235            2240
Leu Pro Ala Ala Glu Leu Lys Ser Val Leu Ser Lys Glu Leu Pro Ala
            2245            2250            2255
Tyr Met Ile Pro Ala Tyr Leu Ile Gln Leu Glu Arg Leu Pro Leu Thr
            2260            2265            2270
Thr Asn Gly Lys Val Asp Arg Arg Ser Leu Pro Ala Pro Glu Glu Ser
        2275            2280            2285
```

```
Leu Gln Pro Gly Gly Gly Ser Thr Pro Pro Arg Thr Pro Leu Glu Ala
        2290            2295                2300

Ser Leu Ala Gly Ile Trp Lys Ser Val Leu Gly Leu Val His Ile Gly
2305            2310                2315                2320

Val His Asp Asn Phe Phe Asp Met Gly Gly His Ser Leu Arg Ala Thr
            2325                2330                2335

Thr Leu Val Ser Lys Val His Gln Glu Leu Asn Val Glu Leu Pro Leu
        2340                2345                2350

Arg Asp Val Phe Arg Tyr Ser Thr Ile Glu Glu Met Ala Leu Ala Ile
            2355                2360                2365

Ser Arg Ile Gly Glu Gln Ser Phe Ser Ser Ile Pro Leu Ala Gly Ala
        2370                2375                2380

Arg Ala Tyr Tyr Pro Leu Ser Ser Ala Gln Lys Arg Leu Phe Ile Leu
2385            2390                2395                2400

Asn Gln Leu Glu Gly Ala Asp Gln Ser Tyr Asn Met Pro Gly Val Leu
            2405                2410                2415

Leu Leu Glu Gly Ser Ile Asp Arg Ser Leu Leu Glu Lys Ala Phe Arg
            2420                2425                2430

Gly Leu Ile Ala Arg His Glu Thr Leu Arg Thr Gly Phe Glu Ile Val
        2435                2440                2445

Gln Gly Glu Ala Val Gln Arg Ile Tyr Glu Ser Val Asp Phe Ala Val
        2450                2455                2460

Glu Tyr Arg His Ala Ser Glu Glu Thr Pro Glu Val Val Gln Ala
2465            2470                2475                2480

Phe Ile Arg Pro Phe Asp Leu Ala Lys Pro Pro Leu Leu Arg Ala Glu
            2485                2490                2495

Leu Val Glu Leu Ala Ile Glu Arg Tyr Leu Leu Met Phe Asp Met His
            2500                2505                2510

His Ile Val Ser Asp Gly Val Ser Met Asp Val Leu Val Glu Glu Leu
        2515                2520                2525

Val Arg Leu Tyr Gly Gly Glu Ser Leu Glu Pro Leu Arg Ile Gln Tyr
        2530                2535                2540

Lys Asp Tyr Ala Val Trp Gln Gln Ser Asp Glu Gln Lys Val Gln Leu
2545            2550                2555                2560

Lys Arg Glu Glu Ala Tyr Trp Leu Asp Arg Tyr Arg Gly Glu Leu Pro
            2565                2570                2575

Val Leu Glu Met Pro Thr Asp Tyr Pro Arg Pro Ala Val Gln Ser Phe
            2580                2585                2590

Glu Gly Gln Thr Leu Thr Ser Phe Val Asp Glu Ala Thr Asn Glu Gly
        2595                2600                2605

Leu Lys Gln Leu Ala Ala Gln Lys Gly Thr Thr Leu Tyr Met Val Leu
        2610                2615                2620

Leu Ala Ala Tyr Thr Val Leu Leu His Lys Tyr Thr Gly Gln Asp Asp
2625            2630                2635                2640

Leu Ile Val Gly Thr Ser Ile Ala Gly Arg Thr His Gly Asp Thr Gln
            2645                2650                2655

Pro Leu Ile Gly Met Phe Val Asn Thr Leu Ala Leu Arg Asn Tyr Pro
            2660                2665                2670

Ala Ser Glu Lys Ser Phe Leu Ser Tyr Leu Glu Glu Val Lys Glu Thr
        2675                2680                2685

Thr Leu Gly Ala Tyr Glu His Gln Asn Tyr Pro Phe Glu Glu Leu Val
        2690                2695                2700
```

```
Asp Lys Val Gln Val Ser Arg Asp Leu Ser Arg Asn Pro Leu Phe Asp
2705                2710                2715                2720

Thr Met Phe Ser Leu Gln Asn Leu Glu Asp Lys Glu Phe Lys Leu Glu
            2725                2730                2735

Gly Leu Lys Leu Ser Pro Tyr Pro Ser Glu Tyr Gly Thr Ala Lys Phe
            2740                2745                2750

Asp Leu Ser Val Asp Val Thr Glu Glu Asn Gly Gly Leu Glu Cys Ile
            2755                2760                2765

Phe Glu Phe Ala Thr Ala Leu Tyr Lys Glu Ser Thr Ile Arg Arg Leu
    2770                2775                2780

Ser Thr His Phe Gly His Leu Leu Ala Ala Ile Val Ser Arg Pro Asp
2785                2790                2795                2800

Ala Lys Ile Ala Glu Leu Asn Leu Leu Thr Ala Glu Glu Asn Glu Gln
                2805                2810                2815

Ile Leu Gly Ala Phe Asn Pro Ala Gln Pro Glu Ala Ala Pro Ala Ala
            2820                2825                2830

Ala Phe His Arg Leu Phe Glu Glu Gln Ala Glu Arg Thr Pro Glu Ala
            2835                2840                2845

Glu Ala Val Val Tyr Glu Asn Asp Arg Leu Thr Tyr Ala Glu Leu Asn
2850                2855                2860

Glu Arg Ala Asn Arg Leu Ala Ala Thr Leu Arg Ala Ser Gly Ile Gly
2865                2870                2875                2880

Arg Glu Ser Ile Val Gly Ile Leu Ser Glu Arg Ser Val Asp Leu Leu
            2885                2890                2895

Val Ala Val Leu Ala Val Trp Lys Ala Gly Gly Ala Tyr Val Pro Leu
            2900                2905                2910

Asp Pro Asp Tyr Pro Ala Asp Arg Val Arg Phe Met Leu Glu Asp Ser
            2915                2920                2925

Gly Ala Lys Val Leu Leu Thr Gln Thr Val Leu Arg Glu Arg Ala Glu
            2930                2935                2940

Ala Trp Leu Gly Glu Glu Leu Ala Leu Ala Ala Val Leu Tyr Leu
2945                2950                2955                2960

Asp Asp Glu Ala Ser Tyr Ser Glu Glu Arg Ala Asn Ala Pro Ile Gly
            2965                2970                2975

Ser Gly Met Val Ser Gly Lys Leu Thr Asp Ala Val Asp Asp Gly Asp
            2980                2985                2990

Val Ser His Gln Lys Val Gly Met Gly Ser Phe His Glu Ala Arg Pro
            2995                3000                3005

Glu Asp Leu Ala Tyr Val Ile Tyr Thr Ser Gly Thr Thr Gly Lys Pro
    3010                3015                3020

Lys Gly Val Met Ile Glu His Arg Ser Leu Val Asn Thr Ala Ala Gly
3025                3030                3035                3040

Tyr Arg Arg Glu Tyr Arg Leu Asp Gln Phe Pro Val Arg Leu Leu Gln
            3045                3050                3055

Leu Ala Ser Phe Ser Phe Asp Val Phe Val Gly Asp Ile Ala Arg Thr
            3060                3065                3070

Leu Tyr Asn Gly Gly Thr Met Val Ile Val Pro Lys Asp Asp Arg Ile
            3075                3080                3085

Asp Pro Ser Arg Leu His His Trp Met Glu Arg Glu Arg Val Thr Ile
            3090                3095                3100

Phe Glu Ser Thr Pro Ala Leu Ile Val Pro Phe Leu Glu Tyr Val His
3105                3110                3115                3120

Glu Gln Gly Leu Asp Met Ser Trp Met Glu Leu Leu Ile Thr Ser Ser
```

```
                      3125              3130              3135

Asp Ser Cys Ser Val Ala Asp Tyr Arg Ile Leu Gln Glu Arg Phe Gly
            3140              3145              3150

Ser Phe Phe Arg Ile Ile Asn Ala Tyr Gly Val Thr Glu Ala Ala Ile
            3155              3160              3165

Asp Ser Ser Phe Tyr Asp Glu Glu Leu Thr Lys Leu Pro Gln Ile Gly
            3170              3175              3180

His Val Pro Ile Gly Lys Ala Trp Leu Asn Ala Lys Phe Tyr Ile Val
3185              3190              3195              3200

Asp Ala His Leu Asn Pro Val Pro Val Gly Val Leu Gly Leu Val
            3205              3210              3215

Ile Gly Gly Val Gly Val Ala Arg Gly Tyr Leu Asn Arg Pro Glu Leu
            3220              3225              3230

Thr Glu Glu Lys Phe Val Asp Ser Pro Phe Ala Ala Gly Glu Arg Leu
            3235              3240              3245

Tyr Arg Thr Gly Asp Leu Ala Arg Trp Met Glu Asp Gly Asn Val Asp
            3250              3255              3260

Phe Ile Gly Arg Ile Asp Asn Gln Ala Lys Ile Arg Gly Tyr Arg Ile
3265              3270              3275              3280

Glu Thr Gly Glu Ile Glu Ser Gln Leu Leu Arg Val Glu Gly Val Arg
            3285              3290              3295

Glu Ala Val Val Leu Val Arg Ser Asp Ala Asn Gly Gln Lys Ala Leu
            3300              3305              3310

Cys Ala Tyr Tyr Thr Leu Asp Thr Gly Ala Glu Leu Ala Val Asn Asp
            3315              3320              3325

Leu Arg Ser Thr Leu Ala Gln Glu Leu Pro Gly Tyr Met Ile Pro Ser
            3330              3335              3340

Tyr Phe Val Glu Leu Glu Gly Leu Pro Leu Thr Pro Asn Gly Lys Ile
3345              3350              3355              3360

Asp Arg Lys Ala Leu Pro Ala Pro Glu Gly Glu Ala Gly Ser Gly Thr
            3365              3370              3375

Glu Tyr Val Ala Pro Arg Asn Glu Leu Glu Thr Lys Leu Ala Ala Ile
            3380              3385              3390

Trp Gln Glu Val Leu Gly Leu Ala Lys Glu Ile Gly Val His Asp Asn
            3395              3400              3405

Phe Phe Asp Ile Gly Gly His Ser Leu Arg Ala Thr Thr Leu Val Ser
            3410              3415              3420

Lys Val His Lys Glu Leu Ser Val Asp Leu Pro Leu Arg Asp Val Phe
3425              3430              3435              3440

Arg His Ser Thr Ile Glu Ser Met Ala Ala Ala Ile Ser Arg Leu Asp
            3445              3450              3455

Glu Gln Thr Phe Val Ala Ile Pro Val Ala Asp Arg Glu Val Tyr
            3460              3465              3470

Pro Gln Ser Phe Ala Gln Lys Arg Leu Phe Ile Leu Asn Gln Leu Glu
            3475              3480              3485

Gly Ala Glu Leu Ser Tyr Asn Met Pro Glu Ala Met Leu Leu Glu Gly
            3490              3495              3500

Ala Leu Asp Arg Ala Arg Phe Glu Glu Ala Phe Arg Lys Leu Val Ala
3505              3510              3515              3520

Arg His Glu Met Leu Arg Thr Gly Phe Glu Met Val Asp Gly Glu Ala
            3525              3530              3535

Ser Gln Arg Val Tyr Gln Asp Leu Asn Phe Ala Val Glu Phe Tyr Arg
            3540              3545              3550
```

-continued

Val Asp Glu Gln Glu Ala Glu Thr Val Arg Arg Phe Val Arg Pro
        3555                3560                3565

Phe Asp Leu Ala Lys Pro Pro Leu Arg Val Gly Leu Val Glu Leu
        3570                3575                3580

Ala Ser Glu Arg His Ile Leu Met Tyr Asp Met His Ile Ile Ser
3585                3590                3595                3600

Asp Gly Val Ser Met Glu Ile Phe Val Glu Gly Phe Val Arg Leu Tyr
            3605                3610                3615

Gly Gly Glu Gln Leu Glu Pro Leu Arg Ile Gln Tyr Lys Asp Tyr Thr
            3620                3625                3630

Val Trp Gln His Ser Gln Glu Gln Lys Glu Arg Leu Gln Arg Gln Glu
            3635                3640                3645

Ala Tyr Trp Leu Asn Met Phe Gln Gly Glu Leu Pro Val Leu Glu Met
        3650                3655                3660

Pro Thr Asp Tyr Pro Arg Pro Ser Val Gln Ser Tyr Glu Gly His Thr
3665                3670                3675                3680

Leu Glu Phe Phe Phe Asp Ala Ser Lys Thr Asp Gly Leu Lys Gln Leu
            3685                3690                3695

Ala Ser Glu Thr Gly Thr Thr Leu Phe Met Val Leu Leu Ala Ala Tyr
            3700                3705                3710

Asn Val Leu Leu His Lys Tyr Ser Gly Gln Glu Asp Val Ile Val Gly
            3715                3720                3725

Thr Pro Ile Ala Gly Arg Asn His Gly Asp Val Gln Pro Leu Ile Gly
            3730                3735                3740

Met Phe Leu Asn Thr Leu Ala Ile Arg Ser Tyr Pro Ala Ser Glu Lys
3745                3750                3755                3760

Thr Phe Leu Ser Tyr Leu Asn Glu Val Lys Glu Thr Thr Leu His Ala
            3765                3770                3775

Phe Glu His Gln Asn Tyr Pro Phe Glu Glu Leu Val Asp Lys Val Gln
            3780                3785                3790

Val Thr Arg Asp Leu Ser Arg Asn Pro Leu Phe Asp Thr Leu Phe Thr
            3795                3800                3805

Met Gln Asn Thr Glu Asn Glu Glu Phe Glu Leu Glu Gly Leu Arg Leu
        3810                3815                3820

Ile Pro Tyr Pro Ser Ala Leu Asp Thr Ala Lys Phe Asp Ile Ser Leu
3825                3830                3835                3840

Asp Val Gly Glu Glu Asn Gly Gly Leu Asp Tyr Ser Phe Glu Tyr Ala
            3845                3850                3855

Thr Ala Leu Tyr Lys Arg Ala Thr Ile Glu Arg Leu Ala Lys His Tyr
            3860                3865                3870

Glu Gln Leu Leu Val Thr Ile Ile Ser Arg Pro Asp Ala Lys Ile Ala
            3875                3880                3885

Glu Leu Asn Leu Leu Thr Ala Glu Glu Lys Glu Gln Ile Leu Gly Thr
            3890                3895                3900

Phe Asn Pro Ala Gln Pro Glu Ala Ala Pro Ala Ala Ala Phe His Arg
3905                3910                3915                3920

Leu Phe Glu Glu Gln Ala Glu Arg Thr Pro Glu Glu Ala Ala Val Val
            3925                3930                3935

Tyr Glu Asn Asp Gln Leu Thr Tyr Ala Glu Leu Asn Glu Arg Ala Asn
                3940                3945                3950

Arg Leu Ala Ala Thr Leu Arg Ala Ser Asp Ile Gly Arg Glu Thr Ile
            3955                3960                3965

-continued

Val Gly Ile Leu Ala Glu Arg Ser Val Asp Leu Leu Val Ser Val Leu
    3970                3975                3980

Ala Val Trp Lys Ala Gly Gly Ala Tyr Val Pro Leu Asp Pro Asp Tyr
3985                3990                3995                4000

Pro Ala Asp Arg Val Arg Phe Met Leu Glu Asp Ser Gly Ala Lys Val
        4005                4010                4015

Leu Leu Thr Gln Met Pro Leu Arg Glu Arg Ala Glu Ala Trp Leu Gly
            4020                4025                4030

Glu Glu Glu Leu Ala Leu Ala Ala Val Leu Tyr Leu Asp Glu Glu Ala
        4035                4040                4045

Ser Tyr Ser Glu Glu Arg Ala Asn Ala Pro Ile Gly Ser Gly Met Val
    4050                4055                4060

Pro Gly Lys Leu Thr Asp Ala Val Asp Asp Gly Asp Glu Thr His Pro
4065                4070                4075                4080

Asn Ile Gly Met Gly Ser Phe His Glu Ala Arg Pro Asp Asp Leu Ala
            4085                4090                4095

Tyr Val Ile Tyr Thr Ser Gly Thr Thr Gly Lys Pro Lys Gly Val Met
        4100                4105                4110

Ile Glu His Arg Ser Leu Val Asn Thr Ala Ala Gly Tyr Arg Arg Glu
        4115                4120                4125

Tyr Arg Leu Asp Gln Phe Pro Val Arg Leu Leu Gln Leu Ala Ser Phe
    4130                4135                4140

Ser Phe Asp Val Phe Val Gly Asp Ile Ala Arg Thr Leu Tyr Asn Gly
4145                4150                4155                4160

Gly Thr Met Val Ile Val Pro Lys Asp Asp Arg Ile Asp Pro Ser Arg
        4165                4170                4175

Leu His His Trp Met Glu Arg Glu Arg Val Thr Ile Phe Glu Ser Thr
        4180                4185                4190

Pro Ala Leu Ile Val Pro Phe Leu Glu Tyr Val His Glu Gln Gly Leu
    4195                4200                4205

Asp Ile Ser Trp Met Glu Leu Leu Ile Thr Ser Ser Asp Ser Cys Ser
    4210                4215                4220

Val Ala Asp Tyr Arg Ile Leu Gln Glu Arg Phe Gly Ser Leu Phe Arg
4225                4230                4235                4240

Ile Ile Asn Ala Tyr Gly Val Thr Glu Ala Ala Ile Asp Ser Ser Phe
        4245                4250                4255

Tyr Asp Glu Glu Leu Ala Lys Leu Pro Gln Thr Gly His Val Pro Ile
        4260                4265                4270

Gly Lys Ala Trp Leu Asn Ala Lys Phe Tyr Ile Val Asp Ala His Leu
    4275                4280                4285

Asn Pro Val Pro Val Gly Val Leu Gly Glu Leu Val Ile Gly Gly Val
    4290                4295                4300

Gly Val Ala Arg Gly Tyr Leu Asn Arg Pro Glu Leu Thr Glu Glu Lys
4305                4310                4315                4320

Phe Val Asp Ser Pro Phe Ala Ala Gly Glu Arg Leu Tyr Arg Thr Gly
            4325                4330                4335

Asp Leu Ala Arg Trp Met Glu Asp Gly Asn Val Asp Phe Ile Gly Arg
        4340                4345                4350

Ile Asp Asn Gln Ala Lys Ile Arg Gly Tyr Arg Ile Glu Thr Gly Glu
        4355                4360                4365

Ile Glu Ser Gln Leu Leu Arg Val Glu Gly Val Arg Glu Ala Val Val
    4370                4375                4380

Leu Val Arg Ser Asp Ala Asn Gly Gln Lys Ala Leu Cys Ala Tyr Tyr

-continued

```
            4385            4390            4395            4400
        Thr Leu Asp Thr Gly Ala Glu Leu Ala Val Asn Asp Leu Arg Ser Thr
                        4405            4410            4415

Leu Ala Gln Glu Leu Pro Gly Tyr Met Ile Pro Ser Tyr Phe Val Glu
                        4420            4425            4430

Leu Glu Gly Leu Pro Leu Thr Pro Asn Gly Lys Ile Asp Arg Lys Ala
                        4435            4440            4445

Leu Pro Ala Pro Glu Gly Glu Ala Gly Ser Gly Thr Glu Tyr Val Ala
                        4450            4455            4460

Pro Arg Asn Glu Leu Glu Thr Lys Leu Ala Ala Ile Trp Gln Glu Val
        4465            4470            4475            4480

Leu Gly Leu Ala Lys Glu Ile Gly Val Tyr Asp Asn Phe Phe Asp Ile
                        4485            4490            4495

Gly Gly His Ser Leu Arg Ala Thr Thr Leu Ala Gly Lys Val Phe Lys
                        4500            4505            4510

Glu Leu Asn Val Asn Leu Pro Leu Arg Asp Val Phe Arg His Ser Thr
                        4515            4520            4525

Ile Ala Ala Met Ala Glu Ala Ile Ala Arg Met Glu Arg Leu Glu His
                        4530            4535            4540

Glu Asp Ile Pro Gln Ala Glu Glu Arg Glu Tyr Tyr Pro Leu Ser Ser
        4545            4550            4555            4560

Ala Gln Lys Arg Leu Phe Ile Gln His Thr Leu Asp Gly Ala Asp Gln
                        4565            4570            4575

Leu Tyr Asn Met Pro Glu Leu Val Gln Val Glu Gly Glu Phe Asp Leu
                        4580            4585            4590

Asp Arg Leu Glu Ala Ala Leu Arg Lys Leu Ile Thr Arg His Glu Ser
                        4595            4600            4605

Leu Arg Thr Gly Phe Glu Leu Val Lys Gly Lys Ala Val Gln Arg Ile
                        4610            4615            4620

Tyr Pro Gln Val Asp Phe Ala Val Glu His His Gln Ala Asp Lys Glu
        4625            4630            4635            4640

Asp Ala Ala Gln Ile Glu Gln Ile Val Arg Ser Phe Val Arg Pro Phe
                        4645            4650            4655

Asp Leu Gly Lys Pro Pro Leu Arg Ala Gly Val Ile Glu Leu Glu
                        4660            4665            4670

Pro Asn Leu Tyr Ile Leu Ile Phe Asp Met His His Met Val Ser Asp
                        4675            4680            4685

Gly Val Ser Met Ala Ile Val Ile Asp Glu Phe Ser Ser Phe Tyr Ala
                        4690            4695            4700

Gly Glu Glu Leu Pro Ser Leu Arg Ile Gln Tyr Lys Asp Tyr Val Val
        4705            4710            4715            4720

Trp Gln Gln Ser Lys Ala Tyr Arg Glu Arg Ile Gly Arg Gln Glu Ala
                        4725            4730            4735

Tyr Trp Leu Gln Thr Phe Lys Gly Glu Leu Pro Thr Ala Asn Leu Pro
                        4740            4745            4750

Met Asp Tyr Lys Arg Ser Ala Ala Arg Ser Tyr Glu Gly Ala His Leu
                        4755            4760            4765

Glu Phe Asp Val Glu Ala Ser Leu Ser Met Arg Leu His Glu Leu Ala
                        4770            4775            4780

Ala Glu Arg Lys Ser Thr Leu Phe Met Val Leu Leu Ala Ala Tyr Thr
        4785            4790            4795            4800

Val Leu Leu Ser Lys Tyr Ser Gly Gln Glu Asp Leu Ile Val Gly Thr
                        4805            4810            4815
```

Pro Val Ala Gly Arg Thr Asn Ala Asp Leu Glu Pro Val Ile Gly Met
            4820                4825                4830

Phe Val Asn Thr Leu Ala Ile Arg Asn Arg Pro Ser Gly Asn Lys Thr
        4835                4840                4845

Phe Leu Ser Tyr Leu Glu Glu Val Lys Glu Thr Ala Leu Gly Ala Phe
    4850                4855                4860

Glu Asn Gln Asp Tyr Pro Phe Glu Leu Val Glu Arg Leu Asn Val
4865            4870                4875                4880

Lys Arg Glu Pro Gly Arg Phe Pro Leu Phe Asp Ala Val Phe Asp Leu
            4885                4890                4895

Gln Asn Ile Glu Glu Arg Asp Val Glu Leu Gly Val Ser Leu Lys
        4900                4905                4910

Asn Tyr Glu Leu Asp His Leu Glu Glu Ala Lys Phe Asp Leu Thr Leu
    4915                4920                4925

Phe Met Tyr Glu Asn Asn Gly Ala Leu Ser Gly Gly Phe Phe Tyr Ala
    4930                4935                4940

Thr Lys Leu Phe Lys Glu Ala Met Ile Arg Thr Leu Thr Glu Asp Tyr
4945            4950                4955                4960

Leu Arg Val Leu Ser Gln Ile Ala Glu Asn Pro Gln Leu Glu Leu Ser
            4965                4970                4975

Arg Ile Glu Cys His Lys Pro Ala Ala Gly Ala Lys Ser Ala Val Asp
            4980                4985                4990

Thr Ile Glu Phe Ala Phe
        4995

<210> SEQ ID NO 26
<211> LENGTH: 14997
<212> TYPE: DNA
<213> ORGANISM: Paenibacillus alvei

<400> SEQUENCE: 26
atgtttgaaa aggcggggag catggctgta gcgttgctgc ggcatatgct ccgccggatt        60
gcttttaccg atgtagagag ggggacgatc caggtggctt ttgaaaaaga aacgttgttt       120
tggaacgaaa aattcggtag tgacgattat accttgacgc ggctgcctta cagcaaagct       180
ccaagctccc aggcgcccat tatgacaacc gtcggcggtt cgctttcgga gaaagcggcg       240
cagcgcgtcc ttcaaatgag caagggcgct ccgctggccg cttttatgat tttgctcgcc       300
ggtgttcagt cactcttgca taaatataca ggcgcttctg acattctggt cggcatgccg       360
gttatacgga aaccgacgga gacgcgccga tccgttaatc atacggtcat tttgaaaagc       420
ttgctttcgg cgggatcgac ttttaaaacg cttctgagcg agctgagaac ttcgttgccg       480
gaaacgattc agcatcaaca tattccgttc ttgaaaatga cggagaagct ggatctgcaa       540
tatgcagacg ggatacccat catccatacg ctagtatccc ttaaggagct gcatctggat       600
gaaattgggc aaaacgtggt cacggattgt cctttgaat tcagcttaac cggcgggacg        660
atacagctag cgctctcata taacgagcac ttatatgact ccaagttcat gactcggatc       720
gtcggccatc tgaatcgcct gctggccgtg gggcttcacg agttggagct ggacatcgtg       780
cgggtggaca tgctgtcgga ggacgagaaa tttcaattgc tgcaaagctt taacgatacc       840
gagaaggact atcctcgaga tcggacgatt catcagctcg tggaggagca ggtgaagagg       900
gtgcccgaag caacggcgat tgtctttgag gggcggcggc tttcgtacgc tgagctgaac       960
gaacgggcga accggctggc gcggacgctg cgatcggtcg gcgtgctgcc caatcagctg      1020

| | |
|---|---|
| gtaggcttga tggccaggag atcgctggag acggtcgttg gcattctggc ggttctgaaa | 1080 |
| gctggcggtg cctacgtgcc gatcgacccg gaatacccgg aagaacgcat ccgctacatt | 1140 |
| ctggagaact cgaacgcgca gctgctgctg actcaaagaa agctgcaaca gcaggtgccg | 1200 |
| ttcgaaggga ctgtgttggc gctggatgac gagcaggcct acagcgatga tggaacgaat | 1260 |
| ctggagccgg ccagcggttc gaatgatctg gcttatgtca tctatacgtc aggtacgacg | 1320 |
| ggcaaaccca aaggggtcat gctggagcat cgcggtttgg tcagcttgaa actgatgttc | 1380 |
| gcggacaggc tcggcatcac ggagcatgac cggatcgttc aattcgccag cctgtcgttc | 1440 |
| gacgcgtcct gctgggaagt gttcaaagcg ctctattttg gcgcgacttt gtacataccg | 1500 |
| acggccgaga cgattctcga caaccgcctg tttgagagtt atatgaacga gcatgcgatt | 1560 |
| acggcggcga ttttgcctcc gacgtacagc gcttatttga acccggaccg ccttcccagc | 1620 |
| ttaacgaagc tcgtaacggg aggctcggcg gtatcggccg aattcgtgca gcagtggaaa | 1680 |
| ccgaaggtcc actatttcaa tgcttacggc cctaccgaag cttcgattgt tacgacgctt | 1740 |
| tgggatgcga atgaggagca gccagagcgc agagtcattc cgattgggcg cccgctggcc | 1800 |
| aatcaccgga tttttatttt ggatgcccac ctgcagcttg tgcctccggg agtggacggc | 1860 |
| gagctgtgcg tggcaggcgt ggggcttgcg agaggttacc tgaaccatcc ggagctgacg | 1920 |
| gcagaaaagt tcgtggaaca tccgttcgcg ccgggagaac gcctttatcg gacgggagat | 1980 |
| ctcgcccgat ggctgccgga cggaaatatt gagtacttgg gccggatcga ccatcaggtg | 2040 |
| aaaatccgtg gattccggat cgagatcggc gagattgaag agcagcttct gaagatcgac | 2100 |
| tccgtgcagg agacgatggt aatcgcgcgg gaaggcaaaa gcgggcaaga attgtgcgct | 2160 |
| tatctggtcg cggaccgccc gcttacgctc ggcgagctga aagcgcgct ggcgcaaaaa | 2220 |
| ttgccgaatt acatgattcc ggcgcatttt gttcagcttc cgcgaatgcc gctcacgccg | 2280 |
| aacgacaaaa tcgaccgcaa ggctttgccc gccccggaag gaaacgcgct gaccggcggc | 2340 |
| ttgtacgtag ctcccccgcaa tgaagccgag cggacacttg tcgatgtgtg gcaggcggta | 2400 |
| ttgaacgccg atcgtgttgg ggtaacggat catttcttcg agctgggtgg agactcgatc | 2460 |
| aagtccattc aagtatcttc gcggcttcat caagccgggt acaagctgga tattcgggat | 2520 |
| ttgttcaaat atccgactat ctcacagctc agcctgcgtg tgaaaccgat cggacgtacc | 2580 |
| atcgatcaag gcgaaataac gggcgaaacg gcgctgacgc cgattcagca ttggtttttc | 2640 |
| gagagctcct ttgcggatcc gcatcatttc aaccagtcgg tgatgctgta ccggaaggaa | 2700 |
| cgcttcgacg aagagacggt gcgtcaggta ctgcaaaagc tggccgagca tcatgacgcc | 2760 |
| ttgcggatgg tgttccgcaa aacggaacaa gggtttagcg aaaggaaccg cgcgattcag | 2820 |
| gaaggcgggc tgttcacgct ggacgtgttc gacttcaagg atgcggagga taccgcacag | 2880 |
| gctctggaag cgaaggcaac ggatattcaa gcgggcatcg atctggagaa agggcccctc | 2940 |
| gtgaaggcgg gactgttccg atgcgcggac ggcgatcatt tactgctcgc ggttcatcat | 3000 |
| gccgtggtgg acgcgtgtc ttggcgcatt ttgatggagg atttcgctct gggttacgag | 3060 |
| caggccggca aaagcgagga aattcgtttc ccggcgaaaa cggatgcgta ccgcacttgg | 3120 |
| tccgagcagc tggccgctta cgcgcaaagc ccggagatag caaggaacg ggcttattgg | 3180 |
| caggccgtgg aacaaattgc ggttccggcc ttgccgaagg atctggaggc ggacgttacg | 3240 |
| acgcagcagg acagcgaatc gctgttcgtc cgtttgactt ccgaagaaac ggagctgctg | 3300 |
| ctgaagcggg tacaccgggc ctacaacacc gaaatgaacg atattttggt aacgcgctc | 3360 |
| ggcatagctg ttcgcaagtg gacgggacac gaacgggtgc ggatcaatct cgaaggacac | 3420 |

```
ggacgcgaat cgatcggaac ggatatcgac atcacgcgca cagtcggctg gtttacgacc    3480
aagtttccgg tcgtcctgga gccgaaacc aaccgggatt tggcctatca gattaaacag     3540
gtcaaggaaa gcttgcgtcg cattccgaac aaggggcttg ggtacggtgt atgccgctat    3600
ctctccaaat cggaggatgg ctttgttttgg ggcgcagagc cggaaattaa ttttaactac   3660
ctcggccagt tcgacgatga tgtcaaccag gacgagatcg gcatatcttc ttattccagc    3720
ggcagcccgg ccagcgaccg gcaggcccgc agctttgtgc tggatatcaa cggcatggtg    3780
ctggacggcg ctctatcgct cgatctcagc tacagccgga agcagtatcg caaggtaacg    3840
atggaagcct tcgctcagcg gcttgagcaa agtctccgag agctcattac ccactgcgca    3900
ggcaaagaaa acaccgaatt gacgcctagc gacgtgcaat ttaaaggctt gaccatcgcg    3960
gaattggagc aaatcggcca gcgctcggtc catgtcgggg aaatcgagaa tatttactcg    4020
cttacgccga tgcagaaggg catgtggttc cacagcgcgc ttgaccggca gacggccgct    4080
tacttcgagc agacgcggtt tacgatgcgg ggagcgctcg acgttcagct tttcgagagg    4140
agctggacgg agcttgcgaa acgtcatctg gtgctgcggg cgaattttgt gaaaggacca    4200
gcgggcgagc cgctgcagat catataccgc gacaaaccag tcggctttga atatgaagag    4260
ctgctacatt tgcaggcgga cgagaaacaa gcgtatttgg ataaaaaggc cgaggatgac    4320
aagcttcgcg gcttcgacct ggaacatgac gcgctcgttc gggttacgat cctgcgcacc    4380
gaagagcaga gctatcatgt gctgtggagt ttccagcata ttttgatgga cggctggtgc    4440
ctgccgcaac tgacgcagga gctgtttgag acatactcgg ccttggcatc cggcaagcag    4500
ccagcgggag ataagggggtc ggattatggc gcttatatcg aatggctgga gaaacaggac   4560
gatcaggcgg catccggcta ttggacggcg ttcctggcag gttacgaagg gcaaactgta    4620
ctcccggggc aaaaggaagc gcagccgaac ggtagattta cggctgatca cgtcaccgcc    4680
gagctgggca aggacttgag cgagcggatg gatcgggtgg cgaaacagcg cctggttaca    4740
gtcaatacgc tgctgcaagc cgcttggggc gtgatgctgc aaaaatataa cggaacaaac    4800
gatgccgtat tcggcagcgt cgtggccgga agaccggcgg aaatcccggg tatagagtcc    4860
atgattggac tgtttatcaa tacggtgccg gttcgcgtca cgagcgaagc ggacaccgtg    4920
ttcgctgacc tgatggcaaa gctccaagag cgggcgctgg agtccgggcg ttatgattac    4980
tatccgctgt atgaaattca agcccgctgc gtgcaaaagc aaaacctgat caaccatatc    5040
atcgctttcg agaactatcc ggtggatgag cagatggagc aggcgggcga ccagcagcac    5100
ggcgacctga cgatcactga cgttcagatg gaggagcaga cgaactataa cttcaatgtg    5160
accgtggtgc caggagccga gatcgaaatt cggttcgatt ttaacgccga agtgtttgat    5220
aaagacagca tcgaacggct caaggggcat ctcgtccatc tgctggagca ggtgacggat    5280
aacccggaaa ttaccgtggg agagctggaa cttgtgacgg aggcggaaaa ggccgacctt    5340
ctcggacgat ttaacgacac caccacggaa tttccgcgcg ggaagacgct cattcaattg    5400
ttcgaagagc aggtagagcg catcccggat gcagccgcca tcaccttgaa tgagcaagag    5460
ctgacctacc gcgagctcaa cgaacgtgtc aaccgccttg cccgtacctt gcgtagccac    5520
gggatatcca aaggtcgtct ggtcgccatt ttggctgagc gttccattga aatggtggtg    5580
ggcatgctgg cggcacacaa agccggagcg gcttacgtac cgattgaccc agaatatccc    5640
gaggagcgta tccgtttctt gatcgaggat tcgggagggc aggtcatgct gacgcaaagc    5700
cgcttgcgcg agcgcctggc gggttcggac cccgtgatct tactggatga cgagtccttc    5760
```

```
tatcacgagg acggcacaaa tctaaatacg ggcatcgaag cgacagatct ggcctgcgtc    5820
atctatacgt caggcacgac gggcaagccg aaaggcaacc ctgtttcgca ccgcaacatc    5880
gtgcgggtcg tgcaaaatac gaattatatc gacatcaccg agcgggatca tgtcctccag    5940
ctttcgagct attcgttcga cggagcgact ttcgatattt tcggcgcttt gaccaacggg    6000
gcgcggctgg tgctggttcc ctacgagact ttgctggaaa tcggccggct ggcggatctc    6060
atccagcgcg agcgcatctc ggtcatgttt attacgacgg ctttcttcaa catccttgta    6120
gatgtgaacg tcgactgcct gcgggatgtc agggcgattt tgttcggagg agagcgtgtg    6180
tcggtcggcc atgtgcgcaa agcgctcgcc catatcggac cgggcaggct caaccatgtg    6240
tacggcccga cggaaagcac ggtttatacc acgtaccttc cggtcgactt cgtcgatgag    6300
ttggcggtta ccgtacccat tggacggccg atcagcaata cgacggtgta tatcgtcgac    6360
agccggaaca aacttctgcc gatcggcgtg gccggggaac tttgcgtcgg cggagaaggc    6420
ttggtaaggg gctacaataa ccggccggag ctgacggcgg agaaatttgt ggacaatccg    6480
tttgtgccgg gagagcgcat gtaccggacg ggggatttgg cgaaatggct gccggacggc    6540
acgatcgaat acgtgggacg gacgacgac caagtgaaaa tccgcggctt ccgaattgag    6600
ctaggcgaga tcgaagctca gcttcagaaa gtggagggaa ttcggaaaac gacggtattc    6660
gcgagggaaa acgcctccgg cgagaagcag ctttgcgcct attatgaagc ggactgcgag    6720
cttccggcgg ccgaactgaa gagcgtgctt tccaaggaac tgccggccta tatgatcccg    6780
gcgtacctga tccagttgga gcggctcccg ctgacgacga acggcaaggt cgaccgccga    6840
tcactcccgg cgccggagga gagcttgcag ccgggcggag gaagtactcc gcctcggact    6900
ccgctggaag ccagcttggc cggaattttgg aaaagcgtgc tcggactagt gcacattggc    6960
gttcatgaca acttcttcga catgggcgga cattccctgc gggcgacgac actggtgagc    7020
aaggtgcatc aggagctgaa cgtcgaactg cctctgcgcg acgtattccg ctactcgacg    7080
atcgaggaga tggctctcgc catctcccgg atcggagagc agtcgttctc gtcgattccg    7140
ctggcaggcg caagagcata ttatccgctt tcctcagctc agaagcggct gtttatcctg    7200
aatcagctga aggggccga tcagagctac aacatgccgg gcgtgctgct gttggaagga    7260
tcgattgacc ggagcctgct ggagaaggct ttccgcggac tgatcgcacg gcacgaaacg    7320
ctgcgaaccg gctttgagat cgtacaaggc gaagcagtac agcgcattta cgagagcgtc    7380
gactttgccg tcgagtaccg tcatgcgagc gaggaagaaa cgcctgaagt cgtgcaggcc    7440
ttcatccggc ctttcgactt ggcaaagcct ccgctgctgc gggcggagct cgtagagctg    7500
gcaatcgaac gttatttgct gatgttcgac atgcaccata tcgtctccga cggggtttcg    7560
atggacgtgt tagtcgagga actcgttcgt ctgtacggcg gcgagtcatt agagcctttg    7620
cgcattcaat acaaggacta tgcggtatgg cagcagtcgg acgagcaaaa agtgcagttg    7680
aaacgcgagg aagcttactg gttggaccgt taccggggcg agctgccggt tctgaaaatg    7740
ccgacggact atccgcgtcc tgccgtgcag agctttgagg acaaacgct gacgtccttc    7800
gtggacgagg caacgaacga aggcttaaag caactggccg ctcaaaaagg aacgacgctg    7860
tatatggtac tgcttgcggc atataccgtg cttttgcata aatacacagg tcaggacgat    7920
ttgatcgtcg gaacgtcgat tgcgggcaga acgcacggag acacgcagcc tttgatcgga    7980
atgttcgtca atacgctggc actccgcaat tatccggctt cggagaagag cttcctgtcg    8040
tatcttgaag aagtgaaaga aacgaccttc ggcgcttacg agcatcagaa ttatccgttc    8100
gaagagctcg ttgataaagt gcaggtcagc cgggatttga gccgcaaccc gctgtttgac    8160
```

```
acgatgttct ccctgcaaaa cttggaggat aaagagttta agctggaagg gctgaaattg    8220
tccccgtacc ctagtgaata cggcacggcc aagttcgatc tgagtgtgga tgttacggaa    8280
gaaaacggcg gcttggagtg catctttgaa ttcgcaacgg ctctttataa agaaagcacg    8340
atccggcggc tgtcgactca ttttggacat ttgcttgcgg cgatcgtaag tcgtccggat    8400
gcgaagatcg ccgagctgaa cttgttgacg gcagaggaaa atgagcaaat tctcggcgcg    8460
ttcaacccgg cgcagccgga agcggctcct gcggccgcgt tccaccggct gttcgaagaa    8520
caggcggagc gcacgccgga agcggaggcc gtcgtgtacg agaacgaccg gctgacgtat    8580
gcggagctga cgagcgggc gaaccgcttg cggctacgc tgcgcgcaag cggcatcggc    8640
cgggagtcga tcgtcggcat tctctccgag cgttcggtgg acttgctggt ggccgtgctg    8700
gccgtctgga aagcgggcgg ggcgtatgtg ccgctcgacc cggattatcc ggcggaccgc    8760
gtgcggttca tgcttgaaga cagtggagcg aaggtgctgc tgacgcaaac ggtgctgcga    8820
gagcgcgccg aagcctggct cggcgaagag gagctggcgc tggcagcggt gctgtacctg    8880
gacgacgaag cgtcgtacag cgaggagcgg gcgaatgcgc cgattggttc cggcatggtc    8940
tccggcaagc tgacggatgc tgtggacgac ggcgatgtga ccatcagaa ggtcggcatg    9000 ggcagcttcc atgaagcccg tccggaggat ctggcgtacg tgatctatac gtcgggaacg    9060
acgggcaagc cgaagggcgt aatgatcgag caccgcagcc tggtgaacac ggcggcgggc    9120
tatcggcggg aataccggtt ggatcagttc ccggtgcggc tgctgcagct cgcaagcttc    9180
tcgttcgacg tattcgtggg cgatatcgcg cggacgctgt ataacggagg cacgatggtg    9240
attgtgccga aggacgaccg gatcgatccg tctcgtctgc accactggat ggagcgggag    9300
cgggtcacca tcttcgaatc gacgccggcg ctgatcgtgc cgttcctgga gtacgtgcac    9360
gagcaggggc tggatatgag ctggatggag ctgttgatca cgagttcgga cagctgcagc    9420
gtggcggatt accggatctt gcaggaacgt ttcggctcgt tcttccggat catcaacgca    9480 tacgcgtga cggaagcggc gatcgactcc agcttctacg acgaggagct gacgaagctg    9540
ccgcagatag gccatgtacc gattggaaaa gcgtggctga atgcgaaatt ctacatcgtg    9600
gatgcgcatc tgaacccggt gccggtcggg gtgctgggcg agctggtcat cggcggagtc    9660
ggtgtggcgc gagggtattt gaaccgtccg gagctgacgg aagagaagtt cgtagacagt    9720
ccgttcgccg cgggcgagcg gctgtaccgc acggagact tggcgcggtg gatgaggac    9780 gggaacgtgg acttcatcgg ccggatcgac aaccaagcga aaatccgggg ctaccggatc    9840
gagacgggtg agatcgagtc gcagctgctg cgggtggaag gcgtgcgcga agcggtggtg    9900
ctggttcgaa gtgacgcaaa cgggcagaag gcgttatgcg cgtattacac gctggatacc    9960
ggagcggaac tggcagtgaa cgatctgcgc agcacgctgg cgcaggagct gccgggctac   10020
atgatcccgt cgtacttcgt ggagctggag ggcctgcctc tgacgccgaa cggaaagatt   10080
gaccggaagg cgctgccggc gccggaagga gaagcgggaa gcgaacgga gtacgtcgca   10140 ccgcgcaatg agctggaaac aaagctggcg gcgatttggc aggaggtgct ggggcttgcg   10200
aaggagattg gcgttcacga caacttcttc gacatcggcg gccactccct gcgggcgacg   10260
acgctggtca gcaaggtgca caaggaactg agcgtggatc tgccgctgcg cgacgtgttc   10320
cgccattcca cgatcgagag catggcggcc gccatttccc ggctggatga gcagacattc   10380
gttgccattc cggtggcgga tgaccggagg gtgtacccgc aatctttttgc tcaaaaacgt   10440 ctctttatcc tgaatcaact ggaaggcgcg gagcttagct acaacatgcc ggaggcgatg   10500
```

```
ctgctggagg gggctttgga tcgggcaagg ttcgaagaag cattccgtaa gctcgtggcg   10560
cggcatgaaa tgctgcgcac cgggttcgaa atggtggatg gcgaagcatc gcagcgggtt   10620
taccaggact tgaattttgc tgtggagttc tatcgagtag atgagcaaga ggccgaagag   10680
acggttcgcc gttttgtccg tccgtttgac ttggcgaagc ctccgctgct gagggtaggc   10740
cttgtcgagc tggcttcgga acgccatatt ctaatgtacg acatgcatca tattatttcc   10800
gacggtgtct ccatggaaat ctttgttgaa gaattcgtcc gcttgtacgg cggtgagcaa   10860
ttggagcctc ttcgcattca gtacaaagac tacacagttt ggcagcattc gcaggagcag   10920
aaggaacggc ttcagcgtca ggaggcgtac tggctgaaca tgttccaagg cgagcttccg   10980
gtgctggaaa tgccaaccga ctatccgcgt ccgtccgtgc agagctacga aggccacacg   11040
ctggagtttt tcttcgacgc ttcgaaaacc gacggcctga gcaactggc ctcggaaacg    11100
ggcacgacgc tgtttatggt gctgcttgcg gcgtataacg tccttctgca taaatattca   11160
ggtcaggaag atgtgatcgt tggtacgccg attgccggaa ggaatcatgg agatgtgcag   11220
ccgttgatcg gaatgttctt aaacacgctg gcgatccgca gttatccggc ttcggagaag   11280
acattcctgt catacctgaa cgaagtcaaa gaaacgaccc tccatgcctt cgagcatcaa   11340
aactatccgt tcgaagaatt ggtagacaag gtgcaagtca cccgtgattt aagccgtaat   11400
ccgcttttcg acacgctgtt tacgatgcag aatacggaga tgaagaatt tgagctggaa    11460
gggcttcgcc tgattcctta tccgagcgca ctggataccg caaagtttga tatcagcttg   11520
gatgtgggcg aggagaacgg cggcttggat tacagcttcg aatatgcgac ggctctctac   11580
aaaagggcga cgattgaacg gctggcgaag cattacgagc agctgctcgt gacgatcata   11640
agccgtccag atgcgaagat cgccgagctg aacttgctga cggcagagga aaaagaacaa   11700
attcttggca cattcaaccc cgcgcagccg gaagcggctc ctgcggccgc gttccaccgg   11760
ctgttcgagg aacaggcgga acgaacgccg gaagaggcgg ccgtcgtgta cgagaacgac   11820
cagctgacgt atgcggagct gaacgagcgg gcgaaccgct tagcggccac gctgcgcgca   11880
agcgacatcg gccgggagac gatcgtcggc attctcgccg agcgttcggt ggatctgctg   11940
gtgtccgtgc tggccgtctg gaaagcgggc ggggcatatg tgccgctcga cccggattat   12000
ccggcggatc gcgtgcggtt catgcttgaa gacagtggag cgaaggtact gttgacgcaa   12060
atgccgctgc gagaacgcgc cgaagcctgg ctcggcgaag aggagctggc gctggcagcg   12120
gtgctgtacc tcgacgacga agcatcgtac agcgaggagc gggcgaatgc gccgattggc   12180
tccggcatgg tccccggcaa gctgacggat gctgtggatg acggcgatga gacccatccg   12240
aatattggca tgggcagctt ccatgaagcc cgtccggatg atctggcgta tgtgatctat   12300
acgtcgggaa cgacgggcaa gccgaaaggc gtgatgatcg agcaccgcag cctggtgaac   12360
acggcggcgg gctaccggcg ggaataccgg ttggatcagt tcccggtacg gctgctgcag   12420
ctcgccagct tctcgtttga cgtgttcgtg ggagatatcg cgcggacgct gtacaacgga   12480
ggcacgatgg tgattgtgcc gaaggacgac cggatcgatc cgtctcgtct gcaccactgg   12540
atggagcgag agcgggtcac cattttcgaa tcaacgccgg cgctgatcgt gccgttctta   12600
gagtacgtgc acgagcaggg gctggatatc agttggatgg agctgttgat cacgagttcg   12660
gacagctgca gcgtggcgga ttaccggatc ttgcaggaac gcttcggctc gttattccgg   12720
atcatcaacg catacggcgt gacggaagcg gcgatcgact ccagcttcta tgacgaggag   12780
ctggcgaagc tgccgcagac aggccatgta ccgattggaa aagcgtggct gaatgcgaaa   12840
ttctacatcg tggatgcgca tctgaacccg gtgccggtcg gggtgctggg cgagctggta   12900
```

```
atcggcggag tcggtgtggc gcgagggtat ttgaaccgtc cggagctgac ggaagagaag    12960
ttcgtagaca gtccgttcgc cgcaggcgag cggctgtacc gcacgggaga cttggcgcgg    13020
tggatggagg acgggaacgt ggacttcatc ggccggatcg acaaccaagc gaaaatccgg    13080
ggctaccgga tcgaaacggg tgagatcgag tcgcagctgc tgcgggtgga aggcgtgcgc    13140
gaagcggtgg tgctggttcg aagtgacgca acgggcagaa aggcgttatg cgcgtattac    13200
acgctggata ccgagcggaa actggcagtg aacgatctgc gcagcacgct ggcgcaggag    13260
ctgccgggct acatgatccc gtcgtacttc gtggagctgg agggcctgcc tctgacgccg    13320
aacggaaaga ttgaccggaa ggcgctgccg gcgccgaagg agaagcgggg aagcggaacg    13380
gagtacgtcg caccgcgcaa tgagctggaa acaaagctgg cggcgatttg caggaggtg    13440 ctggggcttg cgaaggagat tggcgtttac gacaacttct tcgacatcgg tggtcactcc    13500
ctgcgggcaa cgacgctggc gggcaaagta tttaaggaat taaacgtcaa cctgccgctg    13560
cgtgacgtat ttcgtcactc gacgattgca gcgatggccg aggcgatcgc ccgaatggaa    13620
cggctggagc atgaggacat tcctcaagcg gaggagagag agtattaccc tctgtcctct    13680
gcgcagaaac ggctgttcat tcagcacacg ctggatggag cggatcagct ttacaacatg    13740
ccggaactgg tgcaggtgga aggcgagttt gatttagacc ggttggaagc cgccttgcgg    13800
aaattgataa cacggcatga atcgctgcgt accggttttg aactcgtgaa gggcaaagcg    13860
gttcagcgga tttacccgca ggtcgatttt gctgtcgagc atcatcaagc ggataaagag    13920
gatgcggctc aaatcgagca gatcgtccgc agcttcgttc gtccatttga tctcggcaag    13980
ccgccgctgc tgcgcgccgg ggtcatcgag ctggagccga acctgtatat tctcattttc    14040
gacatgcacc atatggtgtc cgacggcgta tcaatggcga ttgtgatcga tgagttctcg    14100
agtttctacg ccggggaaga gctgccgtca ctgcgcattc aatacaagga ttatgtcgtt    14160
tggcagcagt cgaaggccta ccgagaacgg atcgggcggc aggaagcgta ctggctgcaa    14220
accttcaaag gcgagctgcc gacggcgaac ctgccgatgg actacaaacg gtctgcagct    14280
cgcagctacg aaggtgcaca tctggagttt gacgtcgaag cctctctctc tatgcggctg    14340
cacgaattgg cggcagagcg taaaagcacg ctgttcatgg tgctgcttgc ggcttatacc    14400
gtgctgctgt ccaaatacag cgggcaggag gacttgatcg tgggcacccc ggtggcggga    14460
agaacgaacg ccgatttgga accggtcatc ggaatgtttg tcaatacact ggcgatccgc    14520
aatcgtccgt cggcaacaa aacgttttg tcctacctgg aagaagtgaa ggaaacggct    14580
ttgggtgctt tcgagaacca ggattatcca tttgaggagc tcgtggaacg tttgaatgtg    14640
aagcgggagc cgggccgctt cccgctgttc gatgccgttt tcgacttgca aaatatcgaa    14700
gaacgagacg tcgagctgga aggggtcagc ctgaagaatt acgagcttga ccatttggaa    14760
gaagcgaagt tcgatctgac gctgtttatg tatgaaaaca acggggcgct gagcgggggc    14820
ttcttctacg ccaccaagct gttcaaagaa gccatgatcc gcaccttgac cgaggattac    14880
ctgagggtac tgtctcaaat tgcggaaaat ccgcaacttg agctaagtcg gattgaatgt    14940
cataaaccgg cggctggcgc aaagagtgcc gtcgatacga tcgaatttgc gttctaa      14997
```

<210> SEQ ID NO 27
<211> LENGTH: 525
<212> TYPE: PRT
<213> ORGANISM: Paenibacillus alvei

<400> SEQUENCE: 27

```
Val Thr Glu Ala Glu Lys Ala Asp Leu Leu Gly Arg Phe Asn Asp Thr
1               5                   10                  15

Thr Thr Glu Phe Pro Arg Gly Lys Thr Leu Ile Gln Leu Phe Glu Glu
            20                  25                  30

Gln Val Glu Arg Ile Pro Asp Ala Ala Ile Thr Leu Asn Glu Gln
            35                  40                  45

Glu Leu Thr Tyr Arg Glu Leu Asn Glu Arg Val Asn Arg Leu Ala Arg
        50                  55                  60

Thr Leu Arg Ser His Gly Ile Ser Lys Gly Arg Leu Val Ala Ile Leu
65                  70                  75                  80

Ala Glu Arg Ser Ile Glu Met Val Val Gly Met Leu Ala Ala His Lys
                85                  90                  95

Ala Gly Ala Ala Tyr Val Pro Ile Asp Pro Glu Tyr Pro Glu Glu Arg
            100                 105                 110

Ile Arg Phe Leu Ile Glu Asp Ser Gly Gly Gln Val Met Leu Thr Gln
            115                 120                 125

Ser Arg Leu Arg Glu Arg Leu Ala Gly Ser Asp Pro Val Ile Leu Leu
        130                 135                 140

Asp Asp Glu Ser Phe Tyr His Glu Asp Gly Thr Asn Leu Asn Thr Gly
145                 150                 155                 160

Ile Glu Ala Thr Asp Leu Ala Cys Val Ile Tyr Thr Ser Gly Thr Thr
                165                 170                 175

Gly Lys Pro Lys Gly Asn Pro Val Ser His Arg Asn Ile Val Arg Val
            180                 185                 190

Val Gln Asn Thr Asn Tyr Ile Asp Ile Thr Glu Arg Asp His Val Leu
        195                 200                 205

Gln Leu Ser Ser Tyr Ser Phe Asp Gly Ala Thr Phe Asp Ile Phe Gly
        210                 215                 220

Ala Leu Thr Asn Gly Ala Arg Leu Val Leu Val Pro Tyr Glu Thr Leu
225                 230                 235                 240

Leu Glu Ile Gly Arg Leu Ala Asp Leu Ile Gln Arg Glu Arg Ile Ser
                245                 250                 255

Val Met Phe Ile Thr Thr Ala Phe Phe Asn Ile Leu Val Asp Val Asn
            260                 265                 270

Val Asp Cys Leu Arg Asp Val Arg Ala Ile Leu Phe Gly Gly Glu Arg
        275                 280                 285

Val Ser Val Gly His Val Arg Lys Ala Leu Ala His Ile Gly Pro Gly
        290                 295                 300

Arg Leu Asn His Val Tyr Gly Pro Thr Glu Ser Thr Val Tyr Thr Thr
305                 310                 315                 320

Tyr Leu Pro Val Asp Phe Val Asp Glu Leu Ala Val Thr Val Pro Ile
                325                 330                 335

Gly Arg Pro Ile Ser Asn Thr Thr Val Tyr Ile Val Asp Ser Arg Asn
            340                 345                 350

Lys Leu Leu Pro Ile Gly Val Ala Gly Glu Leu Cys Val Gly Gly Glu
        355                 360                 365

Gly Leu Val Arg Gly Tyr Asn Asn Arg Pro Glu Leu Thr Ala Glu Lys
        370                 375                 380

Phe Val Asp Asn Pro Phe Val Pro Gly Glu Arg Met Tyr Arg Thr Gly
385                 390                 395                 400

Asp Leu Ala Lys Trp Leu Pro Asp Gly Thr Ile Glu Tyr Val Gly Arg
                405                 410                 415

Thr Asp Asp Gln Val Lys Ile Arg Gly Phe Arg Ile Glu Leu Gly Glu
```

```
                420              425              430
Ile Glu Ala Gln Leu Gln Lys Val Glu Gly Ile Arg Lys Thr Thr Val
            435              440              445

Phe Ala Arg Glu Asn Ala Ser Gly Glu Lys Gln Leu Cys Ala Tyr Tyr
        450              455              460

Glu Ala Asp Cys Glu Leu Pro Ala Ala Glu Leu Lys Ser Val Leu Ser
465              470              475              480

Lys Glu Leu Pro Ala Tyr Met Ile Pro Ala Tyr Leu Ile Gln Leu Glu
                485              490              495

Arg Leu Pro Leu Thr Thr Asn Gly Lys Val Asp Arg Arg Ser Leu Pro
            500              505              510

Ala Pro Glu Glu Ser Leu Gln Pro Gly Gly Gly Ser Thr
        515              520              525
```

<210> SEQ ID NO 28
<211> LENGTH: 1575
<212> TYPE: DNA
<213> ORGANISM: Paenibacillus alvei

<400> SEQUENCE: 28

| | | | | | |
|---|---|---|---|---|---|
| gtgacggagg | cggaaaaggc | cgaccttctc | ggacgattta | acgacaccac | cacggaattt | 60 |
| ccgcgcggga | agacgctcat | tcaattgttc | gaagagcagg | tagagcgcat | cccggatgca | 120 |
| gccgccatca | ccttgaatga | gcaagagctg | acctaccgcg | agctcaacga | acgtgtcaac | 180 |
| cgccttgccc | gtaccttgcg | tagccacggg | atatccaaag | gtcgtctggt | cgccattttg | 240 |
| gctgagcgtt | ccattgaaat | ggtggtgggc | atgctggcgg | cacacaaagc | cggagcggct | 300 |
| tacgtaccga | ttgacccaga | atatcccgag | gagcgtatcc | gtttcttgat | cgaggattcg | 360 |
| ggagggcagg | tcatgctgac | gcaaagccgc | ttgcgcgagc | gcctggcggg | ttcggacccc | 420 |
| gtgatcttac | tggatgacga | gtccttctat | cacgaggacg | gcacaaatct | aaatacgggc | 480 |
| atcgaagcga | cagatctggc | ctgcgtcatc | tatacgtcag | gcacgacggg | caagccgaaa | 540 |
| ggcaaccctg | tttcgcaccg | caacatcgtg | cgggtcgtgc | aaaatacgaa | ttatatcgac | 600 |
| atcaccgagc | gggatcatgt | cctccagctt | tcgagctatt | cgttcgacgg | agcgactttc | 660 |
| gatattttcg | gcgctttgac | caacggggcg | cggctggtgc | tggttcccta | cgagactttg | 720 |
| ctggaaatcg | gccggctggc | ggatctcatc | cagcgcgagc | gcatctcggt | catgtttatt | 780 |
| acgacggctt | tcttcaacat | ccttgtagat | gtgaacgtcg | actgcctgcg | ggatgtcagg | 840 |
| gcgattttgt | tcggaggaga | gcgtgtgtcg | gtcggccatg | tgcgcaaagc | gctcgcccat | 900 |
| atcggaccgg | gcaggctcaa | ccatgtgtac | ggcccgacgg | aaagcacggt | ttataccacg | 960 |
| taccttccgg | tcgacttcgt | cgatgagttg | gcggttaccg | tacccattgg | acggccgatc | 1020 |
| agcaatacga | cggtgtatat | cgtcgacagc | cggaacaaac | ttctgccgat | cggcgtggcc | 1080 |
| ggggaacttt | cgctcggcgg | agaaggcttg | gtaaggggct | acaataaccg | gccggagctg | 1140 |
| acggcggaga | aatttgtgga | caatccgttt | gtgccgggag | agcgcatgta | ccggacgggg | 1200 |
| gatttggcga | aatggctgcc | ggacggcacg | atcgaatacg | tgggacggac | ggacgaccaa | 1260 |
| gtgaaaatcc | gcggcttccg | aattgagcta | ggcgagatcg | aagctcagct | tcagaaagtg | 1320 |
| gagggaattc | ggaaaacgac | ggtattcgcg | agggaaaacg | cctccggcga | aagcagctt | 1380 |
| tgcgcctatt | atgaagcgga | ctgcgagctt | ccggcggccg | aactgaagag | cgtgcttccc | 1440 |
| aaggaactgc | cggcctatat | gatcccggcg | tacctgatcc | agttggagcg | gctcccgctg | 1500 |
| acgacgaacg | gcaaggtcga | ccgccgatca | ctcccggcgc | cggaggagag | cttgcagccg | 1560 | ggcggaggaa gtact                                                  1575

<210> SEQ ID NO 29
<211> LENGTH: 41172
<212> TYPE: DNA
<213> ORGANISM: Paenibacillus alvei

<400> SEQUENCE: 29

```
atgtttgaaa aggcggggag catggctgta gcgttgctgc ggcatatgct ccgccggatt     60
gcttttaccg atgtagagag ggggacgatc caggtggctt ttgaaaaaga aacgttgttt    120
tggaacgaaa aattcggtag tgacgattat accttgacgc ggctgcctta cagcaaagct    180
ccaagctccc aggcgcccat tatgacaacc gtcggcggtt cgctttcgga gaaagcggcg    240
cagcgcgtcc ttcaaatgag caagggcgct ccgctggccg cttttatgat tttgctcgcc    300
ggtgttcagt cactcttgca taaatataca ggcgcttctg acattctggt cggcatgccg    360
gttatacgga aaccgacgga gacgcgccga tccgttaatc atacggtcat tttgaaaagc    420
ttgctttcgg cgggatcgac ttttaaaacg cttctgagcg agctgagaac ttcgttgccg    480
gaaacgattc agcatcaaca tattccgttc ttgaaaatga cggagaagct ggatctgcaa    540
tatgcagacg ggatacccat catccatacg ctagtatccc ttaaggagct gcatctggat    600
gaaattgggc aaaacgtggt cacgattgt  tcctttgaat tcagcttaac cggcgggacg    660
atacagctag cgctctcata taacgagcac ttatatgact ccaagttcat gactcggatc    720
gtcggccatc tgaatcgcct gctggccgtg gggcttcacg agttggagct ggacatcgtg    780
cgggtggaca tgctgtcgga ggacgagaaa tttcaattgc tgcaaagctt taacgatacc    840
gagaaggact atcctcgaga tcggacgatt catcagctcg tggaggagca ggtgaagagg    900
gtgcccgaag caacggcgat tgtctttgag gggcggcggc tttcgtacgc tgagctgaac    960
gaacgggcga accggctggc gcggacgctg cgatcggtcg gcgtgctgcc caatcagctg   1020
gtaggcttga tggccaggag atcgctggag acggtcgttg gcattctggc ggttctgaaa   1080
gctggcggtg cctacgtgcc gatcgacccg gaatacccgg aagaacgcat ccgctacatt   1140
ctggagaact cgaacgcgca gctgctgctg actcaaagaa agctgcaaca gcaggtgccg   1200
ttcgaaggga ctgtgttggc gctggatgac gagcaggcct acagcgatga tggaacgaat   1260
ctggagccgg ccagcggttc gaatgatctg gcttatgtca tctatacgtc aggtacgacg   1320
ggcaaaccca aggggtcat  gctggagcat cgcggtttgg tcagcttgaa actgatgttc   1380
gcggacaggc tcggcatcac ggagcatgac cggatcgttc aattcgccag cctgtcgttc   1440
gacgcgtcct gctgggaagt gttcaaagcg ctctattttg gcgcgacttt gtacataccg   1500
acggccgaga cgattctcga caaccgcctg tttgagagtt atatgaacga gcatgcgatt   1560
acggcggcga ttttgcctcc gacgtacagc gcttatttga acccggaccg ccttcccagc   1620
ttaacgaagc tcgtaacggg aggctcggcg gtatcggccg aattcgtgca gcagtggaaa   1680
ccgaaggtcc actatttcaa tgcttacggc cctaccgaag cttcgattgt tacgacgctt   1740
tgggatgcga atgaggagca gccagagcgc agagtcattc cgattgggcg cccgctggcc   1800
aatcaccgga tttttatttt ggatgcccac ctgcagcttt gcctccggg  agtggacggc   1860
gagctgtgcg tggcaggcgt ggggcttgcg agaggttacc tgaaccatcc ggagctgacg   1920
gcagaaaagt tcgtgaacac tccgttcgcg ccgggagaac gcctttatcg gacgggagat   1980
ctcgcccgat ggctgccgga cggaaatatt gagtacttgg gccggatcga ccatcaggtg   2040
```

```
aaaatccgtg gattccggat cgagatcggc gagattgaag agcagcttct gaagatcgac    2100
tccgtgcagg agacgatggt aatcgcgcgg aaggcaaaaa gcgggcaaga attgtgcgct    2160
tatctggtcg cggaccgccc gcttacgctc ggcgagctga aagcgcgct ggcgcaaaaa    2220 ttgccgaatt acatgattcc ggcgcatttt gttcagcttc cgcgaatgcc gctcacgccg    2280
aacgacaaaa tcgaccgcaa ggctttgccc gccccggaag gaaacgcgct gaccggcggc    2340
ttgtacgtag ctccccgcaa tgaagccgag cggacacttg tcgatgtgtg gcaggcggta    2400
ttgaacgccg atcgtgttgg ggtaacggat catttcttcg agctgggtgg agactcgatc    2460
aagtccattc aagtatcttc gcggcttcat caagccgggt acaagctgga tattcgggat    2520
ttgttcaaat atccgactat ctcacagctc agcctgcgtg tgaaaccgat cggacgtacc    2580
atcgatcaag gcgaaataac gggcgaaacg cgctgacgc cgattcagca ttggtttttc    2640
gagagctcct ttgcggatcc gcatcatttc aaccagtcgg tgatgctgta ccggaaggaa    2700
cgcttcgacg aagagacggt gcgtcaggta ctgcaaaagc tggccgagca tcatgacgcc    2760
ttgcggatgg tgttccgcaa aacggaacaa gggtttagcg aaaggaaccg cgcgattcag    2820
gaaggcgggc tgttcacgct ggacgtgttc gacttcaagg atgcggagga taccgcacag    2880
gctctggaag cgaaggcaac ggatattcaa gcgggcatcg atctggagaa agggcccctc    2940
gtgaaggcgg gactgttccg atgcgcggac ggcgatcatt tactgctcgc ggttcatcat    3000
gccgtgtgtg acgcgtgtc ttggcgcatt ttgatggagg atttcgctct gggttacgag    3060
caggccggca aaagcgagga aattcgtttc ccggcgaaaa cggatgcgta ccgcacttgg    3120
tccgagcagc tggccgctta cgcgcaaagc ccggagatag caaaggaacg ggcttattgg    3180
caggccgtgg aacaaattgc ggttccggcc ttgccgaagg atctggaggc ggacgttacg    3240
acgcagcagg acagcgaatc gctgttcgtc cgtttgactt ccgaagaaac ggagctgctg    3300
ctgaagcggg tacaccgggc ctacaacacc gaaatgaacg atattttggt aacggcgctc    3360
ggcatagctg ttcgcaagtg gacgggacac gaacgggtgc ggatcaatct cgaaggacac    3420
ggacgcgaat cgatcggaac ggatatcgac atcacgcgca cagtcggctg gtttacgacc    3480
aagtttccgg tcgtcctgga gccggaaacc aaccggggatt tggcctatca gattaaacag    3540
gtcaaggaaa gcttgcgtcg cattccgaac aaggggcttg ggtacggtgt atgccgctat    3600
ctctccaaat cggaggatgg cttttgtttgg ggcgcagagc cggaaattaa ttttaactac    3660
ctcggccagt tcgacgatga tgtcaaccag gacgagatcg gcatatcttc ttattccagc    3720
ggcagcccgg ccagcgaccg gcaggcccgc agctttgtgc tggatatcaa cggcatggtg    3780
ctggacggcg ctctatcgct cgatctcagc tacagccgga agcagtatcg caaggtaacg    3840
atggaagcct tcgctcagcg gcttgagcaa agtctccgag agctcattac ccactgcgca    3900
ggcaaagaaa acaccgaatt gacgcctagc gacgtgcaat ttaaaggctt gaccatcgcg    3960
gaattggagc aaatcggcca gcgctcggtc catgtcgggg aaatcgagaa tatttactcg    4020
cttacgccga tgcagaaggg catgtggttc acagcgcgc ttgaccggca gacggccgct    4080
tacttcgagc agacgcggtt tacgatgcgg ggagcgctcg acgttcagct tttcgagagg    4140
agctggacgg agcttgcgaa acgtcatctg gtgctgcggg cgaattttgt gaaaggacca    4200
gcgggcgagc cgctgcagat catataccgc gacaaaccag tcggctttga atatgaagag    4260
ctgctacatt tgcaggcgga cgagaaacaa gcgtatttgg ataaaaaggc cgaggatgac    4320
aagcttcgcg gcttcgacct ggaacatgac gcgctcgttc gggttacgat cctgcgcacc    4380
gaagagcaga gctatcatgt gctgtggagt ttccagcata ttttgatgga cggctggtgc    4440
```

```
ctgccgcaac tgacgcagga gctgtttgag acatactcgg ccttggcatc cggcaagcag    4500
ccagcgggag ataagggggtc ggattatggc gcttatatcg aatggctgga gaaacaggac    4560
gatcaggcgg catccggcta ttggacggcg ttcctggcag gttacgaagg gcaaactgta    4620
ctcccggggc aaaaggaagc gcagccgaac ggtagattta cggctgatca cgtcaccgcc    4680
gagctgggca aggacttgag cgagcggatg gatcgggtgg cgaaacagcg cctggttaca    4740
gtcaatacgc tgctgcaagc cgcttggggc gtgatgctgc aaaaatataa cggaacaaac    4800
gatgccgtat tcggcagcgt cgtggccgga agaccggcgg aaatcccggg tatagagtcc    4860
atgattggac tgtttatcaa tacggtgccg gttcgcgtca cgagcgaagc ggacaccgtg    4920
ttcgctgacc tgatggcaaa gctccaagag cgggcgctgg agtccgggcg ttatgattac    4980
tatccgctgt atgaaattca gcccgctgc gtgcaaaagc aaaacctgat caaccatatc    5040
atcgctttcg agaactatcc ggtggatgag cagatggagc aggcgggcga ccagcagcac    5100
ggcgacctga cgatcactga cgttcagatg gaggagcaga cgaactataa cttcaatgtg    5160
accgtggtgc caggagccga gatcgaaatt cggttcgatt ttaacgccga agtgtttgat    5220
aaagacagca tcgaacggct caaggggcat ctcgtccatc tgctggagca ggtgacggat    5280
aacccggaaa ttaccgtggg agagctggaa cttgtgacgg aggcggaaaa ggccgacctt    5340
ctcggacgat ttaacgacac caccacggaa tttccgcgcg ggaagacgct cattcaattg    5400
ttcgaagagc aggtagagcg catcccggat gcagccgcca tcaccttgaa tgagcaagag    5460
ctgacctacc gcgagctcaa cgaacgtgtc aaccgccttg cccgtacctt gcgtagccac    5520
gggatatcca aggtcgtct ggtcgccatt ttggctgagc gttccattga aatggtggtg    5580
ggcatgctgg cggcacacaa agccggagcg gcttacgtac cgattgaccc agaatatccc    5640
gaggagcgta tccgtttctt gatcgaggat tcggagggc aggtcatgct gacgcaaagc    5700
cgcttgcgcg agcgcctggc gggttcggac cccgtgatct tactggatga cgagtccttc    5760
tatcacgagg acggcacaaa tctaaatacg ggcatcgaag cgacagatct ggcctgcgtc    5820
atctatacgt caggcacgac gggcaagccg aaaggcaacc ctgtttcgca ccgcaacatc    5880
gtgcgggtcg tgcaaaatac gaattatatc gacatcaccg agcgggatca tgtcctccag    5940
ctttcgagct attcgttcga cggagcgact ttcgatattt cggcgctttt gaccaacggg    6000
gcgcggctgt tgctggttcc ctacgagact ttgctgaaaa tcggccggct ggcggatctc    6060
atccagcgcg agcgcatctc ggtcatgttt attacgacgg ctttcttcaa catccttgta    6120
gatgtgaacg tcgactgcct gcgggatgtc agggcgattt gttcggagg agagcgtgtg    6180 tcggtcggcc atgtgcgcaa agcgctcgcc catatcggac cgggcaggct caaccatgtg    6240 tacgcccga cggaaagcac ggtttatacc acgtaccttc cggtcgactt cgtcgatgag    6300
ttggcggtta ccgtacccat tggacggccg atcagcaata cgacggtgta tatcgtcgac    6360
agccggaaca aacttctgcc gatcggcgtg gccgggaac tttgcgtcgg cggagaaggc    6420
ttggtaaggg gctacaataa ccggccggag ctgacggcgg agaaatttgt ggacaatccg    6480
tttgtgccgg gagagcgcat gtaccggacg ggggatttgg cgaaatggct gccggacggc    6540
acgatcgaat acgtgggacg gacggacgac caagtgaaaa tccgcggctt ccgaattgag    6600
ctaggcgaga tcgaagctca gcttcagaaa gtggagggaa ttcggaaaac gacggtattc    6660
gcgagggaaa acgcctccgg cgagaagcag ctttgcgcct attatgaagc ggactgcgag    6720
cttccggcgg ccgaactgaa gagcgtgctt tccaaggaac tgccggccta tatgatcccg    6780
```

```
gcgtacctga tccagttgga gcggctcccg ctgacgacga acggcaaggt cgaccgccga   6840
tcactcccgg cgccggagga gagcttgcag ccgggcggag gaagtactcc gcctcggact   6900
ccgctggaag ccagcttggc cggaatttgg aaaagcgtgc tcggactagt gcacattggc   6960
gttcatgaca acttcttcga catgggcgga cattccctgc gggcgacgac actggtgagc   7020
aaggtgcatc aggagctgaa cgtcgaactg cctctgcgcg acgtattccg ctactcgacg   7080
atcgaggaga tggctctcgc catctcccgg atcggagagc agtcgttctc gtcgattccg   7140
ctggcaggcg caagagcata ttatccgctt cctcagctc agaagcggct gtttatcctg    7200
aatcagctgg aaggggccga tcagagctac aacatgccgg gcgtgctgct gttggaagga   7260
tcgattgacc ggagcctgct ggagaaggct ttccgcggac tgatcgcacg gcacgaaacg   7320
ctgcgaaccg gctttgagat cgtacaaggc gaagcagtac agcgcattta cgagagcgtc   7380
gactttgccg tcgagtaccg tcatgcgagc gaggaagaaa cgcctgaagt cgtgcaggcc   7440
ttcatccggc ctttcgactt ggcaaagcct ccgctgctgc gggcggagct cgtagagctg   7500
gcaatcgaac gttatttgct gatgttcgac atgcaccata tcgtctccga cggggtttcg   7560
atggacgtgt tagtcgagga actcgttcgt ctgtacggcg gcgagtcatt agagcctttg   7620
cgcattcaat acaaggacta tgcggtatgg cagcagtcgg acgagcaaaa agtgcagttg   7680
aaacgcgagg aagcttactg gttggaccgt taccggggcg agctgccggt tctggaaatg   7740
ccgacggact atccgcgtcc tgccgtgcag agctttgagg acaaacgct gacgtccttc     7800 gtggacgagg caacgaacga aggcttaaag caactggccg ctcaaaaagg aacgacgctg   7860
tatatggtac tgcttgcggc atataccgtg cttttgcata aatacacagg tcaggacgat   7920
ttgatcgtcg gaacgtcgat tgcgggcaga acgcacggag acacgcagcc tttgatcgga   7980
atgttcgtca atacgctggc actccgcaat tatccggctt cggagaagag cttcctgtcg   8040
tatcttgaag aagtgaaaga acgaccttta ggcgcttacg agcatcagaa ttatccgttc   8100
gaagagctcg ttgataaagt gcaggtcagc cgggatttga ccgcaaccc gctgttttgac   8160 acgatgttct ccctgcaaaa cttggaggat aaagagttta agctggaagg gctgaaattg   8220
tccccgtacc ctagtgaata cggcacggcc aagttcgatc tgagtgtgga tgttacggaa   8280
gaaaacggcg gcttggagtg catctttgaa ttcgcaacgg ctctttataa agaaagcacg   8340
atccggcggc tgtcgactca ttttggacat ttgcttgcgg cgatcgtaag tcgtccggat   8400
gcgaagatcg ccgagctgaa cttgttgacg gcagaggaaa atgagcaaat tctcggcgcg   8460
ttcaaccccg gcgcagccgga agcggctcct gcggccgcgt tccaccggct gttcgaagaa   8520
caggcggagc gcacgccgga agcggaggcc gtcgtgtacg agaacgaccg gctgacgtat   8580
gcggagctga cgagcgggc gaaccgcttg gcgctacgc tgcgcgcaag cggcatcggc      8640
cgggagtcga tcgtcggcat tctctccgag cgttcggtgg acttgctggt ggccgtgctg   8700
gccgtctgga aagcgggcgg ggcgtatgtg ccgctcgacc cggattatcc ggcggaccgc   8760
gtgcggttca tgcttgaaga cagtggagcg aaggtgctgc tgacgcaaac ggtgctgcga   8820
gagcgcgccg aagcctggct cggcgaagag gagctggcgc tggcagcggt gctgtacctg   8880
gacgacgaag cgtcgtacag cgaggagcgg gcgaatgcgc cgattggttc cggcatggtc   8940
tccggcaagc tgacggatgc tgtggacgac ggcgatgtga gccatcagaa ggtcggcatg   9000
ggcagcttcc atgaagcccg tccggaggat ctggcgtacg tgatctatac gtcgggaacg   9060
acgggcaagc cgaagggcgt aatgatcgag caccgcagcc tggtgaacac ggcggcgggc   9120
tatcggcggg aataccggtt ggatcagttc ccggtgcggc tgctgcagct cgcaagcttc   9180
```

```
tcgttcgacg tattcgtggg cgatatcgcg cggacgctgt ataacggagg cacgatggtg    9240
attgtgccga aggacgaccg gatcgatccg tctcgtctgc accactggat ggagcgggag    9300
cgggtcacca tcttcgaatc gacgccggcg ctgatcgtgc cgttcctgga gtacgtgcac    9360 gagcagggc tggatatgag ctggatggag ctgttgatca cgagttcgga cagctgcagc    9420
gtggcggatt accggatctt gcaggaacgt ttcggctcgt tcttccggat catcaacgca    9480 tacgcgtga cggaagcggc gatcgactcc agcttctacg acgaggagct gacgaagctg    9540
ccgcagatag gccatgtacc gattggaaaa gcgtggctga atgcgaaatt ctacatcgtg    9600
gatgcgcatc tgaacccggt gccggtcggg gtgctgggcg agctggtcat cggcggagtc    9660
ggtgtggcgc gagggtattt gaaccgtccg gagctgacgg aagagaagtt cgtagacagt    9720
ccgttcgccg cgggcgagcg gctgtaccgc acgggagact ggcgcggtg gatggaggac    9780 gggaacgtgg acttcatcgg ccggatcgac aaccaagcga aaatccgggg ctaccggatc    9840
gagacgggtg agatcgagtc gcagctgctg cgggtggaag gcgtgcgcga agcggtggtg    9900
ctggttcgaa gtgacgcaaa cgggcagaag gcgttatgcg cgtattacac gctggatacc    9960
ggagcggaac tggcagtgaa cgatctgcgc agcacgctgg cgcaggagct gccgggctac    10020
atgatcccgt cgtacttcgt ggagctggag ggcctgcctc tgacgccgaa cggaaagatt    10080
gaccggaagg cgctgccggc gccggaagga gaagcgggaa gcggaacgga gtacgtcgca    10140
ccgcgcaatg agctggaaac aaagctggcg gcgatttggc aggaggtgct ggggcttgcg    10200
aaggagattg gcgttcacga caacttcttc gacatcggcg gccactccct gcgggcgacg    10260
acgctggtca gcaaggtgca caaggaactg agcgtggatc tgccgctgcg cgacgtgttc    10320
cgccattcca cgatcgagag catggcggcc gccatttccc ggctggatga gcagacattc    10380
gttgccattc cggtggcgga tgaccgggag gtgtacccgc aatcttttgc tcaaaaacgt    10440
ctctttatcc tgaatcaact ggaaggcgcg gagcttagct acaacatgcc ggaggcgatg    10500
ctgctggagg gggctttgga tcgggcaagg ttcgaagaag cattccgtaa gctcgtggcg    10560
cggcatgaaa tgctgcgcac cgggttcgaa atggtggatg cgaagcatc gcagcgggtt    10620 taccaggact tgaattttgc tgtggagttc tatcgagtag atgagcaaga ggccgaagag    10680
acggttcgcc gttttgtccg tccgtttgac ttggcgaagc ctccgctgct gagggtaggc    10740
cttgtcgagc tggcttcgga acgccatatt ctaatgtacg acatgcatca tattatttcc    10800
gacggtgtct ccatggaaat ctttgttgaa gaattcgtcc gcttgtacgg cggtgagcaa    10860
ttggagcctc ttcgcattca gtacaaagac tacacagttt ggcagcattc gcaggagcag    10920
aaggaacggc ttcagcgtca ggaggcgtac tggctgaaca tgttccaagg cgagcttccg    10980
gtgctggaaa tgccaaccga ctatccgcgt ccgtccgtgc agagctacga aggccacacg    11040
ctggagtttt tcttcgacgc ttcgaaaacc gacggcctga agcaactggc ctcggaaacg    11100
ggcacgacgc tgtttatggt gctgcttgcg gcgtataacg tccttctgca taaatattca    11160
ggtcaggaag atgtgatcgt tggtacgccg attgccggaa ggaatcatgg agatgtgcag    11220
ccgttgatcg gaatgttctt aaacacgctg gcgatccgca gttatccggc ttcggagaag    11280
acattcctgt catacctgaa cgaagtcaaa gaaacgaccc tccatgcctt cgagcatcaa    11340
aactatccgt tcgaagaatt ggtagacaag gtgcaagtca cccgtgattt aagccgtaat    11400
ccgcttttcg acacgctgtt tacgatgcag aatacggaga atgaagaatt tgagctgaaa    11460
gggcttcgcc tgattccttta tccgagcgca ctggatacccg caaagtttga tatcagcttg    11520
```

```
gatgtgggcg aggagaacgg cggcttggat tacagcttcg aatatgcgac ggctctctac   11580
aaaagggcga cgattgaacg gctggcgaag cattacgagc agctgctcgt gacgatcata   11640
agccgtccag atgcgaagat cgccgagctg aacttgctga cggcagagga aaaagaacaa   11700
attcttggca cattcaaccc cgcgcagccg gaagcggctc ctgcggccgc gttccaccgg   11760
ctgttcgagg aacaggcgga acgaacgccg gaagaggcgg ccgtcgtgta cgagaacgac   11820
cagctgacgt atgcggagct gaacgagcgg gcgaaccgct tagcgccacg ctgcgcgca   11880
agcgacatcg gccgggagac gatcgtcggc attctcgccg agcgttcggt ggatctgctg   11940
gtgtccgtgc tggccgtctg gaaagcgggc ggggcatatg tgccgctcga cccggattat   12000
ccggcggatc gcgtgcggtt catgcttgaa gacagtggag cgaaggtact gttgacgcaa   12060
atgccgctgc gagaacgcgc cgaagcctgg ctcggcgaag aggagctggc gctggcagcg   12120
gtgctgtacc tcgacgacga agcatcgtac agcgaggagc gggcgaatgc gccgattggc   12180
tccggcatgg tccccggcaa gctgacggat gctgtggatg acggcgatga gacccatccg   12240
aatattggca tgggcagctt ccatgaagcc cgtccggatg atctggcgta tgtgatctat   12300
acgtcgggaa cgacgggcaa gccgaaaggc gtgatgatcg agcaccgcag cctggtgaac   12360
acggcggcgg gctaccggcg ggaataccgg ttggatcagt tcccggtacg gctgctgcag   12420
ctcgccagct tctcgtttga cgtgttcgtg ggagatatcg cgcggacgct gtacaacgga   12480
ggcacgatgg tgattgtgcc gaaggacgac cggatcgatc cgtctcgtct gcaccactgg   12540
atggagcgag agcgggtcac cattttcgaa tcaacgccgg cgctgatcgt gccgttctta   12600
gagtacgtgc acgagcaggg gctggatatc agttggatgg agctgttgat cacgagttcg   12660
gacagctgca gcgtggcgga ttaccggatc ttgcaggaac gcttcggctc gttattccgg   12720
atcatcaacg catacggcgt gacggaagcg gcgatcgact ccagcttcta tgacgaggag   12780
ctggcgaagc tgccgcagac aggccatgta ccgattggaa aagcgtggct gaatgcgaaa   12840
ttctacatcg tggatgcgca tctgaacccg gtgccggtcg gggtgctggg cgagctggta   12900
atcggcggag tcggtgtggc gcgagggtat ttgaaccgtc cggagctgac ggaagagaag   12960
ttcgtagaca gtccgttcgc cgcaggcgag cggctgtacc gcacgggaga cttggcgcgg   13020
tggatggagg acgggaacgt ggacttcatc ggccggatcg acaaccaagc gaaaatccgg   13080
ggctaccgga tcgaaacggg tgagatcgag tcgcagctgc tgcgggtgga aggcgtgcgc   13140
gaagcggtgg tgctggttcg aagtgacgca aacgggcaga aggcgttatg cgcgtattac   13200
acgctggata ccggagcgga actggcagtg aacgatctgc gcagcacgct ggcgcaggag   13260
ctgccgggct acatgatccc gtcgtacttc gtggagctgg agggcctgcc tctgacgccg   13320
aacggaaaga ttgaccggaa ggcgctgccg gcgccggaag gagaagcggg aagcggaacg   13380
gagtacgtcg caccgcgcaa tgagctggaa acaaagctgg cggcgatttg gcaggaggtg   13440
ctggggcttg cgaaggagat tggcgtttac gacaacttct tcgacatcgg tggtcactcc   13500
ctgcgggcaa cgacgctggc gggcaaagta tttaaggaat taaacgtcaa cctgccgctg   13560
cgtgacgtat ttcgtcactc gacgattgca gcgatggccg aggcgatcgc ccgaatggaa   13620
cggctggagc atgaggacat tcctcaagcg gaggagagag agtattaccc tctgtcctct   13680
gcgcagaaac ggctgttcat tcagcacacg ctggatggag cggatcagct ttacaacatg   13740
ccggaactgg tgcaggtgga aggcgagttt gatttagacc ggttggaagc cgccttgcgg   13800
aaattgataa cacggcatga atcgctgcgt accggttttg aactcgtgaa gggcaaagcg   13860
gttcagcgga tttacccgca ggtcgatttt gctgtcgagc atcatcaagc ggataaagag   13920
```

```
gatgcggctc aaatcgagca gatcgtccgc agcttcgttc gtccatttga tctcggcaag    13980
ccgccgctgc tgcgcgccgg ggtcatcgag ctggagccga acctgtatat tctcattttc    14040
gacatgcacc atatggtgtc cgacggcgta tcaatggcga ttgtgatcga tgagttctcg    14100
agtttctacg ccggggaaga gctgccgtca ctgcgcattc aatacaagga ttatgtcgtt    14160
tggcagcagt cgaaggccta ccgagaacgg atcgggcggc aggaagcgta ctggctgcaa    14220
accttcaaag gcgagctgcc gacggcgaac ctgccgatgg actacaaacg gtctgcagct    14280
cgcagctacg aaggtgcaca tctggagttt gacgtcgaag cctctctctc tatgcggctg    14340
cacgaattgg cggcagagcg taaaagcacg ctgttcatgg tgctgcttgc ggcttatacc    14400
gtgctgctgt ccaaatacag cgggcaggag gacttgatcg tgggcacccc ggtggcggga    14460
agaacgaacg ccgatttgga accggtcatc ggaatgtttg tcaatacact ggcgatccgc    14520
aatcgtccgt cgggcaacaa aacgttttg tcctacctgg aagaagtgaa ggaaacggct    14580
ttgggtgctt tcgagaacca ggattatcca tttgaggagc tcgtggaacg tttgaatgtg    14640
aagcgggagc cgggccgctt cccgctgttc gatgccgttt tcgacttgca aaatatcgaa    14700
gaacgagacg tcgagctgga aggggtcagc ctgaagaatt acgagcttga ccatttggaa    14760
gaagcgaagt tcgatctgac gctgtttatg tatgaaaaca cggggcgct gagcggggc    14820 ttcttctacg ccaccaagct gttcaaagaa gccatgatcc gcaccttgac cgaggattac    14880
ctgagggtac tgtctcaaat tgcggaaaat ccgcaacttg agctaagtcg gattgaatgt    14940
cataaaccgg cggctggcgc aaagagtgcc gtcgatacga tcgaatttgc gttctaatcc    15000
tataagtgcg cctccgccgt caagcgaaag cggcgcgcat cccaaggaag acggcgaaca    15060
acgtccaagc ccgtaaacgc gcaggccgaa agcaagcttt tcggatctgc gctggggcat    15120
ggtttacttc atttttaggg gaggtacgaa tgaaatcttt atttgaaaag gaagaaaggt    15180
actggagcgg caagtttgac gccgatgaca acctgagctt ccttccctac agtcaatcct    15240
ccaaattatc cgccgacggg gaagctgcgg ccgagccggg cttgcttcac cgtaccctgc    15300
cgagcgaact ctcggagaga atcattcgcc tcgccaacgg ttcggatttg gctatgtaca    15360
tgattgtttt ggcaggagta aaaagcctgc tgttcaaata taccgggcag gaccaagtgc    15420
tggtcggcat gccttcttat agcgcagacc ccgacgggac tccgccgccg catgacatct    15480
tggtgatcaa gacggccgta agccatcaga ctacgctgaa aacgctgctc gggggcatca    15540
aagcctccat tggcgaggcg ctggagcatc agcacctgcc ttttcagaaa atggtggagc    15600
cgctccatct ggactatacg ggggatggcc tcccggtcgt taacaccgtt gcatccttcg    15660
ccccgattca tcccgaaccg ctgggtaacc gggtggcggc cgatacggtt tttcgcttcg    15720
atcgccaaaa ccactccatc gagctggaaa taagctttga cgggcagcgg tacgagcggg    15780
catttgtgga acaggcggcc gaccattttg ttcggctact gtccttgctt ttatttcagc    15840
ctgatctgga gcttggacaa gccgatgtgc tgtccccaga cgagagggag acgctgctga    15900
agcgatttaa tgacaccgaa accgggttcg agcggggaa aacgattcat ggcttgttcg    15960
aagagcaggc ggagctttac ccggacaacg tggccgccgt catgaatgag cggcagctga    16020
cttaccgcga actgaacgag cgatccaacc gccttgcgcg gaagctgcgg gagacgggag    16080
tagaagcgga tcagctggta gcgattctgg ctgaacgctc gctcgatatg gtcgtcggca    16140
ttctggcgat tcttaaagcg gcggagcct acgtgcctgt tgatccccgac tacccggagg    16200 agcgcatccg cttcatgatc gaggattcgg gcgcgccgtt attgttgatt caaaagcatc    16260
```

```
tgcacgagaa gaccgacttc gcaggaacgc gcctcgagtt ggatgatttc gtgtggaacg    16320
acagaggggt ggactccgaa ggtaggctgg atgcttcgaa cctggagccg atttccgggc    16380
cgggcaatct ggcttatgtt atctacacgt cgggaacgac cggcagaccg aaaggaacat    16440
taatcgagca taagaacgtc gtgcggctcc tgttcaacga caagaacctg ttcgacttcg    16500
ggccatccga cacgtggacg ctgttccact cgttctgctt cgatttctcc gtctgggaaa    16560
tgtacggagc gctgctgtac ggaggcaagc tggtcatcgt accgccgctc acggcgaaaa    16620
atccggctga tttcctggtg ctgctgggcc acgaacaggt cacgattttg aaccagacgc    16680
caacgtactt ctaccagctg ctgcgtaagg tcttggcgga ccatccgtac gatctgcgga    16740
ttcgcaacgt catcttcggg ggcgaagcgc tgagtccgct gctgctcaag gcttcaaga    16800 cgaagtaccc ggagacgaag ctgatcaata tgtacggcat taccgagacg acagttcacg    16860
ttacgtataa ggaaatcacc tgggtcgaaa tggaggcggc gaagagcaat atcggcaagc    16920
cgatcccgac gctgagggtg tacgtccttg atgaaaaccg ccgcccagtg ccgatcggcg    16980
tagcaggcga aatgtacgtg gccggggaag gcctggcgag aggatacctg aaccgtccgg    17040
atctgacggc ggagaagttc gtcgattccc cgtttgcgga ggggagaaa ctataccgct    17100 cgggcgactt ggcggtttgg ctgccggacg gcaacatcga atatctgggc cgaatcgacc    17160
accaagtgaa aatccgcggg taccggatcg agctggacga aatcgagacg cagttgctga    17220
agattgccgc cgtgcaagaa gccaaggtgc tcgaccgcga cgacgcgaac ggccaaaagc    17280
agcttgtcgc ttactacgtc gcggaaatga ggctggcggc gcatgaactc aaggaggagc    17340
tcgccaaaca gcttccaggg tatatgattc cttcgcactt cgtgcagctt cgcggatgc    17400 ctctaaccc gaacggaaaa atcgaccgca aagcgctgcc agcgccggag gaagtcgcgg    17460
ccttaggagc ggaatatgtc gcgccagaaa cgctgctcga atgaagatt gcccgcgtct    17520 ggcaggatac gcttggcgtt ccgcaggtcg gcgtaaagga taactttttt gatttgggtg    17580
gcaattcgtt aagtctgatg aggctcgttc aagccgttta cgatgaaacg ggcattgaga    17640
ttccgctgaa tcgccaattt catcatgtaa ccgttgaagc catggctttc gaagaggggg    17700
atctgggcct ggataaaggg ggagactcct tcataaagct gaataaagca ggagatctga    17760
acgtgttctg cttccctccg ggcagcggct tcggcatcgg ttaccgagag ctcgcaagca    17820
ggctcgacgg ccagttcgtg ctctacggca ttgattttat cgacgatacc gccgattacg    17880
aggccatgct gaaccgttat gttgacgaga ttgtccgcat ccagccggaa ggaccttacg    17940
tgctgctcgg ctactgcttc ggaggcaacc tgacgttcga ggtagccaaa acgatggaga    18000
aaagagggta tcccgtaacg gacgtgctca tggtggactc gtggattaag gagacgctga    18060
cgccttccga aacgtcagag aaaagagcttg aagaaatgct tgccgatttc gacgaagaag    18120
agaaggaatt aatgagcaat ccgctcgtgc gggagcgggt tcatcagaag gtcaaagcga    18180
ctttggcgta cgaagcgcag cttattaact ccggcacgat cccggcccgg atttacgaac    18240
tgattgcgaa ggacagcgaa gcgttccgct tggagcacca attgccgtcc tggcgggggg    18300
caacgacgca agcttacacc gattaccggc tggagggcgc gcacgaggaa ttgctggaac    18360
tcgcgcgcgt ggacgaaacg gccgttgtca tccgggatat cttagagcaa gtcaagcggc    18420
agatcgaagt ggaggccggg gtactgcatg gaagctgacc gacagccgtc cgttcaagaa    18480
caaggcacag cggtgccttc caagcgccaa accgcttacg ccacctggaa agcgttccgc    18540
tggctgatgt cctatgtaag ccgtcacata ggctggatga ccgtcggtac cttgtccgca    18600
attgccgccg ccgttattga gatatggacg ggaagtttga tcgagcagct gaccacccag    18660
```

```
gccgagaagg gggcggggcc actcgttctg caaatcgtat acacggtctt tgtggtcatc   18720
ttgatcggtg tgccggcgaa gttttttcatg agcttcggcg tggagcgaag cagcgcctct   18780
gcggttcagg atatccgcaa ccatgtcatg cgtcatatcg gcaaactacc ggtctcctat   18840
ttggaaaagc agcactctgg cgacgtgttg tcgcggatca acaacgacct gcagcttatc   18900
cagcagttta tgattcggga ccttgcccag tggttttatc atccgctatt gttcatcggc   18960
tgtttcgctt atttgatcta cctccaatgg gagctgatgc tgtccagcct gctgttattt   19020
cctgtagcgc tgctggtctc ccaatggatc ggcaagcagt tggagcggtt gacggaggaa   19080
gcccaggcga atatgggccg aatgaatgtc aacctccagg atacgcttgg gggtatgcct   19140
gttgtaaaaa gctacctgct atccggcatg ttatctcgct cctaccaagt gctgctgcaa   19200
ttgacggccc aaaaaaagct ggccgtgaaa agcgggaag cctgggtcaa cccgctgctt   19260
tccacgctga tgatcagccc gatcattttc gccgtcagtt acggaagcta tttgatctac   19320
aacgggcagc taggcgcagg agagttgatc gccttcctgt atttgctgaa tctgtgtctg   19380
gagccgctgg agcatattcc cgagctcatc acgcggacgt tcgaaatggc cggtgccctg   19440
agaagagtct ccgaaatcgt cgagcagccg accgaaacgg aaaatggccg ttcgcttccg   19500
aaagcgagcg ccgcccccat cgagtttcag aacgtaacct cgggtatga ggagagttcc   19560 ccgatcctgc ggaatgttag cttctcggtg ccggaaggga gacgatcgc gcttgtcgga   19620 gcgagcggcg gagggaaaag cacggtgttt aagcttgtat gcggcttta tccgcttccg   19680 gaggatcagg gggagatccg cgtattcggc agcctgatcc acggcgccga tccggagcag   19740
cttcggtcac attttccgt agtaacccag gattcatat tgtttagcgg cacgatcgcc   19800
gaaaatatcg gcttcgggcg ggaagaagcg tcgatggaca agattatcga agccgccaaa   19860
gccgctcaag cgcattcttt cattatgcag cttgagggcg gctaccaaac gtatgtcgga   19920
gagcgcggag gcttcttgtc cggtgggcag cgccagcgta ttgcaatggc ccgggccttt   19980
ctaaaggatg ctcctgtttt gctgctggac gagccaacgt cggctcttga tccggagtcg   20040
gaaagcgcgg ttcagaaagc gctgggcgta ttgatgaagc agagaacgac catggttatt   20100
gcccaccggc tttctacagt acaaaatgcc gacgaaattt gggtcatgga acaaggaaat   20160
attgtggaaa agggcactca tgaacaattg ctggagatga agggactgta cgcccagtca   20220
tactaccagg aatttactga gattgccgaa cgcaggaggg tggcgtacac atgaaaaagg   20280
gcggatggct ctcacaagtg aaagaacttg gctacttgct gaccttttatg aaccgccagc   20340 gcaaaactca gtacgccatt ggcctggccg taacggcgct cacccagaca ttttcctga   20400 tcgctttcag tttggtcgta cataacttgg ttgatttcgc cgtgtcccga gataagtccc   20460
tgatggtgga agcctttatt attttgggcg cggccctgtt cctggaaaat gtgatttctc   20520
catggttcat ttacttatac cagcgcagtg ttgagctgac tgtgctgaat atccgcaaac   20580
gtctttatga caagttgtgc cgggtgcggc cgagattcct agagcagacg caccatgggg   20640
acttgctatc gcgggtgaac aacgacgtaa cgaccgttga gtttacattc tcgcaggttt   20700
acttcgtttt gctgcttcaa gttgtctttt gcatcggctc cattgtctct atgatgttga   20760
tcgattggcg gtttgccggc gtatccttcg tcattctgct gctgtcctcc gtggtcagcc   20820
tgaaatttgc gcgggatatt cgcgccctgt ccgaacaagg cttacagacg ctcggaaaaa   20880
tgaccgaaaa attcaaagat tttatgggcg gcattcaaat tgtgaagctg ttccgcatcc   20940
gcacgattta cggccagtac gaggcgttga acgaacaaat gacgcagacg cttcggcaaa   21000
```

```
ccgcgcagaa aaacggcatg caggctgcgg tgaaccattt tatcagctac gtcacgttct  21060
gcggcatcat agtcatcggc agtcttcttt atgcctacgg actgatgggc atgggaagcg  21120
tcgctgccct ggcggttctg caagtgaatc tgacgcacgc cttgttgaac ttggggatcg  21180
ttctgtcgat gacccagaat tcgctcgcgg gcgctcaccg gattcaagag gtactaagag  21240
aggaagagga accggagcgt ctaggatctc ctctcagcga gctcgtgtcg gaggctgcgg  21300
tggagtttcg cgatgtagag ttttcctatc aggcggataa aaaggtgctt gtcgacatgt  21360
ccatgcaggt gtttcccggc caggtcgccg ctatcgtggg ggccagcggc agcggcaaaa  21420
gtacgctgat caagctgctg ctcggctttt atcctgtgga cagcggagaa atcctgctcc  21480
aaggcaaacc gttcggccat tacacgctgg acgaaatccg gaggcagatt gcatacgttc  21540
cacaggaacc gttcttattt accggcacga ttgaggaaaa cattcgctac ggcaacccgg  21600
atgcaacgga tgaagaagta attgaagcgg ctaaagcggc gtacgctcat catttcattc  21660
aggaacttcc tgaacagtat aaaacgccgg tgggagagag aggagcgtcg ttgtcgggcg  21720
gacaaaggca gcgaattgcg atcgcccggg cgattctcaa aaacgccccg attctgctgc  21780
tggacgaagc gacttctgcg ctggataacg aatcccagca ttgggtacag caggctctga  21840
acgtattgat gaagggcgc accaccattc tgatcgccca tcgtctcagc actgtggaac  21900
atgcggattt gattaccgtt atgaaccaag ggacggtcgt cgagcgtggc cgccatcagg  21960
acctgctggc gcacgggggg tattacgccc ggctgtacgg ctagacccgc tttacggcgg  22020
gaggcttccg acttgcgaat gcgacagagc ctttagtaa ctaaggtatg actttataac  22080
tggtatttac cagaaaacgt agacacgaac aaggggaag agtccacagg agccattccg  22140
ggaatgacct gcgtggttct tcttaagagt gactaagtga gatctaggta caaagcctat  22200
ctataagaat ctctaaaacg ggagtgtgtc gatgtgagag ataataccaa cgggcaatat  22260
gaattaacgc aagcccagcg ccgaatatgg ttcatggaaa ttatgaatcc gggaacgtcc  22320
atcacgatgc tttccgcgac ctaccagatt acgggccaga tcgacacaca gcttctggag  22380
caagctgcgg cggagatcgt caaaacctat gacgctttcc gaatacgcat tagcggggat  22440
ttgcagaatc caacgcagtg gttcgaagag ccggagaatg tccaagccag gataagccgc  22500
ctcgaaatag gcacaaccga acaattctat gcttgggtga agaagtaag cgaaaaaccg  22560
gccagcgtgt tcgacgaaca cctctaccaa tttacgatta tccatttgc gaacggccaa  22620
gtatggctca atttgacggt aaatcatatt atcgccgacg gcttgtccgt cactgctttg  22680
ctgcatgcgg tgatggaaaa atacatggaa ctgcgcaaag gcatctccag cagttaccag  22740
gccccttctt atctggatta tatttccgcg gagcgtgaat atgagcaatc gcagcgttat  22800
caaaaggca aggaatactg gctgacgaag tacagcactt tgcctgaaac gaccggcttt  22860
aaatcgtatc cgccattctc gatcggcagc gaatccaata acgggccac cactttggac  22920
ggttcccggt atgaacgcat tctggccttt agcgaacaat atcaggtcag cttatatacg  22980
ttatttctgt ccgcgatgta tgccttgcta tacaagctga ccgacagcac cgatgttccg  23040
gtcggcacgg tgttcgccaa tcgcaccagc aagaaggaaa agaaacgat cggcatgttc  23100
gtcagcaccg tggctacacg gattcatctg aatccagacg gggacgtgct ttccttgatc  23160
caagcggttt ccaaggagaa tacggcggat ctgcggtatc aaaaatacc ttataaccaa  23220
ttgatccagg attacgcga acaacacggc cgcaacgatc tttcgggact gttccgtacg  23280
tctctgaat atctgccttt gaaatcgtg gaatacgaag aaatcaaggt acgcctggag  23340
gctcacttcg ctaagcacga gatggatgat ttgctgctgc gtttcgacca tatgctgaat  23400
```

```
gaaggccatg tcattctcca cgcttcctat cgcactggct tgttcgagac agccgagatt   23460
gatcggatta tggaacagta tgtaaccgtt ctggaccagt ttcttcagac tcccgaactg   23520
ccggtacgcg aaatttctct gctgagcgat gaggagagac agtgcattct gggcgttttt   23580
aacccgccgg tggcagggct gagcgaggga gaggcgtttc atcggtacgt tgaaaagttt   23640
gcccgcgaaa ttccagatca tccggcagtt gtctacatgg atacacagct gacctacggt   23700
gaattgaacg aacgtgccga gcggctggct tctctcctcc gcgagcaggg cgtgggaaag   23760
gagacgatta cggggatctg gcggagcgt tcggtggaac tgctgatcgg ggtgctcgcc   23820
gtttggaaag ccggcggagc ctatgtaccg cttgaccccg attatccggc ggagcggatt   23880
gagtacatgc tcagcgatag cggtgcgtcg gtgctgctta cgcagcgtca tctgttggag   23940
cgggccggag gttggttggc cgatgaccgg ctgaaactac aagctgtcta tgctatggac   24000
gatgaacaga tttataacag ggatgcctta gccgtggaat ttgagtctgc cgatagtgcc   24060
ccgcaagact tggcttatgt gatttacacc tcgggtacga cgggacgccc gaaaggcgtc   24120
atgatcgaac atggtagtct cttgaatacg gcggatgcgt accgtcgcga gtaccggttg   24180
gatcagttcc cggtgcggct gctgcagttg gccagctttt cgtttgacgt gtttgtcgga   24240
gacatcgctc ggacgctgta taacggaggt acgatggtga ttgtgccaaa ggatgaccgg   24300
attgatccga accgcttata cggctggatt cgggaccaaa acattaccggt attcgaatcg   24360
acgcctgcgc tcatcctgcc attcatgcag catatttatg aagaagggct ggacgttagc   24420
tccatgcagt tgctgattac cagctcggat gcttgcagtg tcaccgatta ccgattgctg   24480
caggaaagat tcggcggaca attccgcatc atcaacagct atggcgttac cgaagcggcc   24540
attgacagca gcttttacga tgagacgctg gacaagctgc cgtcgtcggg tcatgtgccg   24600
atcggcaaag cttggctgaa cgcccggttt tacattgtcg atgccgcgtt aaaaccggtt   24660
cctgtagggg ttccgggcga gcttgtcatc ggaggcgctg gggtggcgcg cggatactgg   24720
aaccgtccgg acctaacggc cgagaagttt gcggacagcc cgtttgtgcc tggcgaacgt   24780
ttgtatcgga caggcgattt ggcccgctgg ctggaagacg gcaacgtcga cttcatcggc   24840
cgaattgact atcaggtgaa aattcgcggg ttccggatcg aactcggcga aattgaaacg   24900
gccttgctgc gtttcccggg cgtcaagcag gctgtggtga cagaccgtac agataagcag   24960
gggcaaaagt atttgtgtgg ctacgtggcg gcagatactt ccttgcagct gagcgatctg   25020
ctgtcccaat gaagcaaga gctgccggcc catatggttc cggcccggct ggtgtctctt   25080
gataagcttc cacttactcc gaacggcaaa attgaccgta aagcgctgcc tgaaccgacc   25140
ggagaggtag aagcaggccg tgagtatgtg gctcctcgca caacgctgga aacaagactt   25200
gctctcattt ggcagcaggt gctgggtatt gcgcgagttg gagtcgaaga cgatttcttt   25260
gacctgggtg gtcattcctt gcgggcctcc acgctggttt ccaagattcg gaaagagctg   25320
caagtcgagg ttccgctgcg ggacgttttc cgctacacca cgatcaaaca gctggcccaa   25380
agaatcggcg gtttaaagca gcaggagacg tatgaaatta caaaggcggc tgaggccgag   25440
tactatccgg tttcatccga gcaaaagcgt ctgtacgtcc tgcgccagct tgacggggcc   25500
gagcgcagct acaatatgtc ggcggcgctt cttctcgaag gcaagctgga tcggacgcgc   25560
gtagagtacg cgttccgggc gctgattcag cgtcatgaga cgctgcgtac cgggatcgag   25620
caggttcaag gcgaacttgt ccagcgcatc tatgacgagg tggagtttgc tgtggattat   25680
ttccaggcga gtgagcggga agtggagcaa ggggtggaag cttactatcg cccgtttgat   25740
```

```
ctgaccaagc cgccacttct ccgcatcggc ctgatcgaag tcaccgagga tcgccacatt   25800
ctgctgttcg atatgcacca tatcgtctcg gacggcatat cgacagcgct gctcttcgac   25860
gagttcagcc gcctgtatcg gggcgaggag ctggctccgc tgcgcattca atacaaagat   25920
tatgccgttt ggcagcattc cgaagcttac gcgcaactgc tccagccgca gaaggagtac   25980
tggctggagc agctgtcagg cgagctgccg gtcttggagc tgccgacgga tttcccgcgg   26040
ccagcggtgc aaagctttga cggccggacc gtgaagtttt atatcgggaa agagcggacg   26100
gagaagctga aagagctggc gtcacggacg ggaacgaccc tgtacatggt gctgctgtcg   26160
gcttatacca tccttatgca taaatattcg ggtcaggaag atctgatcgt cggaacgcca   26220
attgccggaa gaacgcagga tgaagtgcag ccgatcgtag ggatgtttat caacacgctg   26280
accattcgca gccgtccgga gcgttccaag ccataccttt cgtacctgga agaaatcaag   26340
gacatcacgc tcgggctttt cgaacaccaa aattatttgt tcgaagactt ggtggaaagt   26400
cttcacattc cgcgcgcgac cggccggaat ccgctctttg atacgttctt ctccctgcaa   26460
aatacggaga acgagcaaat tgtcattgag gggctggagc aatcgttttta ccgctggaa   26520
aaccgaacat ccaagttcga gctgctcctg gacatttctg agcaggacgg tcagctcgaa   26580
tgccggttgg agtacgcaac ggcttttgtat aaacaggaga ccgcggaacg gttcgccaaa   26640
cattatgaca agctgttaga aaccatcgca gcagcgccgg acggggatat tgcctcgctg   26700
gaaatgctca cggaggagga aatccgcgaa ctagtacgtg gtttcaacga tcggaggcg   26760
gactacccgc ggcagcagac gattcacggc ttgttcgaag agcaggcaga gctttacccg   26820
gacaacgtgc ccgccgtcat gaacgagcgg cagctgacct accgcgagct gaacgagcga   26880
tccaaccgcc ttgcgcggaa gctgcgggag acgggagtag aagcggatca actggtagcg   26940
attctggccg aacgctcgct cgatatggtt gtcggcattc tggcgattct taaagcgggc   27000
ggagcctacg tgcctgtcga tcccgactac ccggaggagc gtatccgctt catgatcgag   27060
gattcgggcg cgccgttatt gctgattcaa aagcatttgc acgagaagac cgacttcgca   27120
ggaacacgcc tcgaattgga tgatttcgtt tggggcgaca gaggtgcgga ctccgaaggt   27180
gcgctggatg cttcgaatct ggatccgatt tccgggccgg gcaacctagc ctatgtcatc   27240
tacacatcgg gaacgaccgg cagaccgaaa ggaactttga tcgagcataa gaacgtcgtg   27300
cgcctcctgt tcaacgacaa gaatctgttc gacttcgggc cgtccgacac gtggacgctg   27360
ttccactcgt tctgcttcga tttctccgtc tgggaaatgt acggagcact gctgtacgga   27420
ggcaagctgg tcatcgtacc gccgctcatg gcgaaaaatc cggccgattt cctagcgctg   27480
ctgggccgcg aacagatcac gattttgaac cagacgccaa cgtacttcta ccagctgctg   27540
cgtgaggtct tggcggacca tccgtacgat ctgcggattc gcaacgtcat cttcggggc   27600
gaagcactga gtccgctgct gctcaagggc ttcaagacga agtacccgga gacgaagctg   27660
atcaatatgt acggcattac cgagacgacg gttcacgtta cgtataagga aatcacgtgg   27720
gtcgaaatgg aggcggcgaa gagcaatatc ggcaagccga tccccgacgct gagggtgtac   27780
gtccttgatg aaaaccgccg ccctgtgccg atcggcgtag cgggcgaaat gtatgtggcc   27840
ggggaaggcc ttgcgagagg ataccggaac cgtccggatc tgacggcgga gaagtttgtc   27900
gattccccgt ttgcggaggg ggagaaactg taccgctcgg gcgacttggc ggcttggcag   27960
ccggacggca acatcgaata cctgggccgg atcgaccacc aggtaaaaat ccgcgggtac   28020
cggatcgagc tggatgaaat cgagacgcag cttctgaacg ttgagggcgt ggaagaagcg   28080
gtggtgcttg ctcgtcagga cggtgggggc gagaaggcgc ttgtcgccta ctttgtggcg   28140
```

```
aaccggacac tgacggtcag tgaaatgaga acctcactgg ccaaggaaat gccggggtac   28200
atgatcccgt cgtacttcgt gcagctggag cgtatgccgc tgacgtccaa cggcaaagtg   28260
gatcgcaaag ccctgccgga ccgcaaggc ggcttgcaaa cgggcgtcga atatgtagcg    28320
ccgcgtaacc ggacggagtc ccagcttgtg aagatctggg aggaagtgct gggttactcc   28380
ggcattggag tcatggacaa tttcttcgag cttggaggcc actccttgcg ggcgacgaac   28440
cttgtcagca agattcggaa ggaaatgaac gtcgaatttc cgctgcgcga tgtgttccgc   28500
tatatgacgg tagagtcgat ggccggggct attgccagct tggaggaaac gcggcatagc   28560
tcgattccga aagcggaaga gagagcgtac tatccggttt cctccgcaca aaaaaggttg   28620
tacgtcctga accagctgga tggctcggag ctgaattaca acctcccaag cgccttgcaa   28680
ttgaaagggg ctttgaacga ggccaaagtg gaaaaggcgc tgactacttt ggtggcccgg   28740
cacgatatgc tgcgcaccgg ttttgaaatc gtagatgggg agccggtaca gcgtattcat   28800
ccgctcgcag ctttcaaggt cgagaagctt caagcaagtg aagatcaggt tgcggccatt   28860
cttgaaggct tcattcagcc ttttgacttg acccagccgc ctttgctgcg tgccctgctg   28920
atcgaactgg agaaagagaa attcctgctt gcgctggata ttcatcatat tggttccgac   28980
ggcctctcca tggacgtgct gctgcgcgaa ttcgtgcggc tttacaatgg ggaagaattg   29040
ccggtgctac ggattcaata caaggattac gccgtttggc agcaatccga ggaacagcgc   29100
cagcgtatca aacagcagga ggaatactgg cgtggggtat tcaactctga gcttccggtt   29160
cttgagctgc ctctcgactt ctcccgtccg gccgtccagc agtttgacgg tcgaacgctc   29220
acgtttacgc tggatgcgga gaaaagcgaa gctctcaaac ggcttgccgg cgattcggga   29280
gcgacgcttt acatgctttt gctggctgcg tactccgtat tgcttcataa atatgcggga   29340
caggaagata tcgtggtcgg aactccgatt gccgcccgat ctcacactga cttacagccg   29400
attatcggca tgttcgtcaa tacgcttgcc cttcgcttgg accggcggc ggagcggacg   29460 ttcctggatt acttacagga agtgaaggaa acgacgctag gagcctacga gcaccaggac   29520
tatccgtttg aggagctggt ggaagctctt caggtgagcc gggatttaag ccggaatccg   29580
ctgtttgaca ccatgttttc tttgcaaaag cacgaaagct tggatttaac cctggaaggc   29640
ttgcaatggt cgctgttcga catcgaggaa aagacggcaa agtttgatct tagctttgat   29700
atcgtggaag ccgataacga gttggttgc aagatcgagt acgctacctc gttgtttaga   29760
caggaaacga tggtacggct ggcgggtcat tacgagcagc ttttggcgtc gatcctggct   29820
cagccgggtg cgcggatttc ggatttggac atattgacgg acagcgaaaa gcatgatttg   29880
ctggtcgggt ttgacgtgtc gtcttcggct cttgcgaagc aatccgccgc agagggtaca   29940
ggtttggaag cggatgaatc gtggagagag aggacgttcc acgagctgtt cgaggagcag   30000
gcggagcgca ctcctggagc gctggctgtt atctacgaag acagcaagct gacgtatgcg   30060
gagctgaacg ccaaagcgaa tcgtctgcg tatgcactgc gggcgcgcgg ggtgaagccg    30120
gagcaggtgg tcggcattct ggccggccgt tcggcggagc tgttgatcgg ggtgctcgcc   30180
gtatggaaag cgggtggcgc ttatgtgccg cttgatccgg actatccggc ggagcggatc   30240
gagtatatgc tcacggacag cggggcgtcg gttctgctca cgcagacccg cctgctggag   30300
caggcggaag tttggcgcag cgacggagct ctagcgttgc aaacggtgct tgcacttgac   30360
gacgctgcga cgtacagtct cggagcggca gaagtggctg tgggcgtaca agctttgggc   30420
gaagcaggcg cagaggcgga ggctttggcg caagcgcaaa cggctgctgc cgagacgtcc   30480
```

```
gccacggcag aagccgagca gaacgtactg gcggcggatc tcgcatcgaa tccggcgaat   30540
gtgaacaagc cgcgcgattt ggcttacgtc atctacacct ccggtacgac tggccgtccg   30600
aagggtgtgg cggtggaaca ccgcagcctg gtgaacacgg cggcgggcta tcggcgggac   30660
taccgcctgg atcagttccc gatccggctg ctgcaactcg ccagcttctc gtttgacgtg   30720
ttcgtcggcg acattgcgcg gacgctgtac aacggcggca ccatggtcat cgtgccgaag   30780
gacgaccgga ttgatccaac ccgcctatac ggctggattc gcgactacgc cgtgacggtg   30840
ttcgaatcga ctccggcgct gatcgtgccg ttcatggagc atgtgtatgc cgagggtctg   30900
gatctcagct cgatgcagtt gctgctcaca agctcggatg cgtgcagcgt agcggattac   30960
cgcaccttgc aggagcgctt cggctcgcag ttccgtatta ttaacagcta cggcgtcacg   31020
gaagcggcga ttgactccag cttctatgac gagccgctgg agaagctgcc gaagacgggc   31080
agcgtgccga tcgggaaagc gtggctgaac gcaaagttct acatcgtgga tgcgagtctg   31140
aagccggtgc cgatcggggt gttgggcgag ctggttatcg gcggagcggg tgtggcccgc   31200
ggttacttga accgcccgga tttgacggcg gagaaattcg tagacagccc gttcactgca   31260
ggggagcggc tgtaccggac gggcgacctg gcgcgctgga tgccggacgg caacgttgac   31320
ttcatcggcc ggatcgacaa ccaggtaaaa attcgcggct atcggatcga gcttggtgaa   31380
attgaagcgg ctatgaaaaa ttttgccggc gttcgtcaag cgcttgtcat cgaccggacg   31440
gacgagcggg ggcagaaata tttgtgcggg tatgtcgtag cggattccag cttcgatctg   31500
gaagggcttg tggcccatct ggacgctgca ctgccttccc atatggtgcc ttcgcgtatc   31560
atgcgcctgg atcaaatgcc gcttacgccg aacgggaaga tcgaccgtaa agggctgcct   31620
gtgccggaag gaagcattcg tgccgaggct gcatacacgg cgcctcgtac tcctgctgag   31680
caagcacttg cgttggtctg gcagtcagtg ctgggcgtgg atcaggtcgg cacgatggac   31740
aatttctttg cgctcggcgg cgattcgatc aaggccttgc aggtatcgtc ccgtcttttg   31800
caaacggggt acaagctgat catgaaagat ttgttccatt acccgacgat ttccgccctt   31860
agtttgcagc tgcaaacggc ggagagaacg gcaagccagg ccgaagtgac gggggaggtc   31920
atcttgaccc cgattcagcg ctggttcttt gaacaaaatc cggccgacgt gcatcacagc   31980
aaccaggcat tcatgcagtt ctccaagcta ggcttcgacg aagaagcttt acgccaagcg   32040
gtgcgtcaac ttgtcgtgca tcacgatgct ctccgtacgg tttaccgcca aaccgaaaac   32100
agctataccg cctggaaccg cggcgccggg gagaacgaag cactgttcga tctggaagtt   32160
gtagatttca ggggagtctg cgacgtgaaa ggcgcggtag aggctaaggc gaatgatatt   32220
caagcgagca tcgatctgga aaacggcccg ctggtgaagc tcggcttgtt ccgctgcgac   32280
gacggcgacc acctgctcat cgcgatccat cacttggtcg tagacggcgt atcatggcgg   32340
attctgcttg aagattttgc tgccggatat gagcaggtgc tgcaagggca gccgatccgt   32400
ctgccgctca aaacggattc attccaaacg tgggcgaaac agctcgctga ttatgcgaac   32460
gatccggcga tggaaagcga aagagagtat tggcagcata tcgagcaatt gagctatgag   32520
ccgcttccaa aagattttga acaaggcaga tccacgctga aggacagcgg tctcgtgacc   32580
gttcgctgga cagcggagga aaccgaacag ctgctgaagc acgcacaccg tgcttaccgt   32640
acggaaatga acgatttgct gcttgccgcg cttggcctcg cggtacaagc ttggagcggc   32700
cggggacgcg tgctggtgaa tctcgaaggc cacggccggg aagatatttt gccggatgtg   32760
gacattacac gcacggtagg ctggtttaca agccaattcc ctgtcgttct ggagccgggt   32820
cacgcccagg agctcggtca tcagctgaaa caggttaaag aaagcttgcg ccgcattccg   32880
```

```
aacaaaggaa tcagctatgg catcctgcgc tatttgtcgg cgccgcgtga cggcgagtgc  32940
ttcgctttgg agccggagat cagctttaac tatttgggtc agttcgacca ggattacgaa  33000
agcagcggct cgcagccgtc tccgttcagc ccgggctccg actcaagccc gaacgcagtg  33060
atggattttg tcctagatat caacggtatg gtgtcggaag gagtgctgga actcacgatc  33120
cgttatgggg aaacccagta taaacgggaa acggtagagc gcctgggcac cctgcttcaa  33180
ttgagcttgc gtgaagtcat caaccattgc gtatcgaaag agcggccgga gcttacgcct  33240
agcgacgtac tgcttcaaga tgtgacggtg gaggaactgg agcggttggc tgaacatacg  33300
gcggcgctcg gcgaactgga gaatgtatac accctgactc cgctgcaaaa agggatgttg  33360
ttccacagcc tgctggatgc cgattcggaa gcttacttcg aacaggtgac cttcgatctg  33420
aacgaagccc tgaatgtcga agccttcacc caaggattgg atacgctggt gcagcggaat  33480
gaggcactgc ggaccaactt tattaccggc tggagggacg agccgattca agtggtattc  33540
cgcgagcgga agtgtgaagt gtacttcgaa gatattcgct cggcaagcga tgaagacccg  33600
gagaagacga tagccgattt cgtcagcgcg ataaagcga acaagttcga tttggctcaa  33660
ggctctctta tgcgcgtgac cgttttgcgc acgggcgacg agtcttacca tgtgatctgg  33720
agtcaccatc acattttgat ggacggctgg tgcatgtcct tcatgatcaa ggaagtgttc  33780
gacacctact tcgcgttcca agagaagcgg acgctggagc ttcctccggt tacctcgtac  33840
tcccggtata tcgaatggct ggaagctcaa gatgccgcga agcttcgcg ttactggtcc  33900
gaatatttgg cgggttacga tcagcagacc aagctgcccc aggagaaaac gcagctgaag  33960
cagggcgctt ttgaagcggc tgaaatcgat gtggaactca gcaaggaact gaccgggcaa  34020
atcgagcggg tggcgcgcca gcagcaggtg acgctcaata cgttcatgca gaccgtatgg  34080
ggactggttc tgcagatata caacaacagc gaggatgtcg tattcggctc cgtcgtatcc  34140
gggcgtccgg cggaaattcc gggcatcgaa agcatgatcg gcctgtttat taatacgatc  34200
ccggttcgta ttcaaggcaa agccgaggag acggtagccg atatcttgag aaaaacccag  34260
gatcaagcac tggcatcggg agcttacgaa acgttcccgc tgttcgaaat tcagtcgctg  34320
agcgagcaaa agcgcgactt gatcaaccat attatggttt ttgaaaatta tccgatggaa  34380
gaacagattg agcaggtcgt cggcggtgac aaagaagcgc tgaaaatcgc taatatccag  34440
tcgccagagc aaacgaacta cgacctggac attaccgtca ttccggaaga gcctattttg  34500
ctgcggttta cgtacaatgc gctgacgtac agagaggaag acatcaggct gatccacggt  34560
cattttgccc aggcactgga gaaggttgcg gctaacccga atatccgcgt gaatcagttg  34620
gagcttttga cggcggcgga aaaagaccaa attctcggtg cgtttaaccc ggcgcagccg  34680
gaagcggctc ctgcggccgc gttccaccgg ctgttcgagg aacaggcgga acgcacgccg  34740
gaagaggcgg ccgtcgtgta tgagaatgac cggctgacgt atgcggagct gaacgagcgg  34800
gcgaaccgct tggcggccac gctgcgcgca agcggcatcg gccgggagac gatcgtcggc  34860
attctcgccg agcgttcggt ggacttgctg gtggccgtgc tggccgtctg gaaagcgggc  34920
ggggcatatg tgccgctcga cccggattat ccggcagacc gcgtgcggtt catgcttgaa  34980
gacagtggag cgaaggtact gttgacgcaa ataccgctgc gagaacgcgc cgaagcctgg  35040
ctcggcgaag aggagctggc gctggcagcg gtgctgtacc tcgacgacga agcgtcgtac  35100
agcgaggagc gggcgaatgc gccgattggt tccggcatgg tctccggcca gctgacggat  35160
gctgtggatg acggcgatga gacccatccg aatattggca tgggcagctt ccatgaagct  35220
```

```
cgtccggagg atctggcgta tgtgatctat acgtcgggaa cgacgggcaa gccgaaaggc    35280
gtgatgatcg agcaccgcag cctggtgaac acggcagcgg gctaccggcg ggaataccgg    35340
ttggatcagt tcccggtacg gctgctgcag ctcgcaagct tctcgttcga cgtgttcgtg    35400
ggagatatcg cgcggacgct gtataacgga ggcacgatgg tgattgtgcc gaaggacgat    35460
cggatcgatc cgtctcgtct gcaccactgg atggagcggg agcgggtcac cattttcgaa    35520
tcaacgccgg cgctgatcgt gccgttctta gagtacgtgc acgagcaggg gctggatatg    35580
agctggatgg agctgttgat cacgagttcg gacagctgca gcgtggcgga ttaccggacc    35640
ttgcaggaac gcttcggctc gttattccgg atcatcaacg catacggcgt gacgaagcg     35700
gcgatcgact ccagcttcta cgacgaggag ctgacgaagc tgccgcagac aggacatgtg    35760
ccgatcggta aagcgtggct gaatgcgaaa ttctacatcg tggacgcgca tctgaacccg    35820
gtgccggtcg gggtgctggg cgagctggtc attggcggag tcggggtagc acgcgggtac    35880
ttgaaccgtc cggagctgac ggaagagaag ttcgtagaca gtccgttcgc cgcgggcgag    35940
cggctgtacc gcacgggaga cttggcgcgg tggatggagg acgggaacgt ggacttcatc    36000
ggccggatcg acaaccaggc gaaaatccgg ggctaccgga ttgagacggg cgaagtcgaa    36060
gcgaagatgc tgagtgtagg tggtgtgaag gaagcggtcg ttgtcgtcag ggaagatcaa    36120
gaaggtcaga aagctttgtg cgcttattat acagtggaag aaggcatgac ggcggcagac    36180
ctgaagcgtg cgatttccag cgagctgccg gggtacatga tcccgtcgta tttcgtggag    36240
ctggagcgtc tgcctttgac gccgaacgga aagatcgacc ggaaggcgct gccggcaccg    36300
gaaggggcag caggcggagg ccgcgaatac gtggcgccac gcaccgaact ggaggcgaag    36360
ctggccgcca tttggcagga ggtgcttgtt agggagaagg cagtaggtgt aacggacaac    36420
ttctttgacc tcgcggaca ctccctgcgg gctacgacgc ttgtcagcaa aatgcataag    36480
gagctaggca ttgaattccc gctacgcgac gtattccgct actcgacggt tgaggaaatg    36540
gccgcggcta tggagtggct ggagatcggc tcgttcatag ctattccggc tgcggaacct    36600
agcgagtatt atccgctatc atccgctcag aaacgtctct atatcttgaa ccagctggaa    36660
ggaggcgagc tgagctacaa cataccggga gcaatgctgc tcgaagggga gctcgaccgg    36720
cagcggtttg aagaagcgtt ccgcgggctc gtagctcgtc atgaaacgct gcgtaccgga    36780
tttgagatgt aaaaggcga agcggttcaa cggatttatg aagaagctgc tttccaggtg    36840
gaatatgtgc agattagcgg ggaacggtg gaagaaacgg tgcgccaatt cgttcgtcca    36900
tttgatctgg cgaagccgcc acttctgcgt gtaggccttg ccgaactggc gccggaccgg    36960
cacattctga tgttcgatac gcatcatatc gtatctgacg gcgtttcgat ggacgtactg    37020
attgaagagt tcgtccgctt gtacagcggg gagccgttgg agccgctacg cattcagtac    37080
aaagattatg cggtatggca gcaatcggac gagcagaaag ctcagcttgc caagcaggaa    37140
gcctactggc tcgacatgtt ccgcggagaa ctgccggttt tggaattgcc aacgactac     37200
ccacgcccag ctatgcagag ctacgagggt cgcacactgc aattgtttat gaatagggag    37260
aaaagcgagg gtctgaaacg gcttgcagcc gagaacggcg caacgcttta catggttctg    37320
cttgctggtt atacaatatt attgcataaa tatactagtc aagaagacgt agtggtcggt    37380
acgccgattg cgggaagaaa tcacagtgac gttcagccgc tgatcggaat gttcgtcaat    37440
actctggcca tccgcagtta tccgactgcg ggtaagacgt tccttgacta cttgaaggaa    37500
atcaaggaga cgacgctggg tgcttttgaa catcagaatt atccgtttga ggaactggtg    37560
gataaggtga acgtagctcg tgatttaagc cgcaatccgc tgttcgatac gatgtttgct    37620
```

```
ttgcagaata cagagaattt ggaaatccag cttcccggac tccatttgtc gacgtatgcc   37680
agcgaagaaa ttgtttctaa attcgatctc agcttggacg tcacggagat cgaggaaggc   37740
ttggaatatc tgtttgaata cgccactgct ctttataaaa ccgaaacggt ggagaaattg   37800
gccgctcact acttgcagct gcttgaatct attctctgca acccttctgc gactattgcc   37860
gagctgggca ttttgacacc agcggaaaaa gaacaaattc tcggcgcgtt caacccggcg   37920
cagccggaag cggctcctgc ggcggcgttc caccggctgt tcgaggaaca gcggagcgc   37980 acgccggaag cggaggctgt cgtgtacgag aacgaccggc tgatttatgc ggagctgaac   38040
gagcgggcga accgcttggc ggctacgctg cgcgcaagcg gcatcggccg ggagtcgatc   38100
gtcggcattc tcgccgagcg ttcggtggac ttgctggtgg ccgtgctggc cgtctggaaa   38160
gcgggcgggc gtatgtgcc gctcgacccg gattatccgg cggaccgcgt gcggttcatg   38220
cttgaagaca gcggagcgaa ggttctgctg acgcaaaagg tgctgcgaga gcgcgccgaa   38280
gcctggctcg cgaagagga gctgacgctg cagcggtgc tgtacctcga cgacgaagcg   38340
tcgtacagcg aggtgcgggc gaatgcgccg attggctccg gcatggtctc cggcaagctg   38400
atggatgctg tgaatgacgg cgatgggacc catccgaatg ttgacatggg cagcttccat   38460
gaagcccgtc cggaggatct ggcgtacgtg atctatacgt cgggaacgac gggcaagccg   38520
aagggcgtga tgatcgagca ccgcagcctg gtgaacacgg cagcgggcta ccggcgggaa   38580
taccggttgg atcagttccc ggtgcggctg ctgcagctcg caagcttctc gttcgacgta   38640
ttcgtgggcg atatcgcgcg gacgctgtat aacggaggca cgatggtgat tgtgacgaag   38700
gacgaccgga tcgatccgtc tcgtctgcac cactggatgg agcgggagcg ggtcaccatc   38760
ttcgaatcga cgccggcgct aatcgtgccg ttcctggagt acgtgcacga gcaggggctg   38820
gatatgagct ggatggagct gttgatcacg agttcggaca gctgcagcgt ggcggattac   38880 cggacccttgc aggaacgctt cggctcgttg ttccggatca tcaatgctta tggcgtgacg   38940
gaagcggcga tcgactccag cttctacgac gaggagctga cgaagctgcc acagacaggc   39000
catgtgccga tcggcaaagc gtggctgaat gcgaaattct acatcgtgga cgcgcatctg   39060
aacccggtgc cggtcggggt gctgggcgag ctggtcatcg gcggagtcgg agtggcgcga   39120
gggtacttga accgtccgga gctgacggaa gagaagttcg tagacagtcc gttcgccgcg   39180
ggcgagcgac tgtaccgcac gggagacttg gcgcggtgga tgaggacgg gaacgtggac   39240 ttcatcggcc ggatcgacaa ccaggcgaaa atcggggggt accggattga gacgggcgaa   39300
gtcgaagcga agctgctaag tgtggaaggc gtgcgcgaag cggtggtgct ggttcgaagt   39360
gacgcgaacg ggcagaaagc gctgtgtgcg tactacacaa ttgatggcga atttacagcg   39420
gcagacctga acgggcgat tgccagcgag ctgccgggt acatgatccc gtcgtacttc   39480
gtggagctgg agcgcctgcc tctgacgccg aacgggaaaa tcgaccggaa ggcgctgccg   39540
gcgccggaag ggggagcaaa cgcaggccgc gaatacgtgg cgccgcgcac cgaactggag   39600
gcgaaactgg tcgccatctg gcaggacgtg ctcgggccgg tcacgattgg cgtaacggac   39660
aacttcttcg acctcggtgg gcactccctg cgggcgacga cgctggtcag caaggtgcac   39720
aaggagctga gcgtggacct gccgttcgcg gatgtgttcc ggcactcgac catcgaagcg   39780
atggccgaag cgataagcca attggagcgg caggaacacc tctccattcc ggttctggat   39840
aagagggatt actatccgct ttcctccgtg cagaaacggc tgtatatcca gcagcagatg   39900
gaaggcgccg agcttagcta caatatgtcc ggcatgacgg ttctcgtcgg gcgtttggaa   39960
```

-continued

```
cggaatcaat tcgaggcggc gctcaaagga ttgatagctc gtcacgaaat tttgcgaacc    40020
ggcttcgaaa tggtcgacgg cgaaccggta caacggattt atccggactt gaagtttgcc    40080
gtcgagtata cgaaagcgat ggaaagtgaa acgaagagca tcgtagacgg ctttgtacgc    40140
gtctttgatt tggagcggcc gccgctgctg cgtgtgggct tagtcgaaat ggaagcggaa    40200
cggcatttgc tcatgctgga cattcatcat atcgtcacgg atggcatgtc gatgggtatc    40260
ttcgtcgaag agctgctgcg cctgtataac ggcgagaatc tggaaccact tcggattcaa    40320
tacaaggaat tcgccgcttg gcagcagtcc gaacctgtaa aagagcggct gaaacgtcag    40380
gaagcctact ggctggacgt gctggaaggc gaactgccga cgcttgaact gccaacggac    40440
tttgtcagac ctgccgctcg cagctttgag ggagatgtgc tgcctttcag catcgacaag    40500
cagatgaccg acagcttgca gcgcatcgcc gatgagaacg gtggcaccct ttatatggtg    40560
ttatcggcgg tctattcaat cctgctcagc aagtactcgg gacaagaaga tttcattgta    40620
ggcacgccgg tttcaggccg cacacatgca gacctggagc cgctcatcgg aatgtttgtc    40680
aacactttgg cgattcgcca ttatccgtcc ggggagaaga cgttcctcgc ttacttgaac    40740
gaagtcaaag aaacgatgct gggggcctac gatcaccagg attatccgtt cgaggagctt    40800
gtgaaaaagc tgcaggttcc gcgagatcta agccgcaatc ctgtattcga tgtcatgttt    40860
gctctggaaa ccaaggaaga taacgttcaa aacttcgggg atatcaggat cgaatcttat    40920
ccggaaactc atacggtttc ccaatttgat ctaaccttga tcatttcgtt gctggatgag    40980
ggaatgaacg ggcagtttga atatgccacc aagttgttca cacgcaatct gatcgacaat    41040
ttcgctcagg acctgctcgt aatcatctct caaatttgcg aacagccttc ggtgctgctg    41100
aaggatattt ccctgaacgg gcaatccgaa caggagcaag atgtgctaga ggccattgat    41160
attattttct aa                                                        41172
```

<210> SEQ ID NO 30
<211> LENGTH: 461
<212> TYPE: PRT
<213> ORGANISM: Paenibacillus alvei

<400> SEQUENCE: 30

```
Val Thr Gly Glu Val Ile Leu Thr Pro Ile Gln Arg Trp Phe Phe Glu
 1               5                   10                  15

Gln Asn Pro Ala Asp Val His His Ser Asn Gln Ala Phe Met Gln Phe
            20                  25                  30

Ser Lys Leu Gly Phe Asp Glu Glu Ala Leu Arg Gln Ala Val Arg Gln
        35                  40                  45

Leu Val Val His His Asp Ala Leu Arg Thr Val Tyr Arg Gln Thr Glu
    50                  55                  60

Asn Ser Tyr Thr Ala Trp Asn Arg Gly Ala Gly Glu Asn Glu Ala Leu
65                  70                  75                  80

Phe Asp Leu Glu Val Val Asp Phe Arg Gly Val Cys Asp Val Lys Gly
                85                  90                  95

Ala Val Glu Ala Lys Ala Asn Asp Ile Gln Ala Ser Ile Asp Leu Glu
            100                 105                 110

Asn Gly Pro Leu Val Lys Leu Gly Leu Phe Arg Cys Asp Asp Gly Asp
        115                 120                 125

His Leu Leu Ile Ala Ile His His Leu Val Val Asp Gly Val Ser Trp
    130                 135                 140

Arg Ile Leu Leu Glu Asp Phe Ala Ala Gly Tyr Glu Gln Val Leu Gln
145                 150                 155                 160
```

Gly Gln Pro Ile Arg Leu Pro Leu Lys Thr Asp Ser Phe Gln Thr Trp
                165                 170                 175

Ala Lys Gln Leu Ala Asp Tyr Ala Asn Asp Pro Ala Met Glu Ser Glu
            180                 185                 190

Arg Glu Tyr Trp Gln His Ile Glu Gln Leu Ser Tyr Glu Pro Leu Pro
        195                 200                 205

Lys Asp Phe Glu Gln Gly Arg Ser Thr Leu Lys Asp Ser Gly Leu Val
    210                 215                 220

Thr Val Arg Trp Thr Ala Glu Glu Thr Glu Gln Leu Leu Lys His Ala
225                 230                 235                 240

His Arg Ala Tyr Arg Thr Glu Met Asn Asp Leu Leu Leu Ala Ala Leu
                245                 250                 255

Gly Leu Ala Val Gln Ala Trp Ser Gly Arg Gly Arg Val Leu Val Asn
            260                 265                 270

Leu Glu Gly His Gly Arg Glu Asp Ile Leu Pro Asp Val Asp Ile Thr
        275                 280                 285

Arg Thr Val Gly Trp Phe Thr Ser Gln Phe Pro Val Val Leu Glu Pro
    290                 295                 300

Gly His Ala Gln Glu Leu Gly His Gln Leu Lys Gln Val Lys Glu Ser
305                 310                 315                 320

Leu Arg Arg Ile Pro Asn Lys Gly Ile Ser Tyr Gly Ile Leu Arg Tyr
                325                 330                 335

Leu Ser Ala Pro Arg Asp Gly Glu Cys Phe Ala Leu Glu Pro Glu Ile
            340                 345                 350

Ser Phe Asn Tyr Leu Gly Gln Phe Asp Gln Asp Tyr Glu Ser Ser Gly
        355                 360                 365

Ser Gln Pro Ser Pro Phe Ser Pro Gly Ser Asp Ser Ser Pro Asn Ala
    370                 375                 380

Val Met Asp Phe Val Leu Asp Ile Asn Gly Met Val Ser Glu Gly Val
385                 390                 395                 400

Leu Glu Leu Thr Ile Arg Tyr Gly Glu Thr Gln Tyr Lys Arg Glu Thr
                405                 410                 415

Val Glu Arg Leu Gly Thr Leu Leu Gln Leu Ser Leu Arg Glu Val Ile
            420                 425                 430

Asn His Cys Val Ser Lys Glu Arg Pro Glu Leu Thr Pro Ser Asp Val
        435                 440                 445

Leu Leu Gln Asp Val Thr Val Glu Glu Leu Glu Arg Leu
    450                 455                 460

<210> SEQ ID NO 31
<211> LENGTH: 430
<212> TYPE: PRT
<213> ORGANISM: Paenibacillus alvei

<400> SEQUENCE: 31

Met Lys Arg Val Ser Ile Phe Glu Lys Leu Glu Ser Asn Val Arg Ser
1               5                   10                  15

Tyr Cys Arg Ser Phe Pro Val Val Phe Asp Arg Ala Lys Gly Asp Leu
            20                  25                  30

Leu Tyr Ser Glu Asp Gly Arg Ser Tyr Ile Asp Phe Ala Gly Ala
        35                  40                  45

Gly Ala Leu Asn Tyr Gly His Asn Asn Asp Tyr Ile Lys Asp Arg Val
    50                  55                  60

Leu Asp Tyr Leu Thr Ser Asp Arg Ile Met His Gly Leu Asp Met Tyr

```
                65                  70                  75                  80
          Thr Met Ala Lys Arg Glu Phe Ile Gln Ser Phe Ser Glu Arg Ile Leu
                            85                  90                  95
          Gln Pro Lys Lys Leu Asn Tyr Lys Leu Gln Phe Cys Gly Pro Thr Gly
                            100                 105                 110
          Thr Asn Ala Val Glu Ala Ala Leu Lys Leu Ala Arg Lys Ala Lys Lys
                            115                 120                 125
          Arg Thr Gly Ile Phe Ala Phe Met Gly Gly Phe His Gly Met Ser Leu
                            130                 135                 140
          Gly Ser Leu Ser Ala Thr Ser Ser Lys Ser Met Arg Glu Gly Ala Gly
          145                 150                 155                 160
          Leu Pro Leu Gly Gly Val Thr Phe Met Pro His Pro Ser Gly Ala Phe
                            165                 170                 175
          Ala Glu Met Asp Thr Leu Gly Tyr Ile Glu Asn Ile Leu Thr Asp Ser
                            180                 185                 190
          His Ser Gly Ile Asp Lys Pro Ala Ala Ile Ile Leu Glu Thr Val Gln
                            195                 200                 205
          Ala Glu Gly Gly Ile His Val Val Asp Ala Gln Trp Leu Arg Gly Leu
                            210                 215                 220
          Gln Gln Leu Cys Arg Arg His Asp Ile Leu Leu Ile Thr Asp Glu Ile
          225                 230                 235                 240
          Gln Val Gly Cys Gly Arg Thr Gly Glu Phe Phe Ser Phe Glu Arg Ala
                            245                 250                 255
          Gly Ile Glu Pro Asp Leu Ile Thr Leu Ser Lys Ser Ile Ser Gly Tyr
                            260                 265                 270
          Gly Leu Pro Met Ser Leu Leu Leu Leu Lys Pro Glu Leu Asp Leu Trp
                            275                 280                 285
          Thr Pro Gly Glu His Asn Gly Thr Phe Arg Gly Asn Gln Leu Ala Phe
                            290                 295                 300
          Val Ala Ala Lys Ala Ala Leu Glu Phe Arg Asp Arg Ala Ala Leu Glu
          305                 310                 315                 320
          Ala Glu Val Lys Gln Lys Glu Glu Phe Val Arg Ser Phe Leu Asp Lys
                            325                 330                 335
          Glu Ile Lys Pro Leu His Pro Ser Ile Ala Ile Arg Gly Leu Gly Leu
                            340                 345                 350
          Ile Trp Gly Ile Asp Val Ser Gly Phe Thr Asp Glu Ala Gly Ala Lys
                            355                 360                 365
          Arg Met Thr Glu Ile Ser Phe Glu Asn Gly Leu Ile Ile Glu Arg Ala
                            370                 375                 380
          Gly Arg Gly Asp His Val Leu Lys Ile Met Pro Pro Leu Thr Val Ser
          385                 390                 395                 400
          Met Glu His Leu Ala Ala Gly Cys Asp Ile Ile Lys Ser Ser Ile Gln
                            405                 410                 415
          Gln Val Leu Ser Gln Glu Thr Gln Glu Leu Leu Val Thr Thr
                            420                 425                 430

<210> SEQ ID NO 32
<211> LENGTH: 1293
<212> TYPE: DNA
<213> ORGANISM: Paenibacillus alvei

<400> SEQUENCE: 32
atgaagcgcg tgagcatttt tgaaaagctg gaatccaatg taagatctta ctgcagaagc      60
tttccggtgg tattcgaccg ggccaagggg gacctcttat attctgagga cggaagatca     120
```

-continued

```
tatattgatt tttttgcagg tgctggggca ctgaattacg gtcataacaa cgattatatc    180
aaggatcggg ttctcgatta cttgacatcc gaccggatta tgcacggtct ggatatgtat    240
acaatggcca agcgcgaatt catccagagc ttctcggagc ggatcctgca gccgaagaag    300
ctgaattaca agcttcaatt ctgcggtccg acggggacga acgcggtgga agcggccttg    360
aagctcgcac gcaaggcgaa gaagagaacc gggatattcg cattcatggg cggcttccac    420
ggtatgtcgc tcggcagcct gtcggcgaca agctccaagt ccatgagaga aggggcgggg    480
cttcctctgg gcggagttac gttcatgccg cacccgagtg ggctttcgc agaaatggat    540
acactcggct atatcgagaa tatcctgact gattcacact ccggaatcga caagccggcc    600
gccatcattc ttgaaacggt acaagccgaa gggggaattc acgtcgtcga cgcgcagtgg    660
ctgcgagggc tgcagcagct ttgccgcagg cacgatatcc tgctcattac cgacgagatt    720
caagtcggct gcggccggac aggcgaattc ttctccttcg aacgtgcggg gattgagccg    780
gatctcatta ccctgtcgaa gtcgatcagc gggtatggcc tgccaatgtc cctcctgctg    840
ctgaagcctg aactggatct ctggacgccg ggcgagcaca acggcacctt ccgcggcaac    900
cagctcgctt ttgtggccgc caaggccgct ctcgagttcc gggacagagc cgccctggaa    960
gccgaggtga agcagaagga agagtttgtg cgctcgttcc ttgacaaaga aatcaagcct   1020
ctgcatccgt cgatcgcgat ccgcggactc ggcctgatct ggggcattga cgtctcgggc   1080
ttcacggatg aagctggggc gaagcggatg acggagatca gcttcgagaa cgggctcatc   1140
attgaaagag ccggcagagg agaccacgtg ctgaagatca tgcctccgct gaccgtctcg   1200
atggagcatc ttgccgccgg ctgtgacatt atcaagtcca gtatacagca ggtgctctct   1260
caggagaccc aggaattgct ggtaacgacc taa                                1293
```

COLISTIN SYNTHETASES AND CORRESPONDING GENE CLUSTER

CROSS-REFERENCE TO RELATED APPLICATIONS

This application is a U.S. National Stage Application pursuant to 35 U.S.C. § 371 of International Patent Application PCT/IB2015/050571, filed on Jan. 26, 2015, and published as WO 2015/111013 on Jul. 30, 2015, which claims priority to French Patent Application 1450641, filed on Jan. 27, 2014, all of which are incorporated herein by reference in their entireties for all purposes.

The present invention relates to bacterial genes and enzymes involved in the synthesis of polymyxin E, an antibiotic molecule used in therapy against infections with gram-negative bacteria.

PRIOR ART

Polymyxins are antibiotic molecules isolated from *Bacillus* species or from *Paenibacillus* species. These molecules are lipopeptides, consisting:
- of a peptide chain comprising ten amino acids, organized in a cyclic heptapeptide and a side chain of three amino acids, and
- of a fatty acid attached at the N-terminal end of the peptide.

At least 16 types of polymyxins have been identified since the discovery of polymyxin B in 1947. Among them, polymyxins B and E have antimicrobial activity on most of the strains of *Escherichia coli* and of *Pseudomonas aeruginosa*, and also on all strains of Salmonellae and Shigellae, and of numerous gram-negative bacteria. These antibiotics have therefore been used as therapeutic agents in many cases. Unfortunately, their toxic effects are such that they have been gradually replaced by antibiotics that are better tolerated.

FIG. 3 shows the general structure of polymyxins, and the two specific amino acids are indicated X and Y. As indicated, polymyxins B and E differ by a single amino acid, the "X" residue being a phenylalanine for polymyxin B and a leucine polymyxin E, it being possible for the "Y" residue to be a leucine, isoleucine or valine.

Because of the increasing demand for new antibiotics for which there is not yet any resistance in the population, new antibiotic agents are sought, and polymyxins are again used clinically in combating multiresistant gram-negative bacteria.

Colistin or polymyxin E, identified under CAS number 1264-72-8, and as described in patent application WO 1998/020836, is an antibiotic of the polymyxin family, making it possible to treat infections due to multiresistant gram-negative bacteria. Its peptide structure is indicated in FIG. 1. Administered by injection, colistin is used in the treatment of neuromeningeal infections, urinary infections, urogenital infections, septicemia and superinfections of wounds, burns and ulcers. Administered by inhalation, colistin is used in the treatment of pulmonary infections, in particular those associated with cystic fibrosis. Finally, in combination with hydrocortisone and bacitracin, colistin is used for treating bacterial and inflammatory infections of the eye, and also infections in ophthalmic surgery.

Colistin is responsible for numerous unwanted effects, in particular nephrotoxic and neurotoxic effects. These toxic effects are attributable to the cationic nature of this molecule, which contains five positive charges, but also to the low degree of purity of the molecule, produced in a fermenter by culturing the original bacterial strain which synthesizes it, and purified from the fermentation medium.

Indeed, polymyxins are currently obtained by isolation and purification from culture media of bacterial strains which produce these molecules, in particular strains of *Paenibacillus polymyxa*. The purification of the molecule from fermentation media is unsatisfactory, and this is why new production techniques are envisioned. In particular, studies are carried out to identify and clone the genes encoding polymyxin synthetases.

Polymyxin synthetases are part of the "Non-Ribosomal Peptide Synthetase" (NRPS) family; the genes encoding these synthetases are organized in a cluster comprising several modules, the order and specificity of which determine the structure of the peptide product. NRPSs allow the synthesis of peptides which exhibit a broader structural variety than that which could be obtained if these peptides were translated from messenger RNA by ribosomes. Furthermore, the peptides thus produced can undergo modifications, in particular through the creation of bonds with hydroxylated acids, and oxidations in the peptide chain making it possible to obtain cyclic structures and also acylations, glycosylations, and an N-methylation of the residues.

Such NRPS complexes have been described in many microorganisms and are involved in the production of tyrocidine, gramicidin, vancomycin, penicillin, and fusaricidins.

NRPS synthetases consist of various modules. Each module is capable of activating an amino acid, optionally of modifying it and of subsequently transferring it onto the activated amino acid in the adjacent module so as to constitute a peptide. Each module is composed of several domains and allow the incorporation of a particular amino acid into the peptide undergoing elongation. Each module contains a minimum of 3 domains:
- an adenylation domain (A): a domain central in the action of peptide synthetases. It allows the binding of a specific amino acid and its activation through a reaction of adenylation of the latter (conversion of the amino acid to adenylated aminoacyl);
- a thiolation domain (T or PCP for Peptidyl Carrier Protein): allows the peptide being synthesized to remain bound to the synthetase throughout the elongation process via a thioester bond;
- a condensation domain (C): allows the formation of the peptide bond between two amino acids of adjacent modules.

The release of the peptide is induced by a specific domain, the Te (thioesterase) domain. This domain will cleave the thioester bond which links the synthesized peptide to the final T domain. This domain also allows the cyclization of certain peptides.

There are also optional secondary domains which make it possible to carry out modifications on the amino acids, such as epimerization (conversion of an amino acid of the L series to an isomer of the D series), methylation (addition of a methyl group) or else formylation (addition of a formyl group).

Figure 2:
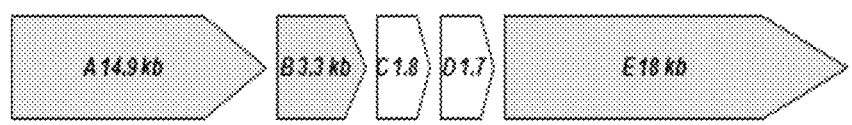

In the case of polymyxins, and as indicated in FIG. 2, three synthetases are essential for the synthesis of the peptide chain:
- the PmxA module has four adenylation domains, organized three-dimensionally as "binding pockets" which each integrate a specific amino acid into the polymyxin molecule;

the PmxB module has one adenylation domain, and is responsible for the integration of a single amino acid;

the PmxE module has five adenylation domains which integrate the other five amino acids which make up the peptide chain of polymyxin.

The article by Choi et al. (Journal of Bacteriology, 2009) and also patent U.S. Pat. No. 8,329,430 describe the isolation of a cluster (group) of genes of the gram-positive strain *Paenibacillus polymyxa* E681 secreting polymyxin A. Five genes constitute this cluster: pmxA, pmxB, pmxC, pmxD and pmxE. The pmxC and pmxD genes encode transport proteins, while the other three genes, pmxA, pmxB and pmxE, encode synthetases. This is in particular demonstrated by a mutant strain which has undergone a mutation by insertion into the pmxE gene: this strain no longer produces polymyxin. Conversely, a strain of *Bacillus subtilis* transformed by the introduction of this gene cluster becomes capable of producing polymyxin A, but only in the presence of L-2,4-diaminobutyric acid (Dab, major residue of the polymyxin peptide chain).

In the polymyxins described in the literature, it is very rare to observe the presence of D-Dab residues, except for polymyxins A, C and P.

Shaheen et al. (Chemistry and Biology, 2011) have described the identification and sequencing of a gene cluster derived from the *Paenibacillus polymyxa* PKB1 strain. The involvement of this genes in polymyxin B biosynthesis is demonstrated by insertional mutation in the pmxE gene: the mutated strain no longer produces polymyxin. During the characterization of the cluster, Shaheen et al. identified an epimerization domain in the third module of the pmx cluster. This suggests the integration of a D-Dab in position 3. Thus, these genes are involved in the biosynthesis of polymyxin B variants, comprising, in position 3, not a D-2,4-diaminobutyrate residue, but its enantiomer, L-2,4-diaminobutyrate.

Other gene clusters derived from *Paenibacillus polymyxa* strains have been isolated, but their functions and specificities are only predicted and in no way functionally demonstrated.

Moreover, "variant" molecules exhibiting slight structural differences with the known polymyxins, and lesser toxic effects, have been reported. Thus, patent application WO 2009/098357 and also the article by Vaara and Vaara (Peptides, 2010) describe polymyxin B variants comprising only three positive charges and having reduced toxic effects. Polymyxin B variants have also been described in the article by Shaheen et al. (2011).

The technique currently used to produce colistin, based on the fermentation of bacterial producer strains in rich media, is not satisfactory, in particular in terms of purity of the molecule, which must be purified from the fermentation medium.

The identification of the genes involved in colistin synthesis would make it possible, by means of genetic engineering processes, to produce a purer polymyxin E molecule, and also to create derived synthetic molecules, having fewer harmful side effects and/or better activity.

SUMMARY OF THE INVENTION

The present invention describes the isolation of a gene cluster derived from a strain of *Paenibacillus alvei* isolated from the environment, producing polymyxin E, and uses thereof.

The present invention relates to a PmxA synthetase involved in polymyxin E synthesis, comprising four adenylation domains, characterized in that the second adenylation domain comprises or has a particular peptide sequence represented in SEQ ID NO 1, this sequence forming a binding pocket specific for a leucine, isoleucine or valine residue.

The present invention also relates to a PmxE synthetase involved in polymyxin E synthesis, comprising five adenylation domains and one epimerization domain.

The present application also relates to a group of genes encoding enzymes involved in polymyxin E synthesis, comprising a gene encoding the PmxA synthetase, genes encoding the PmxB and PmxE synthetases, and genes encoding the PmxC and PmxD transport proteins.

The present invention also relates to transformed microorganisms expressing at least the modified or nonmodified pmxA, pmxB and pmxE genes, said transformed microorganisms producing polymyxin E or variant molecules of this polymyxin.

FIGURES

FIG. 1. Peptide structure of polymyxin E.

FIG. 2. Structure of the NRPS cluster involved in polymyxin E synthesis.

FIG. 3. Chemical structures of the various polymyxins B and E according to Govaerts and collaborators (Govaerts et al., 2002a; Govaerts et al., 2002b).

Figure 4:

FIG. 4. Antimicrobial effect of 20 μl of the culture supernatant of the B-LR bacterium and of mutant 5 on a bacterial layer of *P. aeruginosa*.

FIG. 5. PmxA peptide sequence; in bold: adenylation domain sequences; in bold and underlined: specific motifs of the binding pockets. The entire sequence is set forth in SEQ ID NO:6.

FIG. 6. (A) MS/MS spectrum corresponding to the fragmentation of the doubly charged precursor ion (m/z 585.39). (B) Structure proposed for the corresponding peptide: colistin E1. FA: fatty acid ($C_9H_{17}O$); L-Dab: L-2,4-diaminobutyric acid; Thr: threonine; Leu: leucine. The numbers in boxes correspond to the ions produced in the first series, the encircled numbers correspond to the ions produced in the second series.

FIG. 7. (A) MS/MS spectrum corresponding to the fragmentation of the doubly-charged precursor ion (m/z 578.38). (B) Structure proposed for the corresponding peptide: colistin E2. FA: fatty acid ($C_8H_{15}O$); L-Dab: L-2,4-diaminobutyric acid; Thr: threonine; leu: leucine. The numbers in boxes correspond to the ions produced in the first series.

FIG. 8. (A) MS/MS spectrum corresponding to the fragmentation of the doubly charged precursor ion (m/z 571.38). (B) Structure proposed for the corresponding peptide: Val-E2. FA: fatty acid ($C_8H_{15}O$); L-Dab: L-2,4-diaminobutyric acid; Thr: threonine; Ile: isoleucine; Leu: leucine; Val: valine. The numbers in boxes correspond to the ions produced in the first series, the encircled numbers correspond to the ions produced in the second series.

DETAILED DESCRIPTION

Polypeptides and Polynucleotides

The invention relates to the isolation and identification of new genes encoding polymyxin E synthetases, in particular of a gene encoding the "PmxA" synthetase having a particular adenylation site, forming a specific binding pocket allowing the integration into the polymyxin molecule of a leucine or isoleucine residue.

All the technical terms used in the present application are well known to the person skilled in the art and are defined in the reference book by Sambrook et al. "Molecular Cloning: a Laboratory Manual".

The term "polynucleotide" denotes a chain of covalently bonded nucleotides. For the purposes of the invention, this term denotes nucleic acids such as ribonucleic acid (RNA) and deoxyribonucleic acid (DNA).

For the purposes of the present invention, the "percentage identity" between two nucleic acid sequences is determined by comparing the two optimally aligned sequences through a comparison window.

The part of the nucleotide sequence in the comparison window may comprise additions or deletions (for example gaps) compared with the reference sequence (which does not comprise these additions or these deletions) so as to obtain optimal alignment between the two sequences.

The percentage identity is calculated by determining the number of positions at which an identical nucleic base is observed for the two sequences compared, then by dividing the number of positions at which there is identity between the two nucleic bases by the total number of positions in the comparison window, then by multiplying the result by one hundred in order to obtain the percentage nucleotide identity of the two sequences with respect to one another.

The optical alignment of the sequences for the comparison may be carried out by a computer using known algorithms.

Entirely preferably, the percentage sequence identity is determined using the CLUSTAL W software (version 1.82), the parameters being fixed as follows: (1) CPU MODE=ClustalW mp; (2) ALIGNMENT="full"; (3) OUTPUT FORMAT="aln w/numbers"; (4) OUTPUT ORDER="aligned"; (5) COLOR ALIGNMENT="no"; (6) KTUP (word size)="default"; (7) WINDOW LENGTH="default"; (8) SCORE TYPE="percent"; (9) TOPDIAG="default"; (10) PAIRGAP="default"; (11) PHYLOGENETIC TREE/TREE TYPE="none"; (12) MATRIX="default"; (13) GAP OPEN="default"; (14) END GAPS="default"; (15) GAP EXTENSION="default"; (16) GAP DISTANCES="default"; (17) TREE TYPE="cladogram" and (18) TREE GAP DISTANCES="hide".

The term "polypeptide" denotes a chain of covalently bonded amino acids.

The term "polymyxin E synthetases" denotes the enzymes capable of integrating a specific amino acid into the chain of amino acids forming polymyxin E, and where appropriate of converting the amino acid so as to form a cyclic structure.

The term "adenylation site" or "adenylation domain" denotes, in the polymyxin synthetase molecule, the domain which plays a role in the choice and activation of the amino acid, while the "condensation domain" catalyzes the formation of a peptide bond and the "thiolation domain" is responsible for the transport of the compounds undergoing formation between the modules.

The term "epimerization site" denotes, in a synthetase, a domain which makes it possible to convert a residue which has a levorotary chirality "L" into its enantiomer of dextrorotary chirality "D", in particular an L-α,γ-diaminobutyric acid (L-Dab) into a D-α,γ-diaminobutyric acid (D-Dab).

The term "binding pocket" denotes a zone of the protein which has a three-dimensional structure in the form of a "pocket", in which high-specificity interactions with a substrate or, in the present case, an amino acid, will make it possible to select and activate this amino acid.

The expression "the underlined amino acids being conserved" means that, even if slight sequence variations may be observed between two proteins having the same catalytic activity, the amino acids indicated are essential to the specificity and to the activity of this protein and may not therefore be modified, without risk of losing or reducing the specificity and/or the activity of this protein.

The present invention relates to a PmxA synthetase involved in polymyxin E synthesis, comprising four adenylation sites, characterized in that the second adenylation site has at least 90% identity with the following peptide sequence:

```
                                          (SEQ ID NO 1)
VTEAEKADLLGRFNDTTTEFPRGKTLIQLFEEQVERIPDAAAITLNEQE

LTYRELNERVNRLARTLRSHGISKGRLVAILAERSIEMVVGMLAAHKAG

AAYVPIDPEYPEERIRFLIEDSGGQVMLTQSRLRERLAGSDPVILLDDE

SFYHEDGTNLNTGIEATDLACVIYTSGTTGKPKGNPVSHRNIVRVVQNT

NYIDITERDHVLQLSSYSFDGATFDIFGALTNGARLVLVPYETLLEIGR

LADLIQRERISVMFITTAFFNILVDVNVDCLRDVRAILFGGERVSVGHV

RKALAHIGPGRLNHVYGPTESTVYTTYLPVDFVDELAVTVPIGRPISNT

TVYIVDSRNKLLPIGVAGELCVGGEGLVRGYNNRPELTAEKFVDNPFVP

GERMYRTGDLAKWLPDGTIEYVGRTDDQVKIRGFRIELGEIEAQLQKVE

GIRKTTVFARENASGEKQLCAYYEADCELPAAELKSVLSKELPAYMIPA

YLIQLERLPLTTNGKVDRRSLPAPEESLQPGGG,
``` the underlined amino acids DGFFLGVVYK being conserved and forming a binding pocket specific for a leucine, isoleucine or valine residue.

According to one particular aspect of the invention, the second adenylation site of PmxA has 91%, 92%, 93%, 94%, 95%, 96%, 97%, 98%, 99% or 100% identity with the peptide sequence SEQ ID NO 1, the underlined amino acids DGFFLGVVYK being conserved and forming a binding pocket specific for a leucine, isoleucine or valine residue.

According to one particular aspect of the invention, the second adenylation site of PmxA has a peptide sequence comprising or consisting of the peptide sequence SEQ ID NO 27, the underlined amino acids DGFFLGVVYK being conserved and forming a binding pocket specific for a leucine, isoleucine or valine residue.

According to one particular aspect of the invention, the PmxA synthetase comprises four specific binding pockets comprising the following amino acids:

DAWIVGAIVK (SEQ ID NO 2), specific for a leucine residue;
DGFFLGVVYK (SEQ ID NO 3), specific for a leucine, isoleucine or valine residue;
DVGEISAIDK (SEQ ID NO 4), specific for a diaminobutyric acid residue;
DVGEISAIDK (SEQ ID NO 5), specific for a diaminobutyric acid residue.

It is clearly understood that these sequences SEQ ID NO 2, 3, 4 and 5 group together the essential amino acids forming a functional binding pocket in a three-dimensional structure, but are not consecutive amino acids in a peptide sequence.

According to one particular aspect of the invention, the PmxA synthetase comprises the polypeptide sequence presented in SEQ ID NO 6, and shown in FIG. 5, the adenylation domains being indicated in bold, the amino acids forming the binding pocket being underlined. In particular, this sequence may comprise, in addition to the sequence presented in SEQ ID NO 6, additional amino acids at the N- and C-terminal ends.

According to one particular aspect, the polypeptide sequence of the PmxA synthetase consists of the polypeptide sequence presented in SEQ ID NO 6.

According to another aspect of the invention, the PmxA synthetase has the sequence which comprises, or consists of, the peptide sequence presented in SEQ ID NO 25.

The PmxA synthetase has four adenylation sites at the following positions:
from residue 234L to residue 751Y;
from residue 1741V to residue 2263G;
from residue 2815P to residue 3345T;
from residue 3900E to residue 4428G.

It is understood that these positions are identified according to a particular peptide sequence, in this case according to SEQ ID NO 6 comprising 4967 amino acids, and may be redefined for sequences of larger size.

In particular, when the PmxA synthetase has a sequence consisting of the sequence SEQ ID NO 25, the four adenylation sites are in the following positions:
from residue 265L to residue 782Y;
from residue 1772V to residue 2294G;
from residue 2846P to residue 3376T;
from residue 3931E to residue 4459G.

The present invention also relates to a PmxE synthetase involved in polymyxin E synthesis, comprising five adenylation sites and one epimerization site, characterized in that the epimerization site has at least 90% identity with the peptide sequence as presented in SEQ ID NO 30.

According to one particular aspect of the invention, the peptide sequence of the PmxE synthetase comprises or consists of the sequence represented in sequence SEQ ID NO 14.

This synthetase is responsible for the integration of residues 1 to 5 (see FIG. 1 for the numbering) into the peptide chain of the polymyxin E molecule. This synthetase has the functional characteristic of being able to convert the L-Dab residue into its stereoisomer D-Dab, and of incorporating said stereoisomer in position 3 in a polymyxin E peptide chain. Such a variant polymyxin molecule might have improved antimicrobial properties, as has been proposed in the literature (Hong S Y et al., 1999; Lee D L et al., 2004).

The present invention also relates to a nucleic acid comprising an open reading frame, encoding a synthetase involved in polymyxin E synthesis, having at least 90% identity with the nucleotide sequence SEQ ID NO 7, with the proviso that the nucleotides encoding the underlined amino acids DGFFLGVVYK of the sequence SEQ ID NO 1 are conserved.

According to one particular aspect of the invention, the nucleic acid encoding a synthetase involved in polymyxin E synthesis has 91%, 92%, 93%, 94%, 95%, 96%, 97%, 98%, 99% or 100% identity with the nucleotide sequence SEQ ID NO 7, with the proviso that the nucleotides encoding the underlined amino acids DGFFLGVVYK of the sequence SEQ ID NO 1 are conserved.

The expression "the nucleotides [ . . . ] are conserved" indicate that these nucleotides encoding the amino acids DGFFLGVVYK of the sequence SEQ ID NO 1 must be either identical to those observed in the same position in the sequence SEQ ID NO 7, or different but with the proviso that the codons formed by these nucleotides encode the amino acids DGFFLGVVYK underlined in the sequence SEQ ID NO 1.

This is because, and as indicated above, these amino acids are essential to the specificity and to the activity of this synthetase and may not therefore be modified, without the risk of losing or reducing the specificity of this binding pocket.

According to another particular aspect of the invention, the nucleic acid encoding a PmxA synthetase involved in polymyxin E synthesis comprises a nucleotide sequence encoding the second adenylation site of this PmxA synthetase, consisting of the nucleotide sequence presented in sequence SEQ ID NO 28. This sequence encodes the peptide sequence represented in SEQ ID NO 27 and also encodes the peptide sequence represented in SEQ ID NO 1 which has two amino acids fewer than SEQ ID NO 27 at the C-terminal end of the domain.

The present invention also relates to a group of genes encoding enzymes involved in polymyxin E synthesis, comprising in particular:
a gene encoding the PmxA synthetase as defined above, and
genes encoding respectively the PmxB and PmxE synthetases.

According to one preferred aspect of the invention, this group of genes comprises the pmxE gene encoding a PmxE synthetase comprising an epimerization domain, the peptide sequence of which comprises or consists of the sequence represented in SEQ ID NO 30.

According to one preferred aspect of the invention, this group of genes also comprises genes encoding respectively the PmxC and PmxD transport proteins. The sequences of the PmxC and PmxD proteins isolated from the *Paenibacillus alvei* strain are shown in sequences SEQ ID NO 12 and NO 13, respectively.

According to another particular aspect of the invention, this group of genes involved in polymyxin E synthesis comprises:
a pmxA gene having at least 90% identity with the sequence SEQ ID NO 7, with the proviso that the nucleotides encoding the underlined amino acids DGFFLGVVYK of the sequence SEQ ID NO 1 are conserved,
a pmxB gene having at least 90% identity with the sequence SEQ ID NO 8, and
a pmxE gene having at least 90% identity with the sequence SEQ ID NO 9.

According to another aspect of the invention, this group of genes involved in polymyxin E synthesis comprises:
a pmxA gene having at least 95% identity with the sequence SEQ ID NO 7, with the proviso that the portion of nucleic acid encoding the underlined amino acids DGFFLGVVYK is conserved,
a pmxB gene having at least 95% identity with the sequence SEQ ID NO 8, and
a pmxE gene having at least 95% identity with the sequence SEQ ID NO 9.

According to another aspect of the invention, this group of genes involved in polymyxin E synthesis comprises:
a pmxA gene comprising a nucleotide sequence having 100% identity with the sequence SEQ ID NO 7, and in particular comprising a nucleotide sequence as presented in SEQ ID NO 26,
a pmxB gene comprising a nucleotide sequence having 100% identity with the sequence SEQ ID NO 8, and a pmxE gene comprising a nucleotide sequence having 100% identity with the sequence SEQ ID NO 9.

The present invention also relates to a nucleic acid comprising or consisting of a sequence SEQ ID NO 10, or a sequence SEQ ID NO 29, representing the complete sequence of the cluster derived from the *Paenibacillus alvei* strain, comprising the pmxA, pmxB, pmxC, pmxD and pmxE genes involved in polymyxin E synthesis.

Table 1 below presents the various nucleic acid and protein sequences referenced in the present application:

| Sequence number | Type | Size | Definition |
|---|---|---|---|
| SEQ ID NO 1 | Protein | 523 amino acids | Peptide sequence of the second adenylation site of a PmxA synthetase derived from a *Paenibacillus alvei* strain |
| SEQ ID NO 2 | Protein | 10 amino acids | Binding pocket of the 1$^{st}$ adenylation domain of PmxA, these amino acids forming a binding pocket specific for a leucine residue |
| SEQ ID NO 3 | Protein | 10 amino acids | Binding pocket of the 2$^{nd}$ adenylation domain of PmxA, these amino acids forming a binding pocket specific for a leucine, isoleucine or valine residue |
| SEQ ID NO 4 | Protein | 10 amino acids | Binding pocket of the 3$^{rd}$ adenylation domain of PmxA, these amino acids forming a binding pocket specific for a diaminobutyric acid residue |
| SEQ ID NO 5 | Protein | 10 amino acids | Binding pocket of the 4$^{th}$ adenylation domain of PmxA, these amino acids forming a binding pocket specific for a diaminobutyric acid residue |
| SEQ ID NO 6 | Protein | 4967 amino acids | Complete peptide sequence of a PmxA synthetase derived from a *Paenibacillus alvei* strain; see also FIG. 5 |
| SEQ ID NO 7 | DNA | 14901 base pairs | Coding sequence for the PmxA synthetase having the sequence SEQ ID NO 6 |
| SEQ ID NO 8 | DNA | 3306 base pairs | Coding sequence for the PmxB synthetase derived from *Paenibacillus alvei* |
| SEQ ID NO 9 | DNA | 18876 base pairs | Coding sequence for the PmxE synthetase derived from *Paenibacillus alvei*, having the sequence SEQ ID NO 31 |
| SEQ ID NO 10 | DNA | 41169 base pairs | Sequence encoding a complete cluster comprising the pmxA, pmxB, pmxC, pmxD and pmxE genes derived from *Paenibacillus alvei* |
| SEQ ID NO 11 | Protein | 1102 amino acids | Peptide sequence of the PmxB synthetase derived from a *Paenibacillus alvei* strain |
| SEQ ID NO 12 | Protein | 608 amino acids | Peptide sequence of the PmxC protein derived from a *Paenibacillus alvei* strain |
| SEQ ID NO 13 | Protein | 577 amino acids | Peptide sequence of the PmxD protein derived from a *Paenibacillus alvei* strain |
| SEQ ID NO 14 | Protein | 6292 amino acids | Peptide sequence of the PmxE synthetase derived from a *Paenibacillus alvei* strain |
| SEQ ID NO 15-24 | DNA | 20 base pairs | Artificial sequences - oligonucleotides (see Table 2) |
| SEQ ID NO 25 | Protein | 4999 amino acids | Complete peptide sequence of a PmxA synthetase derived from a *Paenibacillus alvei* strain |
| SEQ ID NO 26 | DNA | 14997 base pairs | Coding sequence for the PmxA synthetase having the sequence SEQ ID NO 25 |
| SEQ ID NO 27 | Protein | 525 amino acids | Peptide sequence of the second adenylation site of a PmxA synthetase derived from a *Paenibacillus alvei* strain |
| SEQ ID NO 28 | DNA | 1575 base pairs | Coding sequence for the 2$^{nd}$ adenylation domain of PmxA, having the sequence SEQ ID NO 27 |
| SEQ ID NO 29 | DNA | 41172 base pairs | Sequence encoding a complete cluster comprising the pmxA, pmxB, pmxC, pmxD and pmxE genes derived from *Paenibacillus alvei* |
| SEQ ID NO 30 | Protein | 461 | Sequence of the epimerization domain of the PmxE synthetase derived from a *Paenibacillus alvei* strain |
| SEQ ID NO 31 | Protein | 431 | Complete peptide sequence of the enzyme allowing Dab biosynthesis, derived from a *Paenibacillus alvei* strain |
| SEQ ID NO 32 | DNA | 1293 base pairs | Sequence encoding the enzyme having the sequence SEQ ID NO 31, derived from *Paenibacillus alvei* |

Expression Vectors

The present invention also relates to an expression vector comprising a gene encoding a PmxA synthetase as defined above, or a nucleic acid encoding a PmxA synthetase as defined above, and/or a gene encoding a PmxE synthetase as defined above.

In the context of the invention, the terms "vector", "expression vector" and "plasmid" are equivalent and are used in accordance with the usual acceptance in the molecular biology, genetic engineering and microbiology field. Very briefly, it is a non-viral DNA molecule housed by a host cell, distinct from the natural chromosomal DNA of said host cell and capable of autonomous replication. A "vector" is obtained by conventional molecular biology and genetic engineering techniques, and is a molecule into which one or more exogenous nucleotide sequences have been inserted (or cloned). The present invention relates to a vector for the expression, by a host cell, of exogenous nucleotide sequences, comprising:
- an origin of replication,
- elements allowing the expression of the genes introduced, such as an appropriate promoter, enhancers, etc.,
- at least one nucleotide sequence of which the expression is desired.

The choice of the vector and, more particularly, of the origin of replication that it carries depends on the host cell that will house it. Depending on the type of host cells, several copies of a vector and/or several different vectors may be introduced into the same host cell, simultaneously or sequentially.

The choice of the vector will also depend on the size of the nucleic acid sequence to be expressed. In particular, for sequences greater than 20 kilobase pairs, fosmids, which are vectors capable of containing large nucleic acid sequences (up to 40 kilobase pairs), will be preferred. It is also possible to use several vectors, each comprising a portion of a set of genes, and to transfer several vectors into the same host cell, this making it possible to express an entire set of genes in the same strain.

Other vectors that may contain sequences of large sizes are cosmids and bacterial artificial chromosomes (BACs).

According to one preferred aspect of the invention, the expression vector totally or partly comprises a group of genes as defined above.

According to another preferred aspect of the invention, the expression vector totally or partly comprises a nucleic acid as defined above, in particular comprising the sequence presented in SEQ ID NO 10 or in SEQ ID NO 29. Preferably, the expression vector is a fosmid comprising all of the DNA sequence encoding the complete cluster comprising the pmxA, pmxB, pmxC, pmxD and pmxE genes derived from *Paenibacillus alvei*, having the sequence SEQ ID NO 10.

Other Enzymes Involved in Polymyxin Synthesis

Other enzymes are involved in polymyxin synthesis, in particular polymyxin E synthesis. These are enzymes which allow the biosynthesis of the Dab residue, this residue being the residue predominantly integrated into the peptide chain of polymyxin E, and enzymes which allow the bonding of the fatty acid on the peptide part.

An enzyme for biosynthesis of the α,γ-diaminobutyric acid (Dab) residue has been identified and isolated from the bacterial strain of *Paenibacillus alvei* described in the examples. In particular, the peptide sequence of this enzyme comprises or consists of the peptide sequence presented in sequence SEQ ID NO 31. The nucleic acid encoding this enzyme comprises or consists of the nucleotide sequence presented in sequence SEQ ID NO 32.

Preferably, this enzyme with transaminase activity may be expressed in a microorganism intended to produce polymyxin E, in combination with the PmxA, PmxB and PmxE synthetases, and preferably also with the PmxC and PmxD transport molecules.

This transaminase comprising 431 residues has a sequence homology with enzymes exhibiting similar functions, derived from other microorganisms, as is shown in Table 2 below:

Host Cells

The term "host cell" or "host microorganism" is used in the context of the present invention to denote a cell which has been transformed, i.e. into which the exogenous DNA has been introduced, this exogenous DNA being in particular in the form of an expression vector comprising a sequence of interest, which will be expressed by means of the cellular machinery of the host cell, capable of synthesizing, from the exogenous DNA, the messenger RNAs and the proteins corresponding to this DNA.

The present application relates in particular to a microorganism transformed by introducing a gene or group of genes as defined above, or one or more expression vectors as presented above.

The invention relates in particular to a microorganism transferred by introducing:

a gene encoding a PmxA synthetase as defined above, or a gene encoding a PmxE synthetase as defined above, or an expression vector comprising a DNA sequence encoding a PmxA synthetase as defined above, in particular the sequence as presented in SEQ ID NO 7 or in SEQ ID NO 26.

The invention also relates to a microorganism transformed by introducing a group of genes as defined above, or a nucleic acid encoding all or part of the pmxA, pmxB and pmxE genes, as defined above, or at least one expression

TABLE 2

| Accession number | Length (AA) | % Identity with sequence derived from B-LR (SEQ ID NO 31) | Function | Microorganism of origin |
|---|---|---|---|---|
| CP000154.1 | 420 | 73 | Diaminobutyrate-- 2-oxoglutarate transaminase | *P. polymyxa* E681 |
| EJW20319.1 | 389 | 89 | Diaminobutyrate-- 2-oxoglutarate transaminase EctB | *P. alvei* DSM 29 |
| YP_005959913.1 | 420 | 74 | diaminobutyrate- 2-oxoglutarate transaminase | *P. polymyxa* M1 |
| EGG38373.1 | 430 | 50 | diaminobutyrate-- 2-oxoglutarate transaminase | *P.* sp. HGF5 |
| EGL19185.1 | 434 | 65 | diaminobutyrate-- 2-oxoglutarate transaminase [*Paenibacillus* sp. HGF7] | *P.* sp. HGF7 |
| ABX39524.1 | 429 | 50 | diaminobutyrate- 2-oxoglutarate transaminase | *Halobacillus halophilus* DSM 2266 |

Enzymes which allow the bonding of the fatty acid on the peptide chain of polymyxin E, said enzymes therefore having acyl transferase activity, have also been identified and isolated from the bacterial strain of *Paenibacillus alvei* described above.

Preferably, at least one acyl transferase will be expressed in a microorganism intended for producing polymyxin E, in combination with the PmxA, PmxB and PmxE synthetases, and preferably also with the PmxC and PmxD transport molecules, and more preferably also with an enzyme for the biosynthesis of the α,γ-diaminobutyric acid (Dab) residue.

Alternatively, the bonding of the fatty acid on the peptide chain of polymyxin E may also be carried out by chemical coupling, according to one of the techniques well known to those skilled in the art.

vector comprising a gene encoding all or part of the pmxA, pmxB and pmxE genes, as defined above.

According to one particular aspect of the invention, the microorganism is in addition transformed so as to comprise at least one nucleic acid encoding an enzyme involved in the biosynthesis of the Dab residue, and in particular a nucleic acid comprising a sequence comprising or consisting of the sequence SEQ ID NO 32.

According to another aspect of the invention, the microorganism is in addition transformed so as to comprise at least one nucleic acid encoding an enzyme with acyl transferase activity, catalyzing the bonding of a fatty acid on the peptide chain of polymyxin E.

The transformation of microorganisms is a technique commonly used in molecular biology laboratories, which makes it possible to introduce exogenous DNA into the microorganism. Various techniques enable the transformation of a microorganism, and in particular of a competent bacterium, and are all well known to those skilled in the art. Mention may in particular be made of electroporation, and the use of calcium chloride followed by a heat shock.

In one preferred aspect of the invention, in the transformed microorganism, the gene or the group of genes introduced is overexpressed.

The overexpression of a gene may be defined by an increased expression of this gene, i.e. a greater production of messenger RNA and the protein encoded by this gene, in the cell. The expression of the protein will in particular be increased by 50%, by 100%, by 150%, by 200%, or even by 300% compared with the level of endogenous expression observed in a bacterium expressing this gene naturally, before any transformation.

The overexpression of a gene may be obtained in several ways, all well known to those skilled in the art. Mention will in particular be made of: using strong promoters for controlling the level of gene expression and increasing the number of copies of the gene in the cell. Preferably, the vector used will comprise a strong promoter under the control of which the gene will be inserted, and said vector will be present in a high number of copies, in particular 10, 20, 50 or 100 copies in the host cell.

Those skilled in the art will know how to choose the host microorganism most suitable for the expression of a vector comprising the gene(s) according to the invention. In particular, gram-positive bacteria will be preferred. A microorganism which is particularly suitable is a bacterium belonging to the *Bacillus* or *Paenibacillus* genus. The species *B. subtilis* and *Paenibacillus polymyxa* are particularly suitable for the expression of polymyxin synthetases and the production of polymyxin E. The strains of the *Paenibacillus* genus, and in particular of *Paenibacillus alvei*, and more particularly the *Paenibacillus alvei* strain isolated from the environment by the inventors, may also be used as host microorganism to be transformed with the vector or the nucleic acid as defined above. Finally, synthetic bacteria may also be used in the context of the present invention, as host cells.

Method for Producing Polymyxin E

The present application also relates to a method for producing polymyxin E, comprising:
 culturing a transformed microorganism as defined above, in an appropriate mineral medium, and
 purifying, from the culture medium, the polymyxin E produced.

The term "appropriate mineral medium" denotes a culture medium which allows the growth of microorganisms, and which comprises in particular mineral salts and nutrients. A preferred medium has the following specific composition: 0.45% (w/v) anhydrous $KH_2PO_4$, 1.13% (w/v) $K_2HPO_4 \cdot 3H_2O$, 0.6% (w/v) $(NH_4)_2SO_4$, 0.6% (w/v) glucose, 0.001%0 (w/v) thiamine, 0.02% (w/v) $MgSO_4 \cdot 7H_2O$. This medium may also comprise, where appropriate, a precursor required for polymyxin synthesis, in particular diaminobutyric acid.

According to one preferred aspect of the invention, the culturing is carried out at a temperature of 30° C., and lasts at least 25 hours.

Preferably, the culturing takes place in 200 ml of mineral medium in 1 L flasks, with shaking, for 30 h at 30° C.

The present invention also relates to a method for producing polymyxin E variants, comprising culturing a microorganism as defined above, in an appropriate mineral medium, and purifying, from the culture medium, the polymyxin E variant(s).

The present invention also relates to polymyxin E variants obtained according to the production method as described above.

The "polymyxin E variants" denote molecules derived from the structure of polymyxin E (see FIG. 1) and which may for example have one or more different amino acids, without however being classified as belonging to another type of polymyxin.

In particular, the types of molecules detected in the culture medium for the *Paenibacillus alvei* strain BL-R are polymyxin E variants which have the following structural difference: the residue in position 3 may be a D-Dab residue in place of an L-Dab residue observed in the conventional structure of polymyxin E.

The variant forms may be natural or synthetic. The term "natural variants" is intended to mean variants synthesized by non-transformed microorganisms; the term "synthetic variants" is intended to mean variant forms synthesized by transformed microorganisms, which have not been identified in the natural state.

In particular, the polymyxin synthetases encoded by the pmxA, pmxB and pmxE genes may be modified so as to become specific for the binding of certain amino acids which are part of the composition of polymyxin E, in order to synthesize polymyxin E variants which have fewer cationic charges and which are therefore less toxic to the human organism.

These polymyxin E variants have advantages and in particular a lower toxicity than polymyxin E.

Moreover, the clinical use of various polymyxin E variants makes it possible to reduce the appearance of antibiotic resistance.

It is probable that, for the variants comprising D-Dab residues in place of L-Dab residues, the antimicrobial activity of these molecules is increased compared with the antimicrobial properties observed with the conventional polymyxins.

The present invention relates to these variants, and also to the use thereof in the treatment of bacterial infections with gram-negative bacteria.

The examples below illustrate the invention claimed, but are not limiting.

EXAMPLES

Example 1. Isolation and Sequencing of the Genetic System for Producing Colistin A microorganism (B-LR) producing colistin (polymyxins E1 and E2), belonging to the *Paenibacillus alvei* species, was isolated from the environment and cultured. A genomic DNA library was constructed in *Escherichia coli* using fosmid vectors (900 clones). The search for the genes encoding the enzymes which synthesize colistin was carried out by degenerate PCRs. The primers used were defined with the aim of amplifying the domains specializing in the integration of diaminobutyric acid (Dab), which is the amino acid most representing the structure of colistin (6 amino acids/12). Three clones of interest were selected from the sequence (Roche GS FLX). The sequences obtained could be assembled over 50 kb. The open reading frames were sought. Five of them called A, B, C, D and E describe a cluster of approximately 41 kb with A (14.9 kb), B (3.3 kb), C (1.8 kb), D (1.7 kb) and E (18.9 kb), which is represented in FIG. 2.

The A, B and E genes were identified, by sequence homology, as encoding synthetases. An in silico study made it possible to predict the involvement of these synthetases in the assembly of colistin (http://nrps.informatik.uni-tuebingen.de/ and http://nrps.igs.umaryland.edu/nrps/). The C and D genes could, for their part, be involved in the export and resistance of the producer microorganism with respect to colistin.

TABLE 3

Primers for amplifying the genes of interest of the colistin cluster of B-LR

| | |
|---|---|
| A | (F) ATGGCTTTTGAAAAAGAAAC |
|   | (R) GAACGCAAATTCGATCGTAT |
| B | (F) ATGAAATCTTTATTTGAAAA |
|   | (R) GCTTCCATGCAGTACCCCGG |
| E | (F) ATGGAAATTATGAATCCGGG |
|   | (R) GAAAATAATATCAATGGCCT |
| C | (F) ATGGAAGCTGACCGACAGCC |
|   | (R) GTGTACGCCACCTCCCTGCG |
| D | (F) ATGAAAAAGGGCGGATGGCT |
|   | (R) GCCGTACAGCCGGGCGTAAT |

These oligonucleotides are represented in SEQ ID NOS 15 to 24.

Example 2. Comparison of the Adenylation Domains of Various *Paenibacillus* Strains Producing Molecules Belonging to the Polymyxin Family The enzymes involved in polymyxin production belong to the non-ribosome synthetase (NRPS) family. These synthetases are capable of producing a particular peptide without relying on the translation of an mRNA template. The specificity of the peptide chain produced depends on a precise sequence of amino acids of the synthetase constituting an adenylation domain. Four adenylation domains were identified in silico for the synthetase A of B-LR, one for B and five for E. Each adenylation domain contains a signature of ten amino acids which confers it on the specificity of integrating a precise amino acid into the non-ribosomal peptide during elongation. These signatures were identified in silico and compared to those described in the literature (Table 4) using the program available at the following web address: http://nrps.informatik.uni-tuebingen.de/.

The E681 and ATCC21830 strains are described in patent U.S. Pat. No. 8,329,430.

The PKB1 strain is described in the article by Shaheen et al., 2011.

The M-1 strain is described in the article by Niu et al., 2013.

TABLE 4

Amino acids conferring the specificity of the adenylation domains of the polymyxin synthetases of the E681, PKB1, ATCC21830, M-1 and B-LR strains Pmx A, 4 domains A

| | 1 | | 2 | | 3 | | 4 | |
|---|---|---|---|---|---|---|---|---|
| E681 | DAWIVGAIVK | Leu | DFWNIGMVHK | Thr | DVGEISAIDK | Dab | DVGEISAIDK | Dab |
| PKB1 | DAWTIAAIAK | Phe | DGFLLGLVYK | Leu | DVGEISAIDK | Dab | DVGEISAIDK | Dab |
| 21830 | DAWIVGAIVK | Leu | DGFLLGLVYK | Leu | DVGEISAIDK | Dab | DVGEISAIDK | Dab |
| M-1 | DAWTIAAIAK | Phe | DFWNIGMVHK | Thr | DVGEISAIDK | Dab | DVGEISAIDK | Dab |
| B-LR | DAWIVGAIVK | Leu | DGFFLGVVYK | Leu/Ileu/Val | DVGEISAIDK | Dab | DVGEISAIDK | Dab |

Pmx B, 1 domain A

| | 1 | |
|---|---|---|
| E681 | DFWNIGMVHK | Thr |
| PKB1 | DFWNIGMVHK | Thr |
| 21830 | DFWNIGMVHK | Thr |
| M-1 | DFWNIGMVHK | Thr |
| B-LR | DFWNIGMVHK | Thr |

Pmx E, 5 domains A

| | 1 | | 2 | | 3 | | 4 | | 5 | |
|---|---|---|---|---|---|---|---|---|---|---|
| E681 | DVGEISSIDK | Dab | DFWNIGMVHK | Thr | DVGEISSIDK | Dab | DVGEISAIDK | Dab | DVGEISAIDK | Dab |
| PKB1 | DVGEISSIDK | Dab | DFWNIGMVHK | Thr | DVGEISSIDK | Dab | DVGEISAIDK | Dab | DVGEISAIDK | Dab |
| 21830 | DVGEISSIDK | Dab | DFWNIGMVHK | Thr | DVGEISSIDK | Dab | DVGEISAIDK | Dab | DVGEISAIDK | Dab |
| M-1 | DVGEISSIVK | Dab | DFWNIGMVHK | Thr | DVGEISSIDK | Dab | DVGEISAIDK | Dab | DVGEISAIDK | Dab |
| B-LR | DVGEISSIDK | Dab | DFWNIGMVHK | Thr | DVGELSSIDK | Dab | DVGEISAIDK | Dab | DVGEISAIDK | Dab |

The synthetases of B-LR differ at the level of the second adenylation domain of the PmxA synthetase and of the third domain of the PmxE synthetase.

The comparisons with the protein sequences derived from the BL-R strain with the protein sequences already known are presented in Table 5 below:

TABLE 5

| | sizes | | % protein sequence ID | | |
|---|---|---|---|---|---|
| | | | | | ATCC |
| Sequences | pb | aa | PKB1 | E681 | 21830 |
| A | 14901 | 4967 | 94 | 90 | 96 |
| A | 14997 | 4999 | 94 | 90 | 95 |
| B | 3306 | 1102 | 96 | 95 | 96 |
| E | 18876 | 6292 | 95 | 96 | 84 |
| C | 1824 | 608 | | | |
| D | 1731 | 577 | | | |

Example 3. Construction of a pmxE-Mutant and Analysis of the Colistin Production Thereof A sequence of 1650 bp beginning at the end of pmxD and finishing at the start of pmxE was selected and amplified. It has the particularity of possessing a unique SacII enzyme restriction site. The amplified sequence was cloned into the pGEM® 7Z plasmid. The gene encoding apramycin resistance was integrated at the SacII restriction site. This construct was introduced into B-LR by electroporation. The selection of the mutants having undergone a double recombination event was carried out by culturing on agar medium supplemented with apramycin. The antiomicrobial activity of the supernatant of the mutants was compared with that of B-LR. The culture supernatant of mutant 5 is less active than that of the wild-type B-LR bacterium on *P. aeruginosa* (FIG. 4).

Example 4. Characteristics of the PmxE Synthetase Derived from *Paenibacillus*

The peptide sequence of the PmxE synthetase is presented in sequence SEQ ID NO 14. The sequence of the epimerization domain is presented in SEQ ID NO 30; it comprises at least 461 residues comprised between and including the residues $Val^{3205}$ to $Leu^{3665}$ of the sequence SEQ ID NO 14. One of the characteristics of non-ribosomal peptides is the presence of amino acids with (L) stereoisomerism. Usually, an (L) amino acid is activated by the A domain, which then incorporates it directly. However, sometimes, this amino acid of the (L) series may be converted into its (D) form by any epimerization domain, before the formation of the peptide bond. According to the in silico predictions, two epimerization domains were identified in modules 3 and 6 of the pmx cluster. This suggests that a stereochemical change in the amino acids present at these sites is possible. Thus, the amino acids present in position 3 (Dab-3) and in position 6 (Leu-6) would be incorporated into the peptide chain in their (D) form. This was known for Leu-6, incorporated in its (D) form into all polymyxins E, but is unusual for the Dab-3 residue.

The PmxE synthetase according to the invention therefore has the property of converting the L-Dab residue into its stereoisomer (D), and of integrating it in position 3 (see FIG. 1) in the polymyxin E molecule synthesized.

Said polymyxin E molecules comprising a D-Dab residue in position 3 are polymyxin E variants.

Example 5. Production of Polymyxin E by a Microorganism Expressing the Combination of a PmxA, a PmxB and a PmxE Characterized in the Preceding Examples The microorganism (B-LR) produces several types of polymyxin E molecules comprising a leucine, isoleucine or valine residue in position 7.

These various types of molecules could be detected in the culture medium by mass spectrometry, according to the protocol detailed below:

A control solution of colistin sulfate at 0.0002% was prepared in the microorganism culture medium (M63T medium). Four fractions were recovered and analyzed by UPLC-MS (Ultra Performance Liquid Chromatography-tandem mass spectrometry). The two peaks corresponding to the polymyxins E1 and E2 present in the positive control were found in the fourth extraction fraction.

The B-LR strain exhibits a maximum level of antimicrobial activity at 30 hours of culture. At this time, the culture supernatant was recovered and filtered (0.22 μm) before being subjected to a solid-phase extraction step. The peptides of the fourth fraction were analyzed by UPLC-MS. Seventeen elution peaks were observed in this fourth fraction. Among them, the main peaks exhibiting retention times of 1.61 and 1.52 minutes have $[M+H]^+$ molecular masses respectively of 1169.7727 and 1155.7555. They correspond respectively to the known polymyxins E1 and E2, which have the same peptide structure and differ by their fatty acids, respectively of formulae $C_9H_{17}O$ and $C_8H_{15}O$.

MS/MS analyses were carried out in order to confirm these structures, as have previously been presented in the articles by Govaerts et al., 2002; and by DeCrescenzo et al., 2007. Tandem mass spectrometry (MS/MS) is used to determine the series of amino acids through fragmentation of the peptide bond. This technique consists in combining two analyzers separated by a collision cell. A first step consists in selecting an ion derived from the source of ionization in the quadrupole: this is the parent or precursor ion. This ion undergoes fragmentation in the collision cell under the effect of a bombardment by argon atoms, and gives "daughter" or "product" ions that will be analyzed and protected by the time-of-flight (TOF) analyzer. The TOF analyzer is based on the measurement of the time taken by the ions to cover a given distance, thereby making it possible to detect the m/z ratios and thus to determine the mass of the corresponding ions.

During these experiments, the leucine and isoleucine residues cannot be differentiated, because of their identical molecular masses.

Three decapeptides with a ring containing seven amino acids were purified from the B-LR supernatant. Their molecular weights range from 1140.74 Da to 1168.77 Da. The comparison of these molecules shows homologies at the level of residues 1 to 6 and 8 to 10 and differences at the level of residue 7 and also at the level of the fatty acid. These three molecules correspond to polymyxins (colistins) $E_1$, $E_2$ and to Val-colistin $E_2$. The deduced chemical formulae thereof are presented in Table 6 below.

TABLE 6

| Name | Fatty acid (FA) | Y | Mass (Da) | Molecular formula |
|---|---|---|---|---|
| Colistin $E_1$ | $C_9H_{17}O$ | Leu/Ile | 1168.77 | $C_{53}H_{101}N_{16}O_{13}$ |
| Colistin $E_2$ | $C_8H_{15}O$ | Leu/Ile | 1154.76 | $C_{52}H_{99}N_{16}O_{13}$ |
| Val-Colistin $E_2$ | $C_8H_{15}O$ | Val | 1140.74 | $C_{51}H_{97}N_{16}O_{13}$ |

The mass spectra obtained for colistin $E_1$, colistin $E_2$ and val-colistin $E_2$ have respective $[M+2H]^{2+}$ values of 585.39, 578.38 and 571.38. The fragmentation of the parent ions of colistins $E_1$ and $E_2$ give daughter ions of m/z 829, 728, 628, 427, 327 and 227 (FIGS. 6 and 7) which are formed by loss of amino acid fragments. The fragmentation of the parent ion of val-colistin $E_2$ gives daughter ions of m/z 815, 714, 614, 514, 413, 313 and 213 (FIG. 8) also formed by loss of amino acid fragments.

These daughter ions obtained are identical to those described in the literature during the fragmentation of colistins $E_1$, $E_2$ and Val-$E_2$ (Govaerts et al., 2002; DeCrescenzo et al., 2007). Colistins $E_1$ and $E_2$ have the same amino acid sequences with a molecular mass difference of 14 Da which corresponds to the loss of a $CH_2$ at the level of the fatty acid.

In conclusion, these results show that the B-LR strain produces colistin $E_1$, colistin $E_2$ and valine-colistin $E_2$ (Val-$E_2$).

Example 6. Heterologous Expression of the pmxA, B and E Genes Derived from *Paenibacillus* in *Bacillus subtilis* and Detection of Colistin

*Bacillus* is a heterologous expression host that is phylogenetically close to B-LR. The fosmid manipulated to house all of the colistin production cluster is transferred into the recipient strain by electroporation. The transformed strains are selected on agar medium supplemented with an antibiotic. The colistin production is carried out in liquid medium supplemented with diaminobutyric acid (synthesis precursor). The colistin is detected after separation of the biomass from the culture supernatant. Extractions make it possible to isolate the colistin before characterization thereof by mass spectrometry.

REFERENCES

Patents

U.S. Pat. No. 8,329,430
WO 1998/020836
WO 2009/098357

Non-Patents

Sambrook et al. '*Molecular Cloning: a Laboratory Manual*'. Second Edition, 1989, Cold Spring Harbor Lab., Cold Spring Harbor, N.Y.

Niu B, Vater J, Rueckert C, Blom J, Lehmann M, Ru J J, Chen X H, Wang Q, Borriss R. "*Polymyxin P is the active principle in suppressing phytopathogenic Erwinia* spp. *by the biocontrol rhizobacterium Paenibacillus polymyxa M*-1". BMC Microbiol. 2013 Jun. 18; 13(1):137.

Choi S K, Park S Y, Kim R, Kim S B, Lee C H, Kim J F, Park S H—"*Identification of a polymyxin synthetase gene cluster of Paenibacillus polymyxa and heterologous expression of the gene in Bacillus subtilis*" J. Bacteriol. May 2009 vol. 191 no. 10-3350-3358

M Shaheen, J Li, A C Ross, J C Vederas, S E Jensen—"*Paenibacillus polymyxa PKB*1 *Produces Variants of Polymyxin B-Type Antibiotics*"—Chemistry & biology, Volume 18, Issue 12, 23 Dec. 2011, Pages 1640-1648

Martti Vaara, Timo Vaara—"*Structure-activity studies on novel polymyxin derivatives that carry only three positive charges*"—Peptides, Volume 31, Issue 12, December 2010, Pages 2318-2321

Govaerts, C., Orwa, J., Van Schepdael, A., Roets, E. & Hoogmartens, J. *Characterization of polypeptide antibiotics of the polymyxin series by liquid chromatography electrospray ionization ion trap tandem mass spectrometry*.—J Pept Sci 8, 45-55. (2002a).

Govaerts, C., Orwa, J., Van Schepdael, A., Roets, E. & Hoogmartens, J. *Liquid chromatography-ion trap tandem mass spectrometry for the characterization of polypeptide antibiotics of the colistin series in commercial samples. J Chromatogr A* 976, 65-78. (2002b).

Hong S Y, Oh J E, Lee K H. *Effect of D-amino acid substitution on the stability, the secondary structure, and the activity of membrane-active peptide*. Biochem Pharmacol. 1999 Dec. 1; 58(11):1775-80.

Lee D L, Powers J P, Pflegerl K, Vasil M L, Hancock R E, Hodges R S. *Effects of single D-amino acid substitutions on disruption of beta-sheet structure and hydrophobicity in cyclic* 14-*residue antimicrobial peptide analogs related to gramicidin S*. J Pept Res. 2004 February; 63(2):69-84.

DeCrescenzo Henriksen, D. R. Phillips and J. B. Doran Peterson. *Polymyxin E production by P. amylolyticus E*. Letters in Applied Microbiology, Volume 45, Issue 5, pages 491-496, November 2007.

The invention claimed is:

1. Method for producing polymyxin E, comprising culturing a microorganism transformed by introducing a gene encoding a PmxA synthetase in an appropriate mineral medium, and purifying, from the culture medium, the polymyxin E produced, said PmxA synthetase comprising four adenylation sites, wherein the second adenylation site has at least 90% identity with the peptide sequence SEQ ID NO:1:

VTEAEKADLLGRFNDTTTEFPRGKTLIQLFEEQVERIPDAAAITLNEQEL

TYRELNERVNRLARTLRSHGISKGRLVAILAERSIEMVVGMLAAHKAGAA

YVPIDPEYPEERIRFLIEDSGGQVMLTQSRLRERLAGSDPVILLDDESFY

HEDGTNLNTGIEATDLACVIYTSGTTGKPKGNPVSHRNIVRVVQNTNYID

ITERDFIVLQLSSYSFDGATFDIFGALTNGARLVLVPYETLLEIGRLADL

IQRERISVMFITTAFFNILVDVNVDCLRDVRAILFGGERVSVGHVRKALA

HIGPGRLNHVYGPTESTVYTTYLPVDFVDELAVTVPIGRPISNTTVYIVD

SRNKLLPIGVAGELCVGGEGLVRGYNNRPELTAEKFVDNPFVPGERMYRT

GDLAKWLPDGTIEYVGRTDDQVKIRGFRIELGEIEAQLQKVEGIRKTTVF
ARENASGEKQLCAYYEADCELPAAELKSVLSKELPAYMIPAYLIQLERLP
LITNGKVDRRSLPAPEESLQPGGG, the bold amino acids D216, G217, F220, F259, L283, G285, V309, V317, Y318, and K505 being conserved and forming a binding pocket specific for a leucine, isoleucine or valine residue.

2. Method for producing polymyxin E, comprising culturing a microorganism transformed by introducing a gene encoding a PmxA synthetase in an appropriate mineral medium, and purifying, from the culture medium, the polymyxin E produced, said PmxA synthetase comprising four adenylation sites, wherein the second adenylation site has at least 90% identity with the peptide sequence SEQ ID NO:1:

VTEAEKADLLGRFNDTTTEFPRGKTLIQLFEEQVERIPDAAAITLNEQEL
TYRELNERVNRLARTLRSHGISKGRLVAILAERSIEMVVGMLAAHKAGAA
YVPIDPEYPEERIRFLIEDSGGQVMLTQSRLRERLAGSDPVILLDDESFY
HEDGTNLNTGIEATDLACVIYTSGTTGKPKGNPVSHRNIVRVVQNTNYID
ITERDFIVLQLSSYSFDGATFDIFGALTNGARLVLVPYETLLEIGRLADL
IQRERISVMFITTAFFNILVDVNVDCLRDVRAILFGGERVSVGHVRKALA
HIGPGRLNHVYGPTESTVYTTYLPVDFVDELAVTVPIGRPISNTTVYIVD
SRNKLLPIGVAGELCVGGEGLVRGYNNRPELTAEKFVDNPFVPGERMYRT
GDLAKWLPDGTIEYVGRTDDQVKIRGFRIELGEIEAQLQKVEGIRKTTVF
ARENASGEKQLCAYYEADCELPAAELKSVLSKELPAYMIPAYLIQLERLP
LITNGKVDRRSLPAPEESLQPGGG, the bold amino acids D216, G217, F220, F259, L283, G285, V309, V317, Y318, and K505 being conserved and forming a binding pocket specific for a leucine, isoleucine or valine residue,
wherein said microorganism belongs to the *Bacillus* or *Paenibacillus* genus.

3. Method for producing polymyxin E according to claim 1, wherein the culturing is carried out at a temperature of 30° C., and lasts at least 25 hours.

4. Method for producing polymyxin E variants, comprising culturing a microorganism transformed by introducing a gene encoding a PmxA synthetase in an appropriate mineral medium, and purifying, from the culture medium, the polymyxin E variant(s), said PmxA synthetase comprising four adenylation sites, wherein the second adenylation site has at least 90% identity with the peptide sequence SEQ ID NO:1:

VTEAEKADLLGRFNDTTTEFPRGKTLIQLFEEQVERIPDAAAITLNEQEL

TYRELNERVNRLARTLRSHGISKGRLVAILAERSIEMVVGMLAAHKAGAA

YVPIDPEYPEERIRFLIEDSGGQVMLTQSRLRERLAGSDPVILLDDESFY

HEDGTNLNTGIEATDLACVIYTSGTTGKPKGNPVSHRNIVRVVQNTNYID

ITERDFIVLQLSSYSFDGATFDIFGALTNGARLVLVPYETLLEIGRLADL

IQRERISVMFITTAFFNILVDVNVDCLRDVRAILFGGERVSVGHVRKALA

HIGPGRLNHVYGPTESTVYTTYLPVDFVDELAVTVPIGRPISNTTVYIVD

SRNKLLPIGVAGELCVGGEGLVRGYNNRPELTAEKFVDNPFVPGERMYRT

GDLAKWLPDGTIEYVGRTDDQVKIRGFRIELGEIEAQLQKVEGIRKTTVF

ARENASGEKQLCAYYEADCELPAAELKSVLSKELPAYMIPAYLIQLERLP

LITNGKVDRRSLPAPEESLQPGGG, the bold amino acids D216, G217, F220, F259, L283, G285, V309, V317, Y318, and K505 being conserved and forming a binding pocket specific for a leucine, isoleucine or valine residue.

* * * * *